(12) United States Patent
Schuster et al.

(10) Patent No.: US 10,781,244 B2
(45) Date of Patent: Sep. 22, 2020

(54) PEPTIDES AND COMBINATION OF PEPTIDES FOR USE IN IMMUNOTHERAPY AGAINST OVARIAN CANCER AND OTHER CANCERS

(71) Applicant: immatics biotechnologies GmbH, Tuebingen (DE)

(72) Inventors: Heiko Schuster, Tuebingen (DE); Janet Peper, Freising (DE); Kevin Roehle, Tuebingen (DE); Phillipp Wagner, Stuttgart (DE); Hans-Georg Rammensee, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/815,965

(22) Filed: Mar. 11, 2020

(65) Prior Publication Data
US 2020/0207832 A1     Jul. 2, 2020

Related U.S. Application Data

(63) Continuation of application No. 15/881,078, filed on Jan. 26, 2018.

(60) Provisional application No. 62/451,255, filed on Jan. 27, 2017.

(30) Foreign Application Priority Data

Jan. 27, 2017 (DE) .......................... 10 2017 101 671

(51) Int. Cl.
| | |
|---|---|
| *A61K 39/00* | (2006.01) |
| *C07K 14/74* | (2006.01) |
| *G16B 30/00* | (2019.01) |
| *C12Q 1/6886* | (2018.01) |
| *A61P 35/00* | (2006.01) |
| *C07K 16/28* | (2006.01) |
| *C07K 14/47* | (2006.01) |

(52) U.S. Cl.
CPC .... *C07K 14/70539* (2013.01); *A61K 39/0011* (2013.01); *A61P 35/00* (2018.01); *C07K 14/4748* (2013.01); *C07K 16/2818* (2013.01); *C07K 16/2833* (2013.01); *C12Q 1/6886* (2013.01); *G16B 30/00* (2019.02); *A61K 39/00* (2013.01); *A61K 2039/892* (2018.08); *C07K 2317/34* (2013.01); *C12Q 2600/156* (2013.01)

(58) Field of Classification Search
CPC ...................................................... A61K 35/17
See application file for complete search history.

(56) References Cited

U.S. PATENT DOCUMENTS

| | | |
|---|---|---|
| 8,080,634 B2 | 12/2011 | Singh et al. |
| 8,669,230 B2 | 3/2014 | Singh et al. |
| 9,283,267 B2 | 3/2016 | Lewandrowski et al. |
| 9,289,478 B2 | 3/2016 | Lewandrowski et al. |
| 9,511,128 B2 | 12/2016 | Singh et al. |
| 9,791,443 B2 | 10/2017 | Weinschenk et al. |
| 9,791,444 B2 | 10/2017 | Weinschenk et al. |
| 9,889,159 B2 | 2/2018 | Schuster et al. |
| 9,950,048 B2 | 4/2018 | Singh et al. |
| 2015/0125477 A1 | 5/2015 | Kuttruff-Coqui et al. |

FOREIGN PATENT DOCUMENTS

| | | |
|---|---|---|
| EP | 2 111 867 A1 | 10/2009 |
| WO | 2003/014151 A2 | 2/2003 |
| WO | 2005/017102 A2 | 2/2005 |
| WO | 2005/049073 A1 | 6/2005 |
| WO | 2009/015842 A2 | 2/2009 |
| WO | 2009/143843 A1 | 12/2009 |
| WO | 2010/037395 A2 | 4/2010 |
| WO | 2010/037397 A1 | 4/2010 |
| WO | 2011/128448 A1 | 10/2011 |
| WO | 2015/063302 A2 | 5/2015 |
| WO | 2014/009400 A1 | 1/2017 |

OTHER PUBLICATIONS

International Search Reporting for PCT/EP2018/051952, dated May 23, 2018.
Schuster et al., "The immunopeptidomic landscape of ovarian carcinomas" PNAS Early Edition. (received for review May 8, 2017) pp. 1-10, followed by supporting information at pp. 11-165.

*Primary Examiner* — Sheela J. Huff
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 30 Drawing Sheets
(19 of 30 Drawing Sheet(s) Filed in Color)
Specification includes a Sequence Listing.

Figure 1E

Gene: VTCN1; Peptide: KVVSVLYNV; SEQ ID No: 75

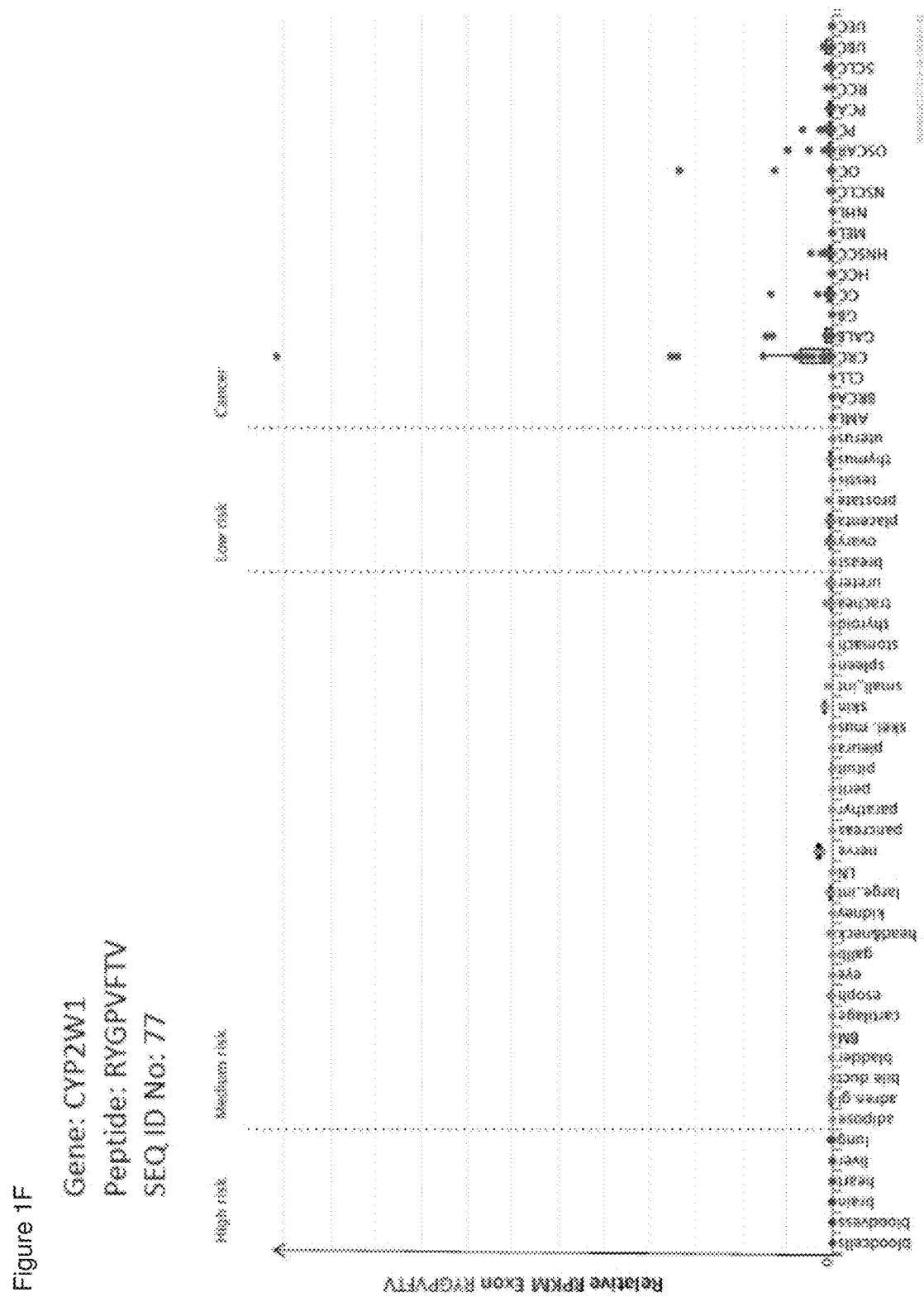

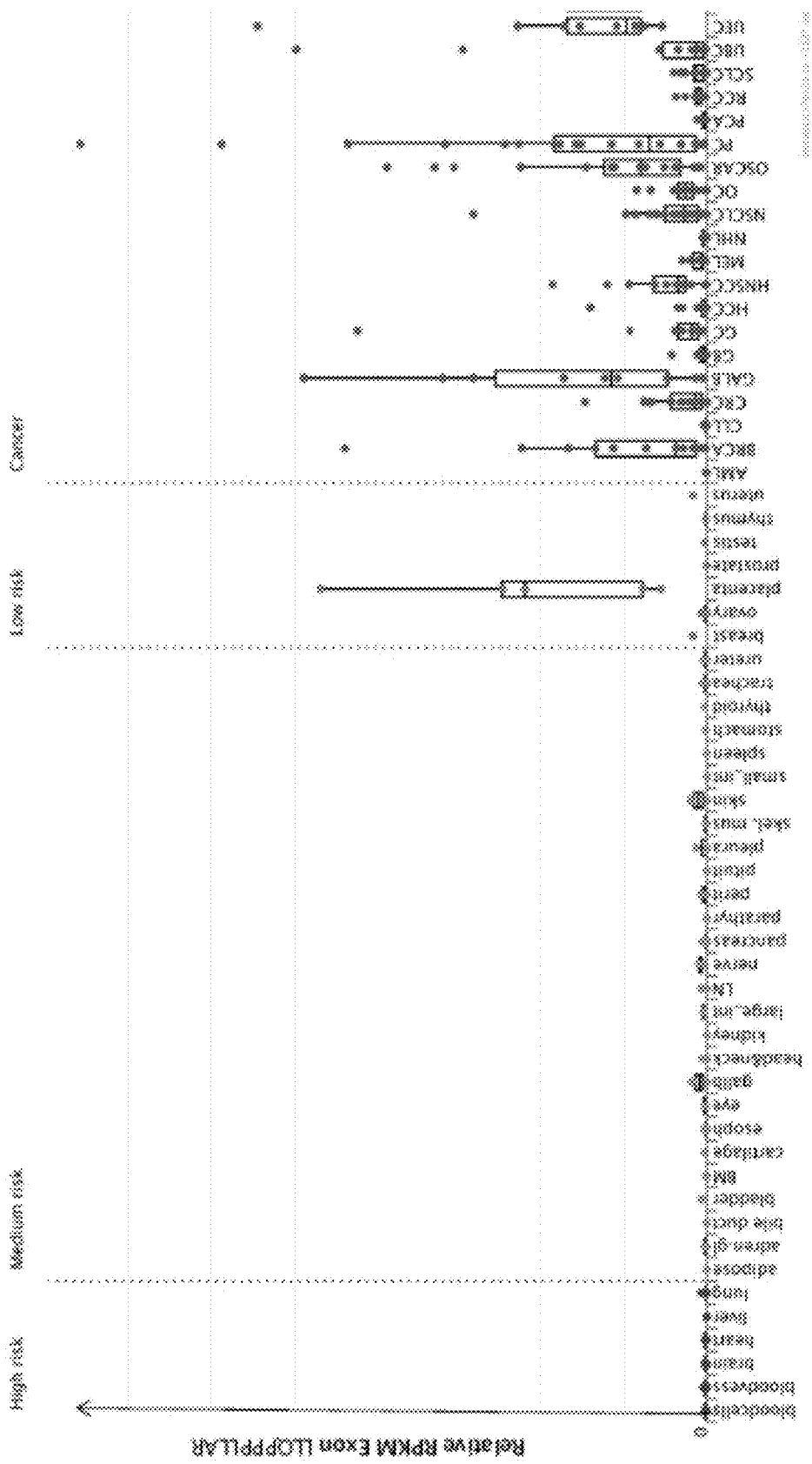

Gene: MMP12; Peptide: FVDNQYWRY; SEQ ID No: 115

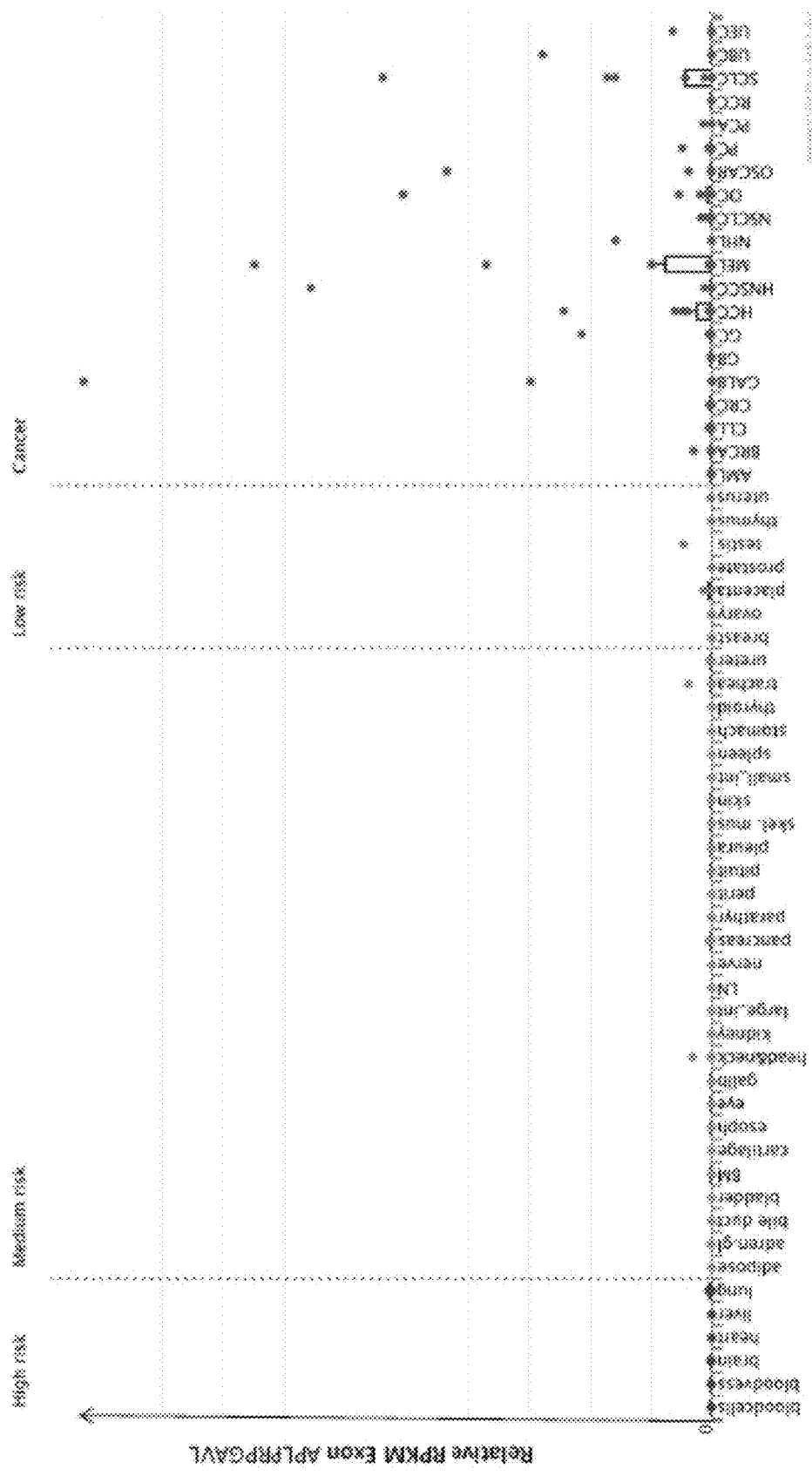
Figure 1}

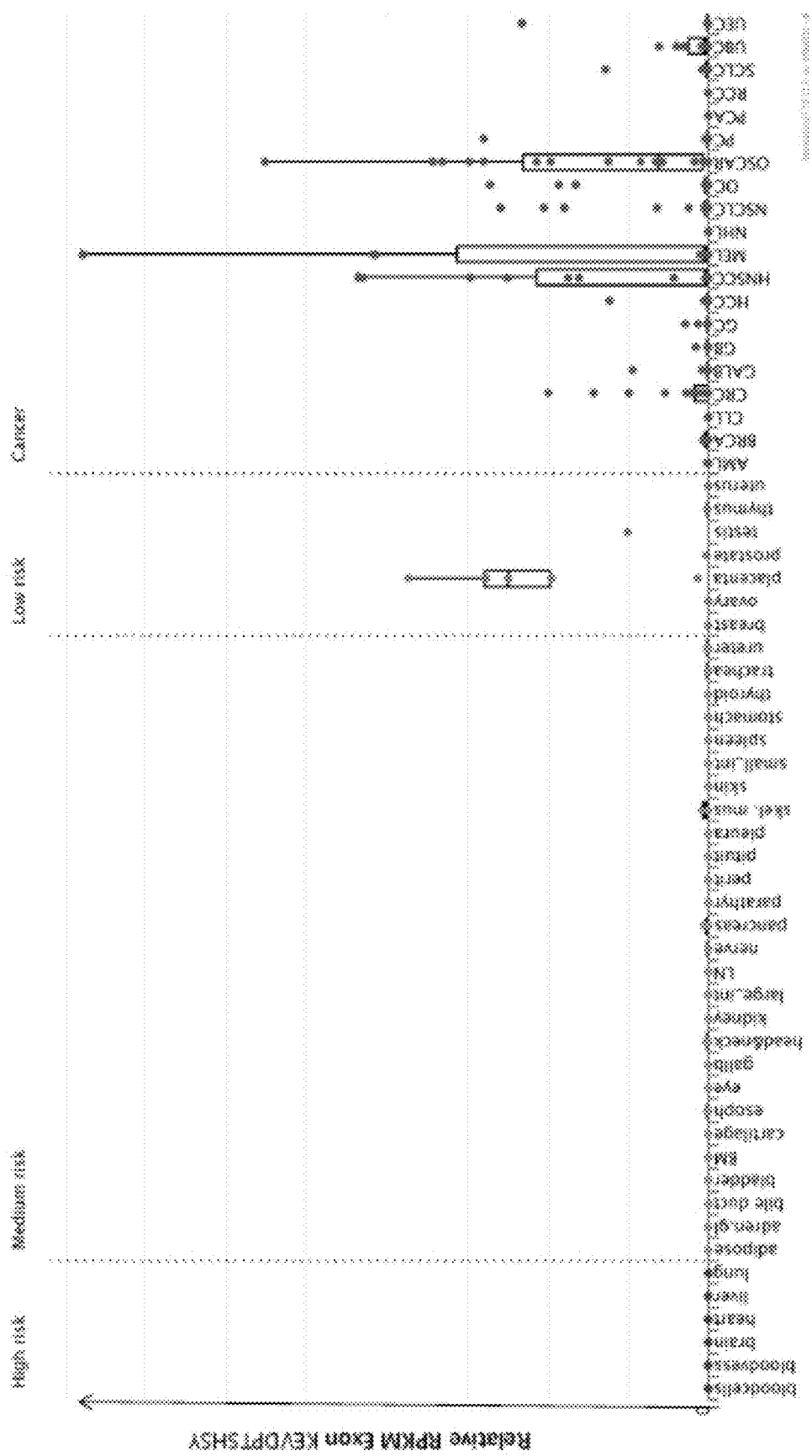
Figure 1M Gene: MAGEA11; Peptide: KEVDPTSHSY; SEQ ID No: 194

Gene: IGF2BP3; Peptide: IEALSGKIEL; SEQ ID No: 413

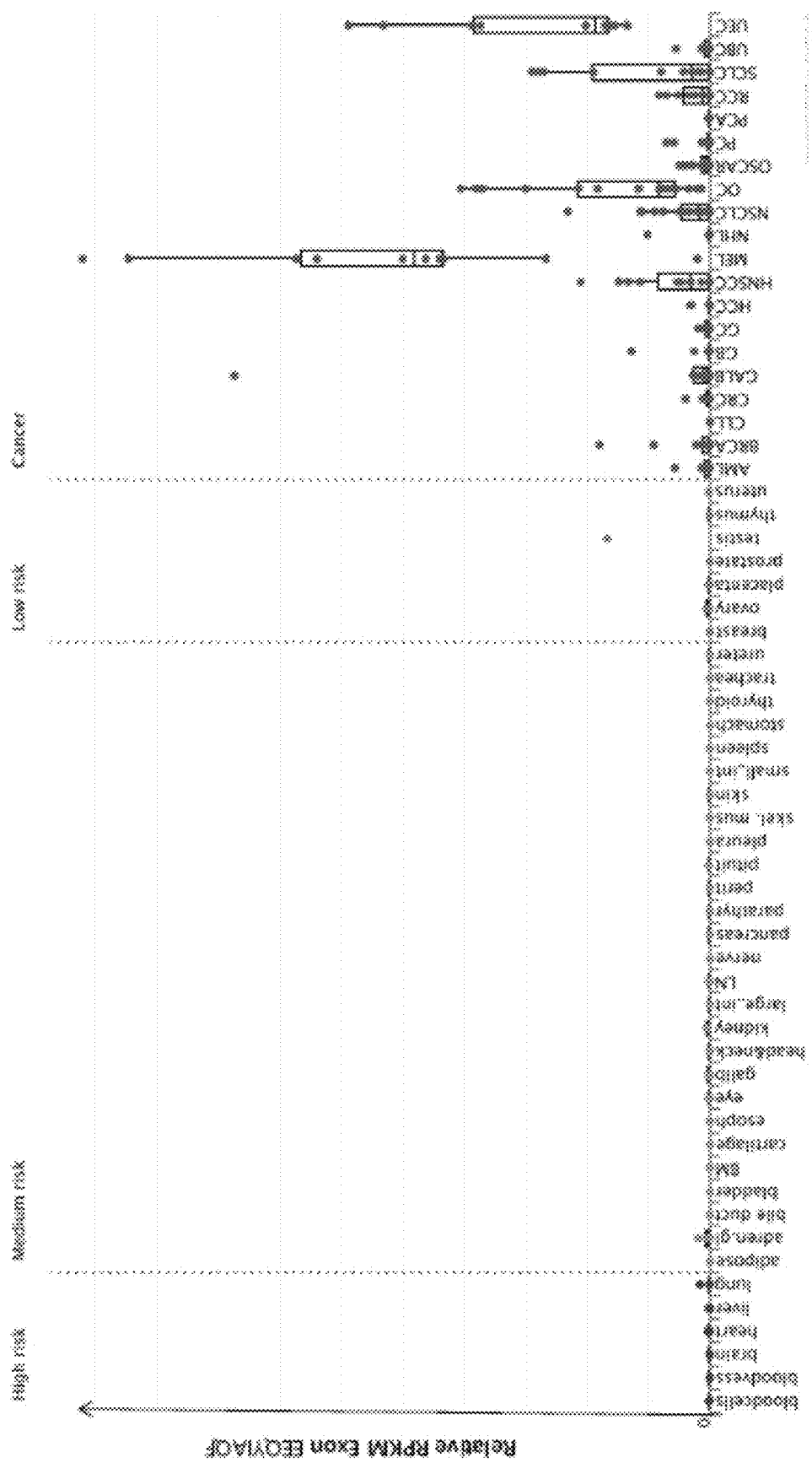
Figure 1S. Gene: PRAME; Peptide: EEQYIAQF; SEQ ID No: 432

Gene: MAGEA4
Peptide: SPDAESLFREALSNKVDEL
SEQ ID: 597

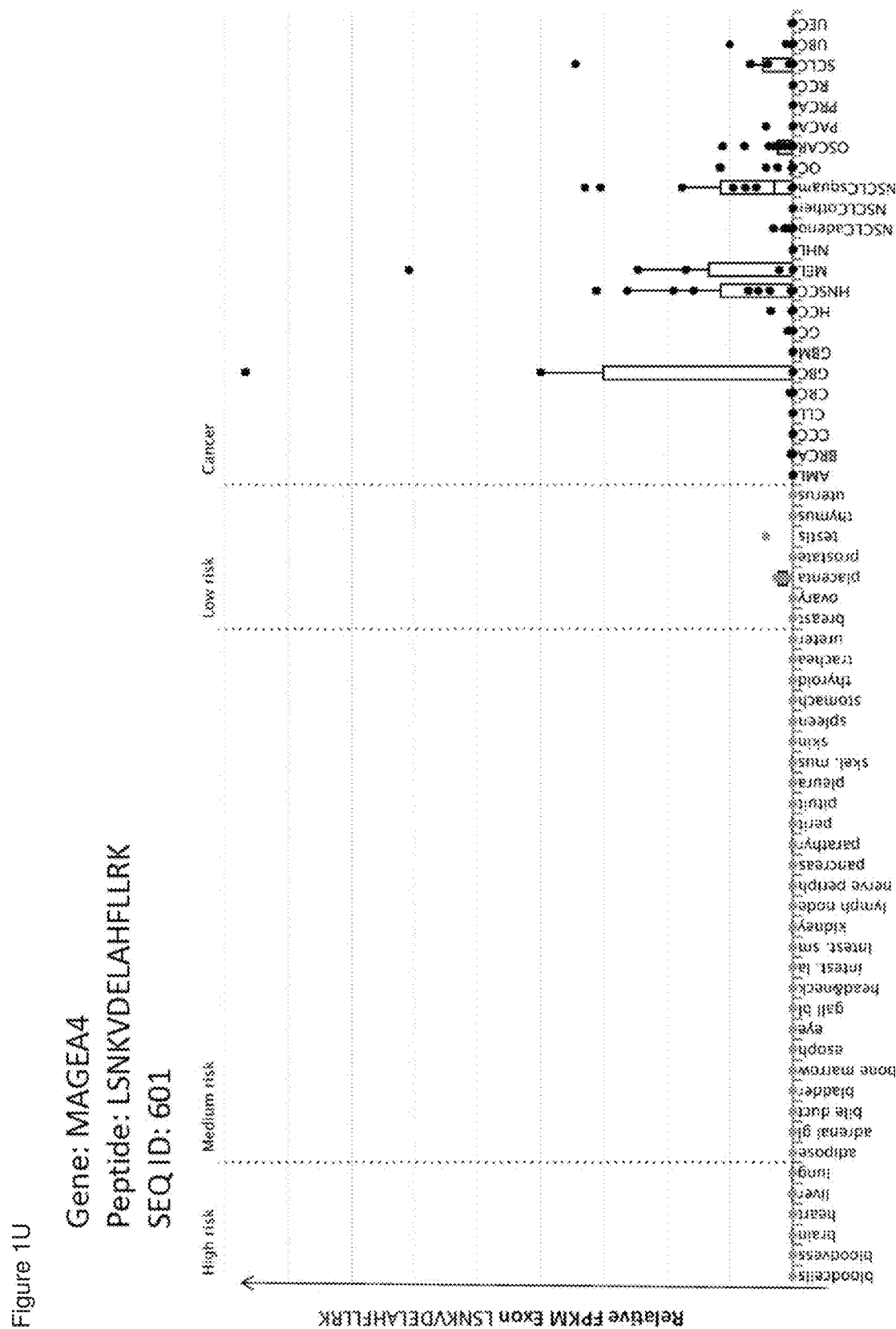

Gene: MAGEB3
Peptide: KLITQDLVKLKYLEYRQ
SEQ ID: 604

PEPTIDES AND COMBINATION OF PEPTIDES FOR USE IN IMMUNOTHERAPY AGAINST OVARIAN CANCER AND OTHER CANCERS

CROSS REFERENCE TO RELATED APPLICATIONS

This application is a continuation of U.S. patent application Ser. No. 15/881,078, filed 26 Jan. 2018, which claims priority to U.S. Provisional Application No. 62/451,255, filed 27 Jan. 2017, and German Patent Application No. 10 2017 101671.6, filed 27 Jan. 2017, the contents of which are incorporated herein by reference in their entirety.

This application is also related to PCT/EP2018/051952 filed 26 Jan. 2018, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-083002_ST25.txt" created on 5 Mar. 2020, and 132,646 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I and HLA class II molecules of human tumor cells that can be used in vaccine compositions for eliciting anti-tumor immune responses, or as targets for the development of pharmaceutically/immunologically active compounds and cells.

DESCRIPTION OF RELATED ART

Ovarian Cancer

With an estimated 239 000 new cases in 2012, ovarian cancer is the seventh most common cancer in women, representing 4% of all cancers in women. The fatality rate of ovarian cancer tends to be rather high relative to other cancers of the female reproductive organs, and case fatality is higher in lower-resource settings. Therefore, ovarian cancer is the eighth most frequent cause of cancer death among women, with 152 000 deaths. In 2012, almost 55% of all new cases occurred in countries with high or very high levels of human development; 37% of the new cases and 39% of the deaths occurred in Europe and North America. Incidence rates are highest in northern and eastern Europe, North America, and Oceania, and tend to be relatively low in Africa and much of Asia. Incidence rates have been declining in certain countries with very high levels of human development, notably in Europe and North America.

The most common ovarian cancers are ovarian carcinomas, which are also the most lethal gynecological malignancies. Based on histopathology and molecular genetics, ovarian carcinomas are divided into five main types: high-grade serous (70%), endometrioid (10%), clear cell (10%), mucinous (3%), and low-grade serous carcinomas (<5%), which together account for more than 95% of cases. Much less common are malignant germ cell tumors (dysgerminomas, yolk sac tumors, and immature teratomas) (3% of ovarian cancers) and potentially malignant sex cord stromal tumors (1-2%), the most common of which are granulosa cell tumors.

Ovarian carcinomas most commonly affect nulliparous women and occur least frequently in women with suppressed ovulation, typically by pregnancy or oral contraceptives. These tumors are generally considered to originate from the cells covering the ovarian surface or the pelvic peritoneum. Malignant transformation of this mesothelium has been explained by the "incessant ovulation" theory (La, 2001).

Family history of ovarian cancer accounts for 10% of cases; the risk is increased 3-fold when two or more first-degree relatives have been affected. Women with germline mutations in BRCA1 or BRCA2 have a 30-70% risk of developing ovarian cancer, mainly high-grade serous carcinomas, by age 70 (Risch et al., 2006).

Surgical resection is the primary therapy in early as well as advanced stage ovarian carcinoma. The ultimate goal is the complete removal of the tumor mass in healthy surrounding tissue. Surgical removal is followed by systemic chemotherapy with platinum analogs, except for very low grade ovarian cancers (stage IA, grade 1), where postoperative chemotherapy is not indicated. In advanced stage, ovarian cancer, the first line chemotherapy comprises a combination of carboplatin with paclitaxel, which can be supplemented with bevacizumab. The standard treatment for platinum-resistant ovarian cancers consists of a monotherapy with one of the following chemotherapeutics: pegylated liposomal doxorubicin, topotecane, gemcitabine or paclitaxel (S3-Leitlinie maligne Ovarialtumore, 2013).

Immunotherapy appears to be a promising strategy to ameliorate the treatment of ovarian cancer patients, as the presence of pro-inflammatory tumor infiltrating lymphocytes, especially CD8-positive T cells, correlates with good prognosis and T cells specific for tumor-associated antigens can be isolated from cancer tissue.

Therefore, a lot of scientific effort is put into the investigation of different immunotherapies in ovarian cancer. A considerable number of pre-clinical and clinical studies has already been performed and further studies are currently ongoing. Clinical data are available for cytokine therapy, vaccination, monoclonal antibody treatment, adoptive cell transfer and immunomodulation.

Cytokine therapy with interleukin-2, interferon-alpha, interferon-gamma or granulocyte-macrophage colony stimulating factor aims at boosting the patient's own anti-tumor immune response and these treatments have already shown promising results in small study cohorts.

Phase I and II vaccination studies, using single or multiple peptides, derived from several tumor-associated proteins (Her2/neu, NY-ESO-1, p53, Wilms tumor-1) or whole tumor antigens, derived from autologous tumor cells revealed good safety and tolerability profiles, but only low to moderate clinical effects.

Monoclonal antibodies that specifically recognize tumor-associated proteins are thought to enhance immune cell-mediated killing of tumor cells. The anti-CA-125 antibodies oregovomab and abagovomab as well as the anti-EpCAM antibody catumaxomab achieved promising results in phase II and III studies. In contrast, the anti-MUC1 antibody HMFG1 failed to clearly enhance survival in a phase III study.

An alternative approach uses monoclonal antibodies to target and block growth factor and survival receptors on tumor cells. While administration of trastuzumab (anti-HER2/neu antibody) and MOv18 and MORAb-003 (anti-folate receptor alpha antibodies) only conferred limited clinical benefit to ovarian cancer patients, addition of bevacizumab (anti-VEGF antibody) to the standard chemotherapy in advanced ovarian cancer appears to be advantageous.

Adoptive transfer of immune cells achieved heterogeneous results in clinical trials. Adoptive transfer of autologous, in vitro expanded tumor infiltrating T cells was shown to be a promising approach in a pilot trial. In contrast, transfer of T cells harboring a chimeric antigen receptor specific for folate receptor alpha did not induce a significant clinical response in a phase I trial. Dendritic cells pulsed with tumor cell lysate or tumor-associated proteins in vitro were shown to enhance the anti-tumor T cell response upon transfer, but the extent of T cell activation did not correlate with clinical effects. Transfer of natural killer cells caused significant toxicities in a phase II study.

Intrinsic anti-tumor immunity as well as immunotherapy are hampered by an immunosuppressive tumor microenvironment. To overcome this obstacle immunomodulatory drugs, like cyclophosphamide, anti-CD25 antibodies and pegylated liposomal doxorubicin are tested in combination with immunotherapy. Most reliable data are currently available for ipilimumab, an anti-CTLA4 antibody, which enhances T cell activity. Ipilimumab was shown to exert significant anti-tumor effects in ovarian cancer patients (Mantia-Smaldone et al., 2012).

Considering the severe side-effects and expense associated with treating cancer, there is a need to identify factors that can be used in the treatment of cancer in general and ovarian cancer in particular. There is also a need to identify factors representing biomarkers for cancer in general and ovarian cancer in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:
a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.
c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.
d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.
e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.
f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way, each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 772 or a variant sequence thereof which is at least 77%, preferably at least 88%, homologous (preferably at least 77% or at least 88% identical) to SEQ ID NO: 1 to SEQ ID NO: 772, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 772 or a variant thereof, which is at least 77%, preferably at least 88%, homologous (preferably at least 77% or at least 88% identical) to SEQ ID NO: 1 to SEQ ID NO: 772, wherein said peptide or variant thereof has an overall length of between 8 and 100, preferably between 8 and 30, and most preferred of between 8 and 14 amino acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1A:
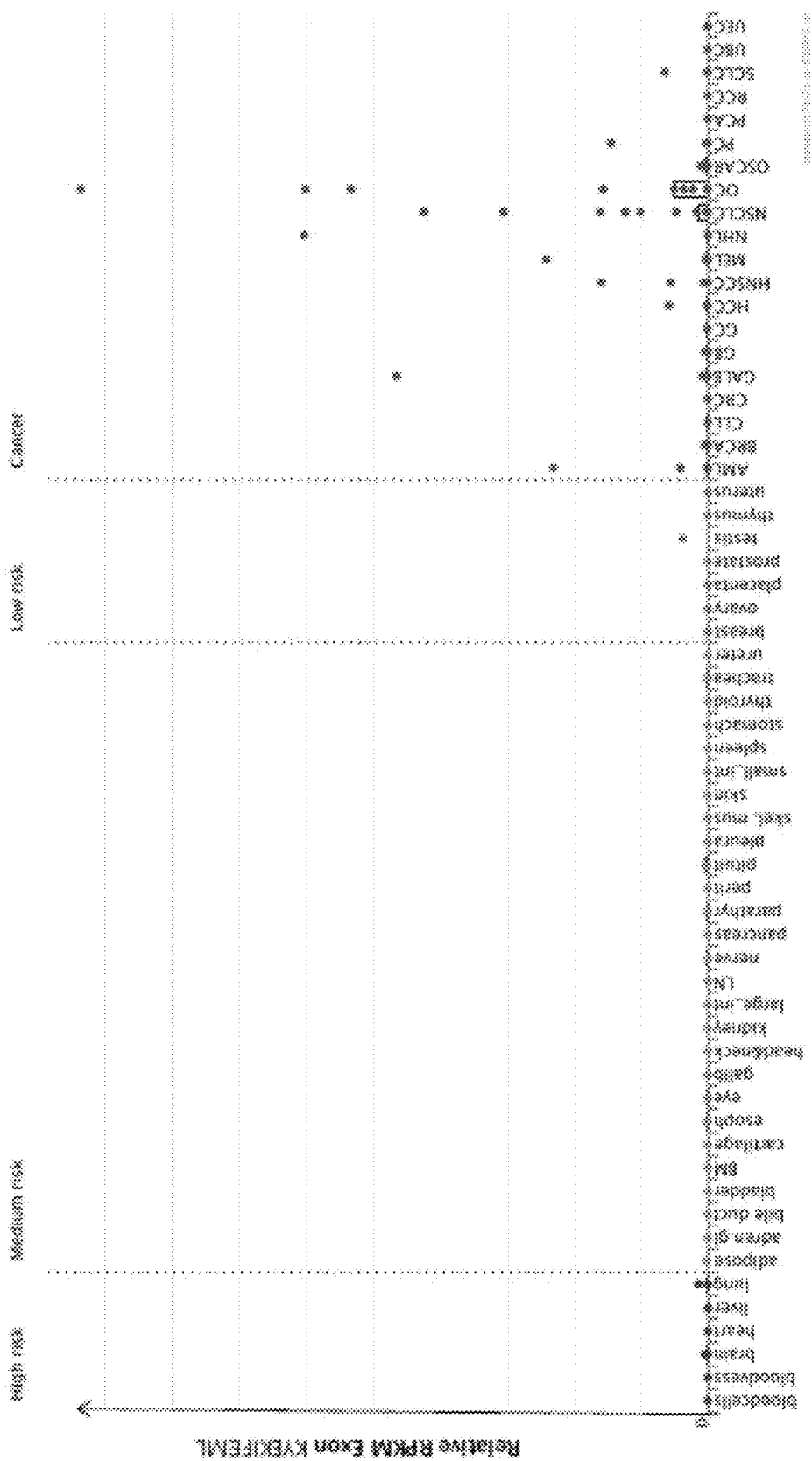
FIGS. 1A-9B depict embodiments as described herein.

The following tables show the peptides according to the present invention, their respective SEQ ID NOs, and the prospective source (underlying) genes for these peptides. In Table 1, peptides with SEQ ID NO: 1 to SEQ ID NO: 9 bind to HLA-A*02, peptides with SEQ ID NO: 10 to SEQ ID NO: 19 bind to HLA-A*24, peptides with SEQ ID NO: 20 to SEQ ID NO: 30 bind to HLA-A*03, peptide with SEQ ID NO: 31 binds to HLA-A*01, peptides with SEQ ID NO: 32 to SEQ ID NO: 41 bind to HLA-B*07, peptides with SEQ ID NO: 42 to SEQ ID NO: 51 bind to HLA-B*08, peptides with SEQ ID NO: 52 to SEQ ID NO: 59 bind to HLA-B*44. In Table 2, peptides with SEQ ID NO: 60 to SEQ ID NO: 75 bind to HLA-A*02, peptides with SEQ ID NO: 76 to SEQ ID NO: 82 bind to HLA-A*24, peptides with SEQ ID NO: 83 to SEQ ID NO: 111 bind to HLA-A*03, peptides with SEQ ID NO: 112 to SEQ ID NO: 116 bind to HLA-A*01, peptides with SEQ ID NO: 117 to SEQ ID NO: 149 bind to HLA-B*07, peptides with SEQ ID NO: 150 to SEQ ID NO: 172 bind to HLA-B*08, peptides with SEQ ID NO: 173 to SEQ ID NO: 215 bind to HLA-B*44. In Table 3, peptides with SEQ ID NO: 216 to SEQ ID NO: 245 bind to HLA-A*02, peptides with SEQ ID NO: 246 to SEQ ID NO: 255 bind to HLA-A*24, peptides with SEQ ID NO: 256 to SEQ ID NO: 287 bind to HLA-A*03, peptides with SEQ ID NO: 288 to SEQ ID NO: 292 bind to HLA-A*01, peptides with SEQ ID NO: 293 to SEQ ID NO: 392 bind to HLA-B*07, peptides with SEQ ID NO: 393 to SEQ ID NO: 395 bind to HLA-B*08, peptides with SEQ ID NO: 396 to SEQ ID NO: 438 bind to HLA-B*44. In Table 4, peptides with SEQ ID NO: 439 to SEQ ID NO: 551 bind to several HLA class I alleles, peptide with SEQ ID NO: 773 binds to HLA-A*02, peptide with SEQ ID NO: 774 binds to HLA-A*24. In Table 5, peptides with SEQ ID NO: 552 to SEQ ID NO: 772 bind to several HLA class II alleles.

TABLE 1

Peptides according to the present invention.

| Seq ID No | Sequence | Gene | Uniprot Accession | HLA allotype |
|---|---|---|---|---|
| 1 | MIPTFTALL | LILRB4 | Q8NHJ6 | A*02 |
| 2 | TLLKALLEI | IDO1 | P14902 | A*02 |
| 3 | ALIYNLVGI | ATP7A, ATP7B, CTAGE1 | P35670 | A*02 |
| 4 | ALFKAWAL | IRF4 | Q15306 | A*02 |
| 5 | RLLDFINVL | OVGP1 | Q12889 | A*02 |
| 6 | SLGKHTVAL | OVGP1 | Q12889 | A*02 |
| 7 | ALQAFEFRV | PCDHB5, PCDHB15, PCDHB11, PCDHB10, PCDHB9, PCDHB8, PCDHB7, PCDHB4, PCDHB3, PCDHB2, PCDHB16 | Q9Y5E7 | A*02 |
| 8 | YLVTKVVAV | PCDHGA12, PCDHB5, PCDHB1, PCDHB18, PCDHGB7, PCDHGB6, PCDHGB5, PCDHGB3, PCDHGB2, PCDHGB1, PCDHGA11, PCDHGA10, PCDHGA9, | O60330, Q96TA0, Q9NRJ7, Q9UN66, O9UN67, Q9UN71, Q9Y5E1, Q9Y5E2, Q9Y5E3, Q9Y5E4, Q9Y5E5, Q9Y5E6, Q9Y5E7, Q9Y5E8, | A*02 |

TABLE 1-continued

Peptides according to the present invention.

| Seq ID No | Sequence | Gene | Uniprot Accession | HLA allotype |
|---|---|---|---|---|
| | | PCDHGA7, PCDHGA6, PCDHGA5, PCDHGA4, PCDHGA3, PCDHGA2, PCDHGA1, PCDHGB8P, PCDHB15, PCDHB14, PCDHB13, PCDHB12, PCDHB11, PCDHB10, PCDHB9, PCDHB8, PCDHB7, PCDHB6, PCDHB4, PCDHB3, PCDHB2, PCDHB16, PCDHGB4, PCDHGA8 | Q9Y5E9, Q9Y5F0, Q9Y5F1, Q9Y5F2, Q9Y5F3, Q9Y5F8, Q9Y5F9, Q9Y5G0, Q9Y5G1, Q9Y5G2, Q9Y5G3, Q9Y5G4, Q9Y5G5, Q9Y5G6, Q9Y5G7, Q9Y5G8, Q9Y5G9, Q9Y5H0, Q9Y5H1, Q9Y5H2, Q9Y5H3, Q9Y5H4 | |
| 9 | VLLAGFKPPL | RNF17 | Q9BXT8 | A*02 |
| 10 | RYSDSVGRVSF | CAPN13 | Q6MZZ7 | A*24 |
| 11 | SYSDLHYGF | CAPN13 | Q6MZZ7 | A*24 |
| 12 | KYEKIFEML | CT45A3, CT45A4, CT45A5, CT45A6, CT45A1, CT45A2 | Q5DJT8 | A*24 |
| 13 | VYTFLSSTL | ESR1 | P03372 | A*24 |
| 14 | FYFPTPTVL | FOLR1 | P15328 | A*24 |
| 15 | VYHDDKQPTF | GXYLT2 | A0PJZ3 | A*24 |
| 16 | IYSPQFSRL | MYO3B | Q8WXR4 | A*24 |
| 17 | RFTTMLSTF | OVGP1 | Q12889 | A*24 |
| 18 | KYPVHIYRL | RAD54B | Q9Y620 | A*24 |
| 19 | KYVKVFHQF | ZNF90, ZNF93, ZNF486 | Q96H40 | A*24 |
| 20 | RMASPVNVK | C2orf88 | Q9BSF0 | A*03 |
| 21 | AVRKPIVLK | CDCA5 | Q96FF9 | A*03 |
| 22 | SLKERNPLK | CDH3 | P22223 | A*03 |
| 23 | GMMKGGIRK | ESR1 | P03372 | A*03 |
| 24 | SMYYPLQLK | GXYLT2 | A0PJZ3 | A*03 |
| 25 | GTSPPSVEK | MUC16 | Q8WXI7 | A*03 |
| 26 | RISEYLLEK | MYO3B | Q8WXR4 | A*03 |
| 27 | VLYGPAGLGK | NLRP2 | Q9NX02 | A*03 |
| 28 | KTYETNLEIKK | NLRP7 | Q8WX94 | A*03 |
| 29 | QQFLTALFY | NLRP7, NLRP2 | Q8WX94 | A*03 |
| 30 | ALEVAHRLK | ZBTB12 | Q9Y330 | A*03 |
| 31 | LLDEGAMLLY | NLRP7 | Q8WX94 | A*01 |
| 32 | SPNKGTLSV | BCAM | P50895 | B*07 |
| 33 | SPTFHLTL | BCAM | P50895 | B*07 |
| 34 | LPRGPLASLL | CDH3 | P22223 | B*07 |
| 35 | FPDNQRPAL | ETV4 | P43268 | B*07 |
| 36 | APAAWLRSA | MMP11 | P24347 | B*07/B*55 |
| 37 | RPLFQKSSM | MUC16 | Q8WXI7 | B*07 |
| 38 | SPHPVTALLTL | MUC16 | Q8WXI7 | B*07 |

TABLE 1-continued

Peptides according to the present invention.

| Seq ID No | Sequence | Gene | Uniprot Accession | HLA allotype |
|---|---|---|---|---|
| 39 | RPAPFEVVF | NXNL2 | Q5VZ03 | B*07 |
| 40 | KPGTSYRVTL | SPON1 | Q9HCB6 | B*07 |
| 41 | RVRSRISNL | TCEA1P2, TCEA1, TCEA2, TCEA3 | Q15560 | B*07 |
| 42 | TLKVTSAL | BCAM | P50895 | B*08 |
| 43 | ALKARTVTF | CCR2, CCR5 | P51681 | B*08 |
| 44 | LNKQKVTF | CTAGE4, CTAGE5 | O15320 | B*08 |
| 45 | VGREKKLAL | CTAGE4, CTAGE5 | O15320 | B*08 |
| 46 | DMKKAKEQL | FUNDC2P2, FUNDC2P3, FUNDC2 | Q9BWH2 | B*08 |
| 47 | MPNLRSVDL | LRRTM1 | Q86UE6 | B*08 |
| 48 | DVKKKIKEV | MFN1 | Q8IWA4 | B*08 |
| 49 | LPRLKAFMI | ST6GALNAC5 | Q9BVH7 | B*08 |
| 50 | DMKYKNRV | TCEA1P2, TCEA1, TCEA2 | Q15560 | B*08 |
| 51 | SLRLKNVQL | VTCN1 | Q7Z7D3 | B*08 |
| 52 | AEFLLRIFL | CAPN13 | Q6MZZ7 | B*44 |
| 53 | MEHPGKLLF | ESR1 | P03372 | B*44 |
| 54 | AEITITTQTGY | MUC16 | Q8WXI7 | B*44 |
| 55 | HETETRTTW | MUC16 | Q8WXI7 | B*44 |
| 56 | SEPDTTASW | MUC16 | Q8WXI7 | B*44 |
| 57 | QESDLRLFL | NLRP7, NLRP2 | Q9NX02 | B*44 |
| 58 | GEMEQKQL | PNOC | Q13519 | B*44 |
| 59 | SENVTMKVV | VTCN1 | Q7Z7D3 | B*44 |

TABLE 2

Additional peptides according to the present invention.

| Seq ID No | Sequence | Gene | Uniprot Accession | HLA allotype |
|---|---|---|---|---|
| 60 | GLLSLTSTLYL | BCAM | P50895 | A*02 |
| 61 | YMVHIQVTL | CD70 | P32970 | A*02 |
| 62 | KVLGVNVML | CRABP2 | P29373 | A*02 |
| 63 | MMEEMIFNL | EYA2 | O00167 | A*02 |
| 64 | FLDPDRHFL | FAM83H | Q6ZRV2 | A*02 |
| 65 | TMFLRETSL | GUCY1A2 | P33402 | A*02 |
| 66 | GLLQELSSI | HTR3A | P46098 | A*02 |
| 67 | SLLLPSIFL | HTR3A | P46098 | A*02 |
| 68 | KLFDTQQFL | IRF4 | O15306 | A*02 |
| 69 | TTYEGSITV | MUC16 | Q8WXI7 | A*02 |

TABLE 2 -continued

Additional peptides according to the present invention.

| Seq ID No | Sequence | Gene | Uniprot Accession | HLA allotype |
|---|---|---|---|---|
| 70 | VLQGLLRSL | MUC16 | Q8WXI7 | A*02 |
| 71 | YLEDTDRNL | NFE2L3 | Q9Y4A8 | A*02 |
| 72 | YLTDLQVSL | NFE2L3 | Q9Y4A8 | A*02 |
| 73 | FLIEELLFA | OVGP1 | Q12889 | A*02 |
| 74 | SQSPSVSQL | PRAME | P78395 | A*02 |
| 75 | KVVSVLYNV | VTCN1 | Q7Z7D3 | A*02 |
| 76 | KYVAELSLL | CCNA1 | P78396 | A*24 |
| 77 | RYGPVFTV | CYP2W1 | Q8TAV3 | A*24 |
| 78 | SFAPRSAVF | HOXD9 | P28356 | A*24 |
| 79 | SYNEHWNYL | LTBR | P36941 | A*24 |
| 80 | TAYMVSVAAF | SDK2 | Q58EX2 | A*24 |
| 81 | VYNHTTRPL | SPINT1 | O43278 | A*24 |
| 82 | SYFRGFTLI | SPON1 | Q9HCB6 | A*24 |
| 83 | GTYAHTVNR | ALPI, ALPP, ALPPL2 | P05187, P09923 | A*03/A*31 |
| 84 | KLQPAQTAAK | ALPP, ALPPL2 | P05187 | A*03 |
| 85 | VLLGSLFSRK | BCL2L1 | O07817 | A*03 |
| 86 | VVLLGSLFSRK | BCL2L1 | O07817 | A*03/A*31/A*66 |
| 87 | AVAPPTPASK | CBX2 | Q14781 | A*03/A*11 |
| 88 | VVHAVFALK | CCR5 | P51681 | A*03 |
| 89 | RVAELLLLH | CDKN2A, CDKN2B | P42771, P42772 | A*03 |
| 90 | KVAGERYVYK | ETV1, ETV4, ETV5 | P41161, P43268, P50549 | A*03 |
| 91 | RSLRYYYEK | ETV1, ETV4, ETV5 | P43268 | A*03 |
| 92 | SVFPIENIY | EYA2 | O00167 | A*03 |
| 93 | KILEEHTNK | FSBP, RAD54B | O95073 | A*03 |
| 94 | ATFERVLLR | GUCY1A2 | P33402 | A*03/A*11 |
| 95 | QSMYYPLQLK | GXYLT2 | A0PJZ3 | A*03 |
| 96 | TAFGGFLKY | LAMA1 | P25391 | A*03 |
| 97 | TMLDVEGLFY | LAMA1 | P25391 | A*03 |
| 98 | LLQPPPLLAR | MMP11 | P24347 | A*03 |
| 99 | KVVDRWNEK | MRPL51 | Q4U2R6 | A*03 |
| 100 | RLFTSPIMTK | MUC16 | Q8WXI7 | A*03 |
| 101 | RVFTSSIKTK | MUC16 | Q8WXI7 | A*03 |
| 102 | SVLTSSLVK | MUC16 | Q8WXI7 | A*03 |
| 103 | TSRSVDEAY | MUC16 | Q8WXI7 | A*03 |
| 104 | VLADSVTTK | MUC16 | Q8WXI7 | A*03 |
| 105 | RLFSWLVNR | MYO1B | Q8WXR4 | A*03 |
| 106 | AAFVPLLLK | NCAPD2 | Q15021 | A*03/A*11 |

TABLE 2 -continued

Additional peptides according to the present invention.

| Seq ID No | Sequence | Gene | Uniprot Accession | HLA allotype |
|---|---|---|---|---|
| 107 | RLQEWKALK | PDCL2 | Q8N4E4 | A*03 |
| 108 | VLYPVPLESY | PRAME | P78395 | A*03 |
| 109 | KTFTIKRFLAK | RPL39L | Q96EH5 | A*03 |
| 110 | SAAPPSYFR | SPON1 | Q9HCB6 | A*03/A*11/A*66 |
| 111 | TLPQFRELGY | WNT7A | O00755 | A*03 |
| 112 | TVTGAEQIQY | CAPN13 | Q6MZZ7 | A*01 |
| 113 | QLDSNRLTY | LRRTM1 | Q86UE6 | A*01 |
| 114 | VMEQSAGIMY | LYPD1 | Q8N2G4 | A*01 |
| 115 | FVDNQYWRY | MMP12 | P39900 | A*01 |
| 116 | VLLDEGAMLLY | NLRP7 | Q8WX94 | A*01 |
| 117 | APRLLLLAVL | BCAM | P50895 | B*07 |
| 118 | SPASRSISL | CD70 | P32970 | B*07 |
| 119 | APLPRPGAVL | CTAG2 | O75638 | B*07 |
| 120 | RPAMNYDKL | ETV1, ETV4, ETV5, SPDEF | P43268 | B*07 |
| 121 | VPNQSSESL | EYA2 | O00167 | B*07/B*35 |
| 122 | YPGFPQSQY | EYA2 | O00167 | B*07/B*35 |
| 123 | KPSESIYSAL | FAM111B | Q6SJ93 | B*07 |
| 124 | LPSDSHFKITF | FAM111B | Q6SJ93 | B*07 |
| 125 | VPVYILLDEM | FAM83H | Q6ZRV2 | B*07/B*35 |
| 126 | KPGPEDKL | FOLR1, FOLR2 | P15328 | B*07 |
| 127 | APRAGSQVV | FUNDC2 | Q9BWH2 | B*07 |
| 128 | YPRTITPGM | KLK14 | Q9P0G3 | B*07 |
| 129 | APRPASSL | MMP11 | P24347 | B*07 |
| 130 | FPRLVGPDF | MMP11 | P24347 | B*07 |
| 131 | APTEDLKAL | MSLN | Q13421 | B*07 |
| 132 | IPGPAQSTI | MUC16 | Q8WXI7 | B*07 |
| 133 | MPNLPSTTSL | MUC16 | Q8WXI7 | B*07 |
| 134 | RPIVPGPLL | MUC16 | Q8WXI7 | B*07 |
| 135 | RVRSTISSL | MUC16 | Q8WXI7 | B*07 |
| 136 | SPFSAEEANSL | MUC16 | Q8WXI7 | B*07 |
| 137 | SPGATSRGTL | MUC16 | Q8WXI7 | B*07 |
| 138 | SPMATTSTL | MUC16 | Q8WXI7 | B*07 |
| 139 | SPQSMSNTL | MUC16 | Q8WXI7 | B*07 |
| 140 | SPRTEASSAVL | MUC16 | Q8WXI7 | B*07 |
| 141 | SPMTSLLTSGL | MUC16 | Q8WXI7 | B*07 |
| 142 | TPGLRETSI | MUC16 | Q8WXI7 | B*07 |

TABLE 2 -continued

Additional peptides according to the present invention.

| Seq ID No | Sequence | Gene | Uniprot Accession | HLA allotype |
|---|---|---|---|---|
| 143 | SPAMTSTSF | MUC16 | Q8WXI7 | B*07/B*35 |
| 144 | SPSPVSSTL | MUC16 | Q8WXI7 | B*07/B*35 |
| 145 | SPSSPMSTF | MUC16 | Q8WXI7 | B*07/B*35 |
| 146 | IPRPEVQAL | PLEKHG4 | O58EX7 | B*07 |
| 147 | APRWFPQPTVV | VTCN1 | O7Z7D3 | B*07 |
| 148 | KPYGGSGPL | ZNF217 | O75362 | B*07 |
| 149 | GPREALSRL | ZSCAN30, ZNF263, ZNF500, ZKSCAN4, ZNF323, ZKSCAN1, ZNF165, ZNF187, ZKSCAN3, ZNF397, ZSCAN12 | O14978, O43309, O60304, P17029, P49910, Q16670, Q86W11, Q8NF99, Q969J2, Q96LW9, Q9BRR0 | B*07 |
| 150 | MAAVKQAL | BCL2L1 | Q07817 | B*08 |
| 151 | HLLLKVLAF | CCNA1 | P78396 | B*08 |
| 152 | MGSARVAEL | CDKN2A, CDKN2B | P42771 | B*08 |
| 153 | NAMLRKVAV | CRABP1 | P29762 | B*08 |
| 154 | MLRKIAVAA | CRABP2 | P29373 | B*08 |
| 155 | NKKMMKRLM | DPPA2 | Q7Z7J5 | B*08 |
| 156 | HVKEKFLL | FAM83H | Q6ZRV2 | B*08 |
| 157 | EAMKRLSYI | LAMC2 | Q13753 | B*08 |
| 158 | LPKLAGLL | LINC00176 | Q6ZNR8 | B*08/B*07 |
| 159 | VLKHKLDEL | MSLN | Q13421 | B*08 |
| 160 | YPKARLAF | MSLN | Q13421 | B*08 |
| 161 | ALKTTTTAL | DNAJC22, MUC16 | Q8WXI7 | B*08 |
| 162 | QAKTHSTL | MUC16 | Q8WXI7 | B*08 |
| 163 | QGLLRPVF | MUC16 | Q8WXI7 | B*08 |
| 164 | SIKTKSAEM | MUC16 | Q8WXI7 | B*08 |
| 165 | SPRFKTGL | MUC16 | Q8WXI7 | B*08 |
| 166 | TPKLRETSI | MUC16 | Q8WXI7 | B*08 |
| 167 | TSHERLTTL | MUC16 | Q8WXI7 | B*08 |
| 168 | TSHERLTTY | MUC16 | Q8WXI7 | B*08 |
| 169 | TSMPRSSAM | MUC16 | Q8WXI7 | B*08 |
| 170 | YLLEKSRVI | MYO3B, MYH15, MYH6, MYH7, MYO1D, MYO3A, MYH7B | A7E2Y1, B0I1T2, O94832, P12883, P13533, Q8NEV4, Q8WXR4, Q9Y2K3 | B*08 |
| 171 | FAFRKEAL | OVGP1 | Q12889 | B*08 |
| 172 | KLKERNREL | OVGP1 | Q12889 | B*08 |
| 173 | AEAQVGDERDY | BCAM | P50895 | B*44 |
| 174 | AEATARLNVF | BCAM | P50895 | B*44 |
| 175 | AEIEPKADG | BCAM | P50895 | B*44 |
| 176 | AEIEPKADGSW | BCAM | P50895 | B*44 |

TABLE 2-continued

Additional peptides according to the present invention.

| Seq ID No | Sequence | Gene | Uniprot Accession | HLA allotype |
|---|---|---|---|---|
| 177 | TEVGTMNLF | BCAT1 | P54687 | B*44 |
| 178 | NELFRDGVNW | BCL2L1 | Q07817 | B*44 |
| 179 | REAGDEFEL | BCL2L1 | Q07817 | B*44 |
| 180 | REAGDEFELRY | BCL2L1 | Q07817 | B*44 |
| 181 | GEGPKTSW | CRABP2 | P29373 | B*44 |
| 182 | KEATEAQSL | CTAGE4, CTAGE10P, CTAGE16P, CTAGE5, CTAGE1 | Q96RT6 | B*44/B*40 |
| 183 | YEKGIMQKV | ETV1, ETV4, ETV5 | P43268 | B*44/B*49 |
| 184 | AELEALTDLW | EYA2 | O00167 | B*44 |
| 185 | AERQPGAASL | FAM83H | Q6ZRV2 | B*44 |
| 186 | REGPEEPGL | FAM83H | Q6ZRV2 | B*44 |
| 187 | GEAQTRIAW | FOLR1 | P15328 | B*44 |
| 188 | AEFAKKQPWW | FUNDC2 | Q9BWH2 | B*44 |
| 189 | KEFLFNMY | HOXA9, HOXA10, HOXB9, HOXC9, HOXC10, HOXD9, HOXD10 | P28356 | B*44 |
| 190 | YEVARILNL | HOXD9 | P28356 | B*44 |
| 191 | EEDAALFKAW | IRF4 | Q15306 | B*44 |
| 192 | YEFKFPNRL | LGALS1 | P09382 | B*44/B*18/B*40 |
| 193 | LEAQQEAL | MAGEA1, MRPL40 | P43355 | B*44 |
| 194 | KEVDPTSHSY | MAGEA11 | P43364 | B*44 |
| 195 | AEDKRHYSV | MFN1 | Q8IWA4 | B*44 |
| 196 | REMPGGPVW | MMP12 | P39900 | B*44 |
| 197 | AEVLLPRLV | MSLN | O13421 | B*44 |
| 198 | QEAARAAL | MSLN | O13421 | B*44 |
| 199 | REIDESLIFY | MSLN | O13421 | B*44 |
| 200 | AESIPTVSF | MUC16 | Q8WXI7 | B*44 |
| 201 | AETILTFHAF | MUC16 | Q8WXI7 | B*44 |
| 202 | HESEATASW | MUC16 | Q8WXI7 | B*44 |
| 203 | IEHSTQAQDTL | MUC16 | Q8WXI7 | B*44 |
| 204 | RETSTSEETSL | MUC16 | Q8WXI7 | B*44 |
| 205 | SEITRIEM | MUC16 | Q8WXI7 | B*44 |
| 206 | SESVTSRTSY | MUC16 | Q8WXI7 | B*44 |
| 207 | TEARATSDSW | MUC16 | Q8WXI7 | B*44 |
| 208 | TEVSRTEAI | MUC16 | Q8WXI7 | B*44 |
| 209 | TEVSRTEL | MUC16 | Q8WXI7 | B*44 |
| 210 | VEAADIFQNF | NXNL2 | Q5VZ03 | B*44 |
| 211 | EEKVFPSPLW | PNOC | Q13519 | B*44 |

TABLE 2 -continued

Additional peptides according to the present invention.

| Seq ID No | Sequence | Gene | Uniprot Accession | HLA allotype |
|---|---|---|---|---|
| 212 | MEQKQLQKRF | PNOC | Q13519 | B*44 |
| 213 | KESIPRWYY | SPINT1 | O43278 | B*44 |
| 214 | VEQTRAGSLL | TDRD5 | Q8NAT2 | B*44 |
| 215 | SEDGLPEGIHL | ZNF217 | O75362 | B*44 |

TABLE 3

Additional peptides according to the present invention.

| Seq ID No | Sequence | Gene | Uniprot Accession | HLA allotype |
|---|---|---|---|---|
| 216 | IMFDDAIERA | ALPP, ALPPL2 | P05187 | A*02 |
| 217 | VSSSLTLKV | BCAM | P50895 | A*02 |
| 218 | TIASQRLTPL | CD70 | P32970 | A*02 |
| 219 | PLPRPGAVL | CTAG2 | O75638 | A*02 |
| 220 | RMTTQLLLL | FOLR1 | P15328 | A*02/B*13 |
| 221 | SLLDLYQL | FTHL17 | Q9BXU8 | A*02/B*35 |
| 222 | ALMRLIGCPL | GPC2 | Q8N158 | A*02 |
| 223 | FAHHGRSL | IRF4 | Q15306 | A*02 |
| 224 | SLPRFQVTL | IRF4 | Q15306 | A*02 |
| 225 | SVFAHPRKL | MAGEA2B, MAGEA2, MAGEA6, MAGEA12 | P43365 | A*02 |
| 226 | QVDPKKRISM | MELK | Q14680 | A*02 |
| 227 | YTFRYPLSL | MMP11 | P24347 | A*02 |
| 228 | RLWDWVPLA | MRPL51 | Q4U2R6 | A*02 |
| 229 | ISVPAKTSL | MUC16 | Q8WXI7 | A*02 |
| 230 | SAFREGTSL | MUC16 | Q8WXI7 | A*02 |
| 231 | SVTESTHHL | MUC16 | Q8WXI7 | A*02 |
| 232 | TISSLTHEL | MUC16 | Q8WXI7 | A*02 |
| 233 | GSDTSSKSL | MUC16 | Q8WXI7 | A*02/B*14 |
| 234 | GVATRVDAI | MUC16 | Q8WXI7 | A*02/B*14 |
| 235 | SAIETSAVL | MUC16 | Q8WXI7 | A*02/B*35 |
| 236 | SAIPFSMTL | MUC16 | Q8WXI7 | A*02/B*35 |
| 237 | SAMGTISIM | MUC16 | Q8WXI7 | A*02/B*35 |
| 238 | PLLVLFTI | MUC16 | Q8WXI7 | A*02/B*51 |
| 239 | FAVPTGISM | MUC16 | Q8WXI7 | A*02/C*03 |
| 240 | FSTDTSIVL | MUC16 | Q8WXI7 | A*02/C*03 |
| 241 | RQPNILVHL | MUC16 | Q8WXI7 | A*02:05 |
| 242 | STIPALHEI | MUC16 | Q8WXI7 | A*02:05 |
| 243 | YASEGVKQV | SPON1 | Q9HCB6 | A*02/B*51 |

TABLE 3 -continued

Additional peptides according to the present invention.

| Seq ID No | Sequence | Gene | Uniprot Accession | HLA allotype |
|---|---|---|---|---|
| 244 | DTDSSVHVQV | TENM4 | Q6N022 | A*02 |
| 245 | LAVEGGQSL | UBXN8 | O00124 | A*02 |
| 246 | RYLAVVHAVF | CCR5 | P51681 | A*24/A*23 |
| 247 | ARPPWMWVL | KLK5 | Q9Y337 | A*24/B*27 |
| 248 | SVIQHLGY | MSLN | Q13421 | A*24 |
| 249 | VYTPTLGTL | DNAJC22, MUC16 | Q8WXI7 | A*24 |
| 250 | HFPEKTTHSF | MUC16 | Q8WXI7 | A*24/C*14 |
| 251 | KQRQVLIFF | PCDHB2 | Q9Y5E7 | A*24/B*15 |
| 252 | LYQPRASEM | PNOC | Q13519 | A*24/A*25 |
| 253 | AYPEIEKF | PTTG2, PTTG1 | O95997 | A*24/C*04 |
| 254 | IIQHLTEQF | STAG3 | Q9UJ98 | A*24/C*03 |
| 255 | VFVSFSSLF | ZNF560 | Q96MR9 | A*24/B*27 |
| 256 | RTEEVLLTFK | GPR64 | Q8IZP9 | A*03 |
| 257 | VTADHSHVF | ALPI, ALPL, ALPP, | P05187 | A*03 |
| 258 | GAYAHTVNR | ALPPL2 | P10696 | A*03 |
| 259 | KTLELRVAY | BCAM | P50895 | A*03/A*32 |
| 260 | GTNTVILEY | C2orf88 | Q9BSF0 | A*03 |
| 261 | HTFGLFYQR | FAM111B | Q6SJ93 | A*03 |
| 262 | RSRLNPLVQR | FAM83H | Q6ZRV2 | A*03 |
| 263 | SSSSATISK | HOXD3 | P31249 | A*03/A*11 |
| 264 | AIKVIPTVFK | IDO1 | P14902 | A*03 |
| 265 | QIHDHVNPK | IDO1 | P14902 | A*03/A*11 |
| 266 | ISYSGQFLVK | IGF2BP1 | Q9NZI8 | A*03 |
| 267 | VTDLISPRK | LAMA1 | P25391 | A*03 |
| 268 | GLLGLSLRY | LRRTM1 | Q86UE6 | A*03/A*11/ A*29 |
| 269 | RLKGDAWVYK | MELK | Q14680 | A*03 |
| 270 | AVFNPRFYRTY | MMP12 | P39900 | A*03/A*11 |
| 271 | RMFADDLHNLNK | MRPL51 | Q4U2R6 | A*03 |
| 272 | RQPERTILRPR | MSLN | Q13421 | A*03 |
| 273 | RVNAIPFTY | MSLN | Q13421 | A*03/A*26 |
| 274 | KTFPASTVF | MUC16 | Q8WXI7 | A*03 |
| 275 | STTFPTLTK | MUC16 | Q8WXI7 | A*03 |
| 276 | VSKTTGMEF | MUC16 | Q8WXI7 | A*03 |
| 277 | TTALKTTSR | DNAJC22, MUC16 | Q8WXI7 | A*03/A*66 |
| 278 | NLSSITHER | MUC16 | Q8WXI7 | A*03/A*68 |
| 279 | SVSSETTKIKR | MUC16 | Q8WXI7 | A*03/A*68 |
| 280 | SVSGVKTTF | MUC16 | Q8WXI7 | A*03/B*15 |

TABLE 3-continued

Additional peptides according to the present invention.

| Seq ID No | Sequence | Gene | Uniprot Accession | HLA allotype |
|---|---|---|---|---|
| 281 | RAKELEATF | NLRP7, NLRP2 | 09NX02 | A*03 |
| 282 | CLTRTGLFLRF | NLRP7, NLRP2 | Q9NX02 | A*03 |
| 283 | IVQEPTEEK | PAGE2, PAGE2B | Q7Z2X7 | A*03/A*11 |
| 284 | KSLIKSWKK | TCEA1P2, TCEA1, TCEA2 | P23193, Q15560 | A*03/A*11 |
| 285 | GTVNPTVGK | TENM4 | Q6N022 | A*03/A*11 |
| 286 | TVAPPQGVVK | ZBTB12 | Q9Y330 | A*03/A*68 |
| 287 | RRIHTGEKPYK | ZNF271, KLF8, ZNF816, ZFP28, ZSCAN29, ZNF597, ZNF480, ZNF714, ZNF836, ZNF600, ZNF320, ZNF100, ZNF721, ZNF841, ZNF678, ZNF860, ZNF429, ZNF888, ZNF761, ZNF701, ZNF83, ZNF695, ZNF471, ZNF22, ZNF28, ZNF137P, ZNF665, ZNF606, ZNF430, ZNF34, ZNF616, ZNF468, ZNF160, ZNF765, ZNF845 | Q8IW36 | A*03/A*11 |
| 288 | SPVTSVHGGTY | LILRB4 | Q8NHJ6 | A*01/B*35 |
| 289 | RWEKTDLTY | MMP11 | P24347 | A*01 |
| 290 | DMDEEIEAEY | MYO3B | Q8WXR4 | A*01/A*25 |
| 291 | ETIRSVGYY | TENM4 | Q6N022 | A*01/A*25 |
| 292 | NVTMKVVSVLY | VTCN1 | Q7Z7D3 | A*01 |
| 293 | VPDSGATATAY | ALPP, ALPPL2 | P05187 | B*07/B*35 |
| 294 | YPLRGSSIF | ALPP, ALPPL2 | P05187 | B*07/B*35 |
| 295 | YPLRGSSIFGL | ALPP, ALPPL2 | P05187 | B*07/B*35 |
| 296 | YPLRGSSI | ALPP, ALPPL2 | P05187 | B*51/B*07 |
| 297 | TVREASGLL | BCAM | P50895 | B*07 |
| 298 | YPTEHVQF | BCAM | P50895 | B*07/B*35 |
| 299 | HPGSSALHY | BCAT1 | P54687 | B*07/B*35 |
| 300 | IPMAAVKQAL | BCL2L1 | Q07817 | B*07 |
| 301 | SPRRSPRISF | CDCA5 | Q96FF9 | B*07 |
| 302 | RVEEVRALL | CDKN2A | P42771 | B*07 |
| 303 | LPMWKVTAF | CLDN6 | P56747 | B*07 |
| 304 | LPRPGAVL | CTAG2 | O75638 | B*07 |
| 305 | TPWAESSTKF | DPEP3 | Q9H4B8 | B*07/B*35 |
| 306 | APVIFSHSA | DPEP2, DPEP3 | Q9H4B8 | B*55/B*56/B*07 |
| 307 | LPYGPGSEAAAF | ESR1 | P03372 | B*07/B*35 |
| 308 | YPEGAAYEF | ESR1 | P03372 | B*07/B*35 |

TABLE 3 -continued

Additional peptides according to the present invention.

| Seq ID No | Sequence | Gene | Uniprot Accession | HLA allotype |
|---|---|---|---|---|
| 309 | FPQSQYPQY | EYA2 | O00167 | B*07/B*35 |
| 310 | RPNPITIIL | FBN2 | P35556 | B*07 |
| 311 | RPLFYVVSL | HTR3A | P46098 | B*07 |
| 312 | LPYFREFSM | HTR3A | P46098 | B*07/B*35 |
| 313 | KVKSDRSVF | HTR3A | P46098 | B*15/B*07 |
| 314 | VPDQPHPEI | IRF4 | Q15306 | B*07/B*35 |
| 315 | SPRENFPDTL | KLK8 | O60259 | B*07 |
| 316 | EPKTATVL | LAMA1 | P25391 | B*42/B*07 |
| 317 | FPFQPGSV | LGALS1 | P09382 | B*51/B*07 |
| 318 | FPNRLNLEA | LGALS1 | P09382 | B*54/B*55/B*07 |
| 319 | SPAEPSVYATL | LILRB4 | Q8NHJ6 | B*07 |
| 320 | FPMSPVTSV | LILRB4 | Q8NHJ6 | B*07/B*51 |
| 321 | SPMDTFLLI | LILRB4 | Q8NHJ6 | B*51/B*07 |
| 322 | SPDPSKHLL | LRRK1 | Q38SD2 | B*07/B*35 |
| 323 | RPMPNLRSV | LRRTM1 | Q86UE6 | B*55/B*07 |
| 324 | VPYRVVGL | MEX3D, MEX3C, MEX3B, MEX3A | A1L020 | B*51/B*07 |
| 325 | GPRNAQRVL | MFN1 | Q8IWA4 | B*07 |
| 326 | VPSEIDAAF | MMP11 | P24347 | B*07/B*35 |
| 327 | SPLPVTSLI | MUC16 | Q8WXI7 | B*07 |
| 328 | EPVTSSLPNF | MUC16 | Q8WXI7 | B*07/B*35 |
| 329 | FPAMTESGGMIL | MUC16 | Q8WXI7 | B*07/B*35 |
| 330 | FPFVTGSTEM | MUC16 | Q8WXI7 | B*07/B*35 |
| 331 | FPHPEMTTSM | MUC16 | Q8WXI7 | B*07/B*35 |
| 332 | FPHSEMTTL | MUC16 | Q8WXI7 | B*07/B*35 |
| 333 | FPHSEMTTVM | MUC16 | Q8WXI7 | B*07/B*35 |
| 334 | FPYSEVTTL | MUC16 | Q8WXI7 | B*07/B*35 |
| 335 | HPDPVGPGL | MUC16 | Q8WXI7 | B*07/B*35 |
| 336 | HPKTESATPAAY | MUC16 | Q8WXI7 | B*07/B*35 |
| 337 | HPVETSSAL | MUC16 | Q8WXI7 | B*07/B*35 |
| 338 | HVTKTQATF | MUC16 | Q8WXI7 | B*07/B*35 |
| 339 | LPAGTTGSLVF | MUC16 | Q8WXI7 | B*07/B*35 |
| 340 | LPEISTRTM | MUC16 | Q8WXI7 | B*07/B*35 |
| 341 | LPLDTSTTL | MUC16 | Q8WXI7 | B*07/B*35 |
| 342 | LPLGTSMTF | MUC16 | Q8WXI7 | B*07/B*35 |
| 343 | LPSVSGVKTTF | MUC16 | Q8WXI7 | B*07/B*35 |
| 344 | LPTQTTSSL | MUC16 | Q8WXI7 | B*07/B*35 |
| 345 | LPTSESLVSF | MUC16 | Q8WXI7 | B*07/B*35 |

TABLE 3-continued

Additional peptides according to the present invention.

| Seq ID No | Sequence | Gene | Uniprot Accession | HLA allotype |
|---|---|---|---|---|
| 346 | LPWDTSTTLF | MUC16 | Q8WXI7 | B*07/B*35 |
| 347 | MPLTTGSQGM | MUC16 | Q8WXI7 | B*07/B*35 |
| 348 | MPNSAIPFSM | MUC16 | Q8WXI7 | B*07/B*35 |
| 349 | MPSLSEAMTSF | MUC16 | Q8WXI7 | B*07/B*35 |
| 350 | NPSSTTTEF | MUC16 | Q8WXI7 | B*07/B*35 |
| 351 | NVLTSTPAF | MUC16 | Q8WXI7 | B*07/B*35 |
| 352 | SPAETSTNM | MUC16 | Q8WXI7 | B*07/B*35 |
| 353 | SPAMTTPSL | MUC16 | Q8WXI7 | B*07/B*35 |
| 354 | SPLPVTSLL | MUC16 | Q8WXI7 | B*07/B*35 |
| 355 | SPLVTSHIM | MUC16 | Q8WXI7 | B*07/B*35 |
| 356 | SPNEFYFTV | MUC16 | Q8WXI7 | B*07/B*35 |
| 357 | SPSPVPTTL | MUC16 | Q8WXI7 | B*07/B*35 |
| 358 | SPSPVTSTL | MUC16 | Q8WXI7 | B*07/B*35 |
| 359 | SPSTIKLTM | MUC16 | Q8WXI7 | B*07/B*35 |
| 360 | SPSVSSNTY | MUC16 | Q8WXI7 | B*07/B*35 |
| 361 | SPTHVTQSL | MUC16 | Q8WXI7 | B*07/B*35 |
| 362 | SPVPVTSLF | MUC16 | Q8WXI7 | B*07/B*35 |
| 363 | TAKTPDATF | MUC16 | Q8WXI7 | B*07/B*35 |
| 364 | TPLATTQRF | MUC16 | Q8WXI7 | B*07/B*35 |
| 365 | TPLATTQRFTY | MUC16 | Q8WXI7 | B*07/B*35 |
| 366 | TPLTTTGSAEM | MUC16 | Q8WXI7 | B*07/B*35 |
| 367 | TPSVVTEGF | MUC16 | Q8WXI7 | B*07/B*35 |
| 368 | VPTPVFPTM | MUC16 | Q8WXI7 | B*07/B*35 |
| 369 | FPHSEMTTV | MUC16 | Q8WXI7 | B*07/B*35/ B*51 |
| 370 | PGGTRQSL | MUC16 | Q8WXI7 | B*14:02/ B*07 |
| 371 | LYVDGFTHW | MUC16 | Q8WXI7 | B*35/B*55/ B*07 |
| 372 | IPRNPPPTLL | MYO3B | Q8WXR4 | B*07 |
| 373 | RPRALRDLRIL | NLRP7, NLRP2 | Q9NX02 | B*07 |
| 374 | NPIGDTGVKF | NLRP7 | Q8WX94 | B*07/B*35 |
| 375 | AAASPLLLL | NMU | P48645 | B*07 |
| 376 | RPRSPAGQVA | NMU | P48645 | B*07/B*55 |
| 377 | RPRSPAGQVAAA | NMU | P48645 | B*07/B*55 |
| 378 | RPRSPAGQVAA | NMU | P48645 | B*07/B*56 |
| 379 | GPFPLVYVL | OVGP1 | Q12889 | B*07/B*35 |
| 380 | IPTYGRTF | OVGP1 | Q12889 | B*07/B*35 |
| 381 | LPEQTPLAF | OVGP1 | Q12889 | B*07/B*35 |
| 382 | SPMHDRWTF | OVGP1 | Q12889 | B*07/B*35 |

TABLE 3 -continued

Additional peptides according to the present invention.

| Seq ID No | Sequence | Gene | Uniprot Accession | HLA allotype |
|---|---|---|---|---|
| 383 | TPTKETVSL | OVGP1 | Q12889 | B*07/B*35 |
| 384 | YPGLRGSPM | OVGP1 | Q12889 | B*07/B*35 |
| 385 | SPALHIGSV | PCDHB5, PCDHB18, PCDHB17, PCDHB15, PCDHB14, PCDHB11, PCDHB10, PCDHB9, PCDHB8, PCDHB6, PCDHB4, PCDHB3, PCDHB2, PCDHB16 | Q96TA0, Q9NRJ7, Q9UN66, Q9UN67, Q9Y5E1, Q9Y5E3, Q9Y5E4, Q9Y5E5, Q9Y5E6, Q9Y5E7, Q9Y5E8, Q9Y5E9, Q9Y5F2 | B*07 |
| 386 | FPFNPLDF | PTTG1 | O95997 | B*07/B*35 |
| 387 | APLKLSRTPA | SPON1 | Q9HCB6 | B*07/B*55 |
| 388 | SPAPLKLSRTPA | SPON1 | Q9HCB6 | B*07/B*55/B*56 |
| 389 | SPGAQRTFFQL | STAG3, STAG3L3, STAG3L2, STAG3L1 | P0CL83, Q9UJ98 | B*07 |
| 390 | NPDLRRNVL | TCEA2 | Q15560 | B*07 |
| 391 | APSTPRITTF | TCEA2 | Q15560 | B*07 |
| 392 | KPIESTLVA | TMEM158 | Q8WZ71 | B*07/B*55 |
| 393 | ASKPHVEI | CRABP1 | P29762 | B*08 |
| 394 | MYKMKKPI | MAGEB3 | O15480 | B*08 |
| 395 | VLLPRLVSC | MSLN | Q13421 | B*08/A*02 |
| 396 | REASGLLSL | BCAM | P50895 | B*44 |
| 397 | REGDTVQLL | BCAM | P50895 | B*44 |
| 398 | SFEQVVNELF | BCL2L1 | Q07817 | B*44 |
| 399 | RELLHLVTL | CAPN13 | Q6MZZ7 | B*44/B*37 |
| 400 | GEIEIHLL | CCDC146 | Q8IYE0 | B*44/B*40 |
| 401 | EDLKEELLL | CPXCR1 | O8N123 | B*44/B*18 |
| 402 | RELANDELIL | CRABP1 | P29762 | B*44 |
| 403 | EEAQWVRKY | FAM111B | Q6SJ93 | B*44 |
| 404 | NEAIMHQY | FAM111B | Q6SJ93 | B*44/B*18 |
| 405 | NEIWTHSY | FOLR1 | P15328 | B*44/B*18 |
| 406 | EDGRLVIEF | FRAS1 | Q86XX4 | B*44/B*18 |
| 407 | AEHEGVSVL | GXYLT2 | A0PJZ3 | B*44 |
| 408 | LEKALQVF | IDO1 | P14902 | B*44 |
| 409 | REFVLSKGDAGL | IDO1 | P14902 | B*44 |
| 410 | SEDPSKLEA | IDO1 | P14902 | B*44 |
| 411 | LELPPILVY | IDO1 | P14902 | B*44/B*18 |
| 412 | QEILTQVKQ | IGF2BP3 | O00425 | B*44/B*40 |
| 413 | IEALSGKIEL | IGF2BP3 | O00425 | B*44/B*45 |
| 414 | EDAALFKAW | IRF4 | Q15306 | B*44 |
| 415 | REEDAALFKAW | IRF4 | Q15306 | B*44 |
| 416 | SEEETRVVF | MELK | Q14680 | B*44 |

TABLE 3-continued

Additional peptides according to the present invention.

| Seq ID No | Sequence | Gene | Uniprot Accession | HLA allotype |
|---|---|---|---|---|
| 417 | AEHFSMIRA | MEX3C, MEX3B, MEX3A | A1L020, Q5U5Q3, Q6ZN04 | B*44/B*50 |
| 418 | FEDAQGHIW | MMP11 | P24347 | B*44 |
| 419 | HEFGHVLGL | MMP11 | P24347 | B*44/B*40 |
| 420 | FESHSTVSA | MUC16 | Q8WXI7 | B*44 |
| 421 | GEPATTVSL | MUC16 | Q8WXI7 | B*44 |
| 422 | SETTFSLIF | MUC16 | Q8WXI7 | B*44 |
| 423 | SEVPTGTTA | MUC16 | Q8WXI7 | B*44 |
| 424 | TEFPLFSAA | MUC16 | Q8WXI7 | B*44 |
| 425 | SEVPLPMAI | MUC16 | Q8WXI7 | B*44/B*18 |
| 426 | PEKTTHSF | MUC16 | Q8WXI7 | B*44/C*04:01 |
| 427 | HESSSHHDL | NFE2L3 | Q9Y4A8 | B*44 |
| 428 | LDLGLNHI | NLRP2 | Q9NX02 | B*44/B*47 |
| 429 | REKFIASVI | OVGP1 | Q12889 | B*44 |
| 430 | DEKILYPEF | OVGP1 | Q12889 | B*44/B*18 |
| 431 | AEQDPDELNKA | POMZP3, ZP3 | P21754, Q6PJE2 | B*44/B*41 |
| 432 | EEQYIAQF | PRAME | P78395 | B*44/B*18 |
| 433 | SDSQVRAF | STAG1, STAG3, STAG2 | Q8N3U4, Q8WVM7, Q9UJ98 | B*44/B*37 |
| 434 | KEAIREHQM | TCEA1P2, TCEA1, TCEA2 | P23193, Q15560 | B*44/B*41 |
| 435 | REEFVSIDHL | TMPRSS3 | P57727 | B*44 |
| 436 | REPGDIFSEL | WISP3 | O95389 | B*44 |
| 437 | TEAVVTNEL | XPR1 | Q9UBH6 | B*44 |
| 438 | SEVDSPNVL | ZNF217 | O75362 | B*44 |

TABLE 4

HLA Class I peptides according to the present invention.

| Seq ID No | Sequence | Gene | Uniprot Accession | HLA allotype |
|---|---|---|---|---|
| 439 | EALAKLMSL | ATP7B | P35670 | B*51 |
| 440 | ELFEGLKAF | BCAT1 | P54687 | A*25 |
| 441 | HQITEVGTM | BCAT1 | P54687 | B*15 |
| 442 | ILSKLTDIQY | BCAT1 | P54687 | B*15 |
| 443 | GTFNPVSLW | BCAT1 | P54687 | B*58 |
| 444 | KLSQKGYSW | BCL2L1 | Q07817 | A*32 |
| 445 | LHITPGTAY | BCL2L1 | Q07817 | B*13 |
| 446 | GRIVAFFSF | BCL2L1 | Q07817 | B*27 |

TABLE 4 -continued

HLA Class I peptides according to the present invention.

| Seq ID No | Sequence | Gene | Uniprot Accession | HLA allotype |
|---|---|---|---|---|
| 447 | MQVLVSRI | BCL2L1 | Q07817 | B*52/B*13 |
| 448 | LSQKGYSW | BCL2L1 | Q07817 | B*57 |
| 449 | RAFSDLTSQL | BCL2L1 | Q07817 | C*15 |
| 450 | KQTFPFPTI | C2orf88 | Q9BSF0 | B*13 |
| 451 | DYLNEWGSRF | CDH3 | P22223 | A*23 |
| 452 | LKVLGVNVM | CRABP2 | P29373 | C*07 |
| 453 | DVKLEKPK | DPPA2 | Q7Z7J5 | A*68 |
| 454 | AQTDPTTGY | LOXL2, ENTPD4 | Q9Y4K0 | B*15 |
| 455 | AAAANAQVY | ESR1 | P03372 | B*35 |
| 456 | IPLERPLGEVY | ESR1 | P03372 | B*35 |
| 457 | NAAAANAQVY | ESR1 | P03372 | B*35 |
| 458 | TDTLIHLM | ESR1 | P03372 | B*37 |
| 459 | KVAGERYVY | ETV1, ETV4, ETV5 | P41161, P43268, P50549 | A*32/A*31 |
| 460 | RLSSATANALY | FAM83H | Q6ZRV2 | A*26 |
| 461 | AQRMTTQLL | FOLR1 | P15328 | B*15 |
| 462 | QRMTTQLLL | FOLR1 | P15328 | B*27/C*07 |
| 463 | VNQSLLDLY | FTHL17 | Q9BXU8 | A*26 |
| 464 | MSALRPLL | GPC2 | Q8N158 | C*15 |
| 465 | DLIESGQLR | IDO1 | P14902 | A*66 |
| 466 | DLIESGQLRER | IDO1 | P14902 | A*66 |
| 467 | MQMQERDTL | IDO1 | P14902 | B*15 |
| 468 | ALAKLLPL | KLK10 | O43240 | B*35 |
| 469 | QEQSSVVRA | KLK6 | Q92876 | B*45 |
| 470 | QGERLLGAAV | LAG3 | P18627 | C*03 |
| 471 | AQRLDPVYF | LAMC2 | Q13753 | B*15 |
| 472 | MRLLVAPL | LRRN2 | O75325 | B*14 |
| 473 | MLNNNALSAL | LRRN2 | O75325 | B*35 |
| 474 | AADGGLRASVTL | LY6E | Q16553 | C*05 |
| 475 | GRDPTSYPSL | MAGEA11 | P43364 | B*39 |
| 476 | ISYPPLHEW | MAGEA3, MAGEA12 | P43357 | B*57 |
| 477 | RIQQQTNTY | MEX3A | A1L020 | B*15 |
| 478 | VVGPKGATI | MEX3D, MEX3C, MEX3B, MEX3A | A1L020, Q5U503, Q6ZN04, Q86XN8 | C*14 |
| 479 | TEGSHFVEA | MFN1 | Q8IWA4 | B*45 |
| 480 | GRADIMIDF | MMP11 | P24347 | B*27 |
| 481 | GRWEKTDLTY | MMP11 | P24347 | B*27 |
| 482 | GRWEKTDLTYR | MMP11 | P24347 | B*27 |
| 483 | VRFPVHAALVW | MMP11 | P24347 | B*27 |

TABLE 4 -continued

HLA Class I peptides according to the present invention.

| Seq ID No | Sequence | Gene | Uniprot Accession | HLA allotype |
|---|---|---|---|---|
| 484 | AWLRSAAA | MMP11 | P24347 | B*56 |
| 485 | VRFPVHAAL | MMP11 | P24347 | C*07 |
| 486 | DRFFWLKV | MMP12 | P39900 | B*14 |
| 487 | GMADILVVF | MMP12 | P39900 | B*15 |
| 488 | RSFSLGVPR | MRPL51 | Q4U2R6 | A*31 |
| 489 | EVSGLSTER | MSLN | Q13421 | A*68 |
| 490 | AEVQKLLGP | MSLN | Q13421 | B*50 |
| 491 | EAYSSTSSW | MUC16 | Q8WXI7 | A*25 |
| 492 | EVTPWISLTL | MUC16 | Q8WXI7 | A*25 |
| 493 | DTNLEPVTR | MUC16 | Q8WXI7 | A*68 |
| 494 | ETTASLVSR | MUC16 | Q8WXI7 | A*68 |
| 495 | EVPSGATTEVSR | MUC16 | Q8WXI7 | A*68 |
| 496 | EVPTGTTAEVSR | MUC16 | Q8WXI7 | A*68 |
| 497 | EVSRTEVISSR | MUC16 | Q8WXI7 | A*68 |
| 498 | EVYPELGTQGR | MUC16 | Q8WXI7 | A*68 |
| 499 | SSETTKIKR | MUC16 | Q8WXI7 | A*68 |
| 500 | AHVLHSTL | MUC16 | Q8WXI7 | B*14 |
| 501 | IQIEPTSSL | MUC16 | Q8WXI7 | B*14 |
| 502 | SGDQGITSL | MUC16 | Q8WXI7 | B*14 |
| 503 | TVFDKAFTAA | MUC16 | Q8WXI7 | B*14 |
| 504 | TVSSVNQGL | MUC16 | Q8WXI7 | B*14 |
| 505 | YVPTGAITQA | MUC16 | Q8WXI7 | B*14 |
| 506 | HQFITSTNTF | MUC16 | Q8WXI7 | B*15 |
| 507 | TSIFSGQSL | MUC16 | Q8WXI7 | B*15 |
| 508 | TVAKTTTTF | MUC16 | Q8WXI7 | B*15 |
| 509 | GRGPGGVSW | MUC16 | Q8WXI7 | B*27 |
| 510 | RRIPTEPTF | MUC16 | Q8WXI7 | B*27 |
| 511 | SRIPQDVSW | MUC16 | Q8WXI7 | B*27 |
| 512 | SRSPENPSW | MUC16 | Q8WXI7 | B*27 |
| 513 | SRTEISSSR | MUC16 | Q8WXI7 | B*27 |
| 514 | SRTEVASSR | MUC16 | Q8WXI7 | B*27 |
| 515 | TRIEMESTF | MUC16 | Q8WXI7 | B*27 |
| 516 | TASTPISTF | MUC16 | Q8WXI7 | B*35 |
| 517 | TAETILTFHAF | MUC16 | Q8WXI7 | B*35 |
| 518 | TSDFPTITV | MUC16 | Q8WXI7 | B*35 |
| 519 | VTSLLTPGMV | MUC16 | Q8WXI7 | B*35 |
| 520 | THSAMTHGF | MUC16 | Q8WXI7 | B*38 |

TABLE 4-continued

HLA Class I peptides according to the present invention.

| Seq ID No | Sequence | Gene | Uniprot Accession | HLA allotype |
|---|---|---|---|---|
| 521 | THSTASQGF | MUC16 | Q8WXI7 | B*38 |
| 522 | THSTISQGF | MUC16 | Q8WXI7 | B*38 |
| 523 | APKGIPVKPTSA | MUC16 | Q8WXI7 | B*55 |
| 524 | AVSPTVQGL | MUC16 | Q8WXI7 | C*07 |
| 525 | QRFPHSEM | MUC16 | Q8WXI7 | C*07 |
| 526 | SVPDILST | MUC16 | Q8WXI7 | C*07 |
| 527 | QSTPYVNSV | MUC16 | Q8WXI7 | C*16 |
| 528 | TRTGLFLRF | NLRP7, NLRP2 | Q9NX02 | B*27 |
| 529 | PFSNPRVL | NLRP2 | Q9NX02 | C*04 |
| 530 | MLPRAALL | NLRP7 | Q8WX94 | B*51 |
| 531 | QGAQLRGAL | NLRP7, NLRP2 | Q8WX94 | B*52 |
| 532 | AISFSYKAW | OVGP1 | Q12889 | A*25 |
| 533 | GQHLHLETF | FRAME | P78395 | B*15 |
| 534 | CRPGALQIEL | RAD54B | Q9Y620 | C*02 |
| 535 | IKDVRKIK | RNF17 | Q9BXT8 | B*13 |
| 536 | VQDQACVAKF | RNF17 | Q9BXT8 | B*15 |
| 537 | IRRLKELKDQ | RPL37A, RPL37AP8 | A6NKH3, P61513 | n/a |
| 538 | QLEKALKEI | SAGE1 | Q9NXZ1 | C*05 |
| 539 | IPIPSTGSVEM | SPINT1 | O43278 | B*35/B*42 |
| 540 | AGIPAVALW | SPINT1 | O43278 | B*58 |
| 541 | RLSPAPLKL | SPON1 | Q9HCB6 | B*13 |
| 542 | QIIDEEETQF | SPON1 | Q9HCB6 | B*15 |
| 543 | MRLSPAPLK | SPON1 | Q9HCB6 | B*27 |
| 544 | LRNPSIQKL | SPON1 | Q9HCB6 | C*07 |
| 545 | RVGPPLLI | TMEM158 | Q8WZ71 | B*15 |
| 546 | GRAFFAAAF | TMEM158 | Q8WZ71 | B*27 |
| 547 | EVNKPGVYTR | TMPRSS3 | P57727 | A*68 |
| 548 | VSEASLVSSI | ZBTB12 | Q9Y330 | C*05 |
| 549 | ARSKLQQGL | ZNF217 | O75362 | B*27 |
| 550 | RRFKEPWFL | ZNF217, ZNF516, ZNF536 | O15090, O75362, Q92618 | B*27 |
| 551 | RLHTGEKPYK | ZNF816, ZNF813, ZNF578, ZNF599, ZNF600, ZNF320, ZNF525, ZNF485, ZNF860, ZNF429, ZNF808, ZNF888, ZNF761, ZNF701, ZNF83, ZNF167, ZFP62, ZNF28, ZSCAN21, ZNF91, ZNF229, ZNF702P, ZNF528, ZNF468, ZNF765, ZNF845 | A2RRD8, A6NHJ4, A6NK21, A6NK53, A6NK75, A6NN14, A6NNF4, A6NP11, A8MTY0, A8MUV8, B4DU55, B4DX44, B4DXR9, O14628, O14709, O15090, O43309, O43345, O43361, O75346, O75373, O75437, O75820, O95600, O95780, P0CB33, P0CJ79, P0DKX0, | A*30 |

TABLE 4-continued

HLA Class I peptides according to the present invention.

| Seq ID No | Sequence | Gene | Uniprot Accession | HLA allotype |
|---|---|---|---|---|
| | | | P10073, P17019, P17026, P17035, P17038, P17040, P17097, P35789, P51522, P51815, P52742, Q02386, Q03923, Q03924, Q03936, Q03938, Q05481, Q08AN1, Q09FC8, Q0VGE8, Q14584, Q14586, Q14590, Q14591, Q14593, Q15928, Q15929, Q15937, Q16587, Q2M3W8, Q2M3X9, Q2VY69, Q3KP31, Q3MI56, Q3SXZ3, Q4V348, Q53GI3, Q5HY98, Q5JNZ3, Q5SXM1, Q5VIY5, Q5VV52, Q68DY1, Q6AZW8, Q6P280, Q6P9G9, Q6PDB4, Q6ZMV8, Q6ZMW2, Q6ZN06, Q6ZN08, Q6ZN19, Q6ZN57, Q6ZNA1, Q6ZNG1, Q6ZR52, Q76KX8, Q7L2R6, Q7L945, Q7Z3V5, Q7Z7L9, Q86TJ5, Q86UE3, Q86V71, Q86XN6, Q86XU0, Q86Y25, Q8IW36, Q8IWY8, Q8IYN0, Q8IZ26, Q8N4W9, Q8N782, Q8N703, Q8N823, Q8N859, Q8N8C0, Q8N8J6, Q8N972, Q8N988, Q8N9F8, Q8NB50, Q8NCK3, Q8NDQ6, Q8NEM1, Q8NF99, Q8NHY6, Q8TAQ5, Q8TBZ5, Q8TD23, Q8TF20, Q8TF32, Q8TF39, Q8WV37, Q8WX64, Q96CX3, Q96IR2, Q96JC4, Q96LX8, Q96MR9, Q96N22, Q96N38, Q96N58, Q96NI8, Q96NL3, Q96PE6, Q96RE9, Q96SE7, Q99676, Q9BX82, Q9H5H4, Q9H7R5, Q9H8G1, Q9H963, Q9HBT7, Q9HCG1, Q9HCL3, Q9NQX6, Q9NV72, Q9POL1, Q9P255, Q9P2F9, Q9P2J8, Q9UEG4, Q9UI15, Q9UJW7, Q9UL36, Q9Y201, Q9Y473, Q9Y5A6 | |
| 773 | ALYGKLLKL | VPS13B | | A*02 |
| 774 | VYVDDIYVI | CASC5 | | A*24 |

TABLE 5

HLA Class II peptides according to the present invention.

| Seq ID No | Sequence | Additional Sequence variants | Gene |
|---|---|---|---|
| 552 | GVNAMLRKVAVAAASKPHVE | | CRABP1 |
| 553 | | VNAMLRKVAVAAASKPHVE | CRABP1 |
| 554 | | GVNAMLRKVAVAAASKPH | CRABP1 |
| 555 | | VNAMLRKVAVAAASKPH | CRABP1 |
| 556 | | NAMLRKVAVAAASKPH | CRABP1 |
| 557 | | AMLRKVAVAAASKPH | CRABP1 |
| 558 | | LRKVAVAAASKPH | CRABP1 |
| 559 | | RKVAVAAASKPH | CRABP1 |
| 560 | PNFSGNWKIIRSENFEELLK | | CRABP1 |
| 561 | | PNFSGNWKIIRSENFEELL | CRABP2 |
| 562 | | GNWKIIRSENFEELLKVL | CRABP2 |
| 563 | | PNFSGNWKIIRSENFEEL | CRABP2 |
| 564 | | GNWKIIRSENFEELLKV | CRABP2 |
| 565 | | NWKIIRSENFEELLKV | CRABP2 |
| 566 | | NWKIIRSENFEELLK | CRABP2 |
| 567 | | NWKIIRSENFEELL | CRABP2 |
| 568 | | WKIIRSENFEELLK | CRABP2 |
| 569 | | WKIIRSENFEELL | CRABP2 |
| 570 | | GNWKIIRSENF | CRABP2 |
| 571 | | PNFSGNWKIIR | CRABP2 |
| 572 | INFKVGEEFEEQTV | | CRABP2 |
| 573 | RLLSADTKGWVRLQ | | DPPA2 |
| 574 | LPDFYNDWMFIAKHLPDL | | IDO1 |
| 575 | VGDDHLLLLQGEQLRRT | | KLK10 |
| 576 | | VGDDHLLLLQGEQLRR | KLK10 |
| 577 | | GDDHLLLLQGEQLRR | KLK10 |
| 578 | | DDHLLLLQGEQLRR | KLK10 |
| 579 | SGGPLVCDETLQGILS | | KLK10 |
| 580 | | GGPLVCDETLQGILS | KLK10 |
| 581 | | GGPLVCDETLQGIL | KLK10 |
| 582 | GSQPWQVSLFNGLSFH | | KLK10 |
| 583 | LTVKLPDGYEFKFPNRLNLEAIN | | LGALS1 |
| 584 | | TVKLPDGYEFKFPNRLNLEAINY | LGALS1 |
| 585 | | LTVKLPDGYEFKFPNRLNL | LGALS1 |
| 586 | | TVKLPDGYEFKFPNRLNL | LGALS1 |
| 587 | DQANLTVKLPDGYEFKFPNRLNL | | LGALS1 |
| 588 | VAPDAKSFVLNLGKDSNNL | | LGALS1 |
| 589 | | APDAKSFVLNLGKDSNNL | LGALS1 |

TABLE 5-continued

HLA Class II peptides according to the present invention.

| Seq ID No | Sequence | Additional Sequence variants | Gene |
|---|---|---|---|
| 590 | RVRGEVAPDAKSFVLNLG | | LGALS1 |
| 591 | | VRGEVAPDAKSFVLNL | LGALS1 |
| 592 | | VRGEVAPDAKSFVLNLG | LGALS1 |
| 593 | | GEVAPDAKSFVLNLG | LGALS1 |
| 594 | | VRGEVAPDAKSFVLN | LGALS1 |
| 595 | | VRGEVAPDAKSFVL | LGALS1 |
| 596 | MAADGDFKIKCVAFD | | LGALS1 |
| 597 | SPDAESLFREALSNKVDEL | | MAGEA4 |
| 598 | | AESLFREALSNKVDEL | MAGEA4 |
| 599 | | AESLFREALSNKVDE | MAGEA4 |
| 600 | FREALSNKVDE | | MAGEA4 |
| 601 | LSNKVDELAHFLLRK | | MAGEA4 |
| 602 | KDPVAWEAGMLMH | | MAGEB1 |
| 603 | KARDETRGLNVPQ | | MAGEB2 |
| 604 | KLITQDLVKLKYLEYRQ | | MAGEB3 |
| 605 | LTVAEVQKLLGPHVEGLKAEERHRP | | MSLN |
| 606 | | LTVAEVQKLLGPHVEGLKAEER | MSLN |
| 607 | | LTVAEVQKLLGPHVEGLKAEE | MSLN |
| 608 | | LTVAEVQKLLGPHVEGLKAE | MSLN |
| 609 | | LTVAEVQKLLGPHVEGLKA | MSLN |
| 610 | | LTVAEVQKLLGPHVEGLK | MSLN |
| 611 | | LTVAEVQKLLGPHVEGL | MSLN |
| 612 | | TVAEVQKLLGPHVEGLK | MSLN |
| 613 | | LTVAEVQKLLGPHVEG | MSLN |
| 614 | | TVAEVQKLLGPHVEGL | MSLN |
| 615 | | VAEVQKLLGPHVEGLK | MSLN |
| 616 | | TVAEVQKLLGPHVEG | MSLN |
| 617 | | VAEVQKLLGPHVEGL | MSLN |
| 618 | | VAEVQKLLGPHVEG | MSLN |
| 619 | | VAEVQKLLGPHVE | MSLN |
| 620 | | EVQKLLGPHVEG | MSLN |
| 621 | | LTVAEVQKLLG | MSLN |
| 622 | MDALRGLLPVLGQPIIRSIPQGIVA | | MSLN |
| 623 | | ALRGLLPVLGQPIIRSIPQGIVA | MSLN |
| 624 | | LRGLLPVLGQPIIRSIPQGIVA | MSLN |
| 625 | | DALRGLLPVLGQPIIRSIPQG | MSLN |
| 626 | | RGLLPVLGQPIIRSIPQGIVA | MSLN |

TABLE 5 -continued

HLA Class II peptides according to the present invention.

| Seq ID No | Sequence | Additional Sequence variants | Gene |
|---|---|---|---|
| 627 | | ALRGLLPVLGQPIIRSIPQG | MSLN |
| 628 | | DALRGLLPVLGQPIIRSIPQ | MSLN |
| 629 | | GLLPVLGQPIIRSIPQGIVA | MSLN |
| 630 | | ALRGLLPVLGQPIIRSIPQ | MSLN |
| 631 | | DALRGLLPVLGQPIIRSIP | MSLN |
| 632 | | LLPVLGQPIIRSIPQGIVA | MSLN |
| 633 | | LRGLLPVLGQPIIRSIPQ | MSLN |
| 634 | | DALRGLLPVLGQPIIRS | MSLN |
| 635 | | ALRGLLPVLGQPIIRS | MSLN |
| 636 | | DALRGLLPVLGQPIIR | MSLN |
| 637 | | ALRGLLPVLGQPIIR | MSLN |
| 638 | | LRGLLPVLGQPIIRS | MSLN |
| 639 | | ALRGLLPVLGQPII | MSLN |
| 640 | | ALRGLLPVLGQPI | MSLN |
| 641 | | RGLLPVLGQPIIR | MSLN |
| 642 | | GLLPVLGQPIIR | MSLN |
| 643 | | LRGLLPVLGQPI | MSLN |
| 644 | | RGLLPVLGQPI | MSLN |
| 645 | RGLLPVLGQPIIRSIPQGIVAAWRQ | | MSLN |
| 646 | | GLLPVLGQPIIRSIPQGIVAAWRQ | MSLN |
| 647 | | LPVLGQPIIRSIPQGIVAAWRQ | MSLN |
| 648 | | GLLPVLGQPIIRSIPQGIVAA | MSLN |
| 649 | | LLPVLGQPIIRSIPQGIVAA | MSLN |
| 650 | | LPVLGQPIIRSIPQGIVAAW | MSLN |
| 651 | | LPVLGQPIIRSIPQGIVAA | MSLN |
| 652 | | PVLGQPIIRSIPQGIVAAW | MSLN |
| 653 | | LPVLGQPIIRSIPQGIVA | MSLN |
| 654 | | PVLGQPIIRSIPQGIVA | MSLN |
| 655 | | LGQPIIRSIPQGIVAA | MSLN |
| 656 | | VLGQPIIRSIPQGIVA | MSLN |
| 657 | | QPIIRSIPQGIVA | MSLN |
| 658 | VSTMDALRGLLPVLGQPIIRSIPQG | | MSLN |
| 659 | | VSTMDALRGLLPVLGQPIIRSIPQ | MSLN |
| 660 | | VSTMDALRGLLPVLGQPIIR | MSLN |
| 661 | | LRGLLPVLGQPIIRSIPQG | MSLN |
| 662 | LRTDAVLPLTVAEVQKLLGPHVEG | | MSLN |
| 663 | | ERTDAVLPLTVAEVQKLLGPHVG | MSLN |
| 664 | | AVLPLTVAEVQKLLGPHVEG | MSLN |

TABLE 5-continued

HLA Class II peptides according to the present invention.

| Seq ID No | Sequence | Additional Sequence variants | Gene |
|---|---|---|---|
| 665 | | VLPLTVAEVQKLLGPHVEG | MSLN |
| 666 | | LPLTVAEVQKLLGPHVEG | MSLN |
| 667 | | TDAVLPLTVAEVQ | MSLN |
| 668 | | AVLPLTVAEVQK | MSLN |
| 669 | VLPLTVAEVQKLLGPHVEGLKAEE | | MSLN |
| 670 | | VLPLTVAEVQKLLGPHVEGLK | MSLN |
| 671 | | LPLTVAEVQKLLGPHVEGLK | MSLN |
| 672 | LRGLLPVLGQPIIRSIPQGIVAA | | MSLN |
| 673 | IPFTYEQLDVLKHKLDELYPQ | | MSLN |
| 674 | | IPFTYEQLDVLKHKLDE | MSLN |
| 675 | | IPFTYEQLDVLKHKLD | MSLN |
| 676 | VPPSSIWAVRPQDLDTCDPR | | MSLN |
| 677 | | IWAVRPQDLDTCDPR | MSLN |
| 678 | | AVRPQDLDTCDPR | MSLN |
| 679 | WGVRGSLLSEADVRALGGLA | | MSLN |
| 680 | | GVRGSLLSEADVRALGGLA | MSLN |
| 681 | | WGVRGSLLSEADVRALGGL | MSLN |
| 682 | | GVRGSLLSEADVRALGGL | MSLN |
| 683 | | VRGSLLSEADVRALGGLA | MSLN |
| 684 | | WGVRGSLLSEADVRALGG | MSLN |
| 685 | | GVRGSLLSEADVRALGG | MSLN |
| 686 | | VRGSLLSEADVRALGGL | MSLN |
| 687 | | WGVRGSLLSEADVRALG | MSLN |
| 688 | | GVRGSLLSEADVRALG | MSLN |
| 689 | | WGVRGSLLSEADVRAL | MSLN |
| 690 | | GSLLSEADVRALGGL | MSLN |
| 691 | | GVRGSLLSEADVRAL | MSLN |
| 692 | | RGSLLSEADVRALGG | MSLN |
| 693 | | WGVRGSLLSEADVRA | MSLN |
| 694 | | GSLLSEADVRALGG | MSLN |
| 695 | | RGSLLSEADVRALG | MSLN |
| 696 | | WGVRGSLLSEADVR | MSLN |
| 697 | | GSLLSEADVRALG | MSLN |
| 698 | | VRGSLLSEADVRA | MSLN |
| 699 | | LLSEADVRALGG | MSLN |
| 700 | | SLLSEADVRALG | MSLN |
| 701 | | GSLLSEADVRA | MSLN |

TABLE 5 -continued

HLA Class II peptides according to the present invention.

| Seq ID No | Sequence | Additional Sequence variants | Gene |
|---|---|---|---|
| 702 | | LLSEADVRALG | MSLN |
| 703 | | LSEADVRALGG | MSLN |
| 704 | | SEADVRALGG | MSLN |
| 705 | | EADVRALGG | MSLN |
| 706 | LSTERVRELAVALAQKNVK | | MSLN |
| 707 | | LSTERVRELAVALAQKN | MSLN |
| 708 | | ERVRELAVALAQKNVK | MSLN |
| 709 | | LSTERVRELAVALAQK | MSLN |
| 710 | | LSTERVRELAVALAQ | MSLN |
| 711 | | STERVRELAVALAQK | MSLN |
| 712 | | TERVRELAVALAQKN | MSLN |
| 713 | | VRELAVALAQKNVK | MSLN |
| 714 | AIPFTYEQLDVLKHKLDE | | MSLN |
| 715 | GLSTERVRELAVALAQKN | | MSLN |
| 716 | | GLSTERVRELAVALAQ | MSLN |
| 717 | IPQGIVAAWRQRSSRDPS | | MSLN |
| 718 | | GIVAAWRQRSSRDPS | MSLN |
| 719 | | IPQGIVAAWRQRSSR | MSLN |
| 720 | ALGGLACDLPGRFVAES | | MSLN |
| 721 | RELAVALAQKNVKLSTE | | MSLN |
| 722 | LKALLEVNKGHEMSPQ | | MSLN |
| 723 | TFMKLRTDAVLPLTVA | | MSLN |
| 724 | | FMKLRTDAVLPLTVA | MSLN |
| 725 | | FMKLRTDAVLPLT | MSLN |
| 726 | FMKLRTDAVLPL | | MSLN |
| 727 | TLGLGLQGGIPNGYLV | | MSLN |
| 728 | DLPGRFVAESAEVLL | | MSLN |
| 729 | | DLPGRFVAESAEVL | MSLN |
| 730 | | LPGRFVAESAEVL | MSLN |
| 731 | | DLPGRFVAESA | MSLN |
| 732 | ERHRPVRDWILRQRQ | | MSLN |
| 733 | SPRQLLGFPCAEVSG | | MSLN |
| 734 | SRTLAGETGQEAAPL | | MSLN |
| 735 | VTSLETLKALLEVNK | | MSLN |
| 736 | LGLQGGIPNGYLVL | | MSLN |
| 737 | | LQGGIPNGYLVL | MSLN |
| 738 | | GGIPNGYLVL | MSLN |
| 739 | LQGGIPNGYLVLDL | | MSLN |

TABLE 5-continued

HLA Class II peptides according to the present invention.

| Seq ID No | Sequence | Additional Sequence variants | Gene |
|---|---|---|---|
| 740 | APERQRLLPAALA | | MSLN |
| 741 | FVKIQSFLGGAPT | | MSLN |
| 742 | | FVKIQSFLGG | MSLN |
| 743 | | FVKIQSFLG | MSLN |
| 744 | FLKMSPEDIRK | | MSLN |
| 745 | WELSQLTNSVTELGPYTLDRD | | MUC16 |
| 746 | EITITTQTGYSLATSQVTLP | | MUC16 |
| 747 | ATTPSWVETHSIVIQGFPH | | MUC16 |
| 748 | GIKELGPYTLDRNSLYVNG | | MUC16 |
| 749 | | GIKELGPYTLDRNSL | MUC16 |
| 750 | | GPYTLDRNSLYVNG | MUC16 |
| 751 | | GIKELGPYTLDRN | MUC16 |
| 752 | | LGPYTLDRNSLYV | MUC16 |
| 753 | | LGPYTLDRNSLY | MUC16 |
| 754 | | LGPYTLDRNSL | MUC16 |
| 755 | IELGPYLLDRGSLYVNG | | MUC16 |
| 756 | | LGPYLLDRGSLYVNG | MUC16 |
| 757 | | LGPYLLDRGSLYVN | MUC16 |
| 758 | | LGPYLLDRGSLYV | MUC16 |
| 759 | EELGPYTLDRNSLYVNG | | MUC16 |
| 760 | LKPLFKSTSVGPLYSG | | MUC16 |
| 761 | | LKPLFKSTSVGPLYS | MUC16 |
| 762 | | LKPLFKSTSVGPLY | MUC16 |
| 763 | | LKPLFKSTSVGPL | MUC16 |
| 764 | FDKAFTAATTEVSRTE | | MUC16 |
| 765 | ELGPYTLDRDSLYVN | | MUC16 |
| 766 | GLLKPLFKSTSVGPL | | MUC16 |
| 767 | | LLKPLFKSTSVGPL | MUC16 |
| 768 | SDPYKATSAVVITST | | MUC16 |
| 769 | | SDPYKATSAVVITS | MUC16 |
| 770 | SRKFNTMESVLQGLL | | MUC16 |
| 771 | | SRKFNTMESVLQG | MUC16 |
| 772 | LGFYVLDRDSLFIN | | MUC16 |

The present invention furthermore generally relates to the peptides according to the present invention for use in the treatment of proliferative diseases, such as, for example, hepatocellular carcinoma, colorectal carcinoma, glioblastoma, gastric cancer, esophageal cancer, non-small cell lung cancer, small cell lung cancer, pancreatic cancer, renal cell carcinoma, prostate cancer, melanoma, breast cancer, chronic lymphocytic leukemia, Non-Hodgkin lymphoma, acute myeloid leukemia, gallbladder cancer and cholangiocarcinoma, urinary bladder cancer, uterine cancer, head and neck squamous cell carcinoma, mesothelioma.

Particularly preferred are the peptides—alone or in combination—according to the present invention selected from the group consisting of SEQ ID NO: 1 to SEQ ID NO: 772. More preferred are the peptides—alone or in combination—selected from the group consisting of SEQ ID NO: 1 to SEQ ID NO: 215 (see Tables 1 and 2), and their uses in the immunotherapy of ovarian cancer, hepatocellular carcinoma, colorectal carcinoma, glioblastoma, gastric cancer, esophageal cancer, non-small cell lung cancer, small cell lung cancer, pancreatic cancer, renal cell carcinoma, prostate cancer, melanoma, breast cancer, chronic lymphocytic leukemia, Non-Hodgkin lymphoma, acute myeloid leukemia, gallbladder cancer and cholangiocarcinoma, urinary bladder cancer, uterine cancer, head and neck squamous cell carcinoma, mesothelioma, and preferably ovarian cancer.

Thus, another aspect of the present invention relates to the use of the peptides according to the present invention for the—preferably combined—treatment of a proliferative disease selected from the group of ovarian cancer, hepatocellular carcinoma, colorectal carcinoma, glioblastoma, gastric cancer, esophageal cancer, non-small cell lung cancer, small cell lung cancer, pancreatic cancer, renal cell carcinoma, prostate cancer, melanoma, breast cancer, chronic lymphocytic leukemia, Non-Hodgkin lymphoma, acute myeloid leukemia, gallbladder cancer and cholangiocarcinoma, urinary bladder cancer, uterine cancer, head and neck squamous cell carcinoma, mesothelioma.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 772.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and functional fragments thereof, and methods of making these, as well as NK cells or other cells bearing said TCR or cross-reacting with said TCRs.

The antibodies and TCRs are additional embodiments of the immunotherapeutic use of the peptides according to the present invention.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 772, preferably containing SEQ ID No. 1 to SEQ ID No. 215, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are ovarian cancer, hepatocellular carcinoma, colorectal carcinoma, glioblastoma, gastric cancer, esophageal cancer, non-small cell lung cancer, small cell lung cancer, pancreatic cancer, renal cell carcinoma, prostate cancer, melanoma, breast cancer, chronic lymphocytic leukemia, Non-Hodgkin lymphoma, acute myeloid leukemia, gallbladder cancer and cholangiocarcinoma, urinary bladder cancer, uterine cancer, head and neck squamous cell carcinoma, mesothelioma, and preferably ovarian cancer cells.

The present invention further relates to biomarkers based on the peptides according to the present invention, herein called "targets" that can be used in the diagnosis of cancer, preferably ovarian cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following more detailed description of the underlying expression products (polypeptides) of the peptides according to the invention.

ALPP, also known as ALP, PLAP or PALP, encodes an alkaline phosphatase, a metallo-enzyme that catalyzes the hydrolysis of phosphoric acid monoesters (RefSeq, 2002). ALPP was described to be hyper-expressed in various human tumors and their cell lines, particularly in cancers of the testis and ovary (Millan and Fishman, 1995). ALPP was identified as an independent prognostic factor for the survival of osteosarcoma patients which also correlates with lung metastasis. Furthermore, ALPP was described as an immunohistochemical marker of gastrointestinal smooth muscle neoplasms, germ cell tumor precursors, such as carcinoma in situ and gonadoblastoma, and as a promising ovarian cancer biomarker (Ravenni et al., 2014; Wong et al., 2014b; Faure et al., 2016; Han et al., 2012).

ALPPL2, also known as GCAP, encodes a membrane bound glycosylated enzyme, localized to testis, thymus and certain germ cell tumors, which is closely related to both the placental and intestinal forms of alkaline phosphatase (RefSeq, 2002). ALPPL2 was shown to be ectopically expressed in seminoma as well as in many pancreatic cancer cell lines at both mRNA and protein levels and to be involved in cancer cell growth and invasion. Additionally, ALPPL2 was described as a potential diagnostic marker of pancreatic ductal adenocarcinoma (Hofmann and Millan, 1993; Dua et al., 2013; Fishman, 1995). RT-PCR for ALPPL2 was described to be suitable for the sensitive detection of residual germ cell tumor cells in peripheral blood and progenitor cell harvests (Hildebrandt et al., 1998).

BCAM encodes the basal cell adhesion molecule (Lutheran blood group), a member of the immunoglobulin superfamily and a receptor for the extracellular matrix protein, laminin (RefSeq, 2002). BCAM is a specific receptor for laminin alpha5 (LAMA5), a subunit of laminin-511 (LM-511) that is a major component of basement membranes in various tissues; the BCAM/LAMA5 system plays a functional role in the metastatic spreading of KRAS-mutant colorectal cancer as well as in the migration of hepatocellular carcinoma (Kikkawa et al., 2013; Kikkawa et al., 2014; Bartolini et al., 2016). Serum levels of BCAM were found to be significantly increased in breast cancer patients and its over-expression was found to be associated with skin, ovarian and pancreatic cancers as well as with endometrioid endometrial carcinoma, ovarian endometrioid carcinoma and cutaneous squamous cell carcinoma (Kikkawa et al., 2008; Planaguma et al., 2011; Latini et al., 2013; Kim et al., 2015a; Li et al., 2017). Being able to form a fusion protein with AKT2, BCAM was identified as AKT2 kinase activator in high-grade serous ovarian cancer (Kannan et al., 2015).

CBX2 encodes chromobox 2 which is a component of the polycomb multiprotein complex, which is required to maintain the transcriptionally repressive state of many genes throughout development via chromatin remodeling and modification of histones (RefSeq, 2002). CBX2 is involved in cell proliferation and metastasis (Clermont et al., 2016). CBX2 is regulated by SMARCE1 leading to suppressed EGFR transcription. CBX2 is involved in the regulation of three tumor suppressor genes encoded in the INK4A/ARF locus (Papadakis et al., 2015; Agherbi et al., 2009; Miyazaki et al., 2008). CBX2 is over-expressed in cancer including breast cancer, ovarian cancer, lung cancer, metastatic castration-resistant and neuroendocrine prostate cancer and basal-like endometrioid endometrial carcinoma (Parris et al., 2010; Clermont et al., 2016; Clermont et al., 2014; Clermont et al., 2015; Jiang et al., 2015; Xu et al., 2016). CBX2 is associated with lower patient survival and metastatic progression. CBX2 is linked to peritumoral inflammatory infiltration, metastatic spread to the cervical lymph nodes, and tumor size (Parris et al., 2014; Clermont et al., 2014; Xu et al., 2016). CBX2 over-expression results in hematopoietic stem cell differentiation and exhaustion (Klauke et al., 2013).

CCNA1 encodes cyclin A1, which belongs to the highly conserved cyclin family involved in the regulation of CDK kinases (RefSeq, 2002). Elevated levels of CCNA1 were detected in epithelial ovarian cancer, lymphoblastic leukemic cell lines as well as in childhood acute lymphoblastic leukemia patients. Others have observed over-expression of CCNA1 protein and mRNA in prostate cancer and in tumor tissues of anaplastic thyroid carcinoma patients (Holm et al., 2006; Wegiel et al., 2008; Marlow et al., 2012; Arsenic et al., 2015). Recent studies have shown that silencing of CCNA1 in highly cyclin A1 expressing ML1 leukemic cells slowed S phase entry, decreased proliferation and inhibited colony formation (Ji et al., 2005).

CD70 encodes CD70 molecule which is a cytokine that belongs to the tumor necrosis factor (TNF) ligand family. It induces proliferation of co-stimulated T cells, enhances the generation of cytolytic T cells, and contributes to T cell activation. This cytokine is also reported to play a role in regulating B-cell activation, cytotoxic function of natural killer cells, and immunoglobulin synthesis (RefSeq, 2002). Targeting of CD70 may be used to specifically target and kill cancer cells. It may be a potential target in oral cancer (Bundela et al., 2014; Jacobs et al., 2015b; Wang et al., 2016a). CD70 is expressed in head-and-neck squamous cell carcinoma. It is ectopically expressed in lymphomas, renal cell carcinomas, and glioblastomas. CD70 expression levels decrease during melanoma progression. CD70 is highly expressed on CD4+CD25+ T-cells from patients with acute-type adult T-cell leukemia/lymphoma (Jacobs et al., 2015b; Curran et al., 2015; De et al., 2016; Jacobs et al., 2015a; Masamoto et al., 2016; Pich et al., 2016b; Ruf et al., 2015a). CD70 is involved in immune response, cancer development, and cancer progression (Petrau et al., 2014; Pich et al., 2016a). CD70 up-regulation in clear cell renal cell carcinoma is associated with worse survival (Ruf et al., 2015b). Cisplatin mediates cytotoxicity through APCs expressing relatively higher levels of CD70 (Beyranvand et al., 2016). CD70 expression is almost not affected by ionizing radiation. It is associated with radio sensitivity in lung cancer. Single-dose external beam radiation up-regulates CD70 in PC3 cells (Bernstein et al., 2014; Kumari and Garnett-Benson, 2016; Pu et al., 2014).

CDH3 (also known as P-cadherin) encodes cadherin 3 which is a classical cadherin of the cadherin superfamily. This calcium-dependent cell-cell adhesion protein is comprised of five extracellular cadherin repeats, a transmembrane region and a highly conserved cytoplasmic tail. This gene is located in a gene cluster in a region on the long arm of chromosome 16 that is involved in loss of heterozygosity events in breast and prostate cancer. In addition, aberrant expression of this protein is observed in cervical adenocarcinomas (RefSeq, 2002). CDH3 is involved in oncogenic signaling and activates integrins, receptor tyrosine kinases, small molecule GTPases, EMT transcription factors, and other cadherin family members. CDH3 signaling induces invasion and metastasis (Albergaria et al., 2011; Paredes et al., 2012; Bryan, 2015; Vieira and Paredes, 2015). Oncogenic activation of CDH3 is involved in gastric carcinogenesis (Resende et al., 2011). CDH3 over-expression promotes breast cancer, bladder cancer, ovarian cancer, prostate cancer, endometrial cancer, skin cancer, gastric cancer, pancreas cancer, and colon cancer (Albergaria et al., 2011; Paredes et al., 2007; Bryan and Tselepis, 2010; Reyes et al., 2013; Vieira and Paredes, 2015). CDH3 is a basal epithelial marker expressed in basal-like breast cancer. BRCA1 carcinomas are characterized by the expression of basal markers like CDH3 and show a high-grade, highly proliferating, ER-negative, and HER3-negative phenotype (Honrado et al., 2006; Palacios et al., 2008; Rastelli et al., 2010; Dewar et al., 2011). CDH3 is a tumor suppressor in melanoma and oral squamous cell carcinoma (Haass et al., 2005; Vieira and Paredes, 2015). CDH3 may be used as EMT marker. There is a shift from E-cadherin to N-cadherin and CDH3 expression during tumor formation and progression (Piura et al., 2005; Bonitsis et al., 2006; Bryan and Tselepis, 2010; Ribeiro and Paredes, 2014). Competitive interaction between CDH3 and beta-catenin causes impaired intercellular interactions and metastases in gastric cancer (Moskvina and Mal'kov, 2010). CDH3 may be an early marker of cancer formation in colon cancer (Alrawi et al., 2006). Dys-regulation of CDH3 is a marker for poor prognosis and increased malignancy (Knudsen and Wheelock, 2005).

CDKN2A (also known as p16 and p16INK4a) encodes cyclin dependent kinase inhibitor 2A which generates several transcript variants which differ in their first exons. At least three alternatively spliced variants encoding distinct proteins have been reported, two of which encode structurally related isoforms known to function as inhibitors of CDK4 kinase. The remaining transcript includes an alternate first exon located 20 Kb upstream of the remainder of the gene; this transcript contains an alternate open reading frame (ARF) that specifies a protein which is structurally unrelated to the products of the other variants. This ARF product functions as a stabilizer of the tumor suppressor protein p53 as it can interact with, and sequester, the E3 ubiquitin-protein ligase MDM2, a protein responsible for the degradation of p53 (RefSeq, 2002). CDKN2A is mutated in pancreatic ductal adenocarcinoma, cutaneous malignant melanoma, vulvar squamous cell carcinoma, and biliary tract cancer. Mutations may be inherited and increase the risk for developing pancreatic cancer. CDKN2A is deleted in malignant pleural mesothelioma. CDKN2A is down-regulated in bladder cancer (Clancy et al., 2016; Fabbri et al., 2017; Gan et al., 2016; Kleeff et al., 2016; Nabeshima et al., 2016; Pacholczyk et al., 2016; Petersen, 2016; Sohal et al., 2016; Tatarian and Winter, 2016). CDKN2A is involved in cancer cell proliferation, tumorigenesis, metastasis, Wnt signaling, senescence, apoptosis, and DNA repair mechanism (Gupta et al., 2016; Ko et al., 2016; Low et al., 2016; Sedgwick and D'Souza-Schorey, 2016; Zhao et al., 2016). CDKN2A is a tumor suppressor gene which is down-regulated upon over-expression of the oncogenic protein UHRF1. CDKN2A interacts with p53 to suppress breast cancer (Alhosin et al., 2016; Fry et al., 2017). CDKN2A promotor hyper-methylation is associated with increased risk for low-grade squamous intra-epithelial lesion, high-grade squamous intra-epithelial lesion, and cervical cancer and with smoking habit. CDKN2A is epigenetically dys-regulated during the development of hepatocellular carcinoma and esophageal squamous cell carcinoma (Han et al., 2017; Khan et al., 2017; Ma et al., 2016a). CDKN2A may be used in the diagnosis of cervical cancer and oropharyngeal squamous cell carcinoma (Mahajan, 2016; Savone et al., 2016; Tjalma, 2017). CDKN2A expression is caused by HPV infection, a virus which is known to have oncogenic potential (Hoff et al., 2017; Lorincz, 2016).

CDKN2B (also known as p15) encodes cyclin dependent kinase inhibitor 2B which lies adjacent to the tumor suppressor gene CDKN2A in a region that is frequently mutated and deleted in a wide variety of tumors. This gene encodes a cyclin-dependent kinase inhibitor, which forms a complex with CDK4 or CDK6, and prevents the activation of the CDK kinases, thus the encoded protein functions as a cell growth regulator that controls cell cycle G1 progression. The expression of this gene was found to be dramatically induced by TGF beta, which suggested its role in the TGF beta induced growth inhibition (RefSeq, 2002). CDKN2B is involved in the regulation of the cell cycle progression and the inhibition of cell proliferation (Hu and Zuckerman, 2014; Roy and Banerjee, 2015). CDKN2B deletion is associated with schistosomal-associated bladder cancer. Mutations in CDKN2B may be involved in inherited susceptibility to glial tumors. CDKN2B is altered in meningiomas and mutated in non-muscle-invasive urothelial carcinoma (Mawrin and Perry, 2010; Melin, 2011; Pollard et al., 2010; Alentorn et al., 2013; Idbaih, 2011; Koonrungsesomboon et al., 2015). CDKN2B is hyper-methylated in acute myeloid leukemia and pituitary adenomas. CDKN2B is aberrantly regulated in cutaneous malignant melanoma (Bailey et al., 2010; Jiang et al., 2014; Popov and Gil, 2010; van den Hurk et al., 2012; Wolff and Bies, 2013; Zhou et al., 2014). CDKN2B interacts with the tumor suppressor RB and is regulated by Miz-1 and TGF-beta (Zhou et al., 2014; Geyer, 2010; Moroy et al., 2011). CDKN2B is a tumor suppressor gene which is affected by long non-coding RNAs. CDKN2B itself in association with AS1 is part of a long non-coding RNA (ANRIL) which may be involved in cancer development (Popov and Gil, 2010; Aguilo et al., 2016; Shi et al., 2013; Wanli and Ai, 2015).

CLDN6, also known as claudin 6, encodes a member of the claudin family which is a component of tight junction strands and an integral membrane protein (RefSeq, 2002). CLDN6 expression was shown to be associated with lymph node metastasis and TNM stage in non-small cell lung cancer (Wang et al., 2015b). Furthermore, low expression of CLDN6 was shown to be associated with significantly lower survival rates in patients with non-small cell lung cancer (Wang et al., 2015b). Thus, low CLDN6 expression is an independent prognostic biomarker that indicates worse prognosis in patients with non-small cell lung cancer (Wang et al., 2015b). CLDN6 was shown to be down-regulated in cervical carcinoma and gastric cancer (Zhang et al., 2015e; Lin et al., 2013b). CLDN6 was shown to be up-regulated in BRCA1-related breast cancer and ovarian papillary serous carcinoma (Wang et al., 2013; Heerma van Voss et al., 2014). CLDN6 was described as a tumor suppressor for breast cancer (Zhang et al., 2015e). Gain of CLDN6 expression in the cervical carcinoma cell lines HeLa and C33A was shown to suppress cell proliferation, colony formation in vitro, and tumor growth in vivo, suggesting that CLDN6 may function as a tumor suppressor in cervical carcinoma cells (Zhang et al., 2015e). CLDN6 may play a positive role in the invasion and metastasis of ovarian cancer (Wang et al., 2013). CLDN6 was shown to be consistently expressed in germ cell tumors and thus is a novel diagnostic marker for primitive germ cell tumors (Ushiku et al., 2012). CLDN6 expression was shown to be positive in most tumors of an assessed set of atypical teratoid/rhabdoid tumors of the central nervous system, with strong CLDN6 positivity being a potential independent prognostic factor for outcome of the disease (Dufour et al., 2012).

CT45A1, also known as CT45, encodes the cancer/testis antigen family 45 member A1 protein and is located on chromosome Xq26.3 (RefSeq, 2002). CT45 genes were shown to be potential prognostic biomarkers and therapeutic targets in epithelial ovarian cancer (Zhang et al., 2015d). The CT45A1 protein which is usually only expressed in testicular germ cells was shown to be also expressed in lung cancer, breast cancer and ovarian cancer (Chen et al., 2009). CT45A1 was also shown to be associated with poor prognosis and poor outcomes in multiple myeloma (Andrade et al., 2009). CT45A1 was described as gene up-regulating epithelial-mesenchymal transition (EMT) and metastatic genes, promoting EMT and tumor dissemination. Furthermore, CT45A1 was described as being implicated in the initiation or maintenance of cancer stem-like cells, promoting tumorigenesis and malignant progression (Yang et al., 2015b). CT45A1 over-expression in a breast cancer model was shown to result in the up-regulation of various oncogenic and metastatic genes, constitutively activated ERK and CREB signaling pathways and increased tumorigenesis, invasion and metastasis. Silencing of CT45A1 was shown to reduce cancer cell migration and invasion. Thus, CT45A1 may function as a novel proto-oncogene and may be a target for anticancer drug discovery and therapy (Shang et al., 2014).

CT45A2 encodes one of a cluster of several similar genes, which is a member of the cancer/testis family of antigens and is located on chromosome Xq26.3 (RefSeq, 2002). CT45A2 was shown to be a novel spliced MLL fusion partner in a pediatric patient with de novo bi-phenotypic acute leukemia and thus might be relevant for leukemogenesis (Cerveira et al., 2010). The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015d).

CT45A3 encodes the cancer/testis antigen family 45 member A3 protein and is located on chromosome Xq26.3 (RefSeq, 2002). The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015d).

CT45A4 encodes the cancer/testis antigen family 45 member A4 protein and is located on chromosome Xq26.3 (RefSeq, 2002). The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015d).

CT45A5 encodes the cancer/testis antigen family 45 member A5 and is located on chromosome Xq26.3 (RefSeq, 2002). The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015d).

CT45A6 encodes the cancer/testis antigen family 45 member A6 protein and is located on chromosome Xq26.3 (RefSeq, 2002). The cancer/testis antigen family 45 was shown to be frequently expressed in both cancer cell lines and lung cancer specimens (Chen et al., 2005). CT45 genes were shown to be potential prognostic biomarkers and therapeutic targets in epithelial ovarian cancer (Zhang et al., 2015d).

CTAG2 encodes cancer/testis antigen 2 which is an auto immunogenic tumor antigen that belongs to the ESO/LAGE family of cancer-testis antigens. This protein is expressed in a wide array of cancers including melanoma, breast cancer, bladder cancer and prostate cancer. This protein is also expressed in normal testis tissue (RefSeq, 2002). CTAG2 is involved in cancer cell migration and invasiveness (Maine et al., 2016). CTAG2 expression is up-regulated by LSAMP resulting in reduced cell proliferation (Baroy et al., 2014). CTAG2 is expressed in liposarcoma, lung cancer, urothelial cancer, and colorectal cancer. CTAG2 is over-expressed in several entities including esophageal squamous cell carcinoma (Kim et al., 2012; Dyrskjot et al., 2012; Hemminger et al., 2014; Forghanifard et al., 2011; McCormack et al., 2013; Shantha Kumara et al., 2012). Engineered T cells against CTAG2 may be used in multiple myeloma treatment. Autoantibodies against CTAG2 may be used in cancer diagnosis. CTAG2 may be a target in immunotherapy. CTAG2 expression is associated with shorter progression-free survival (van et al., 2011; Dyrskjot et al., 2012; Hudolin et al., 2013; Pollack et al., 2012; Rapoport et al., 2015; Wang et al., 2015a).

CYP2W1 encodes a member of the cytochrome P450 superfamily of enzymes which are monooxygenases catalyzing many reactions involved in drug metabolism and in the synthesis of cholesterol, steroids and other lipids (RefSeq, 2002). CYP2W1 is over-expressed in a variety of human cancers including hepatocellular, colorectal and gastric cancer. CYP2W1 over-expression is associated with tumor progression and poor survival (Aung et al., 2006; Gomez et al., 2010; Zhang et al., 2014a). Due to tumor-specific expression, CYP2W1 is an interesting drug target or enzymatic activator of pro-drugs during cancer therapy (Karlgren and Ingelman-Sundberg, 2007; Nishida et al., 2010).

DPPA2 encodes developmental pluripotency associated 2 and is located on chromosome 3q13.13 (RefSeq, 2002). DPPA2 is over-expressed in gastric cancer, non-small cell lung cancer, epithelial ovarian cancer, and colorectal cancer. DPPA2 is an oncogene up-regulated in several entities. DPPA2 is reciprocally repressed in teratoma (Tung et al., 2013; Ghodsi et al., 2015; John et al., 2008; Raeisossadati et al., 2014; Shabestarian et al., 2015; Tchabo et al., 2009; Western et al., 2011). DPPA2 expression correlates with tumor invasion depth, stage, lymph node metastasis, and aggressiveness (Ghodsi et al., 2015; Raeisossadati et al., 2014; Shabestarian et al., 2015). DPPA2 is involved in the pathogenesis of non-small cell lung cancer (Watabe, 2012). DPPA2 is differentially methylated in thyroid cancer (Rodriguez-Rodero et al., 2013).

ENTPD4 (UDPase) encodes ectonucleoside triphosphate diphosphohydrolase 4, a member of the apyrase protein family and may play a role in salvaging nucleotides from lysosomes (RefSeq, 2002). UDPase activity is increased in patients with ovarian cancer or testicular cancer and decreased after chemotherapy (Papadopoulou-Boutis et al., 1985).

ESR1 encodes an estrogen receptor, a ligand-activated transcription factor important for hormone binding, DNA binding and activation of transcription, that is essential for sexual development and reproductive function (RefSeq, 2002). Mutations and single nucleotide polymorphisms of ESR1 are associated with risk for different cancer types including liver, prostate, gallbladder and breast cancer. The up-regulation of ESR1 expression is connected with cell proliferation and tumor growth but the overall survival of patients with ESR1 positive tumors is better due to the successfully therapy with selective estrogen receptor modulators (Sun et al., 2015; Hayashi et al., 2003; Bogush et al., 2009; Miyoshi et al., 2010; Xu et al., 2011; Yakimchuk et al., 2013; Fuqua et al., 2014). ESR1 signaling interferes with different pathways responsible for cell transformation, growth and survival like the EGFR/IGFR, PI3K/Akt/mTOR, p53, HER2, NFkappaB and TGF-beta pathways (Frasor et al., 2015; Band and Laiho, 2011; Berger et al., 2013; Skandalis et al., 2014; Mehta and Tripathy, 2014; Ciruelos Gil, 2014).

ETV1 encodes ETS variant 1 which is a member of the ETS (E twenty-six) family of transcription factors. The ETS proteins regulate many target genes that modulate biological processes like cell growth, angiogenesis, migration, proliferation and differentiation (RefSeq, 2002). ETV1 is involved in epithelial-to-mesenchymal transition, DNA damage response, AR and PTEN signaling, cancer cell invasion, and metastasis. ETV1 interacts with JMJD2A to promote prostate carcinoma formation and to increase YAP1 expression affecting the Hippo signaling pathway (Mesquita et al., 2015; Baty et al., 2015; Heeg et al., 2016; Higgins et al., 2015; Kim et al., 2016; Lunardi et al., 2015). ETV1 expression is decreased in prostate cancer. ETV1 is over-expressed in pancreatic cancer, gastrointestinal stromal tumors, oligodendroglial tumors, and renal cell carcinoma. ETV1 may be an oncogene in non-small cell lung cancer (Heeg et al., 2016; Gleize et al., 2015; Ta et al., 2016; Al et al., 2015; Hashimoto et al., 2017; Jang et al., 2015). Increased mRNA levels of ETV1 in microvesicles of prostate cancer cell lines are correlated with prostate cancer progression (Lazaro-lbanez et al., 2017). ETV1 is an oncogene which interacts with the Ewing's sarcoma breakpoint protein EWS. ETV1 interacts with Sparc and Has2 which mediate in part cancer cell metastasis and desmoplastic stromal expansion (Heeg et al., 2016; Kedage et al., 2016). ETV1 gene fusion products as well as ETV1 promotor methylation status are diagnostically useful (Angulo et al., 2016; 2015; Kumar-Sinha et al., 2015; Linn et al., 2015).

ETV4 (also called E1AF or PEA3) encodes a member of the Ets oncogene family of transcription factors and is involved in the regulation of metastasis gene expression and in the induction of differentiation-associated genes in embryonic stem cell (Akagi et al., 2015; Coutte et al., 1999; Ishida et al., 2006). ETV4 is over-expressed in different cancer entities including breast, lung, colorectal and gastric cancer and is associated with migration, invasion, metastasis and poor prognosis (Benz et al., 1997; Horiuchi et al., 2003; Yamamoto et al., 2004; Keld et al., 2011; Hiroumi et al., 2001). ETV4 is up-regulated by different pathways like ERK/MAPK, HER2, PI3K and Ras following an induction of several targets including MMPs and IL-8 (Maruta et al., 2009; Keld et al., 2010; Chen et al., 2011b; Aytes et al., 2013).

ETV5 encodes the ETS variant 5 protein and is located on chromosome 3q28 (RefSeq, 2002). Pathways including ETV5 were described as being deeply related to the epithelial to mesenchymal process in endometrial cancer (Colas et al., 2012). ETV5 was shown to interact with several signaling pathways such as cell-cycle progression and the TGF-beta signaling pathway in the OV90 ovarian cancer cell line, and ETV5 expression was shown to be associated with the expression of the oncogenic transcription factor FOXM1 in ovarian cancer (Llaurado et al., 2012b). Furthermore, ETV5 was shown to be up-regulated in ovarian cancer. In the spheroid model, the inhibition and up-regulation of ETV5 effected cell proliferation, cell migration, cell adhesion to extracellular matrix components, cell-cell adhesion and cell survival. Thus, ETV5 may play a role in ovarian cancer progression, cell dissemination and metastasis (Llaurado et al., 2012a). Chromosomal rearrangements of ETV5 among other members of the oncogenic PEA3 subfamily, were described to occur in prostate tumors and are thought to be one of the major driving forces in the genesis of prostate cancer. Furthermore, ETV5 was also described as an oncoprotein which is implicated in melanomas, breast and some other types of cancer (Oh et al., 2012). ETV5 was suggested to have a significant role in regulating matrix metalloproteinase 2 expression and therefore resorption in human chondrosarcoma, and thus may be a targetable up-stream effector of the metastatic cascade in this cancer (Power et al., 2013).

EYA2 encodes EYA transcriptional coactivator and phosphatase 2, a member of the eyes absent (EYA) family of proteins involved in eye development (RefSeq, 2002). EYA2 over-expression has been observed in several tumor types such as epithelial ovarian tumor, prostate, breast cancer, urinary tract cancers, glioblastoma, lung adenocarcinoma, cervical cancer, colon and hematopoietic cancers (Bierkens et al., 2013; Zhang et al., 2005; Guo et al., 2009; Patrick et al., 2013; Kohrt et al., 2014). Studies have revealed that EYA2 influences transcription of TGF beta pathway members as well as phosphorylation of TGFBR2, implying a dual role of EYA2 in the pancreas (Vincent et al., 2014).

FAM111B encodes the family with sequence similarity 111 member B, a protein with a trypsin-like cysteine/serine peptidase domain in the C-terminus which leads, in case of a mutation, to mottled pigmentation, telangiectasia, epidermal atrophy, tendon contractures, and progressive pulmonary fibrosis (RefSeq, 2002). FAM111B was found to be down-regulated during metformin and aspirin induced inhibition of pancreatic cancer development (Yue et al., 2015).

FAM83H encodes family with sequence similarity 83 member H which plays an important role in the structural development and calcification of tooth enamel. Defects in this gene are a cause of amelogenesis imperfecta type 3 (AI3) (RefSeq, 2002). The long non-coding RNA FAM83H-AS1 is involved in cell proliferation, migration, and invasion and regulates MET/EGFR signaling (Zhang et al., 2017). The long non-coding RNA FAM83H-AS1 is over-expressed in lung cancer and colorectal cancer. FAM83H is an oncogene over-expressed in several entities including breast cancer and colorectal cancer (Zhang et al., 2017; Kuga et al., 2013; Snijders et al., 2017; Yang et al., 2016c; Yang et al., 2016b). Increased expression of long non-coding RNA FAM83H-AS1 is associated with shorter overall survival. FAM83H-AS1 is associated with poor prognosis (Yang et al., 2016c; Yang et al., 2016b). FAM83H may be involved in androgen independent prostate cancer (Nalla et al., 2016). FAM83H interacts with CK1alpha to form keratin filaments and desmosomes (Kuga et al., 2016).

FBN2, also known as fibrillin 2, encodes a protein which is a component of the connective tissue and may be involved in elastic fiber assembly (RefSeq, 2002). FBN2 was described as an extracellular matrix regulatory protein of TGF-beta signaling activity (Lilja-Maula et al., 2014). Hyper-methylation of FBN2 was described as an epigenetic biomarker for clear cell renal cell carcinoma and early detection of colorectal cancer and as being associated with poor prognosis by colorectal cancer patients (Ricketts et al., 2014; Rasmussen et al., 2016; Yi et al., 2012). FBN2 was shown to be a candidate cell surface target enriched in medulloblastoma which could be used for the development of tumor-specific probes for guided resection in medulloblastoma (Haeberle et al., 2012).

FOLR1 encodes the folate receptor 1, which binds folic acid and its reduced derivatives, and transports 5-methyl-tetrahydrofolate into cells; FOLR1 is a secreted protein that either anchors to membranes via a glycosyl-phosphatidylinositol linkage or exists in a soluble form (RefSeq, 2002). Being a major part of the FOLR1/cSrc/ERK1/2/NFκB/p53 pathway, which is required for the up-take of folic acid, FOLR1 is able to regulate the proliferation of cancer cells such as breast, lung and colon cancer (Kuo and Lee, 2016; Cheung et al., 2016). FOLR1 was found to be widely expressed in epithelial ovarian cancer, where its expression increases with tumor stage and might represent a potential therapeutic target (Leung et al., 2016; Ponte et al., 2016; Moore et al., 2016; Hou et al., 2017; Notaro et al., 2016; Bergamini et al., 2016). Reducing FOLR1 expression during colorectal cancer therapy was shown to increase the effectiveness of 5-fluorouracil treatment (Tsukihara et al., 2016). FOLR1 represents an ideal tumor-associated marker for immunotherapy for triple-negative breast cancer as well as colon cancer (Liang et al., 2016; Song et al., 2016).

GPR64 encodes adhesion G protein-coupled receptor G2, a member of the G protein-coupled receptor family described as an epididymis-specific transmembrane protein (RefSeq, 2002). In breast cancer cell lines, knockdown of GPR64 resulted in a strong reduction in cell adhesion as well as in cell migration (Peeters et al., 2015).

HOXA10 encodes homebox A10. This gene is part of the A cluster on chromosome 7 and encodes a DNA-binding transcription factor that may regulate gene expression, morphogenesis, and differentiation. More specifically, it may function in fertility, embryo viability, and regulation of hematopoietic lineage commitment. Read-through transcription exists between this gene and the downstream homeobox A9 (HOXA9) gene (RefSeq, 2002). HOXA10 is a stem cell factor whose expression correlates with CD133 expression in glioma and may be involved in cancer progression. HOXA10 is involved in cancer cell proliferation, migration, invasion, and metastasis. HOXA10 is involved in multidrug resistance by inducing P-gp and MRP1 expression. HOXA10 promotes epithelial-to-mesenchymal transition. HOXA10 may be a downstream target of miR-218/PTEN/AKT/PI3K signaling. HOXA10 promotes expression of the AML-associated transcription factor Prdm16. HOXA10 may mediate G1 cell cycle arrest in a p21-dependent manner. HOXA10 is involved in TGF-beta2/p38 MAPK signaling promoting cancer cell invasion in a MMP-3-dependent manner (Carrera et al., 2015; Cui et al., 2014; Emmrich et al., 2014; Han et al., 2015; Li et al., 2014a; Li et al., 2016a; Sun et al., 2016; Xiao et al., 2014; Yang et al., 2016a; Yi et al., 2016; Yu et al., 2014; Zhang et al., 2014b; Zhang et al., 2015b). HOXA10 is up-regulated in gastric cancer and acute myeloid leukemia. HOXA10 is differentially expressed in oral squamous cell carcinoma. HOXA10 is differentially methylated in non-serous ovarian carcinoma and glioblastoma (Carrera et al., 2015; Han et al., 2015; Kurscheid et al., 2015; Niskakoski et al., 2014; Oue et al., 2015; Shima et al., 2014). HOXA10 methylation status may be used in breast cancer diagnosis. HOXA10 and CD44 co-expression is correlated with tumor size and patient survival in gastric cancer. HOXA10 and miR-196b co-expression is correlated with poor prognosis in gastric cancer (Han et al., 2015; Lim et al., 2013; Uehiro et al., 2016). SGI-110 treatment hypomethylate HOXA10 which sensitizes ovarian cancer cells for chemotherapy (Fang et al., 2014a).

HOXA9 encodes homebox protein A9. This gene is part of the A cluster on chromosome 7 and encodes a DNA-binding transcription factor which may regulate gene expression, morphogenesis, and differentiation. A specific translocation event which causes a fusion between this gene and the NUP98 gene has been associated with myeloid leukemogenesis (RefSeq, 2002). HOXA9 is expressed in acute myeloid leukemia and high expression is associated with adverse prognosis. HOXA9 and MEIS1 co-expression induces AML. HOXA9 is down-regulated in cervical cancer. HOXA9 is frequently methylated in endometrial cancer (Alvarado-Ruiz et al., 2016; Chen et al., 2015; Li et al., 2016b; Li et al., 2016e; Sykes et al., 2016). The gene fusion product NUP98-HOXA9 acts as oncogene (Abe et al., 2016; Sontakke et al., 2016). Response to cisplatin-based chemotherapy is linked to HOXA9 promotor methylation status. HOXA9, MEIS1, and MN1 co-expression in leukemia make the cells sensitive to pharmacologic inhibition of DOT1L (Li et al., 2016c; Riedel et al., 2016; Xylinas et al., 2016). HOXA9 is a tumor suppressor whose expression may be used to diagnose cancer (Ma et al., 2016b). HOXA9 mediates leukemic stem cell self-renewal and HIF-2alpha deletion accelerates this process (Vukovic et al., 2015; Zhu et al., 2016).

HOXB9 encodes homebox B9 which is a member of the Abd-B homeobox family and encodes a protein with a homeobox DNA-binding domain. It is included in a cluster of homeobox B genes located on chromosome 17. The encoded nuclear protein functions as a sequence-specific transcription factor that is involved in cell proliferation and differentiation. Increased expression of this gene is associated with some cases of leukemia, prostate cancer and lung cancer (RefSeq, 2002). HOXB9 is involved in angiogenic pathways which are regulated by miR-192. HOXB9 is a downstream target of Wnt/beta-catenin signaling induced by N-acetylgalactosaminyltransferase resulting in metastasis. HOXB9 may regulate mesenchymal-to-epithelial transition in gastric carcinoma and colon adenocarcinoma and epithelial-to-mesenchymal transition in breast cancer and hepatocellular carcinoma in a TGF-beta1-dependent manner. HOXB9 is involved in cell proliferation, migration, and invasion. TGF-beta1 down-regulates HOXB9 in a Kindlin-2/PDAC-dependent manner (Chang et al., 2015b; Darda et al., 2015; Hoshino et al., 2014; Huang et al., 2014; Kwon et al., 2015; Seki et al., 2012; Sha et al., 2015; Wu et al., 2016; Zhan et al., 2014; Zhan et al., 2015; Zhussupova et al., 2014). HOXB9 is differentially expressed in PBRM1 mutated clear cell renal cell carcinoma. HOXB9 is overexpressed in platinum-resistant high-grade serous ovarian cancer, breast cancer, glioma, colon adenocarcinoma, hepatocellular carcinoma, and head and neck squamous cell carcinoma. HOXB9 expression is decreased in gastric carcinoma. HOXB9 is mutated in leukemia (Menezes et al., 2014; Chang et al., 2015b; Darda et al., 2015; Zhan et al., 2014; Zhussupova et al., 2014; Fang et al., 2014b; Hayashida et al., 2010; Kelly et al., 2016; Sha et al., 2013; Shrestha et al., 2012; Wang et al., 2016b; Yuan et al., 2014). HOXB9 expression is regulated by E2F1 and FAT10 (Zhussupova et al., 2014; Yuan et al., 2014). HOXB9 expression is correlated with tumor size in oral cancer. HOXB9 expression is associated with advanced clinical stage in glioma. HOXB9 down-regulation is associated with decreased patient survival in gastric carcinoma (Fang et al., 2014b; Sha et al., 2013; Oliveira-Costa et al., 2015; Tomioka et al., 2010). HOXB9 regulates bladder cancer progression (Zhang et al., 2016b). Long non-coding RNA nc-HOXB9-205 is down-regulated in urothelial carcinoma of the bladder (Luo et al., 2014). BCAS3-HOXB9 gene fusion product is expressed in breast cancer (Schulte et al., 2012).

HOXC10 encodes homeobox C10 which belongs to the homeobox family of genes. The homeobox genes encode a highly conserved family of transcription factors that play an important role in morphogenesis in all multicellular organisms. This gene is one of several homeobox HOXC genes located in a cluster on chromosome 12. The protein level is controlled during cell differentiation and proliferation, which may indicate this protein has a role in origin activation (RefSeq, 2002). HOXC10 is involved in chemo resistance by suppressing apoptosis and up-regulating NF-kappaB and DNA damage repair. HOXC10 induces apoptosis and inhibits cell growth. HOXC10 may be involved in cervical cancer progression and invasion (Pathiraja et al., 2014; Sadik et al., 2016; Zhai et al., 2007). HOXC10 is up-regulated in thyroid cancer, cervical squamous cell carcinoma, and breast cancer (Abba et al., 2007; Zhai et al., 2007; Ansari et al., 2012; Feng et al., 2015). HOXC10 expression correlates with shorter recurrence-free and overall survival in ER-negative breast cancer. HOXC10 expression is associated with advanced stage, poor pathologic stage, poor prognosis, cytokine-cytokine receptor interaction, and chemokine signaling pathways in thyroid cancer (Sadik et al., 2016; Feng et al., 2015). HOXC10 is differentially methylated in oral squamous cell carcinoma and small B cell lymophoma (Marcinkiewicz and Gudas, 2014a; Marcinkiewicz and Gudas, 2014b; Rahmatpanah et al., 2006).

HOXC9 encodes homebox C9 which belongs to the homeobox family of genes. The homeobox genes encode a highly conserved family of transcription factors that play an important role in morphogenesis in all multicellular organisms. This gene is one of several homeobox HOXC genes located in a cluster on chromosome 12 (RefSeq, 2002). HOXC9 is involved in cancer cell invasion and proliferation. HOXC9 knock-down results in reduced cell viability, migration, invasion, tumorigenicity, and increased autophagy. HOXC9 is involved in chemo resistance in bladder cancer in a miR-193a-3p-dependent manner. HOXC9 is involved in retinoic acid signaling and is involved in cell growth and differentiation (Hur et al., 2016; Kocak et al., 2013; Lv et al., 2015a; Mao et al., 2011; Simeone et al., 1991; Stornaiuolo et al., 1990; Xuan et al., 2016; Zha et al., 2012). HOXC9 is differentially expressed in breast cancer, lung cancer, and neuroblastoma. HOXC9 is methylated in stage I non-small cell lung cancer. HOXC9 is up-regulated in astrocytoma. HOXC9 is expressed in esophageal cancer and cervical cancer (Hur et al., 2016; Xuan et al., 2016; Gu et al., 2007; Lin et al., 2009; Lopez et al., 2006; Okamoto et al., 2007). HOXC9 may be transcriptionally repressed by Smad4 (Zhou et al., 2008). HOXC9 expression is inversely associated with disease-free survival and distant metastasis-free survival in breast cancer. HOXC9 expression is associated with poor prognosis in glioblastoma (Hur et al., 2016; Xuan et al., 2016). HOXC9 inhibits DAPK1 resulting in disturbed autophagy induced by Beclin-1 (Xuan et al., 2016).

HOXD10 encodes homeobox D10 protein, which functions as a sequence-specific transcription factor that is expressed in the developing limb buds and is involved in differentiation and limb development (RefSeq, 2002). HOXD10 was identified as target gene of miR-10b, which is up-regulated in gastric cancer (GC) and may have a key role in GC pathogenesis and development (Ma et al., 2015; Wang et al., 2015c). HOXD10 was found to be up-regulated in neck squamous cell carcinoma and urothelial cancer promoting cell proliferation and invasion and may represent a new biomarker for ductal invasive breast carcinoma (Sharpe et al., 2014; Vardhini et al., 2014; Heubach et al., 2015). However, HOXD10 also showed tumor-suppressive functions in cholangiocellular carcinoma by inactivating the RHOC/AKT/MAPK pathway and inducing G1 phase cell cycle arrest (Yang et al., 2015a). As part of the miR-224/HOXD10/p-PAK4/MMP-9 signaling pathway, HOXD10 is contributed to the regulation of cell migration and invasion and provides a new bio target for hepatocellular carcinoma treatment (Li et al., 2014b).

HOXD9 encodes homeobox D9 which belongs to the homeobox family of genes. The homeobox genes encode a highly conserved family of transcription factors that play an important role in morphogenesis in all multicellular organisms. This gene is one of several homeobox HOXD genes located at 2q31-2q37 chromosome regions. Deletions that removed the entire HOXD gene cluster or 5' end of this cluster have been associated with severe limb and genital abnormalities. The exact role of this gene has not been determined (RefSeq, 2002). HOXD9 is involved in epithelial-to-mesenchymal transition, cancer cell migration, invasion, and metastasis in a ZEB1-dependent manner. Overexpressed HOXD9 increases anchorage-independent growth and reduces contact inhibition. HOXD9 is involved in growth arrest and neuronal differentiation. Depletion of HOXD9 results in decreased cell proliferation, cell cycle arrest, and induction of apoptosis (Zha et al., 2012; Lawrenson et al., 2015b; Lv et al., 2015b; Tabuse et al., 2011). HOXD9 is up-regulated in lung squamous carcinoma and invasive hepatocellular carcinoma. HOXD9 is expressed in esophageal carcinoma, astrocytomas and glioblastomas. HOXD9 is differentially expressed in cervical cancer (Bao et al., 2016; Gu et al., 2007; Lv et al., 2015b; Tabuse et al., 2011; Li et al., 2002; Liu et al., 2005). HOXD9 expression is induced by retinoic acid and Wnt signaling (Ishikawa and Ito, 2009). HOXD9 may be involved in cervical carcinogenesis (Lopez-Romero et al., 2015). HOXD9 hyper-methylation is associated with poorer disease-free and overall survival in lymph node metastasis (Marzese et al., 2014). HOXD9 is hyper-methylated in cholangiocarcinoma and melanoma brain metastasis (Marzese et al., 2014; Sriraksa et al., 2013). HOXD9 may be involved in mucinous ovarian carcinoma susceptibility (Kelemen et al., 2015). HOXD9 may be an oncogene (Wu et al., 2013).

HTR3A encodes a 5-hydroxytryptamine (serotonin) receptor belonging to the ligand-gated ion channel receptor superfamily that causes fast, depolarizing responses in neurons after activation (RefSeq, 2002). HTR3A (also called 5-HT3) is de-regulated in several cancer types for example a down-regulation in mantle cell lymphomas, a differential expression in diverse B cell tumors and a decreased expression in breast cancer cell lines (Pai et al., 2009; Rinaldi et al., 2010; Ek et al., 2002).

IGF2BP1, also known as CRD-BP, encodes a member of the insulin-like growth factor 2 mRNA-binding protein family which functions by binding to the mRNAs of certain genes and regulating their translation (RefSeq, 2002). Two members of the IGF2 mRNA binding protein family, including IGF2BP1 were described as bona fide oncofetal proteins which are de novo synthesized in various human cancers and which may be powerful post-transcriptional oncogenes enhancing tumor growth, drug-resistance and metastasis (Lederer et al., 2014). Expression of IGF2BP1 was reported to correlate with an overall poor prognosis and metastasis in various human cancers (Lederer et al., 2014). Thus, IGF2BP1 was suggested to be a powerful biomarker and candidate target for cancer therapy (Lederer et al., 2014). IGF2BP family members were described to be highly associated with cancer metastasis and expression of oncogenic factors such as KRAS, MYC and MDR1 (Bell et al., 2013). IGF2BP1 was shown to interact with C-MYC and was found to be expressed in the vast majority of colon and breast tumors and sarcomas as well as in benign tumors such as breast fibroadenomas and meningiomas (Ioannidis et al., 2003). IGF2BP1 was shown to be up-regulated in hepatocellular carcinoma and basal cell carcinoma (Noubissi et al., 2014; Zhang et al., 2015c). Up-regulation of IGF2BP1 and other genes was shown to be significantly associated with poor post-surgery prognosis in hepatocellular carcinoma (Zhang et al., 2015c). IGF2BP1 was shown to be a target of the tumor suppressor miR-9 and miR-372 in hepatocellular carcinoma and in renal cell carcinoma, respectively (Huang et al., 2015; Zhang et al., 2015c). Loss of stromal IGF2BP1 was shown to promote a tumorigenic microenvironment in the colon, indicating that IGF2BP1 plays a tumor-suppressive role in colon stromal cells (Hamilton et al., 2015). IGF2BP1 was shown to be associated with stage 4 tumors, decreased patient survival and MYCN gene amplification in neuroblastoma and may therefore be a potential oncogene and an independent negative prognostic factor in neuroblastoma (Bell et al., 2015). IGF2BP1 was described as a direct target of WNT/B-catenin signaling which regulates GLI1 expression and activities in the development of basal cell carcinoma (Noubissi et al., 2014).

IGF2BP3 encodes insulin-like growth factor II mRNA binding protein 3, an oncofetal protein, which represses translation of insulin-like growth factor II (RefSeq, 2002). Several studies have shown that IGF2BP3 acts in various important aspects of cell function, such as cell polarization, migration, morphology, metabolism, proliferation and differentiation. In vitro studies have shown that IGF2BP3 promotes tumor cell proliferation, adhesion, and invasion. Furthermore, IGF2BP3 has been shown to be associated with aggressive and advanced cancers (Bell et al., 2013; Gong et al., 2014). IGF2BP3 over-expression has been described in numerous tumor types and correlated with poor prognosis, advanced tumor stage and metastasis, as for example in neuroblastoma, colorectal carcinoma, intrahepatic cholangiocarcinoma, hepatocellular carcinoma, prostate cancer, and renal cell carcinoma (Bell et al., 2013; Findeis-Hosey and Xu, 2012; Hu et al., 2014; Szarvas et al., 2014; Jeng et al., 2009; Chen et al., 2011a; Chen et al., 2013; Hoffmann et al., 2008; Lin et al., 2013a; Yuan et al., 2009).

IRF4 encodes the interferon regulatory factor 4, a transcription factor that negatively regulates Toll-like-receptor (TLR) signaling in lymphocytes, what is central to the activation of innate and adaptive immune system (RefSeq, 2002). IRF4 is considered to be a key regulator of several steps in lymphoid, myeloid, and dendritic cell differentiation and maturation and is characterized by varying within the hematopoietic system in a lineage and stage-specific way (Shaffer et al., 2009; Gualco et al., 2010). IRF4 plays a pivotal role in adaptive immunity, cell growth, differentiation and tumorigenesis of chronic myeloid leukemia, primary central nervous system lymphoma, T-cell lymphoma, HTLV-I-induced adult T cell leukemia and intravascular large B-cell lymphoma (Mamane et al., 2002; Orwat and Batalis, 2012; Bisig et al., 2012; Ponzoni et al., 2014; Manzella et al., 2016). IRF4 is a well-known oncogene that is regulated by enhancer of zeste homolog 2 (EZH2) in multiple myeloma (Alzrigat et al., 2016).

KLK14 encodes kallikrein related peptidase 14 which is a member of the kallikrein subfamily of serine proteases that have diverse physiological functions such as regulation of blood pressure and desquamation. The altered expression of this gene is implicated in the progression of different cancers including breast and prostate tumors. The encoded protein is a precursor that is proteolytically processed to generate the functional enzyme. This gene is one of the fifteen kallikrein subfamily members located in a cluster on chromosome 19 (RefSeq, 2002). KLK14 is involved in cell proliferation via phosphorylation of ERK1/2/MAP kinase and tumorigenesis. KLK14 induces PAR-2 signaling. KLK14 may be involved in tumor progression, growth, invasion, and angiogenesis (Walker et al., 2014; Borgono et al., 2007; Chung et al., 2012a; Devetzi et al., 2013; Gratio et al., 2011; Sanchez et al., 2012; Zhang et al., 2012a). KLK14 is down-regulated by miR-378/422a and androgen receptor signaling. Androgen receptor signaling up-regulates KLK14 expression in breast cancer (Paliouras and Diamandis, 2008b; Lose et al., 2012; Paliouras and Diamandis, 2007; Paliouras and Diamandis, 2008a; Samaan et al., 2014). KLK14 is over-expressed in chronic lymphocytic leukemia, non-small cell lung cancer, salivary gland tumors, and ovarian cancer. KLK14 is differentially expressed in breast cancer (Planque et al., 2008b; Fritzsche et al., 2006; Hashem et al., 2010; Kontos et al., 2016; Papachristopoulou et al., 2013; Planque et al., 2008a). KLK14 expression is inversely associated with overall survival. KLK14 expression may be used as biomarker and to predict risk of disease recurrence. KLK14 expression correlates with clinical tumor stage and positive nodal status (Devetzi et al., 2013; Lose et al., 2012; Fritzsche et al., 2006; Kontos et al., 2016; Borgono et al., 2003; Obiezu and Diamandis, 2005; Rabien et al., 2008; Rajapakse and Takahashi, 2007; Talieri et al., 2009).

KLK8 encodes the kallikrein related peptidase 8, a serine protease that may be involved in proteolytic cascade in the skin and may serve as a biomarker for ovarian cancer (RefSeq, 2002). KLK8 expression was shown to correlate with the progression of breast cancer colorectal cancer (CRC), endometrial carcinoma and ovarian cancer and might represent a potential independent prognostic indicator for colorectal, breast and ovarian cancer (Liu et al., 2017; Jin et al., 2006; Kountourakis et al., 2009; Darling et al., 2008; Michaelidou et al., 2015; Borgono et al., 2006). KLK8 is able to undergo alternative splicing that generates an mRNA transcript missing exon 4; this alternative variant is, in contrast to KLK8, significantly down-regulated in cancer cells (Angelopoulou and Karagiannis, 2010). Nevertheless, the KLK8-T4 alternative splice variant, alone or in combination, may be a new independent marker of unfavorable prognosis in lung cancer (Planque et al., 2010). KLK8 expression confers a favorable clinical outcome in non-small cell lung cancer by suppressing tumor cell invasiveness (Sher et al., 2006).

LAMA1 encodes an alpha 1 subunit of laminin an extracellular matrix glycoprotein with heterotrimeric structure, which constitute a major component of the basement membrane (RefSeq, 2002). LAMA1 is de-regulated in different cancer types including up-regulation in glioblastomas, hyper-methylation in colorectal cancer, abnormal methylation in breast cancer and frameshift mutations in gastric cancer (Scrideli et al., 2008; Choi et al., 2015; Simonova et al., 2015; Kim et al., 2011). TGFbeta can induce the expression of LAMA1. LAMA1 in turn promotes collagenase IV production, which leads to an invasive phenotype in benign tumor cells, but is not sufficient to confer metastatic potential (Chakrabarty et al., 2001; Royce et al., 1992).

LAMC2 belongs to the family of laminins, a family of extracellular matrix glycoproteins. Laminins are the major non-collagenous constituent of basement membranes. They have been implicated in a wide variety of biological processes including cell adhesion, differentiation, migration, signaling, neurite outgrowth and metastasis. LAMC2 encodes a protein which is expressed in several fetal tissues and is specifically localized to epithelial cells in skin, lung and kidney (RefSeq, 2002). LAMC2 is highly expressed in anaplastic thyroid carcinoma and is associated with tumor progression, migration, and invasion by modulating signaling of EGFR (Garg et al., 2014). LAMC2 expression predicted poorer prognosis in stage II colorectal cancer patients (Kevans et al., 2011). LAMC2 expression together with three other biomarkers was found to be significantly associated with the presence of LN metastasis in oral squamous cell carcinoma patients (Zanaruddin et al., 2013).

LILRB4 (also known as ILT-3) encodes leukocyte immunoglobulin like receptor B4 which is a member of the leukocyte immunoglobulin-like receptor (LIR) family, which is found in a gene cluster at chromosomal region 19q13.4. The receptor is expressed on immune cells where it binds to MHC class I molecules on antigen-presenting cells and transduces a negative signal that inhibits stimulation of an immune response. The receptor can also function in antigen capture and presentation. It is thought to control inflammatory responses and cytotoxicity to help focus the immune response and limit autoreactivity (RefSeq, 2002). Over-expression of LILRB4 may be involved in tolerance of dendritic cells during cancer. LILRB4 may be involved in immune suppression. LILRB4 is involved in cancer immune escape (Zhang et al., 2012b; Trojandt et al., 2016; Cortesini, 2007; de Goeje et al., 2015; Suciu-Foca et al., 2007). LILRB4 expression is induced by TNF-alpha. Over-expression of LILRB4 inhibits NF-kappaB activation, transcription of inflammatory cytokines, and co-stimulatory molecules. LILRB4 is over-expressed by cyclosporine resulting in decreased tumor cytotoxicity by natural killer cells (Si et al., 2012; Thorne et al., 2015; Vlad and Suciu-Foca, 2012). LILRB4 is over-expressed on dendritic cells in cancer. LILRB4 is expressed in monocytic acute myeloid leukemia. LILRB4 is over-expressed in ovarian cancer (Dobrowolska et al., 2013; Khan et al., 2012; Orsini et al., 2014). LILRB4 expression is associated with shorter survival in non-small cell lung cancer. LILRB4 expression may be used in chronic lymphocytic leukemia prognosis (Colovai et al., 2007; de Goeje et al., 2015).

LOXL2 encodes an extracellular copper-dependent amine oxidase, known as lysyl oxidase like 2. The enzyme is essential to the biogenesis of connective tissue and catalyses the first step in the formation of crosslinks between collagens and elastin (RefSeq, 2002). LOXL2 was shown to be involved in regulation of extracellular and intracellular cell signaling pathways. Extracellularly, LOXL2 remodels the extracellular matrix of the tumor microenvironment. Intracellularly, it regulates the epithelial-to-mesenchymal transition (Cano et al., 2012; Moon et al., 2014). In general, LOXL2 has been associated with tumor progression including the promotion of cancer cell invasion, metastasis, angiogenesis, and the malignant transformation of solid tumors in various tumors. A high expression of LOXL2 is associated with a poor prognosis (Wu and Zhu, 2015). LOXL2 was shown to be overexpressed in colon, esophageal squamous cell, breast cell, clear cell renal cell, hepatocellular, cholangio-, lung squamous cell and head and neck squamous cell carcinomas. In various cancer types, the high expression of LOXL2 was associated with higher recurrence, progression, or metastasis. In various cancer cell lines, the high expression of LOXL2 was associated with increased cell mobility and invasion and its silencing showed the opposite effects (Xu et al., 2014a; Kim et al., 2014; Wong et al., 2014a; Hase et al., 2014; Lv et al., 2014; Torres et al., 2015). In gastric cancer, fibroblast-derived LOXL2 was shown potentially to stimulate the motility of gastric cancer cells. The expression of LOXL2 in stromal cells could serve as a prognostic marker (Kasashima et al., 2014). A number of micro RNAs family is significantly reduced in cancer tissues. LOXL2 was shown to be a direct regulator of those tumor-suppressive micro-RNAs (Fukumoto et al., 2016; Mizuno et al., 2016).

EGF induces LRRK1 translocation as it is an EGF receptor specific interaction partner (Ishikawa et al., 2012; Hanafusa and Matsumoto, 2011; Reyniers et al., 2014). LRRK1 is a component of the Grb2/Gab2/Shc1 complex and interacts with Arap1. It may be a component of the MAPK signaling in response to cellular stress (Titz et al., 2010). Arsenic trioxide which is used for acute promyelocytic leukemia treatment up-regulates LRRK1 in breast cancer cells (Wang et al., 2011). LRRK1 shows extreme allele-specific expression in familial pancreatic cancer (Tan et al., 2008). LRRK1 encodes leucine rich repeat kinase 1 and is located on chromosome 15q26.3. It belongs to the ROCO proteins, a novel subgroup of Ras-like GTPases (RefSeq, 2002; Korr et al., 2006).

LYPD1 encodes LY6/PLAUR domain containing 1 and is located on chromosome 2q21.2 (RefSeq, 2002). LYPD1 is over-expressed in brain metastases derived from breast cancer. LYPD1 is over-expressed in metastasis. LYPD1 is differentially expressed in ovarian cancer. LYPD1 is a tumor suppressor which is down-regulated in CD133+ cancer stem cell-like cells derived from uterine carcinosarcoma (Burnett et al., 2015; Choijamts et al., 2011; Dat et al., 2012; Ge et al., 2015b; Lawrenson et al., 2015a). LYPD1 is a negative regulator of cell proliferation (Salazar et al., 2011).

MAGEA11 encodes MAGE family member A11 which is a member of the MAGEA gene family. The members of this family encode proteins with 50 to 80% sequence identity to each other. The promoters and first exons of the MAGEA genes show considerable variability, suggesting that the existence of this gene family enables the same function to be expressed under different transcriptional controls. The MAGEA genes are clustered at chromosomal location Xq28 (RefSeq, 2002). MAGEA11 is a cancer germline antigen which is involved in tumor progression and correlates with poor prognosis and survival in silico. MAGEA11 is involved in PR-B signaling and acts as co-regulator for the androgen receptor. MAGEA11 directly interacts with TIF2. MAGEA11 is involved in hypoxic signaling and knock-down leads to decreased HIF-1alpha expression (Aprelikova et al., 2009; Askew et al., 2009; James et al., 2013; Liu et al., 2011; Su et al., 2012; Wilson, 2010; Wilson, 2011). MAGEA11 is up-regulated in oral squamous cell carcinoma, paclitaxel-resistant ovarian cancer, and during prostate cancer progression (Duan et al., 2003; Wilson, 2010; Ge et al., 2015a; Karpf et al., 2009). MAGEA11 expression is associated with hypo-methylation in prostate and epithelial ovarian cancer (James et al., 2013).

MAGEA12 encodes MAGE family member A12 and is closely related to several other genes clustered on chromosome X (RefSeq, 2002). MAGEA12 is expressed in 20.5% of multiple myeloma patients (Andrade et al., 2008). The surfacing of systemic immune reactivity toward a cryptic epitope from the MAGEA12, after temporary regression of a single melanoma metastasis, in response to specific vaccination was reported (Lally et al., 2001). MAGEA12 was expressed at the highest frequencies, relative to the other MAGE antigens, in early stage lesions of malignant melanoma (Gibbs et al., 2000).

MAGEA3 encodes melanoma-associated antigen family member A3. MAGEA3 is widely known as cancer-testis antigen (RefSeq, 2002; Pineda et al., 2015; De et al., 1994). MAGEA3 has been known long time for being used in therapeutic vaccination trials of metastatic melanoma cancer. The currently performed percutaneous peptide immunization with MAGEA3 and 4 other antigens of patients with advanced malignant melanoma was shown to contribute significantly to longer overall survival by complete responders compared to incomplete responders (Coulie et al., 2002; Fujiyama et al., 2014). In NSCLC, MAGEA3 was shown to be frequently expressed. The expression of MAGEA3 correlated with higher number of tumor necrosis in NSCLC tissue samples and was shown to inhibit the proliferation and invasion and promote the apoptosis in lung cancer cell line. By the patients with adenocarcinomas, the expression of MAGEA3 was associated with better survival. The whole cell anti MAGEA3 vaccine is currently under the investigation in the promising phase III clinical trial for treatment of NSCLC (Perez et al., 2011; Reck, 2012; Hall et al., 2013; Grah et al., 2014; Liu et al., 2015b). MAGEA3 together with 4 other genes was shown to be frequently expressed in HCC. The expression of those genes was correlated with the number of circulating tumor cells, high tumor grade and advanced stage in HCC patients. The frequency of liver metastasis was shown to be significantly higher in cases with tumor samples that expressed MAGE3 than in those that did not express this gene (Bahnassy et al., 2014; Hasegawa et al., 1998). Cancer stem cell-like side populations isolated from a bladder cancer cell line as well as from lung, colon, or breast cancer cell lines showed expression of MAGEA3 among other cancer-testis antigens. In general, cancer stem cells are known for being resistant to current cancer therapy and cause post-therapeutic cancer recurrence and progression. Thus, MAGEA3 may serve as a novel target for immunotherapeutic treatment in particular of bladder cancer (Yamada et al., 2013; Yin et al., 2014). In head and neck squamous cell carcinoma, the expression of MAGEA3 was shown to be associated with better disease-free survival (Zamuner et al., 2015). Furthermore, MAGEA3 can be used as a prognostic marker for ovarian cancer (Szajnik et al., 2013).

MAGEA4, also known as MAGE4, encodes a member of the MAGEA gene family and is located on chromosome Xq28 (RefSeq, 2002). MAGEA4 was described as a cancer testis antigen which was found to be expressed in a small fraction of classic seminomas but not in non-seminomatous testicular germ cell tumors, in breast carcinoma, Epstein-Barr Virus-negative cases of Hodgkin's lymphoma, esophageal carcinoma, lung carcinoma, bladder carcinoma, head and neck carcinoma, and colorectal cancer, oral squamous cell carcinoma, and hepatocellular carcinoma (Ries et al., 2005; Bode et al., 2014; Li et al., 2005; Ottaviani et al., 2006; Hennard et al., 2006; Chen et al., 2003). MAGEA4 was shown to be frequently expressed in primary mucosal melanomas of the head and neck and thus may be a potential target for cancer testis antigen-based immunotherapy (Prasad et al., 2004). MAGEA4 was shown to be preferentially expressed in cancer stem-like cells derived from LHK2 lung adenocarcinoma cells, SW480 colon adenocarcinoma cells and MCF7 breast adenocarcinoma cells (Yamada et al., 2013). Over-expression of MAGEA4 in spontaneously transformed normal oral keratinocytes was shown to promote growth by preventing cell cycle arrest and by inhibiting apoptosis mediated by the p53 transcriptional targets BAX and CDKN1A (Bhan et al., 2012). MAGEA4 was shown to be more frequently expressed in hepatitis C virus-infected patients with cirrhosis and late-stage hepatocellular carcinoma compared to patients with early stage hepatocellular carcinoma, thus making the detection of MAGEA4 transcripts potentially helpful to predict prognosis (Hussein et al., 2012). MAGEA4 was shown to be one of several cancer/testis antigens that are expressed in lung cancer and which may function as potential candidates in lung cancer patients for polyvalent immunotherapy (Kim et al., 2012). MAGEA4 was described as being up-regulated in esophageal carcinoma and hepatocellular carcinoma (Zhao et al., 2002; Wu et al., 2011). A MAGEA4-derived native peptide analogue called p286-1Y2L9L was described as a novel candidate epitope suitable to develop peptide vaccines against esophageal cancer (Wu et al., 2011).

MAGEA6 encodes melanoma-associated antigen family member A6. MAGEA3 is widely known as cancer-testis antigen (RefSeq, 2002; Pineda et al., 2015; De et al., 1994). MAGEA6 was shown to be frequently expressed in melanoma, advanced myeloma, pediatric rhabdomyosarcoma, sarcoma, lung, bladder, prostate, breast, and colorectal cancers, head and neck squamous cell, esophageal squamous cell, and oral squamous cell carcinomas (Ries et al., 2005; Hasegawa et al., 1998; Gibbs et al., 2000; Dalerba et al., 2001; Otte et al., 2001; van der Bruggen et al., 2002; Lin et al., 2004; Tanaka et al., 1997). MAGEA6 expression has been associated with shorter progression-free survival in multiple myeloma patients. In contrast in head and neck squamous cell carcinoma, the expression of MAGEA6 was shown to be associated with better disease-free survival (van et al., 2011; Zamuner et al., 2015). MAGEA6 was among a set of genes overexpressed in a paclitaxel-resistant ovarian cancer cell line. Moreover, transfection of MAGEA6 also conferred increased drug resistance to paclitaxel-sensitive cells (Duan et al., 2003). MAGEA6 can be used as a prognostic marker for ovarian cancer (Szajnik et al., 2013). Cancer stem cell-like side populations isolated from lung, colon, or breast cancer cell lines showed expression of MAGEA6 among other cancer-testis antigens (Yamada et al., 2013).

MAGEB2 is classified as cancer testis antigen, since it is expressed in testis and placenta, and in a significant fraction of tumors of various histological types, amongst others multiple myeloma and head and neck squamous cell carcinoma (Pattani et al., 2012; van et al., 2011).

MELK encodes maternal embryonic leucine zipper kinase and is located on chromosome 9p13.2 (RefSeq, 2002). MELK is a member of the SNF1/AMPK family of serine-threonine kinases and is a cell cycle dependent protein kinase. It plays a key role in multiple cellular processes such as the proliferation, cell cycle progression, mitosis and spliceosome assembly and has recently emerged as an oncogene and a biomarker over-expressed in multiple cancer stem cells (Du et al., 2014). MELK is over-expressed in various cancers, including colon, gastric, breast, ovaries, pancreas, prostate and brain cancer and over-expression correlates with poor prognosis (Pickard et al., 2009; Kuner et al., 2013; Gu et al., 2013; Liu et al., 2015a). Inhibition of MELK is under investigation as a therapeutic strategy for a variety of cancers, including breast cancer, lung cancer and prostate cancer. MELK-T1 inhibits catalytic activity and MELK protein stability and might sensitize tumors to DNA-damaging agents or radiation therapy by lowering the DNA-damage threshold. MELK inhibitor OTSSP167 is undergoing phase I clinical trials (Chung et al., 2012b; Ganguly et al., 2014; Beke et al., 2015).

MEX3A encodes a member of the mex-3 RNA binding family which consists of evolutionarily conserved RNA-binding proteins recruited to P bodies and potentially involved in post-transcriptional regulatory mechanisms (Buchet-Poyau et al., 2007). MEX3A is over-expressed and the gene is amplified in Wilms tumors associated with a late relapse (Krepischi et al., 2016). MEX3A regulates CDX2 via a post-transcriptional mechanism with impact in intestinal differentiation, polarity and stemness, contributing to intestinal homeostasis and carcinogeneses (Pereira et al., 2013).

MMP-11, also named stromelysin-3, is a member of the stromelysin subgroup belonging to MMPs superfamily, which has been detected in cancer cells, stromal cells and adjacent microenvironment. Differently, MMP-11 exerts a dual effect on tumors. On the one hand MMP-11 promotes cancer development by inhibiting apoptosis as well as enhancing migration and invasion of cancer cells, on the other hand MMP-11 plays a negative role against cancer development via suppressing metastasis in animal models. Overexpression of MMP-11 was discovered in sera of cancer patients compared with normal control group as well as in multiple tumor tissue specimens, such as gastric cancer, breast cancer, and pancreatic cancer (Zhang et al., 2016c). MMP-11 was demonstrated to be over-expressed at mRNA level and protein level in CRC tissue than paired normal mucosa. Further MMP-11 expression was correlated with CRC lymph node metastasis, distant metastasis and TNM stage (Tian et al., 2015). MMP-11 overexpression is associated with aggressive tumor phenotype and unfavorable clinical outcome in upper urinary tract urothelial carcinomas (UTUC) and urinary bladder urothelial carcinomas (UBUC), suggesting it may serve as a novel prognostic and therapeutic target (Li et al., 2016d).

MMP12 (also called MME) encodes a member of the matrix metalloproteinase family which is involved in the breakdown of extracellular matrix in normal physiological processes, such as embryonic development, reproduction and tissue remodeling as well as in disease processes, such as arthritis and metastasis (RefSeq, 2002). De-regulation of MMP12 is shown for different cancer entities. MMP12 is up-regulated in lung, skin, pancreatic and gastric cancer and related to tumor invasion and metastasis. In contrast, overexpression of MMP12 mRNA was found in gastric and colorectal cancer and correlated with a better prognosis (Zhang et al., 2007; Yang et al., 2001; Balaz et al., 2002; Zheng et al., 2013; Wen and Cai, 2014; Zhang et al., 2015f). MMP12 is up-regulated by TNF-alpha or EGF via the NF-kappaB/MAPK and JNK/AP-1 pathways (Yu et al., 2010; Yang et al., 2012).

MYO3B encodes the myosin IIIB, a member of a myosin-class that is characterized by an amino-terminal kinase domain and shown to be present in photoreceptors (RefSeq, 2002). MYO3B was identified as an antagonist to trastuzumab treatment among HER2+ cell lines (Lapin et al., 2014). Nucleotide polymorphisms in the MYOB3 gene were found to be associated with changes in the AUA Symptom Score after radiotherapy for prostate cancer (Kerns et al., 2013).

NFE2L3 encodes nuclear factor, erythroid 2 like 3, a member of the cap 'n' collar basic-region leucine zipper family of transcription factors (RefSeq, 2002). Recent work has revealed that loss of NFE2L3 predisposes mice to lymphoma development. Others have observed high levels of NFE2L3 in colorectal cancer cells, whereas aberrant expression of NFE2L3 was found in Hodgkin lymphoma. Furthermore, NFE2L3 exhibited hyper-methylation in ER positive tumors (Kuppers et al., 2003; Chevillard et al., 2011; Palma et al., 2012; Rauscher et al., 2015).

NLRP2 (also known as NALP2) encodes the NLR family, pyrin domain containing 2 protein and is involved in the activation of caspase-1 and may also form protein complexes activating proinflammatory caspases. NLRP7 is a paralog of NLRP2 (RefSeq, 2002; Wu et al., 2010; Slim et al., 2012). The PYRIN domain of NLRP2 inhibits cell proliferation and tumor growth of glioblastoma (Wu et al., 2010). An ATM/NLRP2/MDC1-dependent pathway may shut down ribosomal gene transcription in response to chromosome breaks (Kruhlak et al., 2007). Mutations in NLRP2 can cause rare human imprinting disorders such as familial hydatidiform mole, Beckwith-Wiedemann syndrome and familial transient neonatal diabetes mellitus (Aghajanova et al., 2015; Dias and Maher, 2013; Ulker et al., 2013). NLRP2 inhibits NF-kappaB activation (Kinoshita et al., 2005; Kinoshita et al., 2006; Fontalba et al., 2007; Bruey et al., 2004).

NLRP7 encodes the NLR family pyrin domain containing 7, a member of the NACHT, leucine rich repeat, and PYD containing (NLRP) protein family that may act as a feedback regulator of caspase-1-dependent interleukin 1-beta secretion (RefSeq, 2002). NLRP7 expression correlates significantly with the depth of tumor invasion and poor prognosis in endometrial cancer and was identified as one of the genes highly expressed in embryonal carcinomas (Ohno et al., 2008; Skotheim et al., 2005). NLRP7 might play a crucial role in cell proliferation in testicular tumorigenesis and represents a promising therapeutic target for testicular germ cell tumors (Okada et al., 2004).

OVGP1 or oviduct-specific glycoprotein, encodes a large, carbohydrate-rich, epithelial glycoprotein which is secreted from non-ciliated oviductal epithelial cells and associates with ovulated oocytes, blastomeres and spermatozoan acrosomal regions (RefSeq, 2002). Gain of OVGP1 was shown to be associated with the development of endometrial hyperplasia and endometrial cancer (Woo et al., 2004). OVGP1 was described as a molecular marker for invasion in endometrial tumorigenesis and a differentiation-based marker of different ovarian cancers (Maines-Bandiera et al., 2010; Wang et al., 2009).

PAGE2 encodes a member of the PAGE protein family, which is predominantly expressed in testis (Brinkmann et al., 1998). The cancer-testis gene PAGE2 is up-regulated by de-methylation during spontaneous differentiation of colorectal cancer cells resulting in mesenchymal-to-epithelial transition (MET). Accordingly, down-regulation of PAGE2 has been shown in EMT (Yilmaz-Ozcan et al., 2014). A genome-wide screening identifies PAGE2 as a possible regulator of telomere signaling in human cells (Lee et al., 2011).

PNOC encodes prepronociceptin which is a preproprotein that is proteolytically processed to generate multiple protein products. These products include nociceptin, nocistatin, and orphanin FQ2 (OFQ2). Nociceptin, also known as orphanin FQ, is a 17-amino acid neuropeptide that binds to the nociceptin receptor to induce increased pain sensitivity, and may additionally regulate body temperature, learning and memory, and hunger.

Another product of the encoded preproprotein, nocistatin, may inhibit the effects of nociception (RefSeq, 2002). Inhibition of cancer pain also inhibits tumor growth and lung metastasis. PNOC is involved in morphine tolerance development. PNOC is involved in neuronal growth. PNOC is involved in cell damage, viability, inflammation and impaired immune function (Caputi et al., 2013; Chan et al., 2012; Kirkova et al., 2009; Kuraishi, 2014; Stamer et al., 2011). PNOC is up-regulated in ganglioglioma. PNOC expression is down-regulated in end-stage cancer. PNOC is highly expressed in the plasma of hepatocellular carcinoma patients (Chan et al., 2012; Stamer et al., 2011; Horvath et al., 2004; Spadaro et al., 2006; Szalay et al., 2004). Cebranopadol is an analgesic PNOC peptide may be used in bone cancer treatment and buprenorphine in lung cancer treatment (Davis, 2012; Linz et al., 2014). PNOC is involved in c-Fos expression (Gottlieb et al., 2007; Kazi et al., 2007).

PRAME encodes an antigen that is preferentially expressed in human melanomas and acts as a repressor of retinoic acid receptor, likely conferring a growth advantage to cancer cell via this function (RefSeq, 2002). PRAME was shown to be up-regulated in multiple myeloma, clear cell renal cell carcinoma, breast cancer, acute myeloid leukemia, melanoma, chronic myeloid leukemia, head and neck squamous cell carcinoma and osteosarcoma cell lines (Dannenmann et al., 2013; Yao et al., 2014; Zou et al., 2012; Szczepanski and Whiteside, 2013; Zhang et al., 2013; Beard et al., 2013; Abdelmalak et al., 2014; Qin et al., 2014). PRAME is associated with myxoid and round-cell liposarcoma (Hemminger et al., 2014). PRAME is associated with shorter progression-free survival and chemotherapeutic response in diffuse large B-cell lymphoma treated with R-CHOP, markers of poor prognosis in head and neck squamous cell carcinoma, poor response to chemotherapy in urothelial carcinoma and poor prognosis and lung metastasis in osteosarcoma (Tan et al., 2012; Dyrskjot et al., 2012; Szczepanski et al., 2013; Mitsuhashi et al., 2014). PRAME is associated with lower relapse, lower mortality and overall survival in acute lymphoblastic leukemia (Abdelmalak et al., 2014). PRAME may be a prognostic marker for diffuse large B-cell lymphoma treated with R-CHOP therapy (Mitsuhashi et al., 2014).

RAD54 encodes a protein belonging to the DEAD-like helicase superfamily. It shares similarity with Saccharomyces cerevisiae RAD54 and RDH54, both of which are involved in homologous recombination and repair of DNA. This protein binds to double-stranded DNA, and displays ATPase activity in the presence of DNA. This gene is highly expressed in testis and spleen, which suggests active roles in meiotic and mitotic recombination (RefSeq, 2002). Homozygous mutations of RAD54B were observed in primary lymphoma and colon cancer (Hiramoto et al., 1999). RAD54B counteracts genome-destabilizing effects of direct binding of RAD51 to dsDNA in human tumor cells (Mason et al., 2015).

RNF17 encodes ring finger protein 17 which is similar to a mouse gene that encodes a testis-specific protein containing a RING finger domain. Alternatively spliced transcript variants encoding different isoforms have been found (RefSeq, 2002). RNF17 is involved in cytokine production and apoptosis. RNF17 enhances c-Myc function (Jnawali et al., 2014; Lee et al., 2013; Yin et al., 1999; Yin et al., 2001). RNF17 is up-regulated upon RHOXF1 knock-down (Seifi-Alan et al., 2014). RNF17 is expressed in liver cancer (Yoon et al., 2011). RNF17 is a cancer-associated marker (de Matos et al., 2015).

SDK2 encodes the sidekick cell adhesion molecule 2, a member of the immunoglobulin superfamily that contains two immunoglobulin domains and thirteen fibronectin type III domains which represent binding sites for DNA, heparin and the cell surface (RefSeq, 2002). It was shown that SDK2 guides axonal terminals to specific synapses in developing neurons and promotes lamina-specific targeting of retinal dendrites in the inner plexiform layer (Kaufman et al., 2004; Yamagata and Sanes, 2012).

SPDEF (also called PDEF) encodes SAM pointed domain containing ETS transcription factor, a member of the E26 transformation-specific (ETS) family of transcription factors. It is highly expressed in prostate epithelial cells where it functions as an androgen-independent transactivator of prostate specific antigen (PSA) promoter (RefSeq, 2002). SPDEF expression is often lost or down-regulated in late-stage of tumor progression which means that it plays a role in tumor cell invasion and metastasis. In earlier stages of tumor progression SPDEF is sometimes up-regulated. De-regulation of SPDEF is described for several cancer entities including breast, prostate and colorectal cancer (Moussa et al., 2009; Schaefer et al., 2010; Steffan and Koul, 2011). SPDEF induces the transcription of E-cadherin and suppresses thereby cell invasion and migration (Pal et al., 2013). SPDEF interacts with beta-catenin and blocks the transcriptional activity resulting in lower protein levels of the oncogenes cyclin D1 and c-Myc (Noah et al., 2013).

SPON1 encodes spondin 1 and is located on chromosome 11p15.2 (RefSeq, 2002). SPON1 is involved in cancer cell proliferation, migration, invasion, and metastasis. SPON1 is involved in Fak and Src signaling. SPON1 is involved in IL-6 maintenance via MEKK/p38 MAPK/NF-kappaB signaling and this may support murine neuroblastoma survival (Chang et al., 2015a; Cheng et al., 2009; Dai et al., 2015). SPON1 is down-regulated by miR-506 (Dai et al., 2015). SPON1 is over-expressed in ovarian cancer (Davidson et al., 2011; Jiao et al., 2013; Pyle-Chenault et al., 2005). SPON1 may have diagnostic potential in cancer prognosis (Pagnotta et al., 2013).

STAG3 encodes stromal antigen 3, which is expressed in the nucleus and is a subunit of the cohesin complex which regulates the cohesion of sister chromatids during cell division (RefSeq, 2002). Researchers have reported the involvement of a common allele of STAG3 in the development of epithelial ovarian cancer. Another group has identified STAG3 to be capable of effectively discriminating lung cancer, chronic obstructive lung disease and fibrotic interstitial lung diseases. Others have detected expression of the STAG3 gene in p53 mutated lymphoma cells (Notaridou et al., 2011; Wielscher et al., 2015; Kalejs et al., 2006).

TDRD5 encodes tudor domain containing 5 and is located on chromosome 1q25.2 (RefSeq, 2002). TDRD5 may be over-expressed in breast cancer (Jiang et al., 2016). TDRD5 methylation is altered upon resveratrol treatment in triple negative breast cancer (Medina-Aguilar et al., 2017). TDRD5 is part of a run of homozygosity associated with thyroid cancer (Thomsen et al., 2016).

TENM4 encodes teneurin transmembrane protein 4 which is expressed in the nervous systems and mesenchymal tissues and is a regulator of chondrogenesis (Suzuki et al., 2014). Among the four most frequently mutated genes was TENM4 showing protein-changing mutations in primary CNS lymphomas (Vater et al., 2015). MDA-MB-175 cell line contains a chromosomal translocation that leads to the fusion of TENM4 and receptors of the ErbB family. Chimeric genes were also found in neuroblastomas (Wang et al., 1999; Boeva et al., 2013).

TMPRSS3 encodes transmembrane protease, serine 3 which is a protein that belongs to the serine protease family. The encoded protein contains a serine protease domain, a transmembrane domain, an LDL receptor-like domain, and a scavenger receptor cysteine-rich domain. Serine proteases are known to be involved in a variety of biological processes, whose malfunction often leads to human diseases and disorders. This gene was identified by its association with both congenital and childhood onset autosomal recessive deafness. This gene is expressed in fetal cochlea and many other tissues, and is thought to be involved in the development and maintenance of the inner ear or the contents of the perilymph and endolymph. This gene was also identified as a tumor-associated gene that is overexpressed in ovarian tumors (RefSeq, 2002). TMPRSS3 is involved in cell proliferation, invasion, and migration. TMPRSS3 induces ERK1/2 signaling (Zhang et al., 2016a). TMPRSS3 affects E-cadherin, vimentin, and Twist expression. TMPRSS3 is down-regulated by hexamethylene bisacetamide (Zhang et al., 2016a; Zhang et al., 2004). TMPRSS3 is up-regulated in breast cancer, pancreatic cancer, and ovarian cancer. TMPRSS3 is de-regulated in gastric cancer and pancreatic ductal adenocarcinoma (Rui et al., 2015; Zhang et al., 2016a; Zhang et al., 2004; Amsterdam et al., 2014; Iacobuzio-Donahue et al., 2003; Luo et al., 2017; Underwood et al., 2000; Wallrapp et al., 2000). TMPRSS3 is associated with TNM stage, lymph node metastasis, distant organ metastasis, shorter survival, shorter disease-free survival, and poor prognosis. TMPRSS3 may be used as biomarker in cancer. TMPRSS3 mutations are associated with cancer risk. TMPRSS3 may be used for early pancreatic ductal adenocarcinoma detection (Rui et al., 2015; Amsterdam et al., 2014; Luo et al., 2017; Dorn et al., 2014; Luostari et al., 2014; Pelkonen et al., 2015; Sawasaki et al., 2004). TMPRSS3 is hypo-methylated in cancer (Guerrero et al., 2012).

VTCN1, also known as B7-H4, encodes a member of the B7 costimulatory protein family which is present on the surface of antigen-presenting cells and interacts with ligands bound to receptors on the surface of T cells (RefSeq, 2002). VTCN1 was shown to be up-regulated in lung cancer, colorectal cancer, hepatocellular carcinoma, osteosarcoma, breast cancer, cervical cancer, urothelial cell carcinoma, gastric cancer, endometrial cancer, thyroid cancer and laryngeal carcinoma (Klatka et al., 2013; Zhu et al., 2013; Vanderstraeten et al., 2014; Shi et al., 2014; Fan et al., 2014; Wang et al., 2014; Leong et al., 2015; Dong and Ma, 2015; Zhang et al., 2015a; Peng et al., 2015; Xu et al., 2015a). VTCN1 is associated with poor overall survival and higher recurrence probability in hepatocellular carcinoma and poor overall survival in osteosarcoma, urothelial cell carcinoma, pancreatic cancer, gastric cancer, cervical cancer, melanoma and thyroid cancer (Zhu et al., 2013; Seliger, 2014; Liu et al., 2014b; Chen et al., 2014; Fan et al., 2014; Dong and Ma, 2015; Zhang et al., 2015a). VTCN1 is associated with clear cell renal cell carcinoma (Xu et al., 2014b). VTCN1 expression levels were shown to be inversely correlated with patient survival in ovarian cancer (Smith et al., 2014). VTCN1 may be a potential prognostic indicator of urothelial cell carcinoma and gastric cancer (Shi et al., 2014; Fan et al., 2014).

WNT7A encodes Wnt family member 7A which is a member of the WNT gene family. These proteins have been implicated in oncogenesis and in several developmental processes, including regulation of cell fate and patterning during embryogenesis. This gene is involved in the development of the anterior-posterior axis in the female reproductive tract, and also plays a critical role in uterine smooth muscle pattering and maintenance of adult uterine function. Mutations in this gene are associated with Fuhrmann and Al-Awadi/Raas-Rothschild/Schinzel phocomelia syndromes (RefSeq, 2002). WNT7A is induced by STAT4 resulting in the activation of cancer-associated fibroblasts. WNT7A potentiates TGF-beta receptor signaling. WNT7A is involved in cell proliferation and migration. WNT7A is an upstream inducer of senescence. PG545 interacts with WNT7A resulting in inhibited cell proliferation. WNT7A suppresses tumor growth. WNT7A is involved in Wnt/beta-catenin signaling and regulates hsa-miR29b (Avasarala et al., 2013; Avgustinova et al., 2016; Bikkavilli et al., 2015; Borowicz et al., 2014; Jung et al., 2015; King et al., 2015; Ramos-Solano et al., 2015; Zhao et al., 2017). WNT7A is regulated by miR-15b and down-regulated by DNMT1. Endosulfan disrupts WNT7A. WNT7A is a target gene of miR-199a-5p and miR-195/497. WNT7A is down-regulated by chronic ethanol exposure and rescued by PPAR-delta agonist treatment. Dkk-1 affects WNT7A. Bilobalide enhances WNT7A expression (Kim et al., 2015a; Chandra et al., 2014; Ingaramo et al., 2016; Itesako et al., 2014; Liu et al., 2014a; MacLean et al., 2016; Mercer et al., 2014; Mercer et al., 2015; Xu et al., 2015b). WNT7A is down-regulated and hyper-methylated in cervical cancer. WNT7A is lost in lung cancer. WNT7A is over-expressed in endometrial cancer (Ramos-Solano et al., 2015; Kim et al., 2015b; Liu et al., 2013). WNT7A expression correlates with poor prognosis and poor patient outcome. WNT7A promotor methylation correlates with advanced tumor stage, distant metastasis, and loss of E-cadherin. Decreased WNT7A expression correlates with decreased overall survival in malignant pleural mesothelioma and may be used for chemosensitivity prediction (Avgustinova et al., 2016; King et al., 2015; Kim et al., 2015b; Hirata et al., 2015). WNT7A may be a tumor suppressor gene in nasopharyngeal cancer (Nawaz et al., 2015).

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (elongated variants of the peptides of the invention) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans, there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 6

Expression frequencies F of HLA-A*02, HLA-A*01, HLA-A*03, HLA-A*24, HLA-B*07, HLA-B*08 and HLA-B*44 serotypes. Haplotype frequencies Gf are derived from a study which used HLA-typing data from a registry of more than 6.5 million volunteer donors in the U.S. (Gragert et al., 2013). The haplotype frequency is the frequency of a distinct allele on an individual chromosome. Due to the diploid set of chromosomes within mammalian cells, the frequency of genotypic occurrence of this allele is higher and can be calculated employing the Hardy-Weinberg principle ($F = 1 - (1 - Gf)^2$).

| Allele | Population | Calculated phenotype from allele frequency (F) |
|---|---|---|
| A*02 | African (N = 28557) | 32.3% |
| | European Caucasian (N = 1242890) | 49.3% |
| | Japanese (N = 24582) | 42.7% |
| | Hispanic, S + Cent Amer. (N = 146714) | 46.1% |
| | Southeast Asian (N = 27978) | 30.4% |
| A*01 | African (N = 28557) | 10.2% |
| | European Caucasian (N = 1242890) | 30.2% |
| | Japanese (N = 24582) | 1.8% |
| | Hispanic, S + Cent Amer. (N = 146714) | 14.0% |
| | Southeast Asian (N = 27978) | 21.0% |
| A*03 | African (N = 28557) | 14.8% |
| | European Caucasian (N = 1242890) | 26.4% |
| | Japanese (N = 24582) | 1.8% |
| | Hispanic, S + Cent Amer. (N = 146714) | 14.4% |
| | Southeast Asian (N = 27978) | 10.6% |
| A*24 | African (N = 28557) | 2.0% |
| | European Caucasian (N = 1242890) | 8.6% |
| | Japanese (N = 24582) | 35.5% |
| | Hispanic, S + Cent Amer. (N = 146714) | 13.6% |
| | Southeast Asian (N = 27978) | 16.9% |
| B*07 | African (N = 28557) | 14.7% |
| | European Caucasian (N = 1242890) | 25.0% |
| | Japanese (N = 24582) | 11.4% |
| | Hispanic, S + Cent Amer. (N = 146714) | 12.2% |
| | Southeast Asian (N = 27978) | 10.4% |
| B*08 | African (N = 28557) | 6.0% |
| | European Caucasian (N = 1242890) | 21.6% |
| | Japanese (N = 24582) | 1.0% |
| | Hispanic, S + Cent Amer. (N = 146714) | 7.6% |
| | Southeast Asian (N = 27978) | 6.2% |
| B*44 | African (N = 28557) | 10.6% |
| | European Caucasian (N = 1242890) | 26.9% |
| | Japanese (N = 24582) | 13.0% |
| | Hispanic, S + Cent Amer. (N = 146714) | 18.2% |
| | Southeast Asian (N = 27978) | 13.1% |

The peptides of the invention, preferably when included into a vaccine of the invention as described herein bind to A*02, A*01, A*03, A*24, B*07, B*08 or B*44. A vaccine may also include pan-binding MHC class II peptides. Therefore, the vaccine of the invention can be used to treat cancer in patients that are A*02-, A*01-, A*03-, A*24-, B*07-, B*08- or B*44-positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86%.

TABLE 7

HLA alleles coverage in European Caucasian population (calculated from (Gragert et al., 2013)).

| | coverage (at least one A-allele) | combined with B*07 | combined with B*44 | combined with B*07 and B*44 |
|---|---|---|---|---|
| A*02/A*01 | 70% | 78% | 78% | 84% |
| A*02/A*03 | 68% | 76% | 76% | 83% |
| A*02/A*24 | 61% | 71% | 71% | 80% |
| A*01/A*03 | 52% | 64% | 65% | 75% |
| A*01/A*24 | 44% | 58% | 59% | 71% |
| A*03/A*24 | 40% | 55% | 56% | 69% |
| A*02/A*01/A*03 | 84% | 88% | 88% | 91% |
| A*02/A*01/A*24 | 79% | 84% | 84% | 89% |
| A*02/A*03/A*24 | 77% | 82% | 83% | 88% |
| A*01/A*03/A*24 | 63% | 72% | 73% | 81% |
| A*02/A*01/A*03/A*24 | 90% | 92% | 93% | 95% |

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=100[1−(C/R)]

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iiii) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 772 or a variant thereof which is 88% homologous to SEQ ID NO: 1 to SEQ ID NO: 772, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 772. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 772, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 8

Variants and motif of the peptides according to SEQ ID NO: 3, 225, 13, 17, 84, 108, 113, 114, 147, 36, 51, 172, 54, and 57

| Position | 1 | 2 | 3 | 4 | 5 | 6 | 7 | 8 | 9 |
|---|---|---|---|---|---|---|---|---|---|
| SEQ ID No 3 | A | L | I | Y | N | L | V | G | I |
| Variant | | | | | | | | | V |
| | | | | | | | | | L |
| | | | | | | | | | A |
| | | | | | M | | | | |
| | | | | | M | | | | |
| | | | | | M | | | | L |
| | | | | | M | | | | A |
| | | | | | A | | | | |
| | | | | | A | | | | |
| | | | | | A | | | | L |
| | | | | | A | | | | A |
| | | | | | V | | | | |
| | | | | | V | | | | |
| | | | | | V | | | | L |
| | | | | | V | | | | A |
| | | | | | T | | | | |
| | | | | | T | | | | |
| | | | | | T | | | | L |
| | | | | | T | | | | A |
| | | | | | Q | | | | |
| | | | | | Q | | | | |
| | | | | | Q | | | | L |
| | | | | | Q | | | | A |

| Position | 1 | 2 | 3 | 4 | 5 | 6 | 7 | 8 | 9 |
|---|---|---|---|---|---|---|---|---|---|
| SEQ ID No 225 | S | V | F | A | H | P | R | K | L |
| Variant | | L | | | | | | | |
| | | L | | | | | | | V |
| | | L | | | | | | | I |
| | | L | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | | | | | | | | V |
| | | | | | | | | | I |
| | | | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |

| Position | 1 | 2 | 3 | 4 | 5 | 6 | 7 | 8 | 9 |
|---|---|---|---|---|---|---|---|---|---|
| SEQ ID No 13 | V | Y | T | F | L | S | S | T | L |
| Variant | | | | | | | | | I |
| | | | | | | | | | F |
| | | | | F | | | | | I |
| | | | | F | | | | | |
| | | | | F | | | | | F |

| Position | 1 | 2 | 3 | 4 | 5 | 6 | 7 | 8 | 9 |
|---|---|---|---|---|---|---|---|---|---|
| SEQ ID No 17 | R | F | T | T | M | L | S | T | F |
| Variant | | Y | | | | | | | I |
| | | Y | | | | | | | L |
| | | Y | | | | | | | |
| | | | | | | | | | I |
| | | | | | | | | | L |

| Position | 1 | 2 | 3 | 4 | 5 | 6 | 7 | 8 | 9 | 10 |
|---|---|---|---|---|---|---|---|---|---|---|
| SEQ ID No 84 | K | L | Q | P | A | Q | T | A | A | K |
| Variant | | | | | | | | | | Y |
| | | | | | | | | | | R |
| | | | | | | | | | | F |
| | | I | | | | | | | | |

TABLE 8-continued

Variants and motif of the peptides according to SEQ ID NO: 3, 225, 13, 17, 84, 108, 113, 114, 147, 36, 51, 172, 54, and 57

| Position | 1 | 2 | 3 | 4 | 5 | 6 | 7 | 8 | 9 | 10 |
|---|---|---|---|---|---|---|---|---|---|---|
|  |  |  | I |  |  |  |  |  | Y |  |
|  |  |  | I |  |  |  |  |  | R |  |
|  |  |  | I |  |  |  |  |  | F |  |
|  |  |  | M |  |  |  |  |  |  |  |
|  |  |  | M |  |  |  |  |  | Y |  |
|  |  |  | M |  |  |  |  |  | R |  |
|  |  |  | M |  |  |  |  |  | F |  |
|  |  |  | V |  |  |  |  |  |  |  |
|  |  |  | V |  |  |  |  |  | Y |  |
|  |  |  | V |  |  |  |  |  | R |  |
|  |  |  | V |  |  |  |  |  | F |  |
|  |  |  | T |  |  |  |  |  |  |  |
|  |  |  | T |  |  |  |  |  | Y |  |
|  |  |  | T |  |  |  |  |  | R |  |
|  |  |  | T |  |  |  |  |  | F |  |

| Position | 1 | 2 | 3 | 4 | 5 | 6 | 7 | 8 | 9 | 10 |
|---|---|---|---|---|---|---|---|---|---|---|
| SEQ ID No 108 | V | L | Y | P | V | P | L | E | S | Y |
| Variant |  |  |  |  |  |  |  |  |  | K |
|  |  |  |  |  |  |  |  |  |  | R |
|  |  |  |  |  |  |  |  |  |  | F |
|  |  |  | I |  |  |  |  |  |  | K |
|  |  |  | I |  |  |  |  |  |  |  |
|  |  |  | I |  |  |  |  |  |  | R |
|  |  |  | I |  |  |  |  |  |  | F |
|  |  |  | M |  |  |  |  |  |  | K |
|  |  |  | M |  |  |  |  |  |  |  |
|  |  |  | M |  |  |  |  |  |  | R |
|  |  |  | M |  |  |  |  |  |  | F |
|  |  |  | V |  |  |  |  |  |  | K |
|  |  |  | V |  |  |  |  |  |  |  |
|  |  |  | V |  |  |  |  |  |  | R |
|  |  |  | V |  |  |  |  |  |  | F |
|  |  |  | T |  |  |  |  |  |  | K |
|  |  |  | T |  |  |  |  |  |  |  |
|  |  |  | T |  |  |  |  |  |  | R |
|  |  |  | T |  |  |  |  |  |  | F |

| Position | 1 | 2 | 3 | 4 | 5 | 6 | 7 | 8 | 9 |
|---|---|---|---|---|---|---|---|---|---|
| SEQ ID No 113 | Q | L | D | S | N | R | L | T | Y |
| Variant |  | S |  |  |  |  |  |  |  |
|  |  | S |  |  |  |  |  |  | A |
|  |  | S | E |  |  |  |  |  |  |
|  |  | S | E |  |  |  |  |  | A |
|  |  | T |  |  |  |  |  |  |  |
|  |  | T |  |  |  |  |  |  | A |
|  |  | T | E |  |  |  |  |  |  |
|  |  | T | E |  |  |  |  |  | A |

| Position | 1 | 2 | 3 | 4 | 5 | 6 | 7 | 8 | 9 | 10 |
|---|---|---|---|---|---|---|---|---|---|---|
| SEQ ID No 114 | V | M | E | Q | S | A | G | I | M | Y |
| Variant |  | S | D |  |  |  |  |  |  |  |
|  |  | S | D |  |  |  |  |  |  | A |
|  |  | S |  |  |  |  |  |  |  |  |
|  |  | S |  |  |  |  |  |  |  | A |
|  |  | T | D |  |  |  |  |  |  |  |
|  |  | T | D |  |  |  |  |  |  | A |
|  |  | T |  |  |  |  |  |  |  |  |
|  |  | T |  |  |  |  |  |  |  | A |

| Position | 1 | 2 | 3 | 4 | 5 | 6 | 7 | 8 | 9 | 10 | 11 |
|---|---|---|---|---|---|---|---|---|---|---|---|
| SEQ ID No 147 | A | P | R | W | F | P | Q | P | T | V | V |
| Variant |  |  |  |  |  |  |  |  |  |  | L |
|  |  |  |  |  |  |  |  |  |  |  | F |
|  |  |  |  |  |  |  |  |  |  |  | M |
|  |  |  |  |  |  |  |  |  |  |  | A |
|  |  |  |  |  |  |  |  |  |  |  | I |

| Position | 1 | 2 | 3 | 4 | 5 | 6 | 7 | 8 | 9 |
|---|---|---|---|---|---|---|---|---|---|
| SEQ ID No 36 | A | P | A | A | W | L | R | S | A |
| Variant |  |  |  |  |  |  |  |  | L |
|  |  |  |  |  |  |  |  |  | F |
|  |  |  |  |  |  |  |  |  | V |
|  |  |  |  |  |  |  |  |  | M |
|  |  |  |  |  |  |  |  |  | I |

| Position | 1 | 2 | 3 | 4 | 5 | 6 | 7 | 8 | 9 |
|---|---|---|---|---|---|---|---|---|---|
| SEQ ID No 51 | S | L | R | L | K | N | V | Q | L |
| Variant |  |  | K |  |  |  |  |  |  |
|  |  |  | K |  |  |  |  |  | V |
|  |  |  | K |  |  |  |  |  | I |
|  |  |  | K |  |  |  |  |  | M |
|  |  |  | K |  |  |  |  |  | F |
|  |  |  | K |  | R |  |  |  |  |
|  |  |  | K |  | R |  |  |  | V |
|  |  |  | K |  | R |  |  |  | I |
|  |  |  | K |  | R |  |  |  | M |
|  |  |  | K |  | R |  |  |  | F |
|  |  |  | K |  | H |  |  |  |  |
|  |  |  | K |  | H |  |  |  | V |
|  |  |  | K |  | H |  |  |  | I |
|  |  |  | K |  | H |  |  |  | M |
|  |  |  | K |  | H |  |  |  | F |
|  |  |  |  |  |  |  |  |  | V |
|  |  |  |  |  |  |  |  |  | I |
|  |  |  |  |  |  |  |  |  | M |
|  |  |  |  |  |  |  |  |  | F |
|  |  |  |  |  | R |  |  |  |  |
|  |  |  |  |  | R |  |  |  | V |
|  |  |  |  |  | R |  |  |  | I |
|  |  |  |  |  | R |  |  |  | M |
|  |  |  |  |  | R |  |  |  | F |
|  |  |  |  |  | H |  |  |  |  |
|  |  |  |  |  | H |  |  |  | V |
|  |  |  |  |  | H |  |  |  | I |
|  |  |  |  |  | H |  |  |  | M |
|  |  |  |  |  | H |  |  |  | F |
|  |  |  | L |  |  |  |  |  |  |
|  |  |  | L |  |  |  |  |  | V |
|  |  |  | L |  |  |  |  |  | I |
|  |  |  | L |  |  |  |  |  | M |
|  |  |  | L |  |  |  |  |  | F |
|  |  |  | L |  | R |  |  |  |  |
|  |  |  | L |  | R |  |  |  | V |
|  |  |  | L |  | R |  |  |  | I |
|  |  |  | L |  | R |  |  |  | M |
|  |  |  | L |  | R |  |  |  | F |
|  |  |  | L |  | H |  |  |  |  |
|  |  |  | L |  | H |  |  |  | V |
|  |  |  | L |  | H |  |  |  | I |
|  |  |  | L |  | H |  |  |  | M |
|  |  |  | L |  | H |  |  |  | F |

| Position | 1 | 2 | 3 | 4 | 5 | 6 | 7 | 8 | 9 |
|---|---|---|---|---|---|---|---|---|---|
| SEQ ID No 172 | K | L | K | E | R | N | R | E | L |
| Variant |  |  | K |  |  |  |  |  |  |
|  |  |  | K |  |  |  |  |  | V |
|  |  |  | K |  |  |  |  |  | I |
|  |  |  | K |  |  |  |  |  | M |
|  |  |  | K |  |  |  |  |  | F |
|  |  |  |  |  |  |  |  |  | V |
|  |  |  |  |  |  |  |  |  | I |
|  |  |  |  |  |  |  |  |  | M |
|  |  |  |  |  |  |  |  |  | F |
|  |  |  |  |  | H |  |  |  |  |
|  |  |  |  |  | H |  |  |  | V |
|  |  |  |  |  | H |  |  |  | I |
|  |  |  |  |  | H |  |  |  | M |
|  |  |  |  |  | H |  |  |  | F |
|  |  | R |  |  | K |  |  |  |  |
|  |  | R |  |  | K |  |  |  | V |
|  |  | R |  |  | K |  |  |  | I |
|  |  | R |  |  | K |  |  |  | M |
|  |  | R |  |  | K |  |  |  | F |
|  |  | R |  |  |  |  |  |  |  |
|  |  | R |  |  |  |  |  |  | V |
|  |  | R |  |  |  |  |  |  | I |
|  |  | R |  |  |  |  |  |  | M |
|  |  | R |  |  |  |  |  |  | F |
|  |  | R |  |  | H |  |  |  |  |

TABLE 8 -continued

Variants and motif of the peptides according to SEQ ID NO: 3, 225, 13, 17, 84, 108, 113, 114, 147, 36, 51, 172, 54, and 57

|  |  |  |  |  |  |  |  |  |  |  |  |
|---|---|---|---|---|---|---|---|---|---|---|---|
|  |  |  |  |  | R | H |  | V |  |  |  |
|  |  |  |  |  | R | H |  | I |  |  |  |
|  |  |  |  |  | R | H |  | M |  |  |  |
|  |  |  |  |  | R | H |  | F |  |  |  |
|  |  |  |  |  | L | K |  |  |  |  |  |
|  |  |  |  |  | L | K |  | V |  |  |  |
|  |  |  |  |  | L | K |  | I |  |  |  |
|  |  |  |  |  | L | K |  | M |  |  |  |
|  |  |  |  |  | L | K |  | F |  |  |  |
|  |  |  |  |  | L |  |  |  |  |  |  |
|  |  |  |  |  | L |  |  | V |  |  |  |
|  |  |  |  |  | L |  |  | I |  |  |  |
|  |  |  |  |  | L |  |  | M |  |  |  |
|  |  |  |  |  | L |  |  | F |  |  |  |
|  |  |  |  |  | L | H |  |  |  |  |  |
|  |  |  |  |  | L | H |  | V |  |  |  |
|  |  |  |  |  | L | H |  | I |  |  |  |
|  |  |  |  |  | L | H |  | M |  |  |  |
|  |  |  |  |  | L | H |  | F |  |  |  |

| Position | 1 | 2 | 3 | 4 | 5 | 6 | 7 | 8 | 9 | 10 | 11 |
|---|---|---|---|---|---|---|---|---|---|---|---|
| SEQ ID No 54 | A | E | I | T | I | T | T | Q | T | G | Y |
| Variant |  |  |  |  |  |  |  |  |  |  | F |
|  |  |  |  |  |  |  |  |  |  |  | W |
|  |  |  |  |  |  |  |  |  |  |  | L |
|  |  |  |  |  | D |  |  |  |  |  | F |
|  |  |  |  |  | D |  |  |  |  |  | W |
|  |  |  |  |  | D |  |  |  |  |  |  |
|  |  | L |  |  | D |  |  |  |  |  |  |

| Position | 1 | 2 | 3 | 4 | 5 | 6 | 7 | 8 | 9 |
|---|---|---|---|---|---|---|---|---|---|
| SEQ ID No 57 | Q | E | S | D | L | R | L | F | L |
| Variant |  |  |  |  |  |  |  |  | F |
|  |  |  |  |  |  |  |  |  | W |
|  |  |  |  |  |  |  |  |  | Y |
|  |  |  |  | D |  |  |  |  | F |
|  |  |  |  | D |  |  |  |  | W |
|  |  |  |  | D |  |  |  |  | Y |
|  |  |  |  | D |  |  |  |  |  |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 9.

TABLE 9

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |

TABLE 9-continued

Combinations of the elongations of peptides of the invention

| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21, 22, 23, 24 or 25 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 772.

"Consisting essentially of" shall mean that a peptide according to the present invention, in addition to the sequence according to any of SEQ ID NO: 1 to SEQ ID NO 772 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention.

Another embodiment of the present invention relates to a non-naturally occurring peptide wherein said peptide consists or consists essentially of an amino acid sequence according to SEQ ID No: 1 to SEQ ID No: 772 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^{2+}$, $Mg^{2+}$, $Ca^{2+}$, $Mn^{2+}$, $Cu^{2+}$ and $Ba^{2+}$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Ck$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNOB$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)_2$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$), such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

For the identification of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from ovarian cancer samples (N≥80 samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from ≥80 ovarian cancer patients (cf. Example 1).

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

HLA-peptide complexes from ovarian cancer tissue samples were purified and HLA-associated peptides were isolated and analyzed by LC-MS (see example 1). All TUMAPs contained in the present application were identified with this approach on primary ovarian cancer samples confirming their presentation on primary ovarian cancer.

Figure 1B:
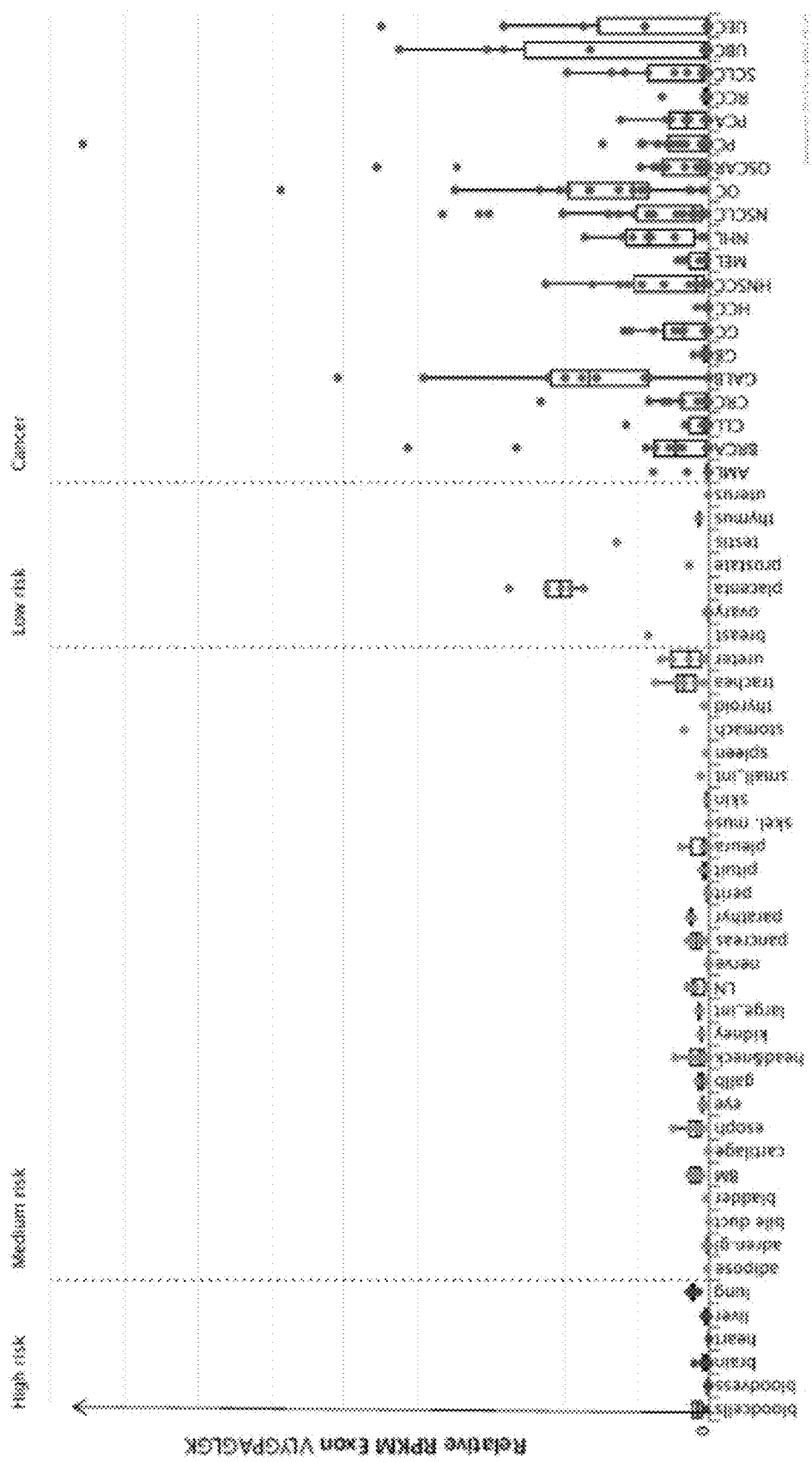
Figure 1C:
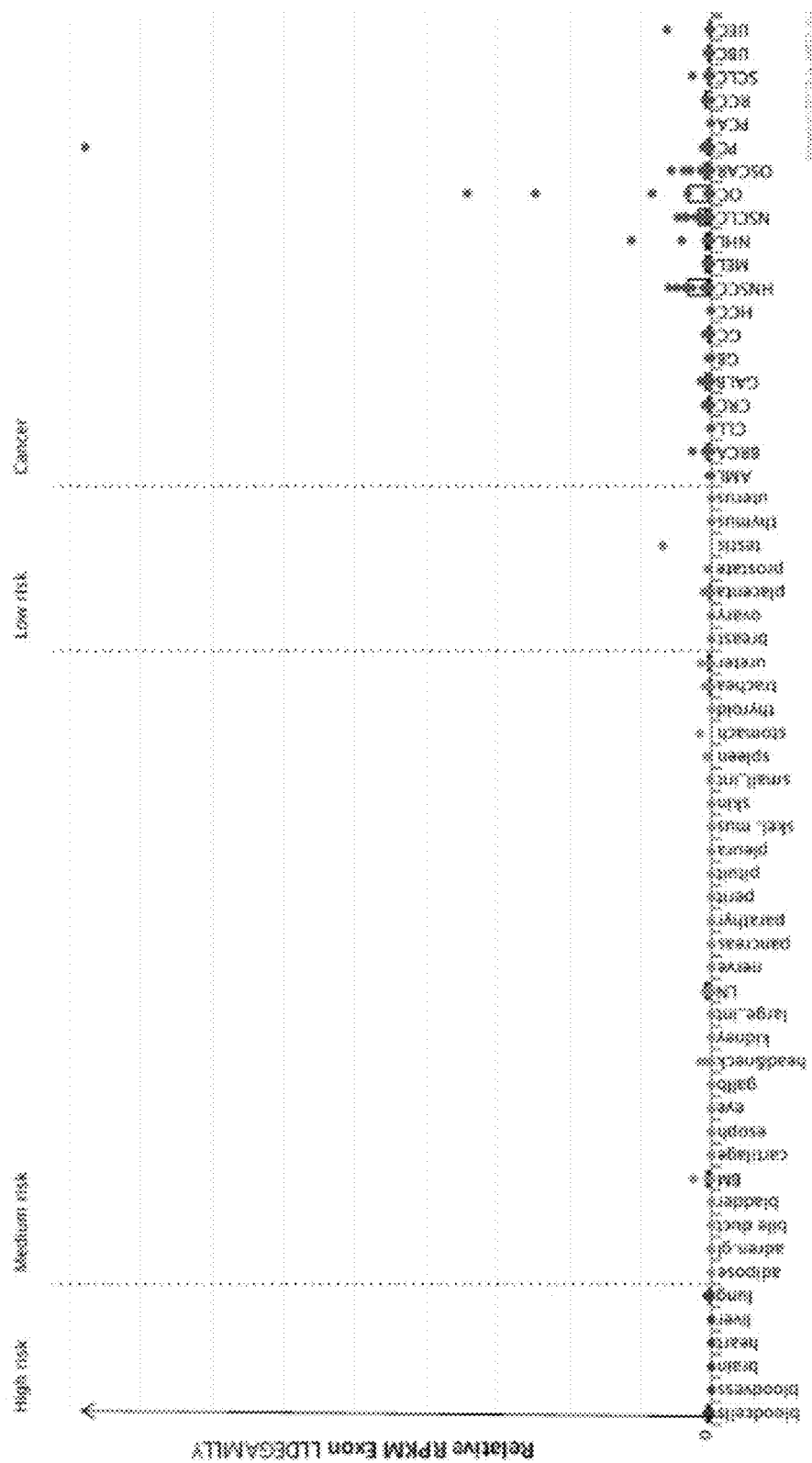
Figure 1D:
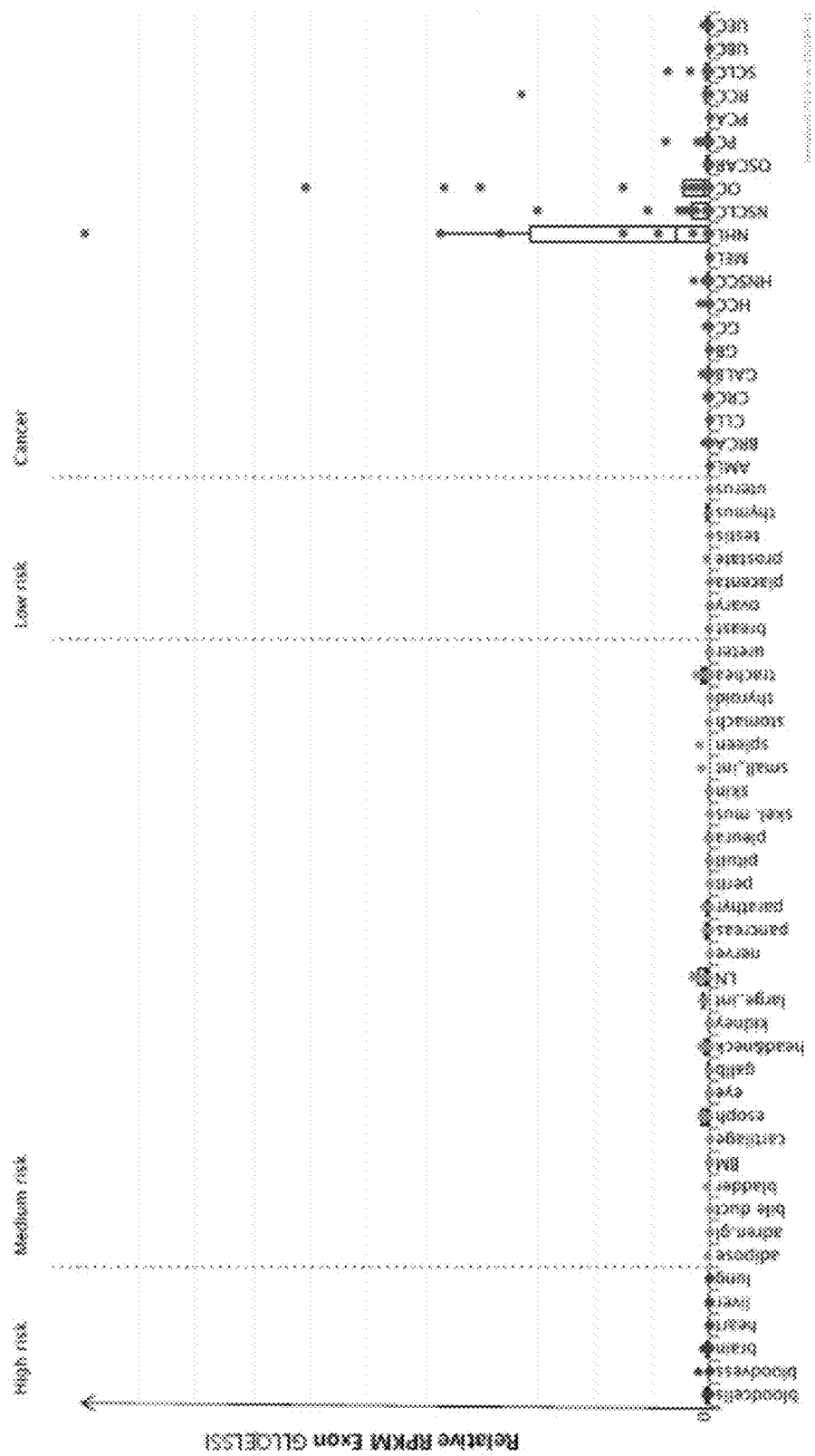
Figure 1E:
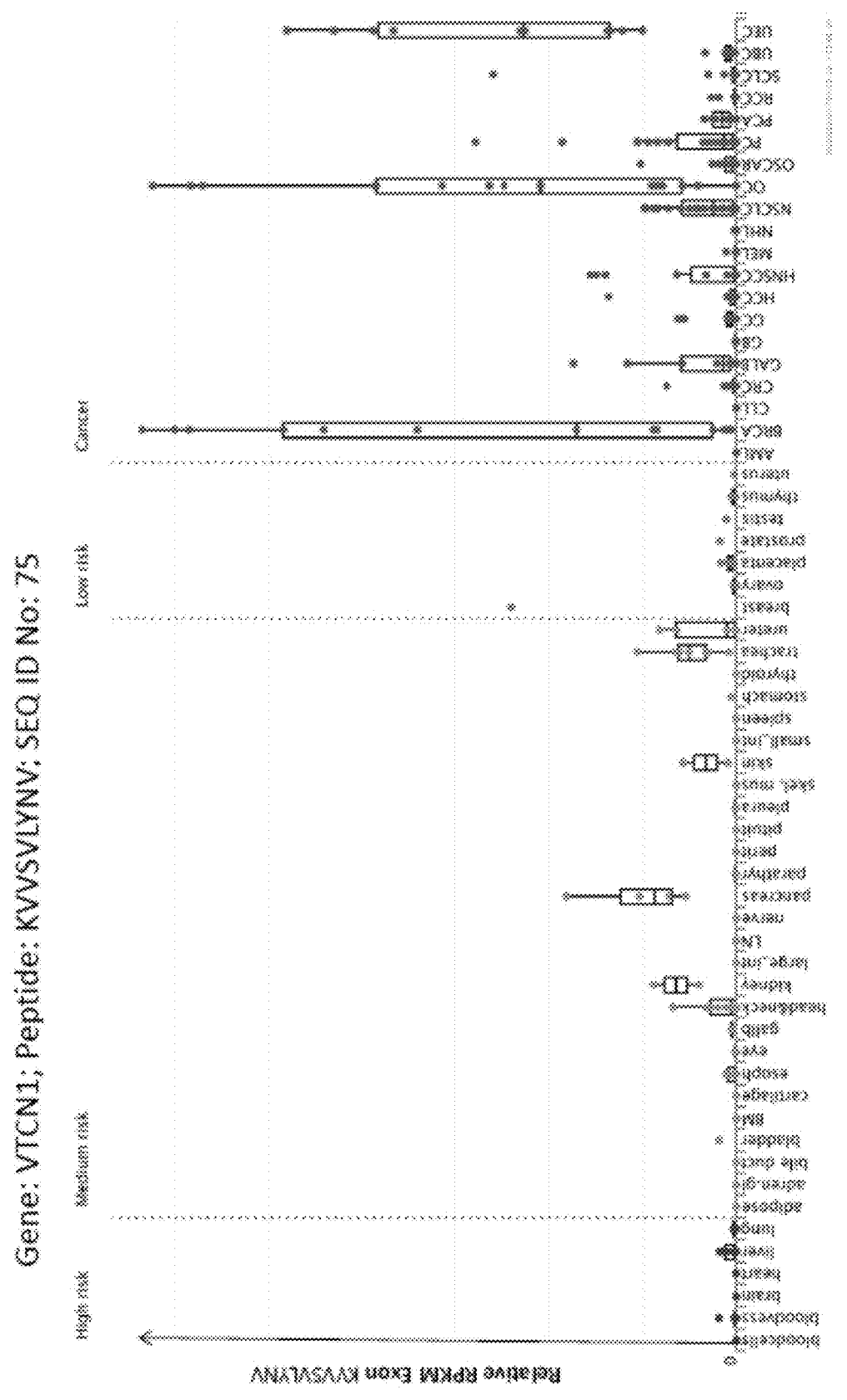
Figure 1H:
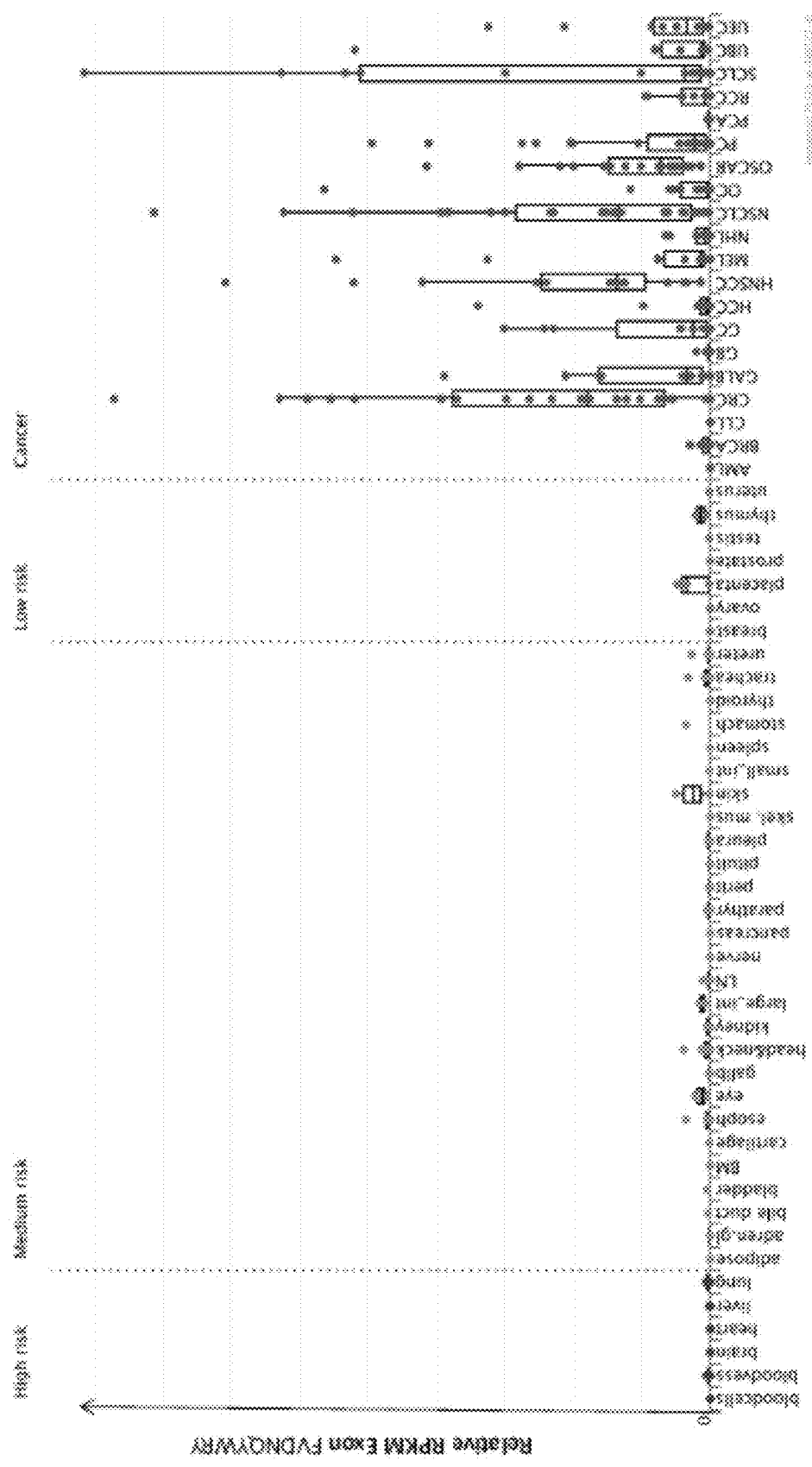
Figure 1J:
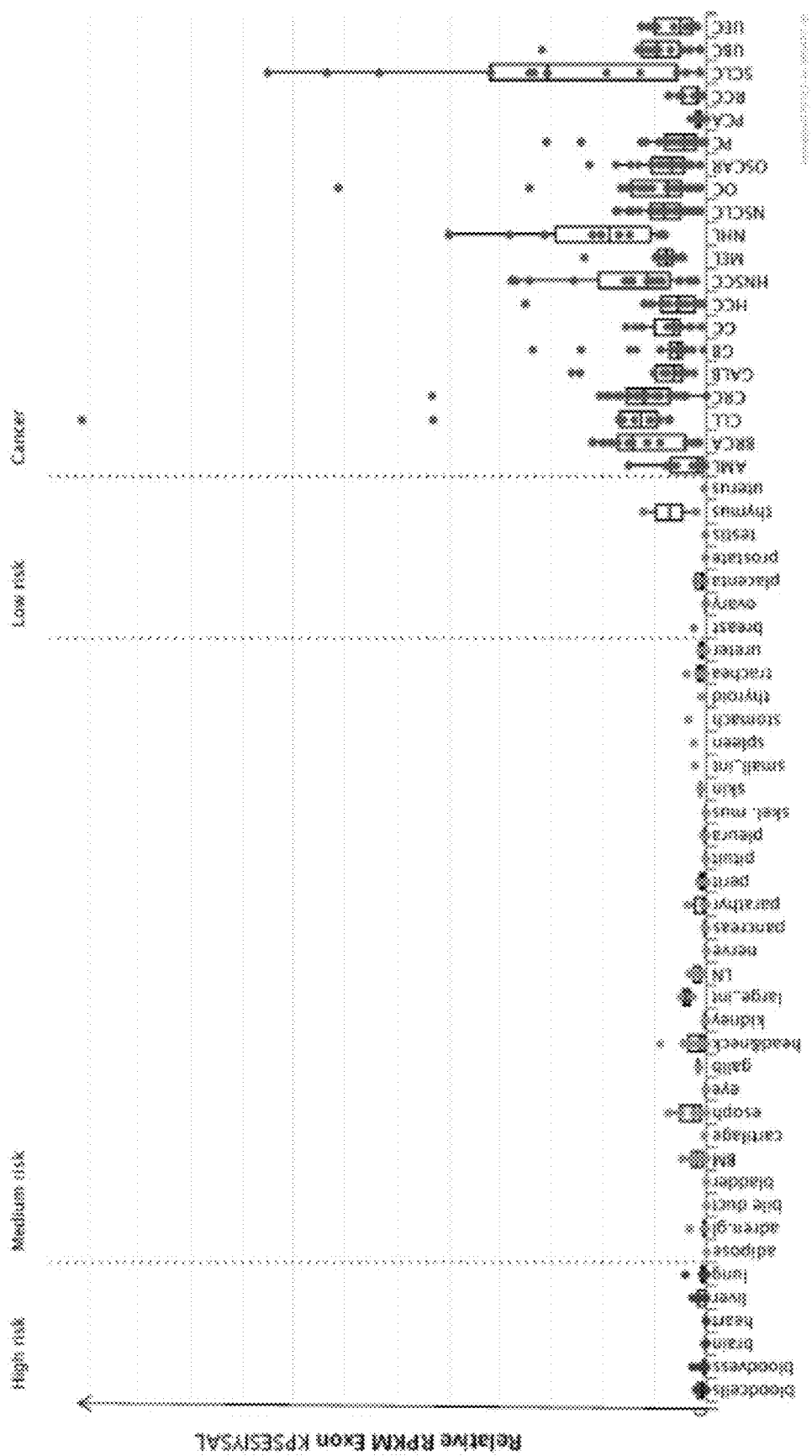
Figure 1K:
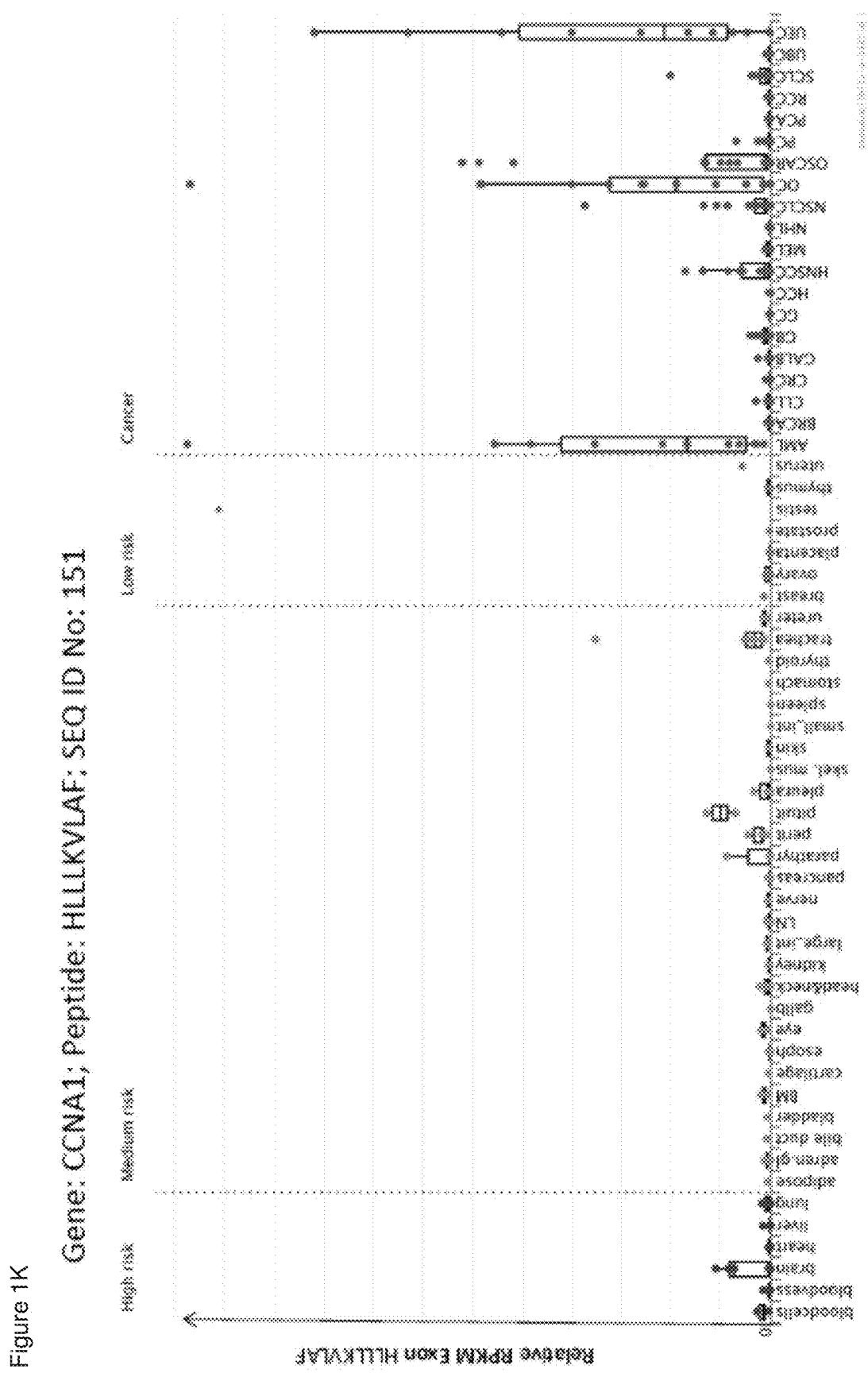
Figure 1L:
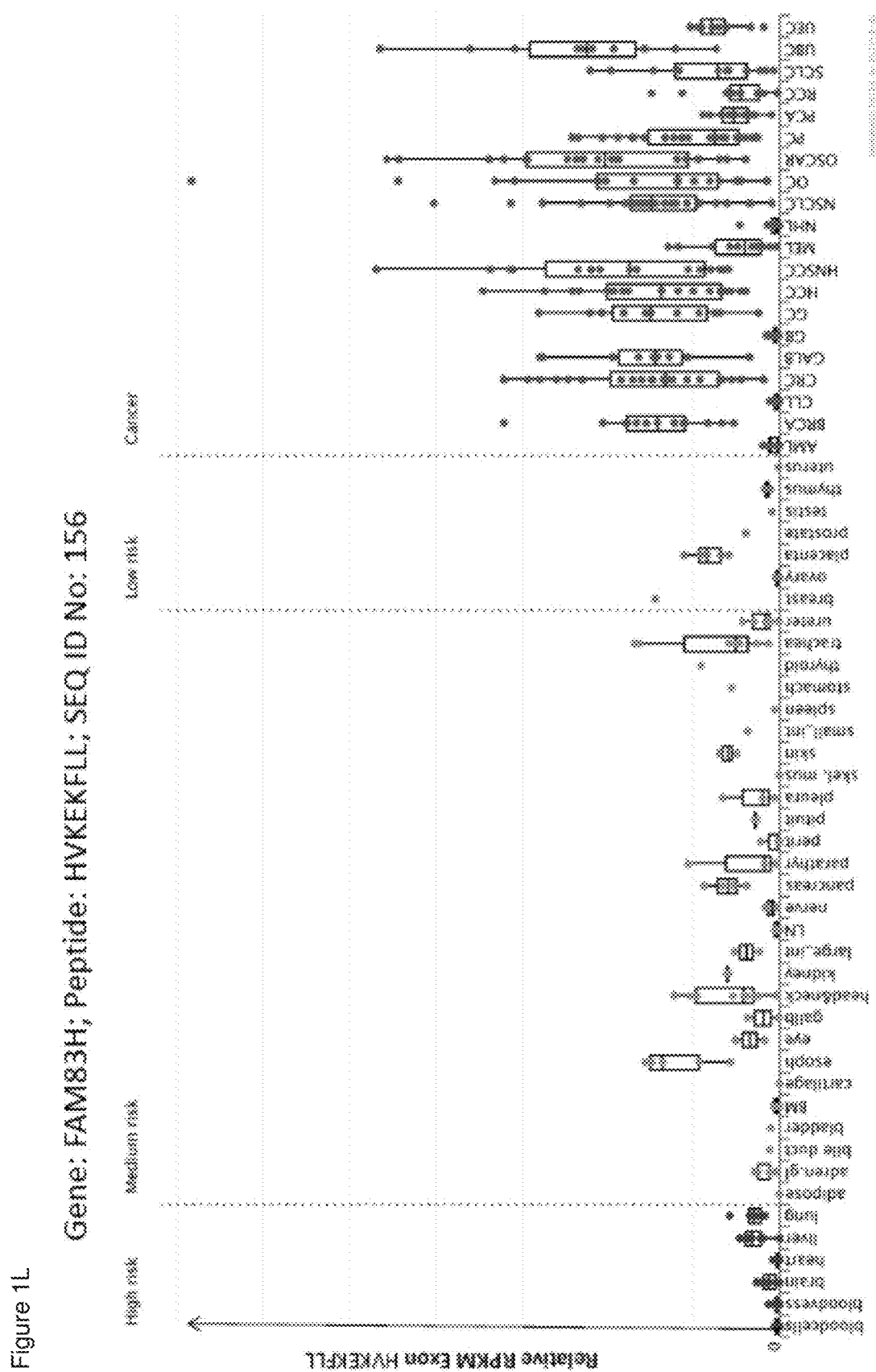
Figure 1N:
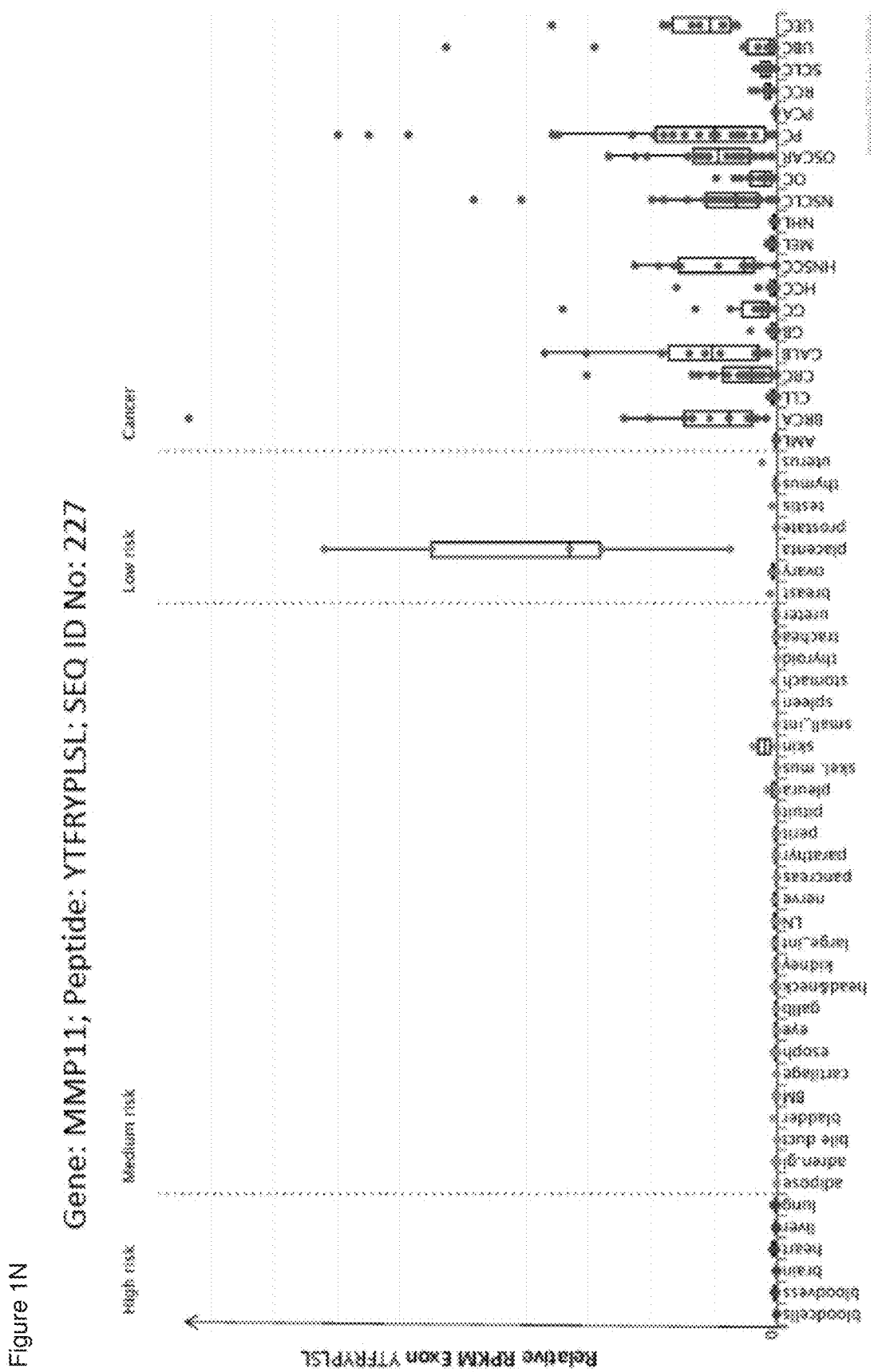
Figure 10:
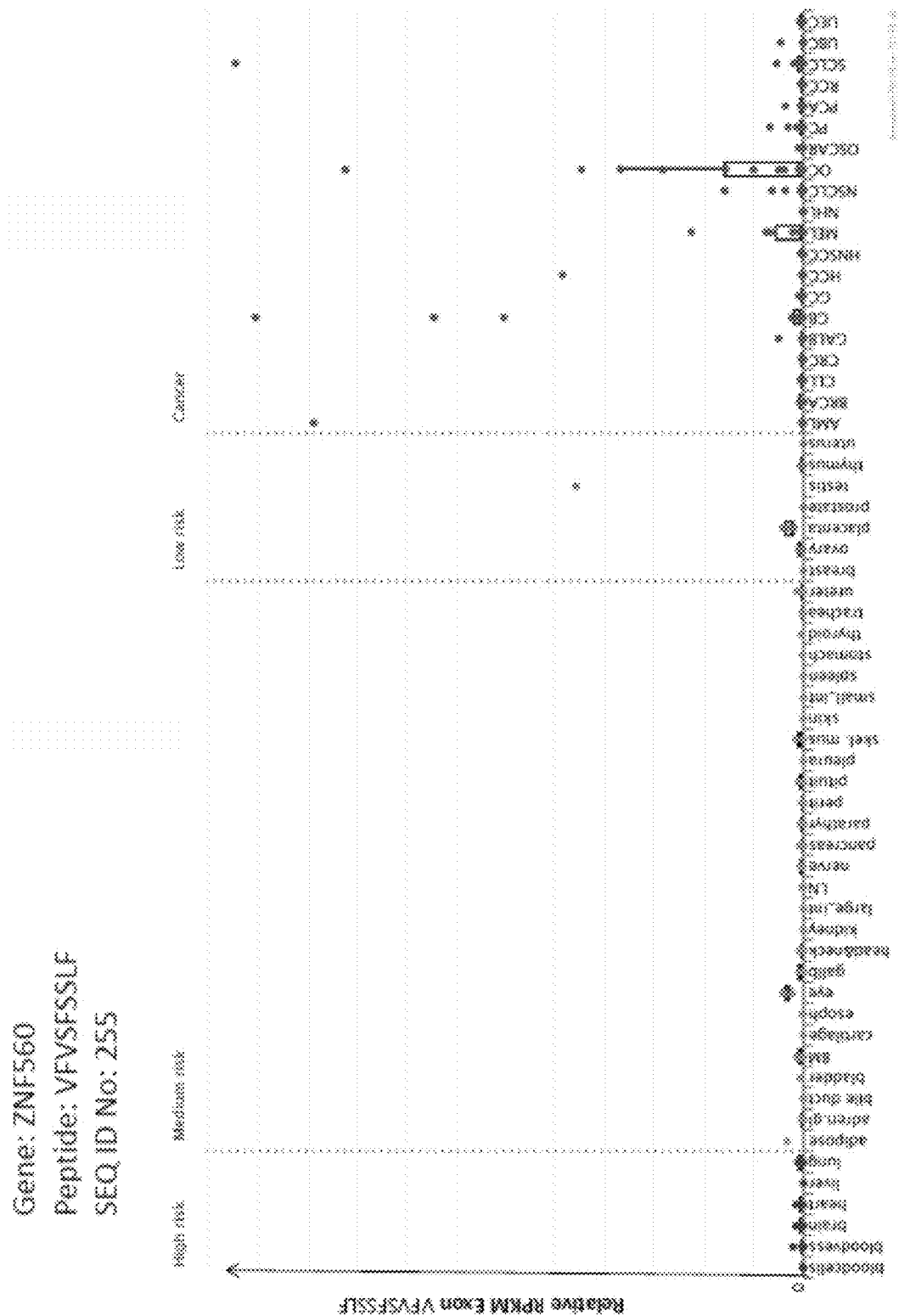
Figure 1P:
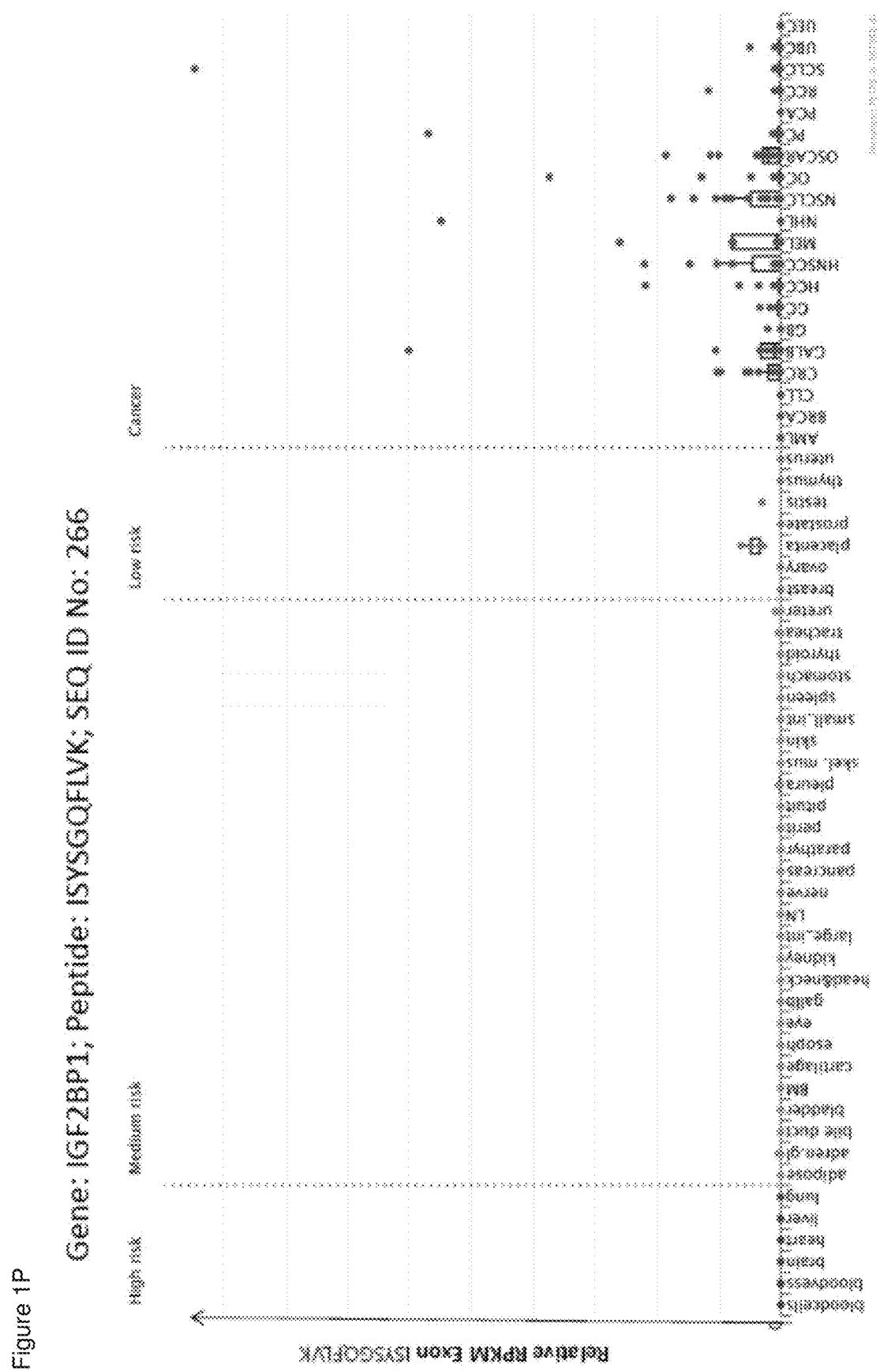
Figure 1Q:
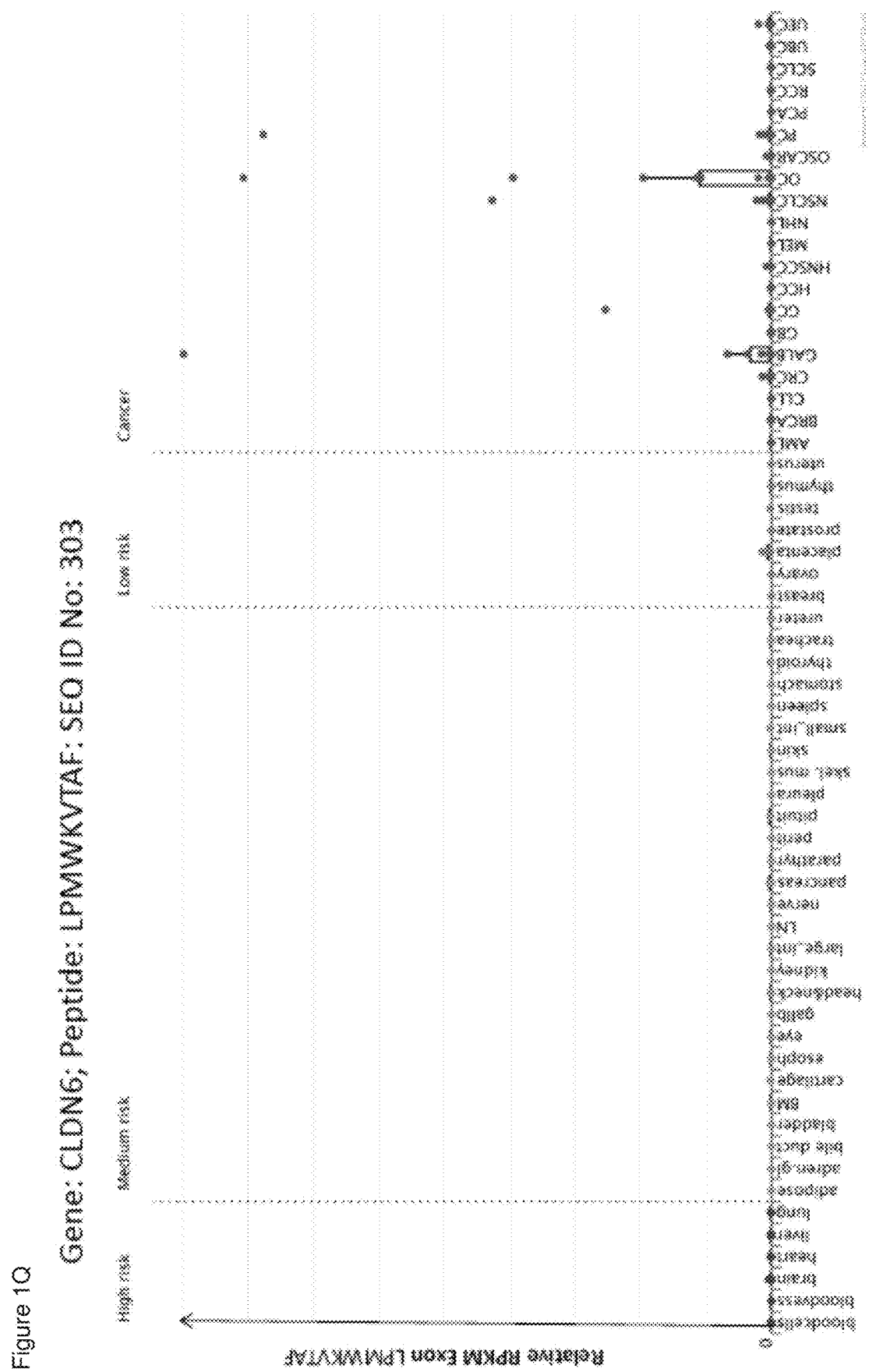
Figure 1R:
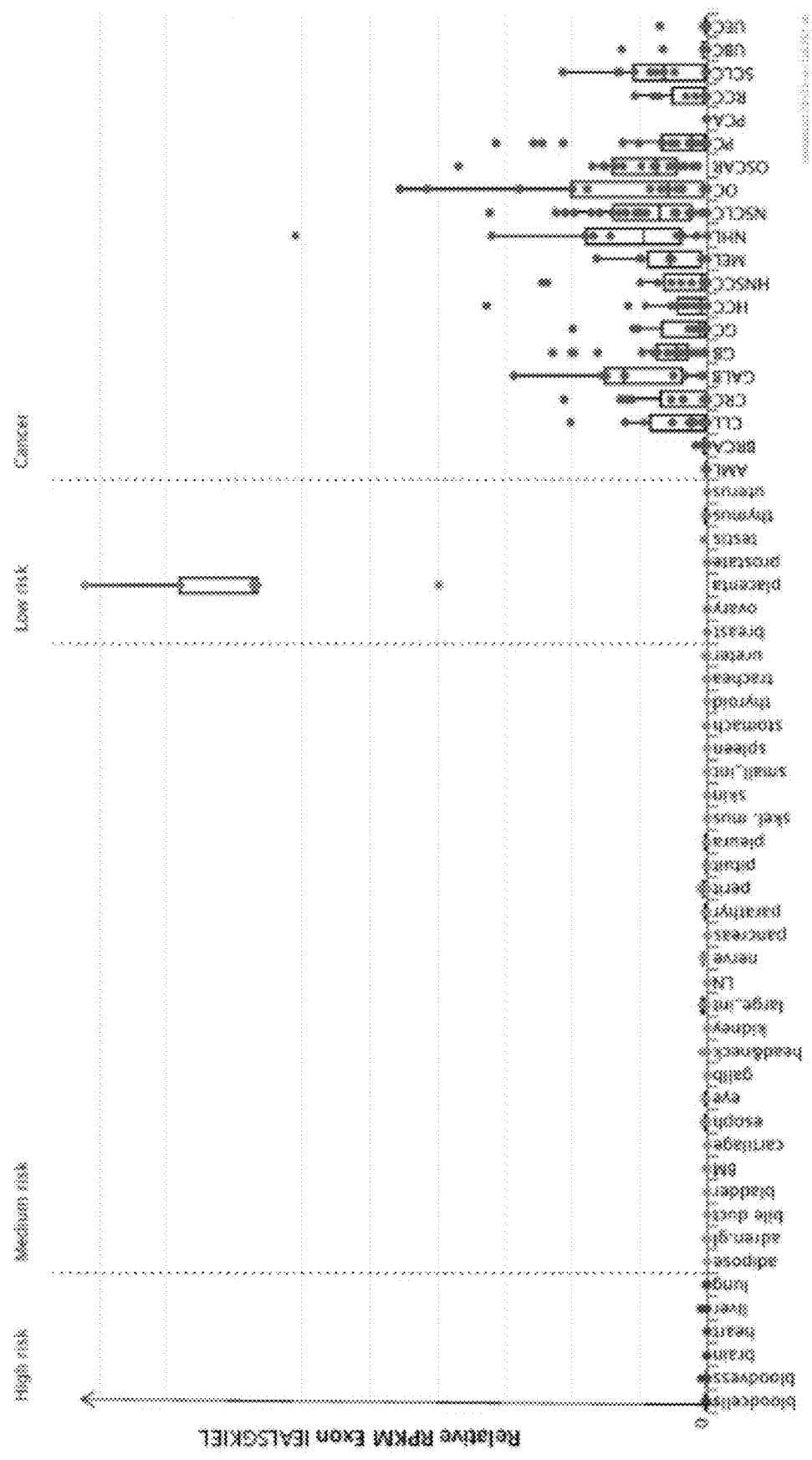
Figure 1T:
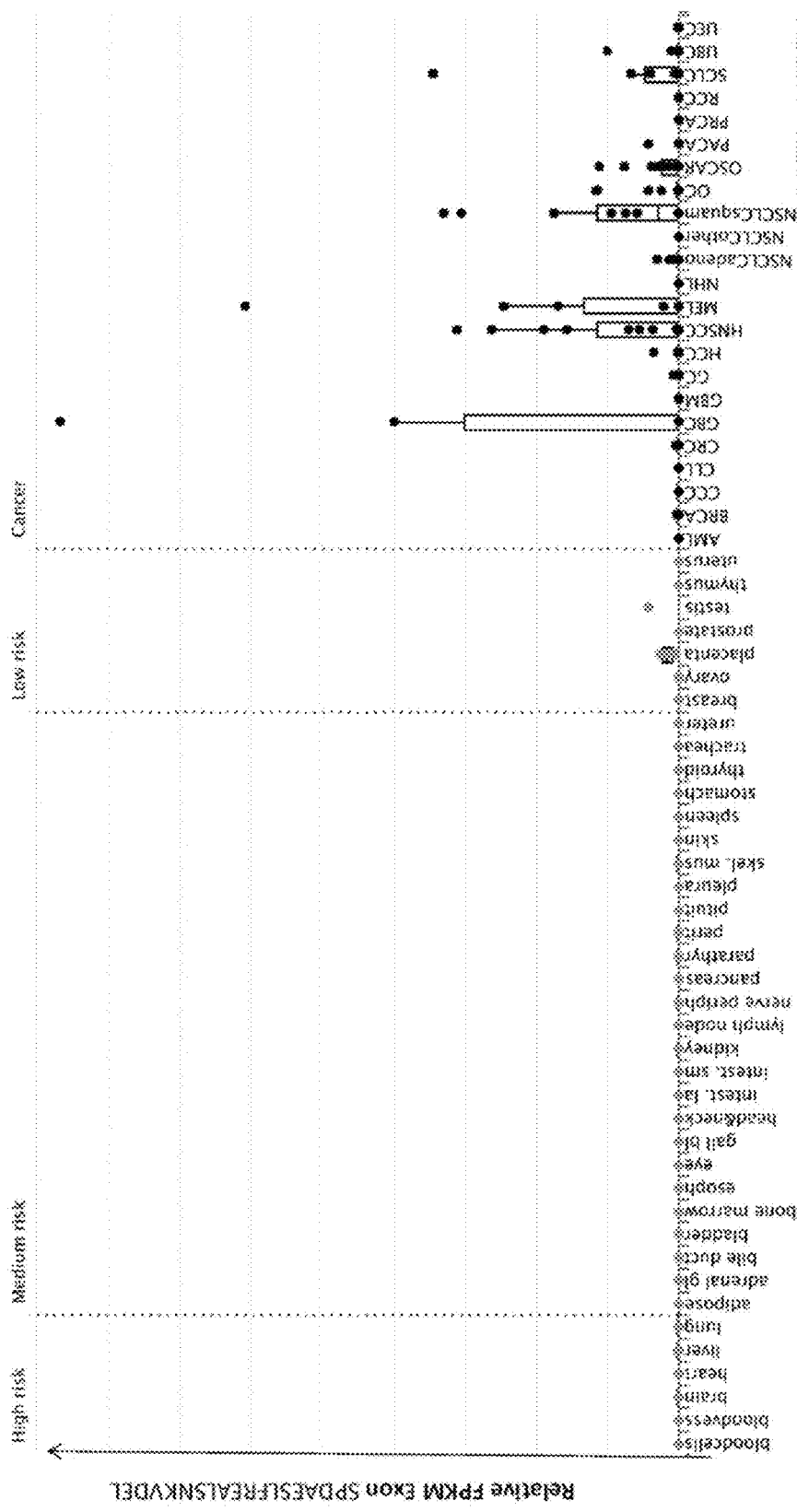
Figure 1V:
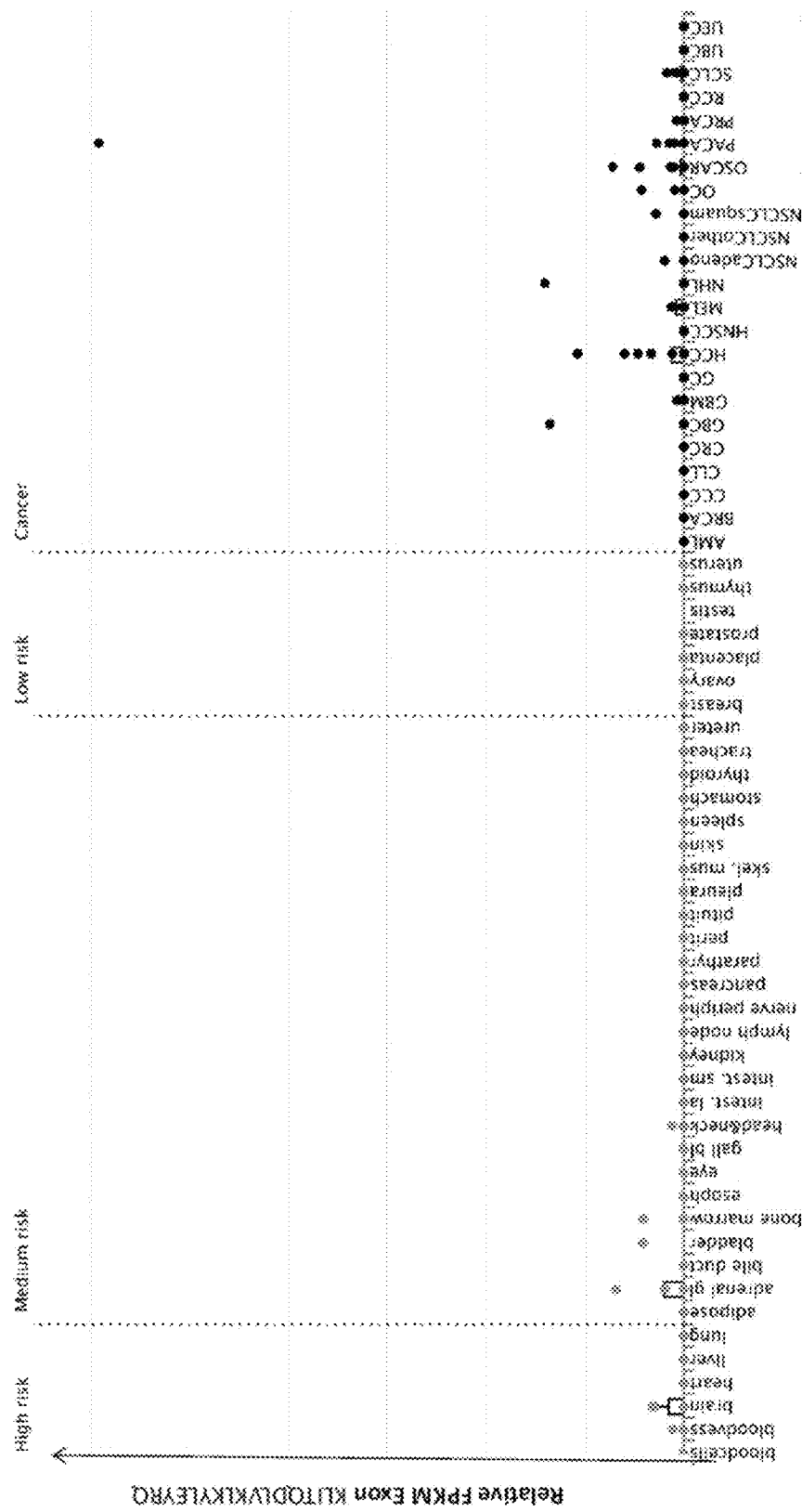

Besides presentation of the peptide, mRNA expression of the underlying gene was tested. mRNA data were obtained via RNASeq analyses of normal tissues and cancer tissues (cf. Example 2, FIGS. 1A-1V). Peptides which are derived from proteins whose coding mRNA is highly expressed in cancer tissue, but very low or absent in vital normal tissues, were preferably included in the present invention.

The present invention provides peptides that are useful in treating cancers/tumors, preferably ovarian cancer that over- or exclusively present the peptides of the invention.

These peptides were shown by mass spectrometry to be naturally presented by HLA molecules on primary human ovarian cancer samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy ovarian cells or other normal tissue cells, demonstrating a high degree of tumor association of the source genes (see Example 2). Moreover, the peptides themselves are presented on tumor tissue—"tumor tissue" in relation to this invention shall mean a sample from a patient suffering from ovarian cancer.

HLA-bound peptides can be recognized by the immune system, specifically T lymphocytes. T cells can destroy the cells presenting the recognized HLA/peptide complex, e.g. ovarian cancer cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well (see also below). Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides according to the invention capable of binding to TCRs and antibodies when presented by an MHC molecule.

The present description also relates to fragments of the TCRs according to the invention that are capable of binding to a peptide antigen according to the present invention when presented by an HLA molecule. The term particularly relates to soluble TCR fragments, for example TCRs missing the transmembrane parts and/or constant regions, single chain TCRs, and fusions thereof to, for example, with Ig.

The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to an peptide-HLA molecule complex with a binding affinity (KD) of about 100 μM or less, about 50 μM or less, about 25 μM or less, or about 10 μM or less. More preferred are high affinity TCRs having binding affinities of about 1 μM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 μM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to peptides can be enhanced by methods well known in the art.

The present description further relates to a method of identifying and isolating a TCR according to the present description, said method comprising incubating PBMCs from HLA-A*02-negative healthy donors with, for example, A2/peptide monomers, incubating the PBMCs with tetramer-phycoerythrin (PE) and isolating the high avidity T-cells by fluo-rescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with a peptide, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced (Schmitt et al., 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion) (Schmitt et al., 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 772, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example E. coli and Bacillus subtilis), yeasts (for example Saccharomyces cerevisiae), filamentous fungi (for example Aspergillus spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment, the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 μg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLRS ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly- (I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28. For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as si RNA into tumor cells.

Aptamers can be selected against complex targets such as cells and tissues and complexes of the peptides comprising, preferably consisting of, a sequence according to any of SEQ ID NO 1 to SEQ ID NO 772, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen (preferably a peptide according to the present invention), the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is thus a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 772, or a variant thereof which is at least 88% homologous (preferably identical) to SEQ ID NO: 1 to SEQ ID NO: 772 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 772 or a variant thereof which is at least 88% homologous (preferably identical) to SEQ ID NO: 1 to SEQ ID NO: 772, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 772.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of ovarian cancer.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, where-in the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 772 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are ovarian cancer cells or other solid or hematological tumor cells such as hepatocellular carcinoma, colorectal carcinoma, glioblastoma, gastric cancer, esophageal cancer, non-small cell lung cancer, small cell lung cancer, pancreatic cancer, renal cell carcinoma, prostate cancer, melanoma, breast cancer, chronic lymphocytic leukemia, Non-Hodgkin lymphoma, acute myeloid leukemia, gallbladder cancer and cholangiocarcinoma, urinary bladder cancer, uterine cancer, head and neck squamous cell carcinoma, mesothelioma.

The present invention further relates to particular marker proteins and biomarkers based on the peptides according to the present invention, herein called "targets" that can be used in the diagnosis and/or prognosis of ovarian cancer. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a ovarian cancer marker (poly)peptide, delivery of a toxin to a ovarian cancer cell expressing a cancer marker gene at an increased level, and/or inhibiting the activity of a ovarian cancer marker polypeptide) according to the invention.

Whenever possible, the antibodies of the invention may be purchased from commercial sources. The antibodies of the invention may also be generated using well-known methods. The skilled artisan will understand that either full length ovarian cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 772 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the ovarian cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating ovarian cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 772, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively eliciting high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, and vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 772.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual"

the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from ovarian cancer, the medicament of the invention is preferably used to treat ovarian cancer.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of ovarian cancer patients with various HLA-A HLA-B and HLA-C alleles. It may contain MHC class I and MHC class II peptides or elongated MHC class I peptides. In addition to the tumor associated peptides collected from several ovarian cancer tissues, the warehouse may contain HLA-A*02, HLA-A*01, HLA-A*03, HLA-A*24, HLA-B*07, HLA-B*08 and HLA-B*44 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, ovarian cancer samples from patients and blood from healthy donors were analyzed in a stepwise approach:
1. HLA ligands from the malignant material were identified by mass spectrometry
2. Genome-wide messenger ribonucleic acid (mRNA) expression analysis was used to identify genes over-expressed in the malignant tissue (ovarian cancer) compared with a range of normal organs and tissues
3. Identified HLA ligands were compared to gene expression data. Peptides presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from ovarian cancer patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory, an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 pg per peptide) will be applied for intradermal injection.

In addition to being useful for treating cancer, the peptides of the present invention are also useful as diagnostics. Since the peptides were generated from ovarian cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for ovarian cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

FIGURES

FIGS. 1A through 1S show exemplary expression profile of source genes of the present invention that are over-expressed in different cancer samples. Tumor (black dots) and normal (grey dots) samples are grouped according to organ of origin, and box-and-whisker plots represent median, 25th and 75th percentile (box), and minimum and maximum (whiskers) RPKM values. Normal organs are ordered according to risk categories. RPKM=reads per kilobase per million mapped reads. Normal samples: blood cells; blood vessel; brain; heart; liver; lung; adipose: adipose tissue; adren.gl.: adrenal gland; bile duct; bladder; BM: bone marrow; cartilage; esoph: esophagus; eye; gallb: gallbladder; head and neck; kidney; large_int: large intestine; LN: lymph node; nerve; pancreas; parathyr: parathyroid; pituit: pituitary; skel.mus: skeletal muscle; skin; small_int: small intestine; spleen; stomach; thyroid; trachea; bladder; breast; ovary; placenta; prostate; testis; thymus; uterus. Tumor samples: AML: acute myeloid leukemia; BRCA: breast cancer; CLL: chronic lymphocytic leukemia; CRC: colorectal cancer; GALB: gallbladder cancer; GB: glioblastoma; GC: gastric cancer; HCC: hepatocellular carcinoma; HNSCC: head-and-neck cancer; MEL: melanoma; NHL: non-hodgkin lymphoma; NSCLC: non-small cell lung cancer; OC: ovarian cancer; OSC_GC: esophageal/gastric cancer; OSCAR: esophageal cancer; PC: pancreatic cancer; PCA: prostate cancer; RCC: renal cell carcinoma; SCLC: small cell lung cancer; UBC: urinary bladder carcinoma; UEC: uterine and endometrial cancer. FIG. 1A) Gene symbol: CT45A2, Peptide: KYEKIFEML (SEQ ID No.: 12), FIG. 1B) Gene symbol: NLRP2, Peptide: VLYGPAGLGK (SEQ ID No.: 27), FIG. 1C) Gene symbol: NLRP7, Peptide: LLDEGAMLLY (SEQ ID No.: 31), FIG. 1D) Gene symbol: HTR3A, Peptide: GLLQELSSI (SEQ ID No.: 66), FIG. 1E) Gene symbol: VTCN1, Peptide: KVVSVLYNV (SEQ ID No.: 75), FIG. 1F) Gene symbol: CYP2W1, Peptide: RYGPVFTV (SEQ ID No.: 98), FIG. 1G) Gene symbol: MMP11, Peptide: LLQPPPLLAR (SEQ ID No.: 98), FIG. 1H) Gene symbol: MMP12, Peptide: FVDNQYWRY (SEQ ID No.: 115), FIG. 1I) Gene symbol: CTAG2, Peptide: APLPRPGAVL (SEQ ID No.: 119), FIG. 1J) Gene symbol: FAM111B, Peptide: KPSESIYSAL (SEQ ID No.: 123), FIG. 1K) Gene symbol: CCNA1, Peptide: HLLLKVLAF (SEQ ID No.: 151), FIG. 1L) Gene symbol: FAM83H, Peptide: HVKEKFLL (SEQ ID No.: 156), FIG. 1M) Gene symbol: MAGEA11, Peptide: KEVDPTSHSY (SEQ ID No.: 194), FIG. 1N) Gene symbol: MMP11, Peptide: YTFRYPLSL (SEQ ID No.: 227), FIG. 1O) Gene symbol: ZNF560, Peptide: VFVSFSSLF (SEQ ID No.: 255), FIG. 1P) Gene symbol: IGF2BP1, Peptide: ISYSGQFLVK (SEQ ID No.: 266), FIG. 1Q) Gene symbol: CLDN6, Peptide: LPMWKVTAF (SEQ ID No.: 303), FIG. 1R) Gene symbol: IGF2BP3, Peptide: IEALSGKIEL (SEQ ID No.: 413), FIG. 1S) Gene symbol: PRAME, Peptide: EEQYIAQF (SEQ ID No.: 432).

FIGS. 1T through 1V show exemplary expression profiles of source genes of the present invention, that are overexpressed in different cancer samples. Tumor (black dots) and normal (grey dots) samples are grouped according to organ of origin. Box-and-whisker plots represent median FPKM value, 25th and 75th percentile (box) plus whiskers that extend to the lowest data point still within 1.5 interquartile range (IQR) of the lower quartile and the highest data point still within 1.5 IQR of the upper quartile. Normal organs are ordered according to risk categories. FPKM: fragments per kilobase per million mapped reads. Normal samples: blood cells; bloodvess (blood vessels); brain; heart; liver; lung; adipose (adipose tissue); adrenal gl (adrenal gland); bile duct; bladder; bone marrow; cartilage; esoph (esophagus); eye; gall bl (gallbladder); head&neck; intest. la (large intestine); intest. sm (small intestine); kidney; lymph node; nerve perith (peripheral nerve); pancreas; parathyr (parathyroid gland); perit (peritoneum); pituit (pituitary); pleura; skel. mus (skeletal muscle); skin; spleen; stomach; thyroid; trachea; ureter; breast; ovary; placenta; prostate; testis; thymus; uterus. Tumor samples: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); HCC (hepatocellular carcinoma); HNSCC (head and neck squamous cell carcinoma); MEL (melanoma); NHL (non-hodgkin lymphoma); NSCLCadeno (non-small cell lung cancer adenocarcinoma); NSCLCother (NSCLC samples that could not unambiguously be assigned to NSCLCadeno or NSCLCsquam); NSCLCsquam (squamous cell non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine and endometrial cancer). FIG. 1T) Gene symbol: MAGEA4, Peptide: SPDAESLFREALSNKVDEL (SEQ ID No.: 597), FIG. 1U) Gene symbol: MAGEA4, Peptide: LSNKVDELAHFLLRK (SEQ ID No.: 601), FIG. 1V) Gene symbol: MAGEB3, Peptide: KLITQDLVKLKYLEYRQ (SEQ ID No.: 604).

Figure 2:
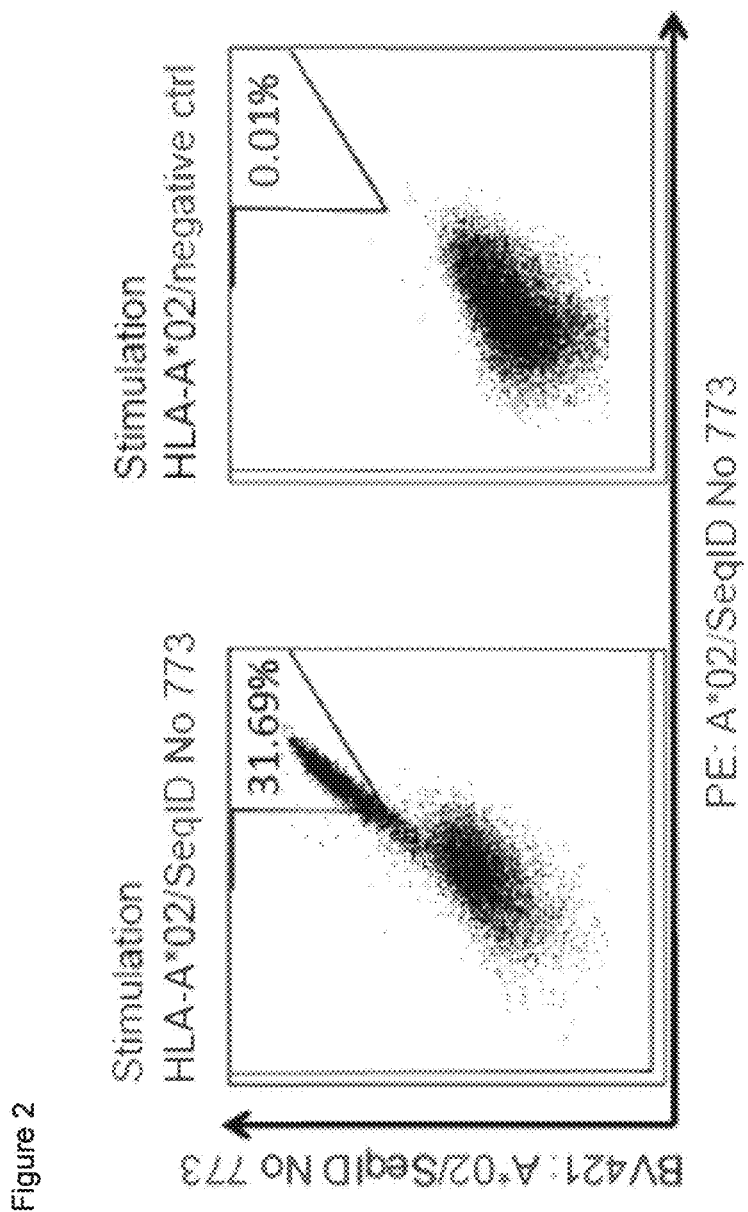

FIG. 2 shows exemplary results of peptide-specific in vitro CD8+ T cell responses of a healthy HLA-A*02+ donor. CD8+ T cells were primed using artificial APCs coated with anti-CD28 mAb and HLA-A*02 in complex with SeqID No 773 peptide (ALYGKLLKL, Seq ID NO: 773) left panel. After three cycles of stimulation, the detection of peptide-reactive cells was performed by 2D multimer staining with A*02/SeqID No 773. Right panel shows control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 3:
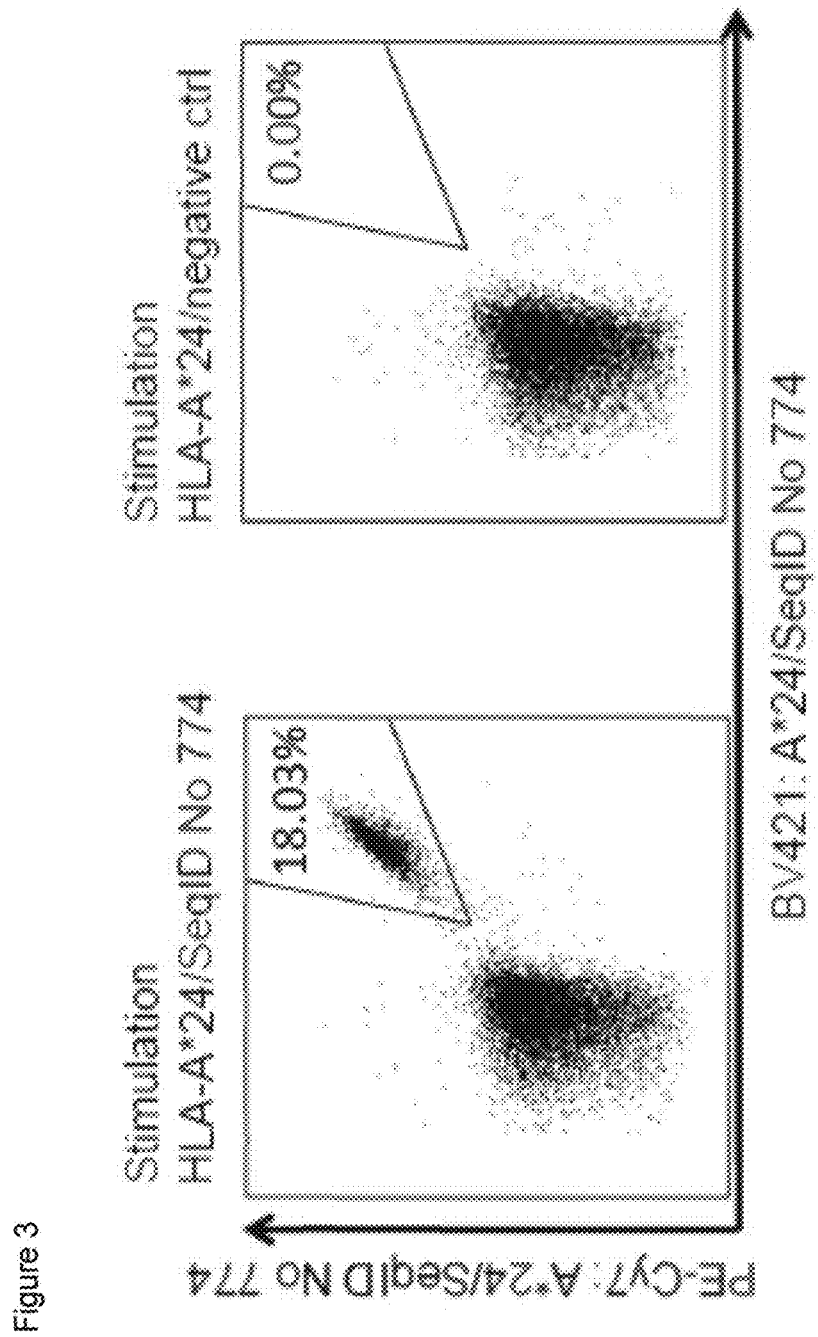

FIG. 3 shows exemplary results of peptide-specific in vitro CD8+ T cell responses of a healthy HLA-A*24+ donor. CD8+ T cells were primed using artificial APCs coated with anti-CD28 mAb and HLA-A*24 in complex with SeqID No 774 peptide (left panel). After three cycles of stimulation, the detection of peptide-reactive cells was performed by 2D multimer staining with A*24/SeqID No 774 (VYVDDIYVI, Seq ID NO: 774). Right panel shows control staining of cells stimulated with irrelevant A*24/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 4A:
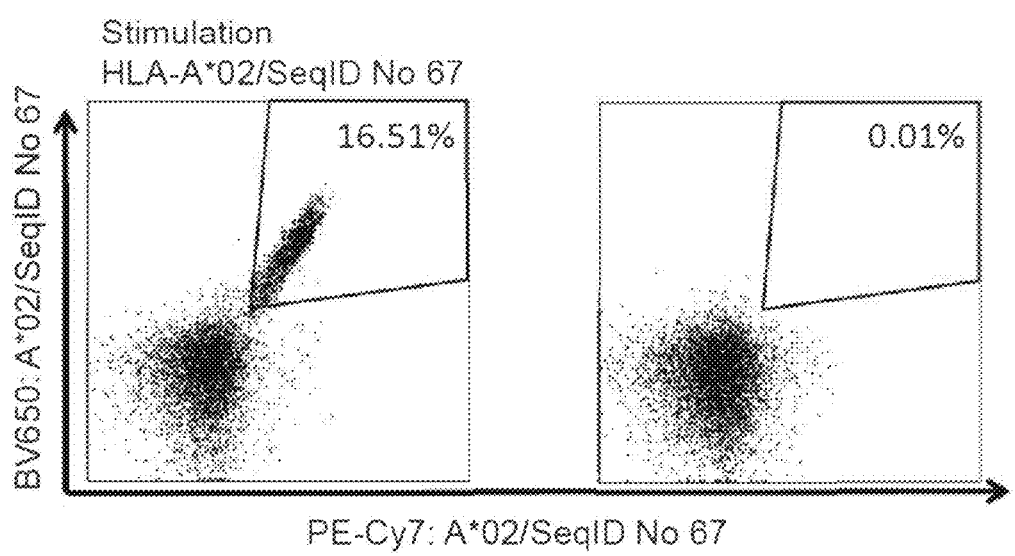
Figure 4B:
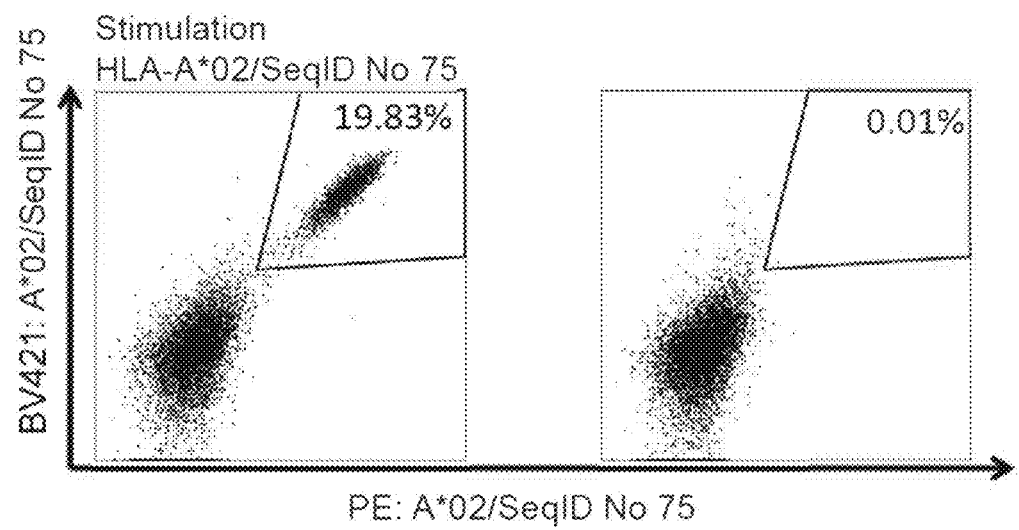

FIGS. 4A and 4B shows exemplary results of peptide-specific in vitro CD8+ T cell responses of a healthy HLA-A*02+ donor. CD8+ T cells were primed using artificial APCs coated with anti-CD28 mAb and HLA-A*02 in complex with SeqID No 67 peptide SLLLPSIFL (FIG. 4A, left panel) and SeqID No 75 peptide KVVSVLYNV (FIG. 4B, left panel), respectively. After three cycles of stimulation, the detection of peptide-reactive cells was performed by 2D multimer staining with A*02/SeqID No 67 (FIG. 4A) or A*02/SeqID No 75 (FIG. 4B). Right panels (FIGS. 4A and 4B) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 5A:
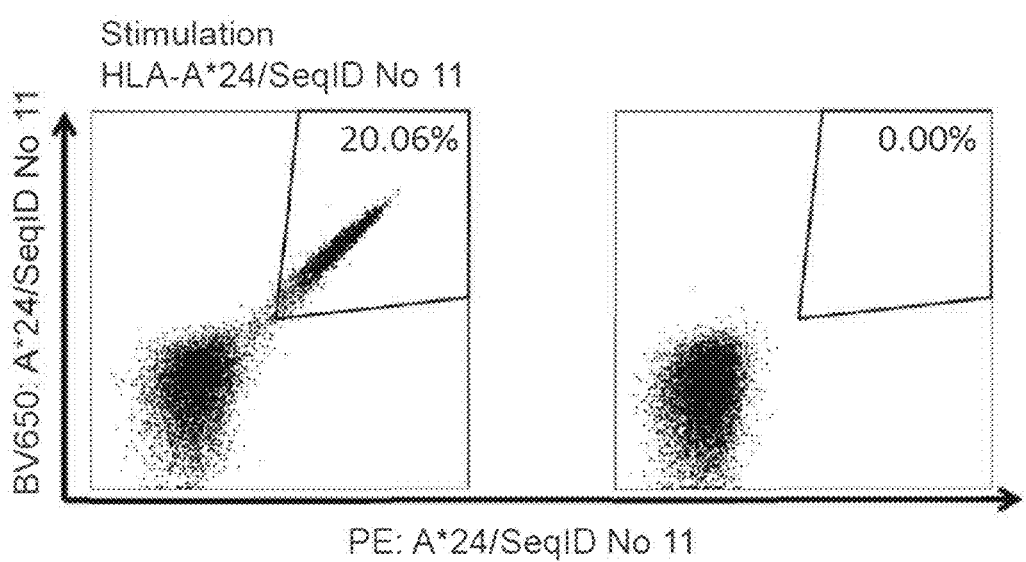
Figure 5B:
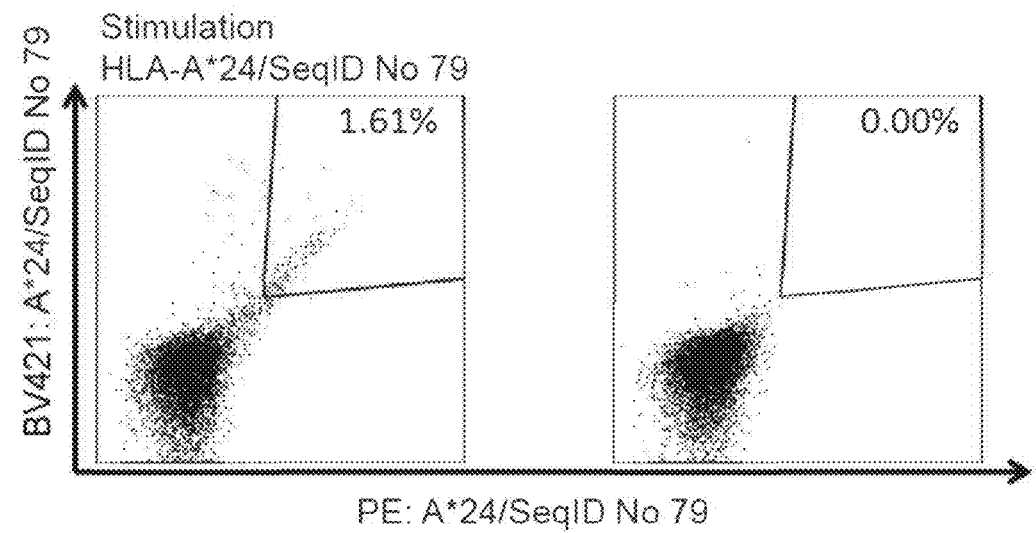

FIGS. 5A and 5B shows exemplary results of peptide-specific in vitro CD8+ T cell responses of a healthy HLA-A*24+ donor. CD8+ T cells were primed using artificial APCs coated with anti-CD28 mAb and HLA-A*24 in complex with SeqID No 11 peptide SYSDLHYGF (FIG. 5A, left panel) and SeqID No 79 peptide SYNEHWNYL (FIG. 5B, left panel), respectively. After three cycles of stimulation, the detection of peptide-reactive cells was performed by 2D multimer staining with A*24/SeqID No 11 (FIG. 5A) or A*24/SeqID No 79 (FIG. 5B). Right panels (FIGS. 5A and 5B) show control staining of cells stimulated with irrelevant A*24/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 6A:
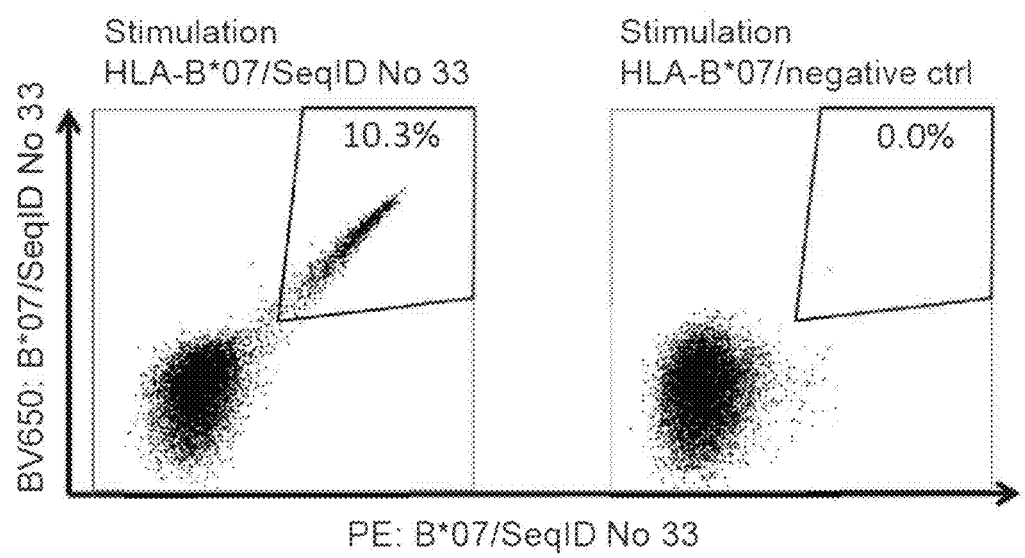
Figure 6B:
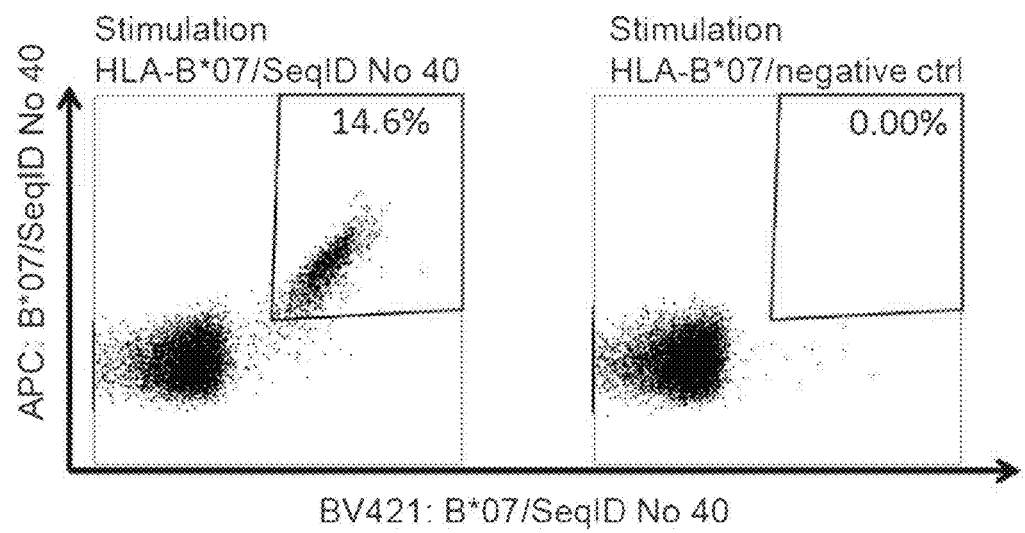

FIGS. 6A and 6B show exemplary results of peptide-specific in vitro CD8+ T cell responses of a healthy HLA-B*07+ donor. CD8+ T cells were primed using artificial APCs coated with anti-CD28 mAb and HLA-B*07 in complex with SeqID No 33 peptide SPTFHLTL (FIG. 6A, left panel) and SeqID No 40 peptide KPGTSYRVTL (FIG. 6B, left panel), respectively. After three cycles of stimulation, the detection of peptide-reactive cells was performed by 2D multimer staining with B*07/SeqID No 33 (FIG. 6A) or B*07/SeqID No 40 (FIG. 6B). Right panels (FIGS. 6A and 6B) show control staining of cells stimulated with irrelevant B*07/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 7A:
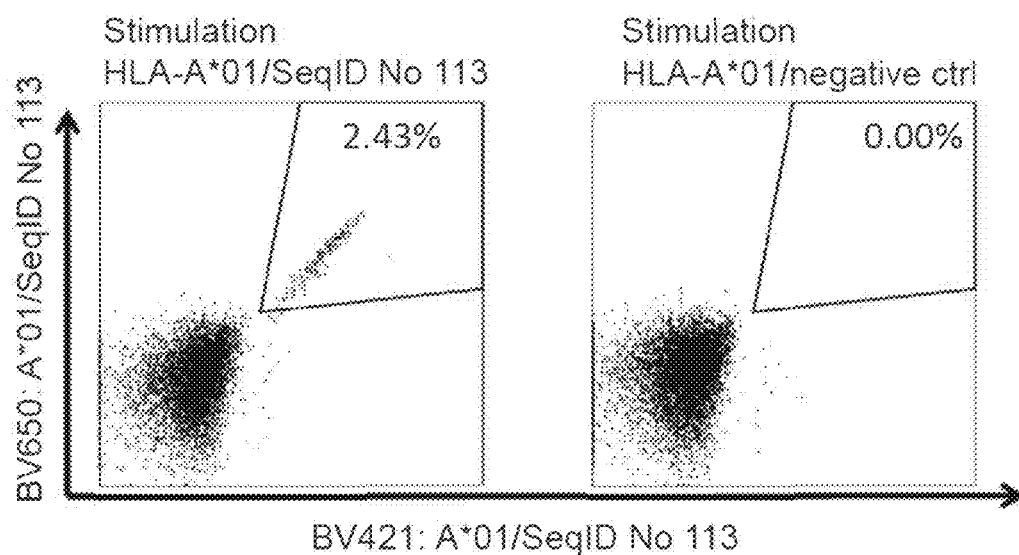
Figure 7B:
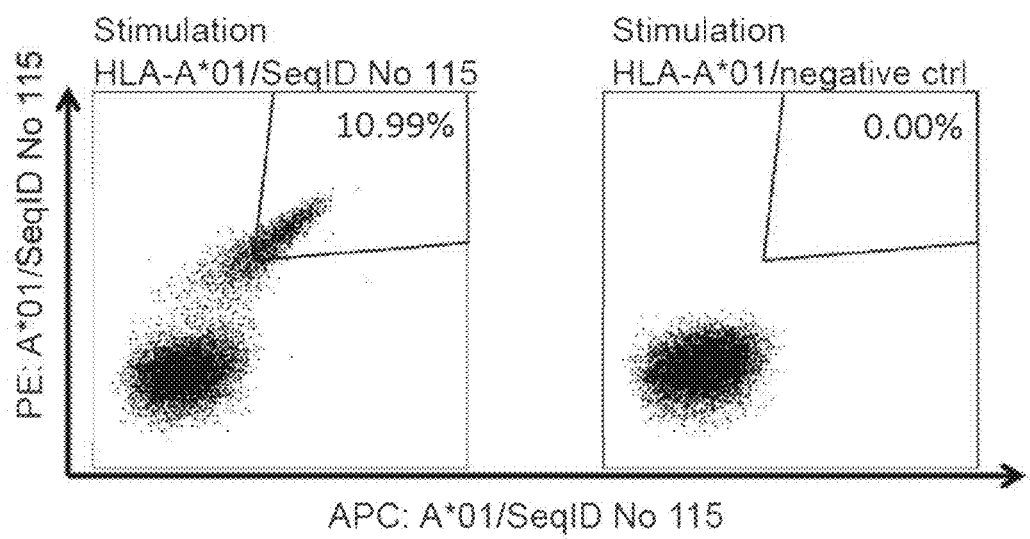

FIGS. 7A and 7B shows exemplary results of peptide-specific in vitro CD8+ T cell responses of a healthy HLA-A*01+ donor. CD8+ T cells were primed using artificial APCs coated with anti-CD28 mAb and HLA-A*01 in complex with SeqID No 113 peptide QLDSNRLTY (FIG. 7A, left panel) and SeqID No 115 peptide FVDNQYWRY (FIG. 7B, left panel), respectively. After three cycles of stimulation, the detection of peptide-reactive cells was performed by 2D multimer staining with A*01/SeqID No 113 (FIG. 7A) or A*01/SeqID No 115 (FIG. 7B). Right panels (FIGS. 7A and 7B) show control staining of cells stimulated with irrelevant A*01/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 8A:
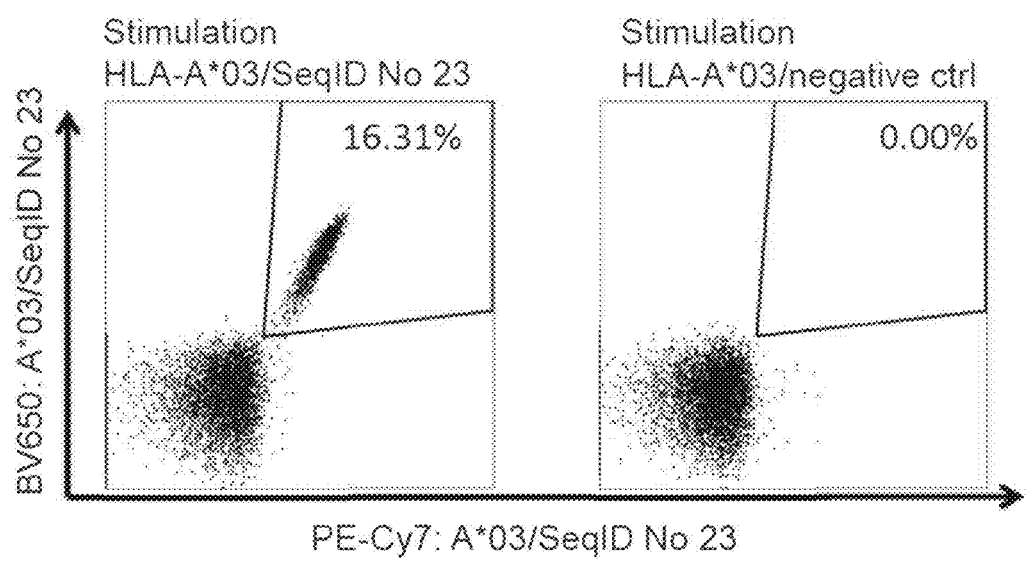
Figure 8B:
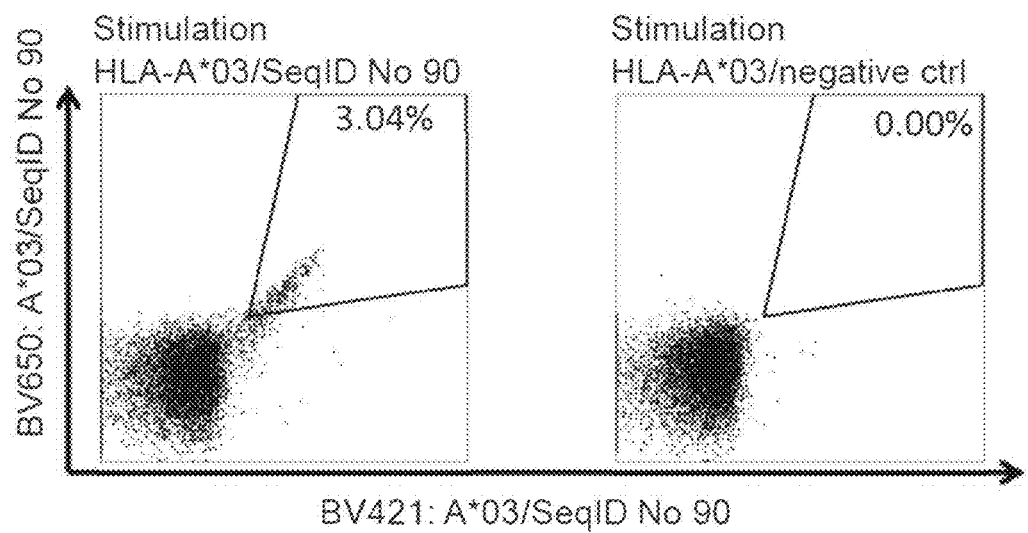

FIGS. 8A and 8B shows exemplary results of peptide-specific in vitro CD8+ T cell responses of a healthy HLA-A*03+ donor. CD8+ T cells were primed using artificial APCs coated with anti-CD28 mAb and HLA-A*03 in complex with SeqID No 23 peptide GMMKGGIRK (FIG. 8A, left panel) and SeqID No 90 peptide KVAGERYVYK (FIG. 8B, left panel), respectively. After three cycles of stimulation, the detection of peptide-reactive cells was performed by 2D multimer staining with A*03/SeqID No 23 (FIG. 8A) or A*03/SeqID No 90 (FIG. 8B). Right panels (FIGS. 8A and 8B) show control staining of cells stimulated with irrelevant A*03/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 9A:
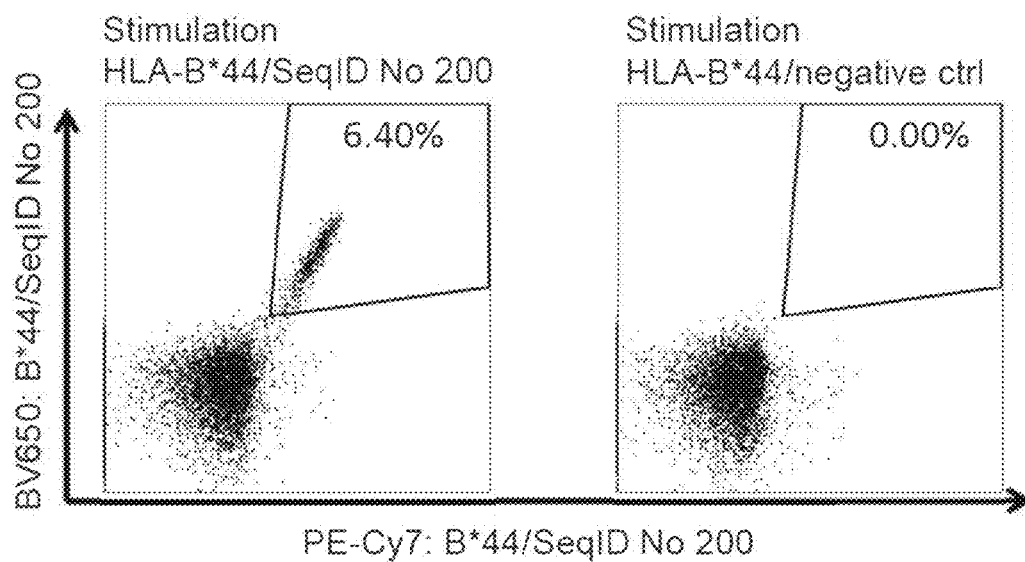
Figure 9B:
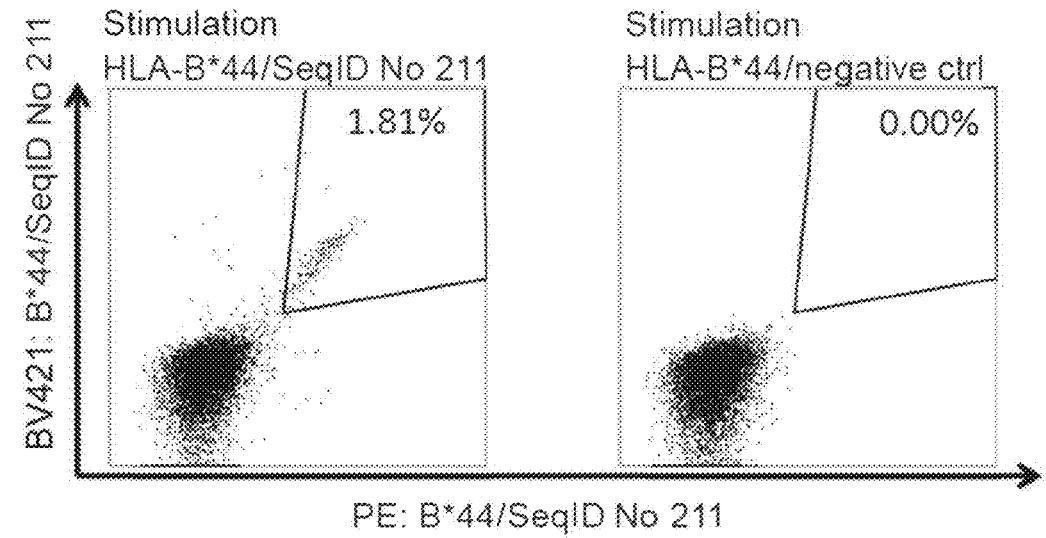

FIGS. 9A and 9B shows exemplary results of peptide-specific in vitro CD8+ T cell responses of a healthy HLA-B*44+ donor. CD8+ T cells were primed using artificial APCs coated with anti-CD28 mAb and HLA-B*44 in complex with SeqID No 200 peptide AESIPTVSF (FIG. 9A, left panel) and SeqID No 211 peptide EEKVFPSPLW (FIG. 9B, left panel), respectively. After three cycles of stimulation, the detection of peptide-reactive cells was performed by 2D multimer staining with B*44/SeqID No 200 (FIG. 9A) or B*44/SeqID No 211 (FIG. 9B). Right panels (FIGS. 9A and 9B) show control staining of cells stimulated with irrelevant B*44/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

EXAMPLES

Example 1

Identification of Tumor Associated Peptides Presented on the Cell Surface

Tissue Samples

Patients' tumor tissues and normal tissues were obtained from the University Hospital Tübingen (Tübingen, Germany). Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, —B, C-specific antibody W6/32, the HLA-DR specific antibody L243 and the pan-HLA class II specific antibody Tü39, CNBr-activated sepharose, acid treatment, and ultrafiltration.

Mass Spectrometry Analyses

The HLA peptide pools as obtained were separated according to their hydrophobicity by reversed-phase chromatography (Ultimate 3000 RSLC Nano UHPLC System, Dionex)) and the eluting peptides were analyzed in LTQ-Orbitrap and Fusion Lumos hybrid mass spectrometers (ThermoElectron) equipped with an ESI source. Peptide samples were loaded with 3% of solvent B (20% $H_2O$, 80% acetonitrile and 0.04% formic acid) on a 2 cm PepMap 100 C18 Nanotrap column (Dionex) at a flowrate of 4 µl/min for 10 min. Separation was performed on either 25 cm or 50 cm PepMap C18 columns with a particle size of 2 µm (Dionex) mounted in a column oven running at 50° C. The applied gradient ranged from 3 to 32% solvent B within 90 min at a flow rate of 300 nl/min (for 25 cm columns) or 140 min at a flow rate of 175 nl/min (for 50 cm columns). (Solvent A: 99% $H_2O$, 1% ACN and 0.1% formic acid; Solvent B: 20% $H_2O$, 80% ACN and 0.1% formic acid).

Mass spectrometry analysis was performed in data dependent acquisition mode employing a top five method (i.e. during each survey scan the five most abundant precursor ions were selected for fragmentation). Alternatively, a Top-Speed method was employed for analysis on Fusion Lumos instruments, Survey scans were recorded in the Orbitrap at a resolution of 60,000 (for Orbitrap XL) or 120,000 (for Orbitrap Fusion Lumos). MS/MS analysis was performed by collision induced dissociation (CID, normalized collision energy 35%, activation time 30 ms, isolation width 1.3 m/z) with subsequent analysis in the linear trap quadrupole (LTQ). Mass range for HLA class I ligands was limited to 400-650 m/z with possible charge states 2+ and 3+ selected for fragmentation. For HLA class II mass range was set to 300-1500 m/z allowing for fragmentation with all positive charge states 2.

Tandem mass spectra were interpreted by MASCOT or SEQUEST at a fixed false discovery rate ($q \leq 0.05$) and additional manual control. In cases where the identified peptide sequence was uncertain it was additionally validated by comparison of the generated natural peptide fragmentation pattern with the fragmentation pattern of a synthetic sequence-identical reference peptide.

Table 19 shows the presentation on various cancer entities for selected peptides, and thus the particular relevance of the peptides as mentioned for the diagnosis and/or treatment of the cancers as indicated (e.g. peptide SEQ ID No. 1 for colorectal cancer, gallbladder cancer, non-hodgkin lymphoma, non-small cell lung cancer, and uterine and endometrial cancer, peptide SEQ ID No. 2 for breast cancer, cholangiocellular carcinoma, colorectal cancer, gallbladder cancer, gastric cancer, head and neck squamous cell carcinoma, melanoma, non-hodgkin lymphoma, non-small cell lung cancer, esophageal cancer, pancreatic cancer, prostate cancer, renal cell carcinoma, small cell lung cancer, and uterine and endometrial cancer).

TABLE 19

Overview of presentation of selected tumor-associated peptides of the present invention across tumor types.

| Seq ID No | Sequence | Peptide Presentation on tumor types |
|---|---|---|
| 1 | MIPTFTALL | CRC, GBC, NHL, NSCLC, UEC |
| 2 | TLLKALLEI | BRCA, CCC, CRC, GBC, GC, HNSCC, MEL, NHL, NSCLC, OSCAR, PACA, PRCA, RCC, SCLC, UEC |
| 3 | ALIYNLVG I | HCC |
| 4 | ALFKAWAL | AML, BRCA, CLL, CRC, GBC, GC, HCC, HNSCC, MEL, NHL, NSCLC, OSCAR, RCC, SCLC, UBC, UEC |
| 5 | RLLDFINVL | UEC |
| 7 | ALQAFEFRV | GC, GEJC, HNSCC, NSCLC, PACA, SCLC, UBC |
| 8 | YLVTKVVAV | AML, BRCA, CCC, CLL, CRC, GBC, GBM, GC, GEJC, HCC, HNSCC, MEL, NHL, NSCLC, OSCAR, PACA, PRCA, RCC, SCLC, UBC, UEC |
| 10 | RYSDSVGRVSF | BRCA, CRC, GBC, GC, NSCLC, SCLC, UBC, UEC |
| 11 | SYSDLHYGF | GC, NSCLC, UEC |
| 12 | KYEKIFEML | AML, NSCLC |
| 13 | VYTFLSSTL | NSCLC |
| 14 | FYFPTPTVL | GBC, NSCLC |
| 15 | VYHDDKQPTF | GBM, GC, NSCLC, OSCAR, UEC |
| 16 | IYSPQFSRL | BRCA, NHL, NSCLC, OSCAR, UBC, UEC |
| 18 | KYPVHIYRL | AML, BRCA, GBC, GC, HNSCC, MEL, NHL, NSCLC, OSCAR, PACA, RCC, UBC, UEC |
| 19 | KYVKVFHQF | AML, BRCA, CLL, CRC, GBC, GBM, GC, HCC, MEL, NHL, NSCLC, OSCAR, PACA, PRCA, RCC, SCLC, UBC, UEC |
| 20 | RMASPVNVK | CLL |
| 21 | AVRKPIVLK | AML, BRCA, CCC, CRC, GBC, GBM, GC, HCC, HNSCC, MEL, NHL, NSCLC, OSCAR, PACA, RCC, SCLC, UBC, UEC |
| 22 | SLKERNPLK | NSCLC |
| 24 | SMYYPLQLK | BRCA, CRC, GBM, HCC, NHL, RCC |
| 25 | GTSPPSVEK | UEC |
| 27 | VLYGPAGLGK | HCC, HNSCC, NSCLC, OSCAR, PACA, SCLC, UBC, UEC |
| 28 | KTYETNLEIKK | NSCLC, UBC |
| 29 | QQFLTALFY | PACA, PRCA |
| 31 | LLDEGAMLLY | GBC, HNSCC, NSCLC, SCLC, UBC |

TABLE 19 -continued

Overview of presentation of selected tumor-associated peptides of the present invention across tumor types.

| Seq ID No | Sequence | Peptide Presentation on tumor types |
|---|---|---|
| 32 | SPNKGTLSV | NSCLC |
| 33 | SPTFHLTL | NSCLC, PRCA, SCLC, UBC, UEC |
| 34 | LPRGPLASLL | HNSCC, NSCLC, OSCAR, PACA, SCLC |
| 35 | FPDNQRPAL | BRCA, CRC, GBC, MEL, NSCLC, PACA, UBC, UEC |
| 36 | APAAWLRSA | BRCA, CCC, CRC, GBC, GC, HCC, HNSCC, NSCLC, OSCAR, PACA, SCLC, UBC, UEC |
| 38 | SPHPVTALLTL | PACA, UEC |
| 40 | KPGTSYRVTL | GBM |
| 43 | ALKARTVTF | BRCA, CCC, GBM, HCC, HNSCC, MEL, NHL, NSCLC, OSCAR, PRCA, SCLC, UBC, UEC |
| 48 | DVKKKIKEV | NSCLC, RCC, SCLC |
| 53 | MEHPGKLLF | UEC |
| 56 | SEPDTTASW | NSCLC, UEC |
| 57 | QESDLRLFL | BRCA, CLL, CRC, GC, GEJC, HNSCC, NHL, NSCLC, PACA, UBC, UEC |
| 59 | SENVTMKVV | UEC |
| 60 | GLLSLTSTLYL | BRCA |
| 62 | KVLGVNVML | BRCA, HNSCC, MEL, NSCLC, SCLC |
| 63 | MMEEMIFNL | UBC |
| 64 | FLDPDRHFL | BRCA, CCC, CRC, GBC, GC, GEJC, HCC, HNSCC, MEL, NSCLC, OSCAR, PACA, PRCA, RCC, SCLC, UBC, UEC |
| 65 | TMFLRETSL | MEL, NHL, NSCLC, PRCA, SCLC |
| 68 | KLFDTQQFL | AML, BRCA, CRC, HCC, HNSCC, MEL, NHL, NSCLC, OSCAR, RCC |
| 69 | TTYEGSITV | NSCLC, UEC |
| 71 | YLEDTDRNL | AML, BRCA, CCC, CRC, GBC, GC, GEJC, HCC, HNSCC, MEL, NHL, NSCLC, OSCAR, PACA, PRCA, RCC, SCLC, UBC, UEC |
| 72 | YLTDLQVSL | AML, BRCA, CCC, CLL, CRC, GBC, GBM, GC, GEJC, HCC, HNSCC, MEL, NHL, NSCLC, OSCAR, PACA, PRCA, RCC, SCLC, UBC, UEC |
| 74 | SQSPSVSQL | UEC |
| 75 | KVVSVLYNV | BRCA, UEC |
| 77 | RYGPVFTV | CCC, GC |
| 78 | SFAPRSAVF | SCLC |
| 79 | SYNEHWNYL | BRCA, CCC, CRC, GBC, GC, HCC, HNSCC, MEL, NHL, NSCLC, OSCAR, PACA, PRCA, RCC, SCLC, UBC, UEC |
| 81 | VYNHTTRPL | OSCAR |

TABLE 19 -continued

Overview of presentation of selected tumor-associated peptides of the present invention across tumor types.

| Seq ID No | Sequence | Peptide Presentation on tumor types |
|---|---|---|
| 85 | VLLGSLFSRK | AML, CRC, HCC, MEL, NHL, NSCLC, RCC, UEC |
| 86 | VVLLGSLFSRK | AML, CRC, GC, HCC, PACA, RCC |
| 87 | AVAPPTPASK | AML, CRC, GBC, MEL, NSCLC, OSCAR, RCC, SCLC, UEC |
| 90 | KVAGERYVYK | CCC, UEC |
| 92 | SVFPIENIY | UEC |
| 94 | ATFERVLLR | BRCA, NSCLC |
| 96 | TAFGGFLKY | OSCAR, RCC |
| 97 | TMLDVEGLFY | GC |
| 99 | KVVDRWNEK | CRC, NHL, RCC |
| 101 | RVFTSSIKTK | NSCLC, PACA, UEC |
| 106 | AAFVPLLLK | AML, BRCA, NHL, NSCLC, SCLC |
| 108 | VLYPVPLESY | AML, MEL, NHL, NSCLC, RCC, SCLC, UEC |
| 109 | KTFTIKRFLAK | BRCA, CCC, MEL, NHL, NSCLC, OSCAR, SCLC, UEC |
| 110 | SAAPPSYFR | RCC, UEC |
| 113 | QLDSNRLTY | HCC |
| 115 | FVDNQYWRY | BRCA, GBC, GC, GEJC, NSCLC, OSCAR, PACA, SCLC |
| 116 | VLLDEGAMLLY | NSCLC, PACA |
| 117 | APRLLLLAVL | BRCA, CRC, HNSCC, MEL, NSCLC, OSCAR, PRCA, RCC, SCLC, UBC, UEC |
| 118 | SPASRSISL | NHL, OSCAR, RCC |
| 119 | APLPRPGAVL | MEL, OSCAR |
| 120 | RPAMNYDKL | CRC |
| 123 | KPSESIYSAL | BRCA, CRC, HNSCC, MEL, NHL, NSCLC, OSCAR, SCLC, UBC |
| 124 | LPSDSHFKITF | CRC, HNSCC, NHL, OSCAR, SCLC |
| 125 | VPVYILLDEM | CCC, GC, HNSCC, UEC |
| 127 | APRAGSQVV | AML, BRCA, CRC, GBM, HCC, HNSCC, MEL, NSCLC, OSCAR, PACA, PRCA, RCC, SCLC, UBC, UEC |
| 129 | APRPASSL | BRCA, CRC, NSCLC, OSCAR, SCLC, UEC |
| 133 | MPNLPSTTSL | UEC |
| 141 | SPMTSLLTSGL | UEC |
| 146 | IPRPEVQAL | AML, CRC, GC, HNSCC, MEL |
| 147 | APRWFPQPTVV | BRCA |
| 148 | KPYGGSGPL | AML, BRCA, NHL, RCC |

TABLE 19 -continued

Overview of presentation of selected tumor-associated peptides of the present invention across tumor types.

| Seq ID No | Sequence | Peptide Presentation on tumor types |
|---|---|---|
| 149 | GPREALSRL | AML, BRCA, CCC, CRC, HCC, MEL, NHL, NSCLC, OSCAR, PACA, PRCA, RCC, SCLC, UEC |
| 150 | MAAVKQAL | CCC, NSCLC, PACA |
| 151 | HLLLKVLAF | HNSCC |
| 152 | MGSARVAEL | HNSCC |
| 156 | HVKEKFLL | CCC, HNSCC |
| 157 | EAMKRLSYI | CCC, HNSCC, PACA |
| 174 | AEATARLNVF | NSCLC |
| 176 | AEIEPKADGSW | CCC, NSCLC, PRCA |
| 178 | NELFRDGVNW | AML, BRCA, CCC, CLL, CRC, HCC, HNSCC, MEL, NHL, NSCLC, OSCAR, PACA, PRCA, SCLC, UBC, UEC |
| 179 | REAGDEFEL | CCC, NSCLC, SCLC |
| 180 | REAGDEFELRY | CRC, HCC, MEL, NSCLC, OSCAR, PACA, RCC, UEC |
| 181 | GEGPKTSW | NSCLC |
| 182 | KEATEAQSL | NSCLC |
| 184 | AELEALTDLW | NHL, NSCLC, NSCLC |
| 186 | REGPEEPGL | GC |
| 188 | AEFAKKQPWW | CCC, CLL, CRC, MEL, NHL, NSCLC |
| 191 | EEDAALFKAW | AML, BRCA, CCC, CLL, CRC, GC, HCC, HNSCC, MEL, NHL, NSCLC, OSCAR, PACA, PRCA, RCC, SCLC, UBC, UEC |
| 192 | YEFKFPNRL | BRCA, HCC, NSCLC, OSCAR, UEC |
| 196 | REMPGGPVW | BRCA, CCC, CRC, GC, HCC, HNSCC, MEL, NHL, NSCLC, OSCAR, PACA, SCLC, UBC, UEC |
| 197 | AEVLLPRLV | NSCLC, PACA, UEC |
| 199 | REIDESLIFY | NSCLC |
| 200 | AESIPTVSF | NSCLC |
| 208 | TEVSRTEAI | NSCLC, UEC |
| 211 | EEKVFPSPLW | NHL |
| 215 | SEDGLPEGIHL | CLL, GC, GEJC, HNSCC, NHL, NSCLC, PACA |
| 216 | IMFDDAIERA | UEC |
| 217 | VSSSLTLKV | BRCA, RCC |
| 224 | SLPRFQVTL | BRCA, HCC, NHL, NSCLC, OSCAR, UBC, UEC |
| 225 | SVFAHPRKL | BRCA, OSCAR |
| 226 | QVDPKKRISM | BRCA, NHL, NSCLC, SCLC |

TABLE 19-continued

Overview of presentation of selected tumor-associated peptides of the present invention across tumor types.

| Seq ID No | Sequence | Peptide Presentation on tumor types |
|---|---|---|
| 227 | YTFRYPLSL | CCC, CRC, GBC, GC, HCC, HNSCC, NSCLC, OSCAR, PACA, SCLC, UBC, UEC |
| 228 | RLWDWVPLA | AML, NHL |
| 235 | SAIETSAVL | NSCLC, UEC |
| 237 | SAMGTISIM | UEC |
| 240 | FSTDTSIVL | PACA |
| 241 | RQPNILVHL | UEC |
| 243 | YASEGVKQV | UEC |
| 245 | LAVEGGQSL | AML, BRCA, CCC, CRC, GBC, GBM, GC, GEJC, HCC, HNSCC, MEL, NHL, NSCLC, OSCAR, PACA, PRCA, RCC, SCLC, UBC, UEC |
| 246 | RYLAVVHAVF | HCC, NHL, NSCLC, PACA, SCLC |
| 247 | ARPPWMWVL | BRCA, GBC, HNSCC, OSCAR |
| 251 | KQRQVLIFF | GBM, NSCLC, OSCAR, PACA, RCC |
| 252 | LYQPRASEM | NHL |
| 256 | RTEEVLLTFK | RCC, SCLC, UEC |
| 257 | VTADHSHVF | UEC |
| 259 | KTLELRVAY | GBC, HNSCC |
| 260 | GTNTVILEY | MEL, PACA, UEC |
| 262 | RSRLNPLVQR | HNSCC, NSCLC |
| 264 | AIKVIPTVFK | HNSCC, MEL, NSCLC, RCC, UEC |
| 268 | GLLGLSLRY | PRCA |
| 269 | RLKGDAWVYK | MEL, NHL, OSCAR, UEC |
| 271 | RMFADDLHNLNK | NSCLC |
| 273 | RVNAIPFTY | GBC |
| 275 | STTFPTLTK | UEC |
| 277 | TTALKTTSR | NSCLC |
| 279 | SVSSETTKIKR | UEC |
| 280 | SVSGVKTTF | HCC, UEC |
| 281 | RAKELEATF | CLL, GC, NSCLC |
| 283 | IVQEPTEEK | HCC, NHL, NSCLC |
| 286 | TVAPPQGVVK | HCC |
| 288 | SPVTSVHGGTY | NHL |
| 289 | RWEKTDLTY | CRC, UEC |
| 291 | ETIRSVGYY | GBM, NSCLC, UBC |
| 295 | YPLRGSSIFGL | UEC |
| 296 | YPLRGSSI | UEC |

TABLE 19 -continued

Overview of presentation of selected tumor-associated peptides of the present invention across tumor types.

| Seq ID No | Sequence | Peptide Presentation on tumor types |
|---|---|---|
| 299 | HPGSSALHY | AML, CCC, CRC, GC, HNSCC, MEL, NHL, NSCLC, OSCAR, PACA, PRCA, RCC, UEC |
| 300 | IPMAAVKQAL | AML, BRCA, CLL, CRC, GC, HCC, HNSCC, MEL, NSCLC, OSCAR, PACA, RCC, UEC |
| 302 | RVEEVRALL | BRCA, CRC, GBM, UBC |
| 306 | APVIFSHSA | AML, CCC, HCC, MEL, NSCLC, UBC |
| 307 | LPYGPGSEAAAF | BRCA, UEC |
| 308 | YPEGAAYEF | PRCA, UEC |
| 314 | VPDQPHPEI | PACA |
| 315 | SPRENFPDTL | HNSCC |
| 317 | FPFQPGSV | AML, BRCA, CLL, CRC, GBC, GBM, GC, HCC, HNSCC, MEL, NHL, NSCLC, OSCAR, PACA, PRCA, RCC, SCLC, UBC, UEC |
| 318 | FPNRLNLEA | CCC, CLL, GC, HNSCC, MEL, NSCLC, PRCA, RCC, SCLC, UBC |
| 319 | SPAEPSVYATL | BRCA, GC, NSCLC, OSCAR |
| 320 | FPMSPVTSV | AML, BRCA, CCC, CRC, GBC, GBM, GC, HCC, HNSCC, MEL, NHL, NSCLC, OSCAR, PACA, PRCA, RCC, SCLC, UBC, UEC |
| 321 | SPMDTFLLI | AML, BRCA, CLL, CRC, GBC, GBM, GC, HCC, HNSCC, MEL, NHL, NSCLC, OSCAR, PACA, PRCA, RCC, SCLC, UBC, UEC |
| 322 | SPDPSKHLL | NHL, NSCLC, PRCA, RCC |
| 324 | VPYRVVGL | CLL, CRC, GC, MEL, NHL, NSCLC, PRCA, SCLC |
| 325 | GPRNAQRVL | CRC, GBC, NHL, NSCLC |
| 326 | VPSEIDAAF | BRCA, CCC, CRC, GBC, GC, NSCLC, OSCAR, PACA, RCC, SCLC, UEC |
| 330 | FPFVTGSTEM | UEC |
| 331 | FPHPEMTTSM | UEC |
| 332 | FPHSEMTTL | NSCLC, PACA |
| 333 | FPHSEMTTVM | NSCLC, SCLC, UEC |
| 334 | FPYSEVTTL | NSCLC, SCLC, UEC |
| 335 | HPDPVGPGL | NSCLC, UEC |
| 337 | HPVETSSAL | UEC |
| 355 | SPLVTSHIM | UEC |
| 363 | TAKTPDATF | CCC |
| 369 | FPHSEMTTV | PACA, UEC |
| 371 | LYVDGFTHW | NSCLC, UEC |
| 376 | RPRSPAGQVA | PACA |

TABLE 19 -continued

Overview of presentation of selected tumor-associated peptides of the present invention across tumor types.

| Seq ID No | Sequence | Peptide Presentation on tumor types |
|---|---|---|
| 378 | RPRSPAGQVAA | NHL, PACA, SCLC |
| 385 | SPALHIGSV | BRCA, GBM, HCC, NSCLC, PRCA, SCLC, UBC, UEC |
| 386 | FPFNPLDF | GC, NHL |
| 388 | SPAPLKLSRTPA | MEL |
| 389 | SPGAQRTFFQL | AML, MEL |
| 391 | APSTPRITTF | HCC, NHL |
| 392 | KPIESTLVA | GBM, MEL, NSCLC, UEC |
| 393 | ASKPHVEI | CRC |
| 395 | VLLPRLVSC | NSCLC |
| 399 | RELLHLVTL | NSCLC, SCLC, UEC |
| 403 | EEAQWVRKY | BRCA, CLL, NHL |
| 404 | NEAIMHQY | BRCA, CCC, CLL, CRC, GBC, GC, HCC, MEL, NHL, NSCLC, OSCAR, SCLC, UBC, UEC |
| 405 | NEIWTHSY | NSCLC, UEC |
| 407 | AEHEGVSVL | NSCLC, UEC |
| 408 | LEKALQVF | CRC, GC, HNSCC, OSCAR, UEC |
| 409 | REFVLSKGDAGL | GBC, GC, GEJC, HNSCC, NSCLC |
| 410 | SEDPSKLEA | BRCA, HNSCC, NSCLC, OSCAR, SCLC, UEC |
| 411 | LELPPILVY | BRCA, CRC, GBC, GBM, GC, NHL, NSCLC, OSCAR, PRCA, SCLC, UBC, UEC |
| 414 | EDAALFKAW | CLL, CRC, MEL, NHL |
| 415 | REEDAALFKAW | BRCA, CLL, CRC, HCC, HNSCC, MEL, NHL, NSCLC, OSCAR, PRCA, UBC, UEC |
| 416 | SEEETRVVF | AML, CRC, HNSCC, NSCLC, UEC |
| 417 | AEHFSMIRA | AML, BRCA, CRC, GBM, GC, HNSCC, NHL, NSCLC, OSCAR, PACA, PRCA, RCC, UEC |
| 418 | FEDAQGHIW | BRCA, CCC, CRC, HCC, NSCLC, OSCAR, PACA, UBC, UEC |
| 419 | HEFGHVLGL | BRCA, CCC, CRC, GC, HNSCC, MEL, NSCLC, OSCAR, PACA, UEC |
| 420 | FESHSTVSA | UEC |
| 423 | SEVPTGTTA | GBC, GBM |
| 425 | SEVPLPMAI | NSCLC, UEC |
| 429 | REKFIASVI | UEC |
| 430 | DEKILYPEF | UEC |
| 431 | AEQDPDELNKA | CRC, OSCAR, SCLC, UEC |
| 432 | EEQYIAQF | OSCAR, SCLC |

TABLE 19 -continued

Overview of presentation of selected tumor-associated peptides of the present invention across tumor types.

| Seq ID No | Sequence | Peptide Presentation on tumor types |
|---|---|---|
| 433 | SDSQVRAF | GBM, GC, HCC, HNSCC, NSCLC, OSCAR, RCC, SCLC, UEC |
| 436 | REPGDIFSEL | CRC |
| 437 | TEAVVTNEL | CRC, GC, NSCLC, SCLC, UEC |
| 438 | SEVDSPNVL | CCC, CLL, CRC, GC, HNSCC, MEL, NHL, NSCLC, SCLC, UBC |
| 442 | ILSKLTDIQY | BRCA, GBM, NHL, NSCLC |
| 443 | GTFNPVSLW | BRCA, GBC, GBM, HNSCC, MEL, NHL, NSCLC, OSCAR, PACA, SCLC |
| 444 | KLSQKGYSW | BRCA, CCC, CRC, GBM, HCC, HNSCC, MEL, NHL, NSCLC, OSCAR, PACA, PRCA, SCLC, UBC |
| 445 | LHITPGTAY | HCC, PRCA |
| 446 | GRIVAFFSF | AML, BRCA, CRC, HCC, HNSCC, MEL, NHL, NSCLC, OSCAR, PACA, PRCA, SCLC, UBC, UEC |
| 447 | MQVLVSRI | GC, NSCLC, PACA, PRCA, RCC, SCLC |
| 448 | LSQKGYSW | NHL, NSCLC, UBC |
| 451 | DYLNEWGSRF | NSCLC, OSCAR, UEC |
| 454 | AQTDPTTGY | GBM, GC, NSCLC |
| 455 | AAAANAQVY | BRCA, UEC |
| 456 | IPLERPLGEVY | BRCA, UEC |
| 457 | NAAAANAQVY | BRCA, NSCLC, UEC |
| 458 | TDTLIHLM | UEC |
| 459 | KVAGERYVY | BRCA, CCC, CRC, GBM, HNSCC, MEL, NSCLC, OSCAR, PACA, PRCA, SCLC, UBC |
| 460 | RLSSATANALY | GBC |
| 461 | AQRMTTQLL | CRC, MEL, NSCLC, RCC |
| 462 | QRMTTQLLL | NSCLC, RCC, UEC |
| 466 | DLIESGQLRER | UEC |
| 467 | MQMQERDTL | GEJC, HNSCC, NHL, NSCLC, OSCAR |
| 471 | AQRLDPVYF | CCC, CRC, GBC, GEJC, NSCLC, OSCAR, PACA, SCLC, UBC |
| 472 | MRLLVAPL | SCLC, UEC |
| 474 | AADGGLRASVTL | BRCA, NSCLC, OSCAR |
| 477 | RIQQQTNTY | GBM, SCLC |
| 479 | TEGSHFVEA | BRCA, SCLC, UEC |
| 480 | GRADIMIDF | BRCA, CRC, HNSCC, MEL, NSCLC, OSCAR, SCLC, UEC |
| 481 | GRWEKTDLTY | BRCA, GBC, HNSCC, MEL, NSCLC, OSCAR, PACA, SCLC, UBC, UEC |
| 482 | GRWEKTDLTYR | HNSCC, NSCLC, OSCAR, PACA, SCLC, UEC |

TABLE 19 -continued

Overview of presentation of selected tumor-associated peptides of the present invention across tumor types.

| Seq ID No | Sequence | Peptide Presentation on tumor types |
|---|---|---|
| 484 | AWLRSAAA | CCC |
| 485 | VRFPVHAAL | MEL, NSCLC, OSCAR |
| 486 | DRFFWLKV | NSCLC, SCLC |
| 487 | GMADILVVF | NSCLC |
| 488 | RSFSLGVPR | AML, CLL, GC, HCC, HNSCC, NHL, NSCLC, PRCA, SCLC, UEC |
| 490 | AEVQKLLGP | HNSCC, NSCLC, OSCAR, UEC |
| 491 | EAYSSTSSW | GBC, UEC |
| 493 | DTNLEPVTR | UEC |
| 495 | EVPSGATTEVSR | UEC |
| 496 | EVPTGTTAEVSR | UEC |
| 498 | EVYPELGTQGR | UEC |
| 503 | TVFDKAFTAA | NSCLC |
| 507 | TSIFSGQSL | UEC |
| 508 | TVAKTTTTF | UEC |
| 509 | GRGPGGVSW | NSCLC |
| 518 | TSDFPTITV | PACA |
| 520 | THSAMTHGF | NHL |
| 527 | QSTPYVNSV | UEC |
| 528 | TRTGLFLRF | HNSCC, NSCLC, UEC |
| 533 | GQHLHLETF | AML, CCC, GBC, GC, HCC, MEL, NHL, NSCLC, OSCAR, RCC, SCLC, UBC, UEC |
| 537 | IRRLKELKDQ | NSCLC |
| 539 | IPIPSTGSVEM | CCC, GC, HNSCC, NSCLC, OSCAR, PRCA, SCLC, UBC, UEC |
| 540 | AGIPAVALW | HCC, NSCLC, OSCAR |
| 541 | RLSPAPLKL | GBM, NSCLC |
| 544 | LRNPSIQKL | GBM |
| 545 | RVGPPLLI | BRCA, CRC, NSCLC, OSCAR, UEC |
| 546 | GRAFFAAAF | CRC, GBM, HNSCC, MEL, NSCLC, OSCAR, PACA, SCLC, UBC, UEC |
| 547 | EVNKPGVYTR | HCC, UEC |
| 549 | ARSKLQQGL | MEL |
| 550 | RRFKEPWFL | BRCA, HCC, MEL, NSCLC, PRCA, SCLC, UBC, UEC |
| 563 | PNFSGNWKIIRSENFEEL | NSCLC |
| 589 | APDAKSFVLNLGKDSNNL | NSCLC |
| 590 | RVRGEVAPDAKSFVLNLG | NSCLC |
| 591 | VRGEVAPDAKSFVLNL | NSCLC, RCC |

TABLE 19 -continued

Overview of presentation of selected tumor-associated peptides of the present invention across tumor types.

| Seq ID No | Sequence | Peptide Presentation on tumor types |
|---|---|---|
| 592 | VRGEVAPDAKSFVLNLG | NSCLC, RCC |
| 593 | GEVAPDAKSFVLNLG | NSCLC, RCC |
| 594 | VRGEVAPDAKSFVLN | NSCLC, RCC |
| 598 | AESLFREALSNKVDEL | NSCLC |
| 599 | AESLFREALSNKVDE | NSCLC |
| 607 | LTVAEVQKLLGPHVEGLKAEE | NSCLC |
| 608 | LTVAEVQKLLGPHVEGLKAE | NSCLC |
| 609 | LTVAEVQKLLGPHVEGLKA | NSCLC |
| 610 | LTVAEVQKLLGPHVEGLK | NSCLC |
| 611 | LTVAEVQKLLGPHVEGL | NSCLC |
| 612 | TVAEVQKLLGPHVEGLK | NSCLC |
| 613 | LTVAEVQKLLGPHVEG | NSCLC |
| 614 | TVAEVQKLLGPHVEGL | NSCLC |
| 615 | VAEVQKLLGPHVEGLK | NSCLC |
| 616 | TVAEVQKLLGPHVEG | NSCLC |
| 617 | VAEVQKLLGPHVEGL | NSCLC |
| 618 | VAEVQKLLGPHVEG | NSCLC |
| 619 | VAEVQKLLGPHVE | NSCLC |
| 620 | EVQKLLGPHVEG | NSCLC |
| 625 | DALRGLLPVLGQPIIRSIPQG | NSCLC |
| 628 | DALRGLLPVLGQPIIRSIPQ | NSCLC |
| 629 | GLLPVLGQPIIRSIPQGIVA | NSCLC |
| 630 | ALRGLLPVLGQPIIRSIPQ | NSCLC |
| 633 | LRGLLPVLGQPIIRSIPQ | NSCLC |
| 634 | DALRGLLPVLGQPIIRS | NSCLC |
| 635 | ALRGLLPVLGQPIIRS | NSCLC |
| 637 | ALRGLLPVLGQPIIR | NSCLC |
| 638 | LRGLLPVLGQPIIRS | NSCLC |
| 639 | ALRGLLPVLGQPII | NSCLC |
| 646 | GLLPVLGQPIIRSIPQGIVAAWRQ | NSCLC |
| 648 | GLLPVLGQPIIRSIPQGIVAA | NSCLC |
| 651 | LPVLGQPIIRSIPQGIVAA | NSCLC |
| 653 | LPVLGQPIIRSIPQGIVA | NSCLC |
| 654 | PVLGQPIIRSIPQGIVA | GC, NSCLC |
| 656 | VLGQPIIRSIPQGIVA | NSCLC |
| 661 | LRGLLPVLGQPIIRSIPQG | NSCLC |
| 666 | LPLTVAEVQKLLGPHVEG | NSCLC |

TABLE 19 -continued

Overview of presentation of selected tumor-associated peptides of the present invention across tumor types.

| Seq ID No | Sequence | Peptide Presentation on tumor types |
|---|---|---|
| 668 | AVLPLTVAEVQK | BRCA, CRC, GBC, GC, NSCLC, PACA, UEC |
| 677 | IWAVRPQDLDTCDPR | NSCLC |
| 680 | GVRGSLLSEADVRALGGLA | NSCLC |
| 682 | GVRGSLLSEADVRALGGL | NSCLC |
| 686 | VRGSLLSEADVRALGGL | NSCLC |
| 694 | GSLLSEADVRALGG | NSCLC |
| 695 | RGSLLSEADVRALG | NSCLC |
| 697 | GSLLSEADVRALG | NSCLC |
| 717 | IPQGIVAAWRQRSSRDPS | GC |
| 730 | LPGRFVAESAEVL | NSCLC |

AML: acute myeloid leukemia;
BRCA: breast cancer;
CCC: cholangiocellular carcinoma;
CLL: chronic lymphocytic leukemia;
CRC: colorectal cancer;
GBC: gallbladder cancer;
GBM: glioblastoma;
GC: gastric cancer;
GEJC: gastro-esophageal junction cancer;
HCC: hepatocellular carcinoma;
HNSCC: head and neck squamous cell carcinoma;
MEL: melanoma;
NHL: non-hodgkin lymphoma;
NSCLC: non-small cell lung cancer;
OC: ovarian cancer;
OSCAR: esophageal cancer;
PACA: pancreatic cancer;
PRCA: prostate cancer;
RCC: renal cell carcinoma;
SCLC: small cell lung cancer;
UBC: urinary bladder carcinoma;
UEC: uterine and endometrial cancer Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, Mich., USA & Royston, Herts, UK); Bio-Options Inc. (Brea, Calif., USA); Geneticist Inc. (Glendale, Calif., USA); ProteoGenex Inc. (Culver City, Calif., USA); Tissue Solutions Ltd (Glasgow, UK).

Total RNA from tumor tissues for RNASeq experiments was obtained from: Asterand (Detroit, Mich., USA & Royston, Herts, UK); BioCat GmbH (Heidelberg, Germany); BioServe (Beltsville, Md., USA); Geneticist Inc. (Glendale, Calif., USA); Istituto Nazionale Tumori "Pascale" (Naples, Italy); ProteoGenex Inc. (Culver City, Calif., USA); University Hospital Heidelberg (Heidelberg, Germany).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in ovarian cancer are shown in FIGS. 1A through 1V. Expression scores for further exemplary genes are shown in Table 10.

TABLE 10

Expression scores.

| Seq ID No | Sequence | Gene Expression |
| --- | --- | --- |
| 1 | MIPTFTALL | ++ |
| 5 | RLLDFINVL | +++ |
| 6 | SLGKHTVAL | +++ |
| 10 | RYSDSVGRVSF | + |
| 11 | SYSDLHYGF | ++ |
| 12 | KYEKIFEML | +++ |
| 13 | VYTFLSSTL | +++ |
| 14 | FYFPTPTVL | ++ |
| 16 | IYSPQFSRL | +++ |
| 17 | RFTTMLSTF | +++ |
| 18 | KYPVHIYRL | + |
| 20 | RMASPVNVK | ++ |
| 21 | AVRKPIVLK | + |
| 22 | SLKERNPLK | ++ |
| 23 | GMMKGGIRK | +++ |
| 25 | GTSPPSVEK | ++ |
| 26 | RISEYLLEK | +++ |
| 27 | VLYGPAGLGK | +++ |
| 28 | KTYETNLEIKK | +++ |
| 29 | QQFLTALFY | +++ |
| 30 | ALEVAHRLK | + |
| 31 | LLDEGAMLLY | +++ |
| 32 | SPNKGTLSV | + |
| 33 | SPTFHLTL | + |

TABLE 10 -continued

Expression scores.

| Seq ID No | Sequence | Gene Expression |
| --- | --- | --- |
| 34 | LPRGPLASLL | ++ |
| 35 | FPDNQRPAL | ++ |
| 36 | APAAWLRSA | +++ |
| 37 | RPLFQKSSM | +++ |
| 38 | SPHPVTALLTL | ++ |
| 39 | RPAPFEVVF | ++ |
| 40 | KPGTSYRVTL | +++ |
| 42 | TLKVTSAL | + |
| 43 | ALKARTVTF | + |
| 47 | MPNLRSVDL | +++ |
| 51 | SLRLKNVQL | +++ |
| 52 | AEFLLRIFL | + |
| 53 | MEHPGKLLF | +++ |
| 54 | AEITITTQTGY | ++ |
| 55 | HETETRTTW | ++ |
| 56 | SEPDTTASW | ++ |
| 57 | QESDLRLFL | +++ |
| 58 | GEMEQKQL | +++ |
| 59 | SENVTMKVV | +++ |
| 60 | GLLSLTSTLYL | + |
| 61 | YMVHIQVTL | ++ |
| 62 | KVLGVNVML | ++ |
| 63 | MMEEMIFNL | ++ |
| 64 | FLDPDRHFL | ++ |
| 66 | GLLQELSSI | +++ |
| 67 | SLLLPSIFL | +++ |
| 69 | TTYEGSITV | ++ |
| 70 | VLQGLLRSL | +++ |
| 71 | YLEDTDRNL | + |
| 72 | YLTDLQVSL | + |
| 73 | FLIEELLFA | +++ |
| 74 | SQSPSVSQL | +++ |
| 75 | KVVSVLYNV | +++ |
| 76 | KYVAELSLL | +++ |
| 77 | RYGPVFTV | +++ |
| 78 | SFAPRSAVF | ++ |
| 82 | SYFRGFTLI | +++ |

TABLE 10 -continued

Expression scores.

| Seq ID No | Sequence | Gene Expression |
|---|---|---|
| 83 | GTYAHTVNR | +++ |
| 84 | KLQPAQTAAK | +++ |
| 87 | AVAPPTPASK | ++ |
| 88 | VVHAVFALK | + |
| 89 | RVAELLLLH | +++ |
| 90 | KVAGERYVYK | ++ |
| 91 | RSLRYYYEK | ++ |
| 92 | SVFPIENIY | ++ |
| 96 | TAFGGFLKY | +++ |
| 97 | TMLDVEGLFY | ++ |
| 98 | LLQPPPLLAR | +++ |
| 100 | RLFTSPIMTK | ++ |
| 101 | RVFTSSIKTK | ++ |
| 102 | SVLTSSLVK | ++ |
| 103 | TSRSVDEAY | ++ |
| 104 | VLADSVTTK | ++ |
| 107 | RLQEWKALK | +++ |
| 108 | VLYPVPLESY | +++ |
| 110 | SAAPPSYFR | +++ |
| 111 | TLPQFRELGY | ++ |
| 112 | TVTGAEQIQY | ++ |
| 113 | QLDSNRLTY | ++ |
| 114 | VMEQSAGIMY | +++ |
| 115 | FVDNQYWRY | +++ |
| 116 | VLLDEGAMLLY | +++ |
| 117 | APRLLLLAVL | ++ |
| 118 | SPASRSISL | ++ |
| 119 | APLPRPGAVL | +++ |
| 120 | RPAMNYDKL | ++ |
| 121 | VPNQSSESL | +++ |
| 122 | YPGFPQSQY | +++ |
| 123 | KPSESIYSAL | +++ |
| 124 | LPSDSHFKITF | +++ |
| 125 | VPVYILLDEM | ++ |
| 126 | KPGPEDKL | ++ |
| 128 | YPRTITPGM | + |
| 129 | APRPASSL | ++ |
| 130 | FPRLVGPDF | + |
| 131 | APTEDLKAL | ++ |
| 132 | IPGPAQSTI | ++ |
| 133 | MPNLPSTTSL | ++ |
| 135 | RVRSTISSL | ++ |
| 136 | SPFSAEEANSL | ++ |
| 137 | SPGATSRGTL | ++ |
| 138 | SPMATTSTL | ++ |
| 139 | SPQSMSNTL | ++ |
| 140 | SPRTEASSAVL | ++ |
| 141 | SPMTSLLTSGL | ++ |
| 142 | TPGLRETSI | ++ |
| 143 | SPAMTSTSF | ++ |
| 144 | SPSPVSSTL | ++ |
| 145 | SPSSPMSTF | ++ |
| 147 | APRWFPQPTVV | +++ |
| 151 | HLLLKVLAF | +++ |
| 152 | MGSARVAEL | +++ |
| 154 | MLRKIAVAA | ++ |
| 155 | NKKMMKRLM | +++ |
| 156 | HVKEKFLL | ++ |
| 157 | EAMKRLSYI | + |
| 159 | VLKHKLDEL | ++ |
| 160 | YPKARLAF | ++ |
| 161 | ALKTTTTAL | ++ |
| 162 | QAKTHSTL | ++ |
| 163 | QGLLRPVF | +++ |
| 164 | SIKTKSAEM | ++ |
| 165 | SPRFKTGL | ++ |
| 166 | TPKLRETSI | ++ |
| 167 | TSHERLTTL | ++ |
| 168 | TSHERLTTY | ++ |
| 169 | TSMPRSSAM | ++ |
| 170 | YLLEKSRVI | +++ |
| 171 | FAFRKEAL | +++ |
| 172 | KLKERNREL | +++ |
| 173 | AEAQVGDERDY | + |
| 174 | AEATARLNVF | + |

TABLE 10 -continued

Expression scores.

| Seq ID No | Sequence | Gene Expression |
|---|---|---|
| 175 | AEIEPKADG | + |
| 176 | AEIEPKADGSW | + |
| 177 | TEVGTMNLF | ++ |
| 181 | GEGPKTSW | + |
| 183 | YEKGIMQKV | ++ |
| 184 | AELEALTDLW | ++ |
| 185 | AERQPGAASL | ++ |
| 186 | REGPEEPGL | ++ |
| 187 | GEAQTRIAW | ++ |
| 189 | KEFLFNMY | ++ |
| 190 | YEVARILNL | ++ |
| 193 | LEAQQEAL | ++ |
| 194 | KEVDPTSHSY | +++ |
| 195 | AEDKRHYSV | + |
| 196 | REMPGGPVW | +++ |
| 197 | AEVLLPRLV | ++ |
| 198 | QEAARAAL | ++ |
| 199 | REIDESLIFY | ++ |
| 200 | AESIPTVSF | ++ |
| 201 | AETILTFHAF | ++ |
| 202 | HESEATASW | ++ |
| 203 | IEHSTQAQDTL | ++ |
| 204 | RETSTSEETSL | ++ |
| 205 | SEITRIEM | ++ |
| 206 | SESVTSRTSY | +++ |
| 207 | TEARATSDSW | ++ |
| 208 | TEVSRTEAI | ++ |
| 209 | TEVSRTEL | ++ |
| 210 | VEAADIFQNF | ++ |
| 211 | EEKVFPSPLW | +++ |
| 212 | MEQKQLQKRF | +++ |
| 214 | VEQTRAGSLL | ++ |
| 216 | IMFDDAIERA | +++ |
| 217 | VSSSLTLKV | + |
| 218 | TIASQRLTPL | ++ |
| 219 | PLPRPGAVL | +++ |
| 220 | RMTTQLLLL | ++ |
| 225 | SVFAHPRKL | ++ |
| 226 | QVDPKKRISM | ++ |
| 227 | YTFRYPLSL | ++ |
| 229 | ISVPAKTSL | ++ |
| 230 | SAFREGTSL | ++ |
| 231 | SVTESTHHL | ++ |
| 232 | TISSLTHEL | ++ |
| 233 | GSDTSSKSL | ++ |
| 234 | GVATRVDAI | +++ |
| 235 | SAIETSAVL | ++ |
| 236 | SAIPFSMTL | ++ |
| 237 | SAMGTISIM | ++ |
| 238 | PLLVLFTI | +++ |
| 239 | FAVPTGISM | ++ |
| 240 | FSTDTSIVL | ++ |
| 241 | RQPNILVHL | ++ |
| 242 | STIPALHEI | ++ |
| 243 | YASEGVKQV | ++ |
| 244 | DTDSSVHVQV | ++ |
| 246 | RYLAVVHAVF | + |
| 247 | ARPPWMWVL | +++ |
| 248 | SVIQHLGY | ++ |
| 249 | VYTPTLGTL | ++ |
| 250 | HFPEKTTHSF | ++ |
| 252 | LYQPRASEM | +++ |
| 254 | IIQHLTEQF | +++ |
| 255 | VFVSFSSLF | +++ |
| 256 | RTEEVLLTFK | ++ |
| 257 | VTADHSVF | +++ |
| 258 | GAYAHTVNR | +++ |
| 259 | KTLELRVAY | + |
| 260 | GTNTVILEY | ++ |
| 261 | HTFGLFYQR | ++ |
| 262 | RSRLNPLVQR | ++ |
| 263 | SSSSATISK | ++ |
| 266 | ISYSGQFLVK | +++ |
| 267 | VTDLISPRK | +++ |
| 268 | GLLGLSLRY | +++ |

TABLE 10 -continued

Expression scores.

| Seq ID No | Sequence | Gene Expression |
|---|---|---|
| 269 | RLKGDAWVYK | ++ |
| 270 | AVFNPRFYRTY | +++ |
| 272 | RQPERTILRPR | ++ |
| 273 | RVNAIPFTY | ++ |
| 274 | KTFPASTVF | ++ |
| 275 | STTFPTLTK | ++ |
| 276 | VSKTTGMEF | ++ |
| 277 | TTALKTTSR | ++ |
| 278 | NLSSITHER | ++ |
| 279 | SVSSETTKIKR | ++ |
| 280 | SVSGVKTTF | ++ |
| 281 | RAKELEATF | +++ |
| 282 | CLTRTGLFLRF | +++ |
| 285 | GTVNPTVGK | ++ |
| 286 | TVAPPQGVVK | + |
| 287 | RRIHTGEKPYK | ++ |
| 288 | SPVTSVHGGTY | + |
| 289 | RWEKTDLTY | ++ |
| 290 | DMDEEIEAEY | +++ |
| 291 | ETIRSVGYY | ++ |
| 292 | NVTMKVVSVLY | +++ |
| 293 | VPDSGATATAY | +++ |
| 294 | YPLRGSSIF | +++ |
| 295 | YPLRGSSIFGL | +++ |
| 296 | YPLRGSSI | +++ |
| 297 | TVREASGLL | + |
| 298 | YPTEHVQF | + |
| 299 | HPGSSALHY | ++ |
| 301 | SPRRSPRISF | + |
| 302 | RVEEVRALL | +++ |
| 303 | LPMWKVTAF | +++ |
| 304 | LPRPGAVL | +++ |
| 305 | TPWAESSTKF | ++ |
| 306 | APVIFSHSA | ++ |
| 307 | LPYGPG-SEAAAF | +++ |
| 308 | YPEGAAYEF | +++ |
| 309 | FPQSQYPQY | +++ |
| 310 | RPNPITIIL | +++ |
| 311 | RPLFYVVSL | +++ |
| 312 | LPYFREFSM | +++ |
| 313 | KVKSDRSVF | +++ |
| 315 | SPRENFPDTL | +++ |
| 316 | EPKTATVL | ++ |
| 320 | FPMSPVTSV | + |
| 321 | SPMDTFLLI | + |
| 322 | SPDPSKHLL | + |
| 323 | RPMPNLRSV | +++ |
| 324 | VPYRVVGL | +++ |
| 326 | VPSEIDAAF | ++ |
| 327 | SPLPVTSLI | ++ |
| 328 | EPVTSSLPNF | ++ |
| 329 | FPAMTESGGMIL | ++ |
| 330 | FPFVTGSTEM | ++ |
| 331 | FPHPEMTTSM | ++ |
| 332 | FPHSEMTTL | ++ |
| 333 | FPHSEMTTVM | ++ |
| 334 | FPYSEVTTL | ++ |
| 335 | HPDPVGPGL | +++ |
| 336 | HPKTESAT-PAAY | ++ |
| 337 | HPVETSSAL | ++ |
| 338 | HVTKTQATF | ++ |
| 339 | LPAGTTGSLVF | ++ |
| 340 | LPEISTRTM | ++ |
| 341 | LPLDTSTTL | ++ |
| 342 | LPLGTSMTF | ++ |
| 343 | LPSVSGVKTTF | ++ |
| 344 | LPTQTTSSL | ++ |
| 345 | LPTSESLVSF | ++ |
| 346 | LPWDTSTTLF | ++ |
| 347 | MPLTTGSQGM | ++ |
| 348 | MPNSAIPFSM | ++ |
| 349 | MPSLSEAMTSF | ++ |
| 350 | NPSSTTTEF | ++ |
| 351 | NVLTSTPAF | ++ |

TABLE 10 -continued

Expression scores.

| Seq ID No | Sequence | Gene Expression |
|---|---|---|
| 352 | SPAETSTNM | ++ |
| 353 | SPAMTTPSL | ++ |
| 354 | SPLPVTSLL | ++ |
| 355 | SPLVTSHIM | ++ |
| 356 | SPNEFYFTV | ++ |
| 357 | SPSPVPTTL | ++ |
| 358 | SPSPVTSTL | ++ |
| 359 | SPSTIKLTM | ++ |
| 360 | SPSVSSNTY | ++ |
| 361 | SPTHVTQSL | ++ |
| 362 | SPVPVTSLF | ++ |
| 363 | TAKTPDATF | ++ |
| 364 | TPLATTQRF | ++ |
| 365 | TPLATTQRFTY | ++ |
| 366 | TPLTTTGSAEM | ++ |
| 367 | TPSVVTEGF | ++ |
| 368 | VPTPVFPTM | ++ |
| 369 | FPHSEMTTV | ++ |
| 370 | PGGTRQSL | ++ |
| 372 | IPRNPPPTLL | +++ |
| 373 | RPRALRDLRIL | +++ |
| 374 | NPIGDTGVKF | +++ |
| 375 | AAASPLLLL | +++ |
| 376 | RPRSPAGQVA | +++ |
| 377 | RPRSPAGQVAAA | +++ |
| 378 | RPRSPAGQVAA | +++ |
| 379 | GPFPLVYVL | +++ |
| 380 | IPTYGRTF | +++ |
| 381 | LPEQTPLAF | +++ |
| 382 | SPMHDRWTF | +++ |
| 383 | TPTKETVSL | +++ |
| 384 | YPGLRGSPM | +++ |
| 387 | APLKLSRTPA | +++ |
| 388 | SPAPLKLSRTPA | +++ |
| 389 | SPGAQRTFFQL | ++ |
| 395 | VLLPRLVSC | ++ |
| 396 | REASGLLSL | + |
| 397 | REGDTVQLL | + |
| 399 | RELLHLVTL | + |
| 400 | GEIEIHLL | + |
| 403 | EEAQWVRKY | ++ |
| 404 | NEAIMHQY | ++ |
| 405 | NEIWTHSY | ++ |
| 411 | LELPPILVY | + |
| 412 | QEILTQVKQ | +++ |
| 413 | 1EALSGKIEL | +++ |
| 416 | SEEETRVVF | ++ |
| 417 | AEHFSMIRA | +++ |
| 418 | FEDAQGHIW | ++ |
| 419 | HEFGHVLGL | ++ |
| 420 | FESHSTVSA | ++ |
| 421 | GEPATTVSL | ++ |
| 422 | SETTFSLIF | ++ |
| 423 | SEVPTGTTA | ++ |
| 424 | TEFPLFSAA | ++ |
| 425 | SEVPLPMAI | ++ |
| 426 | PEKTTHSF | ++ |
| 427 | HESSSHHDL | + |
| 428 | LDLGLNHI | ++ |
| 429 | REKFIASVI | +++ |
| 430 | DEKILYPEF | +++ |
| 432 | EEQYIAQF | +++ |
| 433 | SDSQVRAF | +++ |
| 435 | REEFVSIDHL | +++ |
| 436 | REPGDIFSEL | +++ |
| 437 | TEAVVTNEL | + |

The table lists peptides from genes that are very highly over-expressed in OC tumors compared to a panel of normal tissues (+++), highly over-expressed in OC tumors compared to a panel of normal tissues (++) or over-expressed in OC tumors compared to a panel of normal tissues (+).
The baseline for this score was calculated from measurements of the following relevant normal tissues: adipose tissue, adrenal gland, bile duct, blood cells, blood vessels, bone marrow, brain, cartilage, large intestine, liver, lung, lymph esophagus, eye, gallbladder, heart, head&neck, kidney, node, nerve, parathyroid, pancreas, pituitary, skeletal muscle, skin, small intestine, spleen, stomach, thyroid gland, trachea, urinary bladder.
In case expression data for several samples of the same tissue type were available, the arithmetic mean of all respective samples was used for the calculation.

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201, HLA-A*24:02, HLA-A*01:01, HLA-A*03:01, HLA-B*07:02 and HLA-B*44:02 restricted TUMAPs of the invention, demonstrating that these peptides are T-cell epitopes against which CD8+ precursor T cells exist in humans (Table 11).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02, HLA-A*24, HLA-A*01, HLA-A*03, HLA-B*07 or HLA-B*44 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 775) from modified Melan-A/MART-1) and A*0201/DDX5-001 (YLLPAIVHI from DDX5, SEQ ID NO. 776), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^6$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Ovarian Cancer Peptides

For tested HLA class I peptides, in vitro immunogenicity could be demonstrated by generation of peptide specific T-cell lines. Exemplary flow cytometry results after TUMAP-specific multimer staining for 14 peptides of the invention are shown in FIGS. 2 through 9B together with corresponding negative controls. Results for 118 peptides from the invention are summarized in Table 11a and Table 11b.

TABLE 11a in vitro immunogenicity of HLA class I peptides of the invention. Exemplary results of in vitro immunogenicity experiments conducted by the applicant for the peptides of the invention.
<20% = +; 20%-49% = ++; 50%-69% = +++;
>=70% = ++++

| Seq ID | Sequence | Wells positive [%] |
|---|---|---|
| 773 | ALYGKLLKL | +++ |
| 774 | VYVDDIYVI | +++ |

TABLE 11b in vitro immunogenicity of HLA class I peptides of the invention. Exemplary results of in vitro immunogenicity experiments conducted by the applicant for the peptides of the invention.
<20% = +; 20%-49% = ++; 50%-69% = +++; >=70% = ++++

| Seq ID No | Sequence | Wells positive [%] | HLA |
|---|---|---|---|
| 2 | TLLKALLEI | ++ | A*02 |
| 3 | ALIYNLVGI | ++ | A*02 |
| 4 | ALFKAWAL | ++++ | A*02 |
| 5 | RLLDFINVL | ++ | A*02 |
| 7 | ALQAFEFRV | ++++ | A*02 |
| 60 | GLLSLTSTLYL | + | A*02 |
| 62 | KVLGVNVML | ++ | A*02 |
| 64 | FLDPDRHFL | +++ | A*02 |
| 66 | GLLQELSSI | + | A*02 |
| 67 | SLLLPSIFL | +++ | A*02 |
| 71 | YLEDTDRNL | + | A*02 |
| 73 | FLIEELLFA | +++ | A*02 |
| 75 | KVVSVLYNV | +++ | A*02 |
| 11 | SYSDLHYGF | +++ | A*24 |
| 12 | KYEKIFEML | + | A*24 |
| 13 | VYTFLSSTL | + | A*24 |
| 16 | IYSPQFSRL | + | A*24 |
| 18 | KYPVHIYRL | + | A*24 |
| 79 | SYNEHWNYL | + | A*24 |
| 80 | TAYMVSVAAF | + | A*24 |
| 82 | SYFRGFTLI | + | A*24 |

TABLE 11b-continued in vitro immunogenicity of HLA class I peptides of the invention. Exemplary results of in vitro immunogenicity experiments conducted by the applicant for the peptides of the invention.
<20% = +; 20%-49% = ++; 50%-69% = +++; >=70% = ++++

| Seq ID No | Sequence | Wells positive [%] | HLA |
| --- | --- | --- | --- |
| 113 | QLDSNRLTY | + | A*01 |
| 115 | FVDNQYWRY | + | A*01 |
| 20 | RMASPVNVK | + | A*03 |
| 21 | AVRKPIVLK | + | A*03 |
| 22 | SLKERNPLK | + | A*03 |
| 23 | GMMKGGIRK | ++ | A*03 |
| 24 | SMYYPLQLK | + | A*03 |
| 25 | GTSPPSVEK | +++ | A*03 |
| 26 | RISEYLLEK | + | A*03 |
| 27 | VLYGPAGLGK | + | A*03 |
| 28 | KTYETNLEIKK | + | A*03 |
| 30 | ALEVAHRLK | ++ | A*03 |
| 83 | GTYAHTVNR | + | A*03 |
| 84 | KLQPAQTAAK | + | A*03 |
| 85 | VLLGSLFSRK | + | A*03 |
| 86 | VVLLGSLFSRK | + | A*03 |
| 87 | AVAPPTPASK | + | A*03 |
| 90 | KVAGERYVYK | +++ | A*03 |
| 91 | RSLRYYYEK | ++ | A*03 |
| 94 | ATFERVLLR | + | A*03 |
| 95 | QSMYYPLQLK | + | A*03 |
| 99 | KVVDRWNEK | ++ | A*03 |
| 100 | RLFTSPIMTK | + | A*03 |
| 102 | SVLTSSLVK | + | A*03 |
| 106 | AAFVPLLLK | +++ | A*03 |
| 109 | KTFTIKRFLAK | + | A*03 |
| 110 | SAAPPSYFR | ++ | A*03 |
| 32 | SPNKGTLSV | + | B*07 |
| 33 | SPTFHLTL | ++++ | B*07 |
| 34 | LPRGPLASLL | + | B*07 |
| 35 | FPDNQRPAL | + | B*07 |
| 36 | APAAWLRSA | +++ | B*07 |
| 37 | RPLFQKSSM | + | B*07 |
| 38 | SPHPVTALLTL | + | B*07 |
| 39 | RPAPFEVVF | +++ | B*07 |
| 40 | KPGTSYRVTL | ++++ | B*07 |
| 41 | RVRSRISNL | + | B*07 |
| 118 | SPASRSISL | + | B*07 |
| 119 | APLPRPGAVL | ++ | B*07 |
| 120 | RPAMNYDKL | + | B*07 |
| 121 | VPNQSSESL | + | B*07 |
| 123 | KPSESIYSAL | ++ | B*07 |
| 124 | LPSDSHFKITF | ++ | B*07 |
| 128 | YPRTITPGM | + | B*07 |
| 129 | APRPASSL | + | B*07 |
| 130 | FPRLVGPDF | +++ | B*07 |
| 131 | APTEDLKAL | ++ | B*07 |
| 133 | MPNLPSTTSL | ++++ | B*07 |
| 134 | RPIVPGPLL | ++ | B*07 |
| 139 | SPQSMSNTL | + | B*07 |
| 140 | SPRTEASSAVL | + | B*07 |
| 141 | SPMTSLLTSGL | ++ | B*07 |
| 146 | IPRPEVQAL | +++ | B*07 |
| 147 | APRWFPQPTVV | ++ | B*07 |
| 148 | KPYGGSGPL | + | B*07 |
| 149 | GPREALSRL | ++ | B*07 |
| 52 | AEFLLRIFL | + | B*44 |
| 53 | MEHPGKLLF | + | B*44 |
| 55 | HETETRTTW | +++ | B*44 |
| 57 | QESDLRLFL | + | B*44 |
| 58 | GEMEQKQL | ++++ | B*44 |
| 59 | SENVTMKVV | ++ | B*44 |
| 174 | AEATARLNVF | + | B*44 |
| 175 | AEIEPKADG | ++++ | B*44 |
| 177 | TEVGTMNLF | ++ | B*44 |
| 178 | NELFRDGVNW | + | B*44 |
| 179 | REAGDEFEL | + | B*44 |
| 180 | REAGDEFELRY | ++++ | B*44 |
| 181 | GEGPKTSW | + | B*44 |
| 182 | KEATEAQSL | + | B*44 |
| 183 | YEKGIMQKV | ++++ | B*44 |
| 184 | AELEALTDLW | + | B*44 |
| 186 | REGPEEPGL | + | B*44 |
| 187 | GEAQTRIAW | ++ | B*44 |
| 188 | AEFAKKQPWW | ++ | B*44 |
| 189 | KEFLFNMY | ++++ | B*44 |
| 190 | YEVARILNL | ++++ | B*44 |
| 191 | EEDAALFKAW | +++ | B*44 |
| 192 | YEFKFPNRL | + | B*44 |
| 195 | AEDKRHYSV | +++ | B*44 |
| 197 | AEVLLPRLV | ++ | B*44 |
| 198 | QEAARAAL | ++ | B*44 |
| 199 | REIDESLIFY | + | B*44 |
| 200 | AESIPTVSF | +++ | B*44 |
| 201 | AETILTFHAF | +++ | B*44 |
| 202 | HESEATASW | ++ | B*44 |
| 203 | IEHSTQAQDTL | ++++ | B*44 |
| 205 | SEITRIEM | ++++ | B*44 |
| 207 | TEARATSDSW | + | B*44 |
| 208 | TEVSRTEAI | + | B*44 |
| 209 | TEVSRTEL | ++++ | B*44 |
| 210 | VEAADIFQNF | + | B*44 |
| 211 | EEKVFPSPLW | +++ | B*44 |
| 212 | MEQKQLQKRF | ++ | B*44 |
| 213 | KESIPRWYY | + | B*44 |

Example 4

Synthesis of Peptides

All peptides were synthesized using standard and well-established solid phase peptide synthesis using the Fmoc-strategy. Identity and purity of each individual peptide have been determined by mass spectrometry and analytical RP-HPLC. The peptides were obtained as white to off-white lyophilizes (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated overnight with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100-fold in blocking buffer. Samples were incubated for 1 h at 37° C., washed four times, incubated with 2 ug/ml HRP conjugated anti-β2m for 1 h at 37° C., washed again and detected with TMB solution that is stopped with NH₂SO₄. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 12

MHC class I binding scores. Binding of HLA-class I restricted peptides to HLA-A*02:01 was ranged by peptide exchange yield: >10% = +; >20% = ++; >50 = +++; >75% = ++++

| Seq ID No | Sequence | Peptide exchange |
|---|---|---|
| 1 | MIPTFTALL | +++ |
| 2 | TLLKALLEI | ++++ |
| 3 | ALIYNLVGI | ++++ |
| 4 | ALFKAWAL | ++++ |
| 5 | RLLDFINVL | ++++ |
| 6 | SLGKHTVAL | +++ |
| 7 | ALQAFEFRV | ++++ |
| 8 | YLVTKVVAV | ++++ |
| 9 | VLLAGFKPPL | + |
| 60 | GLLSLTSTLYL | ++++ |
| 61 | YMVHIQVTL | ++++ |
| 62 | KVLGVNVML | ++++ |
| 63 | MMEEMIFNL | ++++ |
| 64 | FLDPDRHFL | ++++ |
| 66 | GLLQELSSI | ++++ |
| 67 | SLLLPSIFL | ++++ |
| 68 | KLFDTQQFL | ++++ |
| 69 | TTYEGSITV | ++++ |
| 70 | VLQGLLRSL | ++++ |
| 71 | YLEDTDRNL | ++++ |
| 72 | YLTDLQVSL | ++++ |
| 73 | FLIEELLFA | ++++ |
| 75 | KVVSVLYNV | ++++ |
| 216 | IMFDDAIERA | ++++ |
| 217 | VSSSLTLKV | + |
| 219 | PLPRPGAVL | + |
| 220 | RMTTQLLLL | +++ |
| 221 | SLLDLYQL | ++ |
| 222 | ALMRLIGCPL | ++++ |
| 223 | FAHHGRSL | + |
| 224 | SLPRFQVTL | ++++ |
| 225 | SVFAHPRKL | +++ |
| 227 | YTFRYPLSL | +++ |
| 228 | RLWDWVPLA | ++++ |
| 229 | ISVPAKTSL | + |
| 231 | SVTESTHHL | +++ |
| 232 | TISSLTHEL | ++++ |
| 234 | GVATRVDAI | ++ |
| 236 | SAIPFSMTL | +++ |
| 241 | RQPNILVHL | ++ |
| 242 | STIPALHEI | +++ |
| 243 | YASEGVKQV | +++ |
| 244 | DTDSSVHVQV | + |

TABLE 13

MHC class I binding scores. Binding of HLA-class I restricted peptides to HLA-A*24:02 was ranged by peptide exchange yield: >10% = +; >20% = ++; >50 = +++; >75% = ++++

| Seq ID No | Sequence | Peptide exchange |
|---|---|---|
| 10 | RYSDSVGRVSF | ++++ |
| 11 | SYSDLHYGF | ++++ |
| 12 | KYEKIFEML | ++++ |
| 13 | VYTFLSSTL | ++++ |
| 14 | FYFPTPTVL | ++++ |
| 15 | VYHDDKQPTF | ++++ |
| 16 | IYSPQFSRL | ++++ |
| 17 | RFTTMLSTF | ++++ |
| 18 | KYPVHIYRL | ++++ |
| 19 | KYVKVFHQF | ++++ |
| 76 | KYVAELSLL | ++++ |
| 77 | RYGPVFTV | ++++ |
| 78 | SFAPRSAVF | ++++ |
| 79 | SYNEHWNYL | ++++ |
| 80 | TAYMVSVAAF | +++ |
| 81 | VYNHTTRPL | ++++ |
| 82 | SYFRGFTLI | ++++ |
| 246 | RYLAVVHAVF | ++++ |
| 249 | VYTPTLGTL | ++++ |
| 252 | LYQPRASEM | +++ |
| 255 | VFVSFSSLF | +++ |

TABLE 14

MHC class I binding scores. Binding of HLA-class I restricted peptides to HLA-A*01:01 was ranged by peptide exchange yield: >10% = +; >20% = ++; >50 = +++; >75% = ++++

| Seq ID No | Sequence | Peptide exchange |
|---|---|---|
| 31 | LLDEGAMLLY | ++++ |
| 112 | TVTGAEQIQY | ++ |
| 113 | QLDSNRLTY | +++ |
| 114 | VMEQSAGIMY | ++ |
| 115 | FVDNQYWRY | +++ |
| 116 | VLLDEGAMLLY | ++ |
| 288 | SPVTSVHGGTY | ++ |
| 289 | RWEKTDLTY | ++ |
| 290 | DMDEEIEAEY | ++ |
| 291 | ETIRSVGYY | +++ |
| 292 | NVTMKVVSVLY | +++ |

TABLE 15

MHC class I binding scores. Binding of HLA-class I restricted peptides to HLA-A*03:01 was ranged by peptide exchange yield: >10% = +; >20% = ++; >50 = +++; >75% = ++++

| Seq ID No | Sequence | Peptide exchange |
|---|---|---|
| 20 | RMASPVNVK | ++++ |
| 21 | AVRKPIVLK | +++ |
| 22 | SLKERNPLK | ++ |
| 23 | GMMKGGIRK | +++ |
| 24 | SMYYPLQLK | +++ |
| 25 | GTSPPSVEK | ++ |
| 26 | RISEYLLEK | ++ |
| 27 | VLYGPAGLGK | +++ |
| 28 | KTYETNLEIKK | +++ |
| 30 | ALEVAHRLK | ++ |
| 83 | GTYAHTVNR | +++ |
| 84 | KLQPAQTAAK | ++ |
| 85 | VLLGSLFSRK | ++ |
| 86 | VVLLGSLFSRK | ++ |
| 87 | AVAPPTPASK | ++ |

TABLE 15-continued

MHC class I binding scores. Binding of HLA-class I restricted peptides to HLA-A*03:01 was ranged by peptide exchange yield: >10% = +; >20% = ++; >50 = +++; >75% = ++++

| Seq ID No | Sequence | Peptide exchange |
|---|---|---|
| 88 | VVHAVFALK | +++ |
| 89 | RVAELLLLH | ++ |
| 90 | KVAGERYVYK | +++ |
| 91 | RSLRYYYEK | ++ |
| 93 | KILEEHTNK | ++ |
| 94 | ATFERVLLR | +++ |
| 95 | QSMYYPLQLK | ++ |
| 98 | LLQPPPLLAR | ++ |
| 99 | KVVDRWNEK | ++ |
| 100 | RLFTSPIMTK | +++ |
| 101 | RVFTSSIKTK | ++ |
| 102 | SVLTSSLVK | ++ |
| 104 | VLADSVTTK | ++ |
| 105 | RLFSWLVNR | +++ |
| 106 | AAFVPLLLK | ++ |
| 107 | RLQEWKALK | +++ |
| 109 | KTFTIKRFLAK | ++ |
| 110 | SAAPPSYFR | ++ |
| 256 | RTEEVLLTFK | ++ |
| 257 | VTADHSHVF | + |
| 258 | GAYAHTVNR | +++ |
| 259 | KTLELRVAY | ++ |
| 260 | GTNTVILEY | +++ |
| 261 | HTFGLFYQR | ++ |
| 262 | RSRLNPLVQR | ++ |
| 263 | SSSSATISK | ++ |
| 264 | AIKVIPTVFK | ++ |
| 265 | QIHDHVNPK | ++ |
| 266 | ISYSGQFLVK | +++ |
| 267 | VTDLISPRK | ++ |
| 269 | RLKGDAWVYK | +++ |
| 270 | AVFNPRFYRTY | ++ |
| 271 | RMFADDLHNLNK | +++ |
| 272 | RQPERTILRPR | ++ |
| 273 | RVNAIPFTY | +++ |
| 274 | KTFPASTVF | + |
| 275 | STTFPTLTK | ++ |
| 276 | VSKTTGMEF | + |
| 277 | TTALKTTSR | + |
| 278 | NLSSITHER | ++ |
| 279 | SVSSETTKIKR | ++ |
| 280 | SVSGVKTTF | ++ |
| 281 | RAKELEATF | + |
| 283 | IVQEPTEEK | ++ |
| 284 | KSLIKSWKK | ++ |
| 285 | GTVNPTVGK | ++ |
| 286 | TVAPPQGVVK | ++ |
| 287 | RRIHTGEKPYK | ++ |

TABLE 16

MHC class I binding scores. Binding of HLA-class I restricted peptides to HLA-B*07:02 was ranged by peptide exchange yield: >10% = +; >20% = 30 +; >50 = +++; >75% = ++++

| Seq ID No | Sequence | Peptide exchange |
|---|---|---|
| 32 | SPNKGTLSV | "+++" |
| 33 | SPTFHLTL | "+++" |
| 34 | LPRGPLASLL | "+++" |
| 35 | FPDNQRPAL | "+++" |
| 36 | APAAWLRSA | "++" |
| 37 | RPLFQKSSM | "+++" |
| 38 | SPHPVTALLTL | "+++" |
| 39 | RPAPFEVVF | "+++" |
| 40 | KPGTSYRVTL | "+++" |
| 41 | RVRSRISNL | "+++" |
| 118 | SPASRSISL | "+++" |
| 119 | APLPRPGAVL | "+++" |
| 120 | RPAMNYDKL | "++" |
| 121 | VPNQSSESL | "+++" |
| 122 | YPGFPQSQY | "++" |
| 123 | KPSESIYSAL | "+++" |
| 124 | LPSDSHFKITF | "+++" |
| 125 | VPVYILLDEM | "++" |
| 126 | KPGPEDKL | "++" |
| 127 | APRAGSQVV | "+++" |
| 128 | YPRTITPGM | "+++" |
| 129 | APRPASSL | "+++" |
| 130 | FPRLVGPDF | "+++" |
| 131 | APTEDLKAL | "+++" |
| 132 | IPGPAQSTI | "++" |
| 133 | MPNLPSTTSL | "+++" |
| 134 | RPIVPGPLL | "+++" |
| 135 | RVRSTISSL | "+++" |
| 136 | SPFSAEEANSL | "+++" |
| 137 | SPGATSRGTL | "+++" |
| 138 | SPMATTSTL | "+++" |
| 139 | SPQSMSNTL | "+++" |
| 140 | SPRTEASSAVL | "+++" |
| 141 | SPMTSLLTSGL | "+++" |
| 142 | TPGLRETSI | "++" |
| 143 | SPAMTSTSF | "++" |
| 144 | SPSPVSSTL | "+++" |
| 145 | SPSSPMSTF | "++" |
| 146 | IPRPEVQAL | "+++" |
| 147 | APRWFPQPTVV | "+++" |
| 148 | KPYGGSGPL | "+++" |
| 149 | GPREALSRL | "+++" |
| 293 | VPDSGATATAY | "++" |
| 294 | YPLRGSSIF | "+++" |
| 295 | YPLRGSSIFGL | "+++" |
| 296 | YPLRGSSI | "++" |
| 297 | TVREASGLL | "+++" |
| 298 | YPTEHVQF | "++" |
| 299 | HPGSSALHY | "++" |
| 300 | IPMAAVKQAL | "+++" |
| 301 | SPRRSPRISF | "++" |
| 302 | RVEEVRALL | "+++" |
| 303 | LPMWKVTAF | "+++" |
| 304 | LPRPGAVL | "+++" |
| 305 | TPWAESSTKF | "++" |
| 306 | APVIFSHSA | "++" |
| 307 | LPYGPGSEAAAF | "+++" |
| 308 | YPEGAAYEF | "++" |
| 309 | FPQSQYPQY | "++++" |
| 311 | RPLFYVVSL | "++" |
| 312 | LPYFREFSM | "+++" |
| 313 | KVKSDRSVF | "+" |
| 314 | VPDQHPEI | "+++" |
| 315 | SPRENFPDTL | "+++" |
| 316 | EPKTATVL | "++" |
| 317 | FPFQPGSV | "+++" |
| 318 | FPNRLNLEA | "+++" |
| 319 | SPAEPSVYATL | "++++" |
| 320 | FPMSPVTSV | "+++" |
| 321 | SPMDTFLLI | "++" |
| 322 | SPDPSKHLL | "++" |
| 323 | RPMPNLRSV | "+++" |
| 324 | VPYRVVGL | "++" |
| 325 | GPRNAQRVL | "+++" |
| 326 | VPSEIDAAF | "++" |
| 327 | SPLPVTSLI | "+++" |
| 328 | EPVTSSLPNF | "++" |
| 329 | FPAMTESGGMIL | "+++" |
| 330 | FPFVTGSTEM | "++" |
| 331 | FPHPEMTTSM | "+++" |
| 332 | FPHSEMTTL | "+++" |
| 333 | FPHSEMTTVM | "+++" |

TABLE 16-continued

MHC class I binding scores. Binding of HLA-class I restricted peptides to HLA-B*07:02 was ranged by peptide exchange yield: >10% = +; >20% = 30 +; >50 = +++; >75% = ++++

| Seq ID No | Sequence | Peptide exchange |
|---|---|---|
| 334 | FPYSEVTTL | "+++" |
| 335 | HPDPVGPGL | "++" |
| 336 | HPKTESATPAAY | "++" |
| 337 | HPVETSSAL | "+++" |
| 338 | HVTKTQATF | "++" |
| 339 | LPAGTTGSLVF | "+++" |
| 340 | LPEISTRTM | "++" |
| 341 | LPLDTSTTL | "+++" |
| 342 | LPLGTSMTF | "+++" |
| 343 | LPSVSGVKTTF | "++" |
| 344 | LPTQTTSSL | "+++" |
| 345 | LPTSESLVSF | "++" |
| 346 | LPWDTSTTLF | "+++" |
| 347 | MPLTTGSQGM | "++" |
| 348 | MPNSAIPFSM | "+++" |
| 349 | MPSLSEAMTSF | "+++" |
| 350 | NPSSTTTEF | "+++" |
| 351 | NVLTSTPAF | "++" |
| 352 | SPAETSTNM | "+++" |
| 353 | SPAMTTPSL | "+++" |
| 354 | SPLPVTSLL | "+++" |
| 355 | SPLVTSHIM | "+++" |
| 356 | SPNEFYFTV | "+++" |
| 357 | SPSPVPTTL | "+++" |
| 358 | SPSPVTSTL | "+++" |
| 359 | SPSTIKLTM | "+++" |
| 360 | SPSVSSNTY | "++" |
| 361 | SPTHVTQSL | "+++" |
| 362 | SPVPVTSLF | "+++" |
| 363 | TAKTPDATF | "++" |
| 364 | TPLATTQRF | "++" |
| 365 | TPLATTQRFTY | "++" |
| 367 | TPSVVTEGF | "++" |
| 368 | VPTPVFPTM | "++" |
| 369 | FPHSEMTTV | "+++" |
| 370 | PGGTRQSL | "+" |
| 371 | LYVDGFTHW | "++" |
| 372 | IPRNPPPTLL | "+++" |
| 373 | RPRALRDLRIL | "+++" |
| 374 | NPIGDTGVKF | "+++" |
| 375 | AAASPLLLL | "++" |
| 376 | RPRSPAGQVA | "+++" |
| 377 | RPRSPAGQVAAA | "+++" |
| 378 | RPRSPAGQVAA | "+++" |
| 379 | GPPPLVYVL | "+++" |
| 380 | IPTYGRTF | "+++" |
| 381 | LPEQTPLAF | "++" |
| 382 | SPMHDRWTF | "+++" |
| 383 | TPTKETVSL | "+++" |
| 384 | YPGLRGSPM | "++++" |
| 385 | SPALHIGSV | "+++" |
| 386 | FPFNPLDF | "++" |
| 387 | APLKLSRTPA | "+++" |
| 388 | SPAPLKLSRTPA | "++" |
| 389 | SPGAQRTFFQL | "+++" |
| 390 | NPDLRRNVL | "+++" |
| 391 | APSTPRITTF | "+++" |
| 392 | KPIESTLVA | "+++" |

TABLE 17

MHC class I binding scores. Binding of HLA-class I restricted peptides to HLA-B*44:02 was measured by peptide exchange yield: >10% = +; >20% = ++; >50 =+++; >75% = ++++

| Seq ID No | Sequence | Peptide exchange |
|---|---|---|
| 52 | AEFLLRIFL | "++" |
| 53 | MEHPGKLLF | "++++" |
| 54 | AEITITTQTGY | "+++" |
| 55 | HETETRTTW | "+++" |
| 56 | SEPDTTASW | "+++" |
| 57 | QESDLRLFL | "+++" |
| 58 | GEMEQKQL | "++" |
| 59 | SENVTMKVV | "+++" |
| 173 | AEAQVGDERDY | "+++" |
| 174 | AEATARLNVF | "++++" |
| 175 | AEIEPKADG | "++" |
| 176 | AEIEPKADGSW | "+++" |
| 177 | TEVGTMNLF | "+++" |
| 178 | NELFRDGVNW | "+++" |
| 179 | REAGDEFEL | "++" |
| 180 | REAGDEFELRY | "++" |
| 181 | GEGPKTSW | "++" |
| 182 | KEATEAQSL | "+++" |
| 183 | YEKGIMQKV | "++" |
| 184 | AELEALTDLW | "+++" |
| 185 | AERQPGAASL | "++" |
| 186 | REGPEEPGL | "++" |
| 187 | GEAQTRIAW | "+++" |
| 188 | AEFAKKQPWW | "+++" |
| 189 | KEFLFNMY | "++" |
| 190 | YEVARILNL | "++" |
| 191 | EEDAALFKAW | "+++" |
| 192 | YEFKPNRL | "+++" |
| 193 | LEAQQEAL | "++" |
| 194 | KEVDPTSHSY | "++" |
| 195 | AEDKRHYSV | "++" |
| 196 | REMPGGPVW | "+++" |
| 197 | AEVLLPRLV | "+++" |
| 198 | QEAARAAL | "++" |
| 199 | REIDESLIFY | "+++" |
| 200 | AESIPTVSF | "+++" |
| 201 | AETILTFHAF | "+++" |
| 202 | HESEATASW | "+++" |
| 203 | IEHSTQAQDTL | "++" |
| 204 | RETSTSEETSL | "+++" |
| 205 | SEITRIEM | "++" |
| 206 | SESVTSRTSY | "+++" |
| 207 | TEARATSDSW | "+++" |
| 208 | TEVSRTEAI | "++" |
| 209 | TEVSRTEL | "++" |
| 210 | VEAADIFQNF | "+++" |
| 211 | EEKVFPSPLW | "+++" |
| 212 | MEQKQLQKRF | "+++" |
| 213 | KESIPRWYY | "++" |
| 214 | VEQTRAGSLL | "++" |
| 215 | SEDGLPEGIHL | "++" |
| 396 | REASGLLSL | "+++" |
| 397 | REGDTVQLL | "++" |
| 398 | SFEQVVNELF | "++" |
| 399 | RELLHLVTL | "+++" |
| 400 | GEIEIHLL | "+" |
| 402 | RELANDELIL | "++" |
| 403 | EEAQWVRKY | "++" |
| 404 | NEAIMHQY | "++" |
| 405 | NEIWTHSY | "+" |
| 406 | EDGRLVIEF | "+" |
| 407 | AEHEGVSVL | "++" |
| 408 | LEKALQVF | "++" |
| 409 | REFVLSKGDAGL | "+++" |
| 410 | SEDPSKLEA | "+" |
| 411 | LELPPILVY | "+" |
| 412 | QEILTQVKQ | "++" |
| 413 | IEALSGKIEL | "++" |
| 414 | EDAALFKAW | "++" |
| 415 | REEDAALFKAW | "+++" |
| 416 | SEEETRVVF | "+++" |
| 417 | AEHFSMIRA | "++" |

TABLE 17-continued

MHC class I binding scores. Binding of HLA-class I restricted peptides to HLA-B*44:02 was measured by peptide exchange yield: >10% = +; >20% = ++; >50 =+++; >75% = ++++

| Seq ID No | Sequence | Peptide exchange |
|---|---|---|
| 418 | FEDAQGHIW | "+++" |
| 419 | HEFGHVLGL | "++" |
| 420 | FESHSTVSA | "+" |
| 421 | GEPATTVSL | "++" |
| 422 | SETTFSLIF | "+++" |
| 423 | SEVPTGTTA | "++" |
| 424 | TEFPLFSAA | "+" |
| 425 | SEVPLPMAI | "+++" |
| 426 | PEKTTHSF | "+" |
| 427 | HESSSHHDL | "++" |
| 429 | REKFIASVI | "++" |
| 431 | AEQDPDELNKA | "++" |
| 432 | EEQYIAQF | "+" |
| 433 | SDSQVRAF | "+" |
| 434 | KEAIREHQM | "++" |
| 435 | REEFVSIDHL | "++" |
| 436 | REPGDIFSEL | "++" |
| 437 | TEAVVTNEL | "++" |
| 438 | SEVDSPNVL | "+++" |

Example 6

Stability of Peptide-MHC Class I Complexes

Peptide-MHC stability assays for HLA-B*08:01 peptides were performed. The data were obtained using a proximity based, homogenous, real-time assay in order to measure the dissociation of peptides from HLA class I molecules. First, human recombinant HLA-B*08:01 and b2m were expressed in *E. coli* and purified in a series of liquid chromatography based steps (Ferre et al., 2003; Ostergaard et al., 2001). Then, the stability of a peptide-MHC complex (pMHC) was determined by measuring the amount of b2m associated with the MHC heavy chain over time at 37° C. (Harndahl et al., 2012). The stability of each pMHC, expressed as the half life of b2m associated with the respective heavy chain, was calculated by fitting the data to a one-phase dissociation equation.

The pMHC stabilities were measured in three independent experiments with the peptides in question, and for HLA-B*08:01 were found to span the range from weak-binders (+) to very stable binders (++++). The mean half-life (T1/2) is shown in Table 18.

TABLE 18

Mean half-life (T1/2) based on three individual measurements. T1/2 > 2 h = +; T1/2 > 4 h = ++; T1/2 > 6 h = +++; T1/2 > 10 h = ++++

| Seq ID No | Sequence | Mean Half-life (T1/2) |
|---|---|---|
| 43 | ALKARTVTF | +++ |
| 44 | LNKQKVTF | ++++ |
| 45 | VGREKKLAL | ++ |
| 46 | DMKKAKEQL | + |
| 47 | MPNLRSVDL | ++ |
| 48 | DVKKKIKEV | + |
| 49 | LPRLKAFMI | ++ |
| 50 | DMKYKNRV | + |
| 51 | SLRLKNVQL | + |
| 150 | MAAVKQAL | ++ |
| 151 | HLLLKVLAF | ++ |
| 152 | MGSARVAEL | ++ |
| 153 | NAMLRKVAV | + |
| 154 | MLRKIAVAA | + |
| 156 | HVKEKFLL | ++ |
| 157 | EAMKRLSYI | + |
| 158 | LPKLAGLL | + |
| 159 | VLKHKLDEL | + |
| 160 | YPKARLAF | +++ |
| 161 | ALKTTTTAL | + |
| 162 | QAKTHSTL | + |
| 163 | QGLLRPVF | ++ |
| 164 | SIKTKSAEM | +++ |
| 166 | TPKLRETSI | ++ |
| 167 | TSHERLTTL | ++ |
| 169 | TSMPRSSAM | +++ |
| 170 | YLLEKSRVI | ++ |
| 171 | FAFRKEAL | ++ |
| 172 | KLKERNREL | +++ |
| 394 | MYKMKKPI | + |
| 395 | VLLPRLVSC | + |

Example 7

Binding Scores of Selected Peptides for HLA Class II Allotypes

Major histocompatibility complex class II (MHC-II) molecules are predominantly expressed on the surface of professional antigen presenting cells, where they display peptides to T helper cells, which orchestrate the onset and outcome of many host immune responses. Understanding which peptides will be presented by the MHC-II molecule is therefore important for understanding the activation of T helper cells and can be used to identify T-cell epitopes. Peptides presented by the MHC class II molecule bind to a binding groove formed by residues of the MHC α- and β-chain. The peptide-MHC binding affinity is primarily determined by the amino acid sequence of the peptide-binding core. HLA class II binding prediction algorithms are only available for the most important class II alleles and have been tested using the SYFPEITHI algorithm (Rammensee et al., 1999). The algorithm has already been successfully used to identify class I and class II epitopes from a wide range of antigens, e.g. from the human tumor-associated antigens TRP2 (class I) (Sun et al., 2000) and SSX2 (class II) (Neumann et al., 2004). Table 20 shows the HLA class II allotypes which are likely to bind the selected peptides. The peptide was considered as binding to an HLA molecule if the SYFPEITHI score was equal to or higher than 18.

TABLE 20

Binding of the class II peptides to various HLA class II allotypes. Based on the prediction by the SYFPEITHI algorithm, the selected peptides are likely to bind to at least 4 of the HLA class II allotypes with known binding motif. Listed are all HLA class II alleles for which a SYFPEITHI prediction matrix is available.

| Seq ID No | Sequence | Best HLA class II binders | HLA Class II binders | No of HLA Class II binder |
|---|---|---|---|---|
| 552 | GVNAMLRKVAVAAASKPHVE | DRB1*11:04 | DQA1*05:01/DQB1*02:01 (DQ2), QA1*05:01/DQB1*03:01 (DQ7), DQB1*06:02, DRB1*01:01, DRB1*04:01, DRB1*04:02, DRB1*04:04, DRB1*04:05, DRB1*07:01, DRB1*09:01, DRB1*11:01, DRB1*11:04, DRB1*13:01, DRB1*13:02, DRB1*15:01 | 15 |
| 560 | PNFSGNWKIIRSENFEELLK | DRB1*07:01 | DQA1*05:01/DQB1*02:01 (DQ2), DRB1*01:01, DRB1*03:01, DRB1*04:01, DRB1*04:04, DRB1*04:05, DRB1*07:01, DRB1*08:02, DRB1*08:03, DRB1*09:01, DRB1*11:01, DRB1*13:02, DRB1*15:01, DRB1*15:02 | 14 |
| 574 | LPDFYNDWMFIAKHLPDL | DRB1*11:01 | DQA1*05:01/DQB1*02:01 (DQ2), DRB1*01:01, DRB1*03:01, DRB1*04:01, DRB1*04:02, DRB1*04:04, DRB1*04:05, DRB1*07:01, DRB1*08:02, DRB1*08:03, DRB1*11:01, DRB1*11:04, DRB1*13:02, DRB1*15:01, DRB1*15:02 | 15 |
| 575 | VGDDHLLLLQGEQLRRT | DRB1*01:01 | DQA1*05:01/DQB1*02:01 (DQ2), DRB1*01:01, DRB1*03:01, DRB1*04:01, DRB1*04:04, DRB1*09:01, DRB1*15:01, DRB1*15:02 | 8 |
| 579 | SGGPLVCDETLQGILS | DQA1*0501/DQB1*0201 (DQ2) | DQA1*05:01/DQB1*02:01 (DQ2), DQA1*05:01/DQB1*03:01 (DQ7), DRB1*01:01, DRB1*03:01, DRB1*04:01, DRB1*04:04, DRB1*04:05, DRB1*15:01 | 8 |
| 582 | GSQPWQVSLFNGLSFH | DRB1*15:01 | DQA1*05:01/DQB1*02:01 (DQ2), DQB1*06:02, DRB1*01:01, DRB1*03:01, DRB1*04:01, DRB1*04:04, DRB1*07:01, DRB1*09:01, DRB1*15:01, DRB1*15:02 | 10 |
| 583 | LTVKLPDGYEFKFPNRLNLEAINY | DQA1*05:01/DQB1*02:01 (DQ2) | DQA1*05:01/DQB1*02:01 (DQ2), DRB1*01:01, DRB1*03:01, DRB1*04:01, DRB1*04:04, DRB1*04:05, DRB1*07:01, DRB1*08:02, DRB1*08:03, DRB1*09:01, DRB1*11:01, DRB1*13:02, DRB1*15:01, DRB1*15:02 | 14 |
| 587 | DQANLTVKLPDGYEFKFPNRLNL | DQA1*05:01/DQB1*02:01 (DQ2) | DQA1*05:01/DQB1*02:01 (DQ2), DRB1*01:01, DRB1*03:01, DRB1*04:01, DRB1*04:04, DRB1*04:05, DRB1*07:01, DRB1*08:02, DRB1*08:03, DRB1*11:01, DRB1*13:02, DRB1*15:01, DRB1*15:02 | 13 |
| 588 | VAPDAKSFVLNLGKDSNNL | DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*08:02, DRB1*08:03, DRB1*09:01, DRB1*11:01, DRB1*11:04, DRB1*13:01, DRB1*13:02 | 16 |
| 590 | RVRGEVAPDAKSFVLNLG | DRB1*03:01 | DQA1*05:01/DQB1*02:01 (DQ2), DQA1*05:01/DQB1*03:01 (DQ7), DRB1*01:01, DRB1*03:01, DRB1*04:01, DRB1*04:04, DRB1*07:01, DRB1*09:01, DRB1*11:04, DRB1*15:01 | 10 |
| 596 | MAADGDFKIKCVAFD | DQA1*05:01/DQB1*02:01 (DQ2); DRB1*03:01; DRB1*07:01 | DQA1*05:01/DQB1*02:01 (DQ2), DRB1*01:01, DRB1*03:01, DRB1*04:01, DRB1*04:04, DRB1*04:05, DRB1*07:01, DRB1*08:03, DRB1*09:01, DRB1*15:01 | 10 |
| 597 | SPDAESLFREALSNKVDEL | DRB1*07:01 | DQA1*05:01/DQB1*02:01 (DQ2), DQA1*05:01/DQB1*03:01 (DQ7), | 8 |

TABLE 20-continued

Binding of the class II peptides to various HLA class II allotypes. Based on the prediction by the SYFPEITHI algorithm, the selected peptides are likely to bind to at least 4 of the HLA class II allotypes with known binding motif. Listed are all HLA class II alleles for which a SYFPEITHI prediction matrix is available.

| Seq ID No | Sequence | Best HLA class II binders | HLA Class II binders | No of HLA Class II binder |
|---|---|---|---|---|
| | | | DRB1*01:01, DRB1*04:01, DRB1*04:04, DRB1*04:05, DRB1*07:01, DRB1*09:01 | |
| 601 | LSNKVDELAHFLLRK | DQA1*05:01/DQB1*02:01 (DQ2) | DQA1*05:01/DQB1*02:01 (DQ2), DRB1*01:01, DRB1*03:01, DRB1*04:01, DRB1*04:02, DRB1*04:04, DRB1*04:05, DRB1*07:01, DRB1*08:02, DRB1*08:03, DRB1*11:01, DRB1*11:04, DRB1*15:01, DRB1*15:02 | 14 |
| 604 | KLITQDLVKLKYLEYRQ | DQA1*05:01/DQB1*02:01 (DQ2) | DQA1*05:01/DQB1*02:01 (DQ2), DRB1*01:01, DRB1*03:01, DRB1*04:01, DRB1*04:04, DRB1*08:02, DRB1*13:01, DRB1*13:02, DRB1*15:01 | 9 |
| 605 | LTVAEVQKLLGPHVEGLKAEERHRP | DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*09:01, DRB1*11:01, DRB1*11:04, DRB1*13:01, DRB1*15:01, DRB1*15:02 | 15 |
| 622 | MDALRGLLPVLGQPIIRSIPQGIVA | DRB1*01:01 | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:02, DRB1*04:04, DRB1*04:05, DRB1*07:01, DRB1*09:01, DRB1*11:01, DRB1*11:04, DRB1*15:01, DRB1*15:02 | 15 |
| 645 | RGLLPVLGQPIIRSIPQGIVAAWRQ | DRB1*01:01; DRB1*09:01 | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:02, DRB1*04:04, DRB1*07:01, DRB1*09:01, DRB1*11:01, DRB1*11:04, DRB1*15:01, DRB1*15:02 | 14 |
| 658 | VSTMDALRGLLPVLGQPIIRSIPQG | DRB1*01:01 | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:02, DRB1*04:04, DRB1*04:05, DRB1*09:01, DRB1*11:01, DRB1*11:04, DRB1*15:01, DRB1*15:02 | 14 |
| 662 | LRTDAVLPLTVAEVQKLLGPHVEG | DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*09:01, DRB1*11:01, DRB1*11:04, DRB1*13:01, DRB1*15:01, DRB1*15:02 | 15 |
| 669 | VLPLTVAEVQKLLGPHVEGLKAEE | DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*09:01, DRB1*11:01, DRB1*11:04, DRB1*13:01, DRB1*15:01, DRB1*15:02 | 15 |
| 672 | LRGLLPVLGQPIIRSIPQGIVAA | DRB1*01:01 | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:02, DRB1*04:04,, DRB1*07:01, DRB1*09:01, DRB1*11:01, DRB1*11:04, DRB1*15:01, DRB1*15:02 | 14 |
| 673 | IPFTYEQLDVLKHKLDELYPQ | DRB1*08:03 | DQA1*05:01/DQB1*02:01 (DQ2), DRB1*01:01, DRB1*03:01, DRB1*04:01, DRB1*04:04, DRB1*04:05, DRB1*07:01, | 15 |

TABLE 20-continued

Binding of the class II peptides to various HLA class II allotypes. Based on the prediction by the SYFPEITHI algorithm, the selected peptides are likely to bind to at least 4 of the HLA class II allotypes with known binding motif. Listed are all HLA class II alleles for which a SYFPEITHI prediction matrix is available.

| Seq ID No | Sequence | Best HLA class II binders | HLA Class II binders | No of HLA Class II binder |
|---|---|---|---|---|
| | | | DRB1*08:02, DRB1*08:03, DRB1*09:01, DRB1*11:01, DRB1*11:04, DRB1*13:02, DRB1*15:01, DRB1*15:02 | |
| 676 | VPPSSIWAVRPQDLDTCDPR | DQA1*05:01/DQB1*02:01 (DQ2) | DQA1*05:01/DQB1*02:01 (DQ2), DRB1*01:01, DRB1*03:01, DRB1*04:01, DRB1*04:04, DRB1*04:05, DRB1*07:01, DRB1*08:03, DRB1*09:01, DRB1*15:01 | 10 |
| 679 | WGVRGSLLSEADVRALGGLA | DRB1*09:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*09:01, DRB1*11:01, DRB1*15:01 | 12 |
| 706 | LSTERVRELAVALAQKNVK | DQA1*05:01/DQB1*03:01 (DQ7) | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:02, DRB1*04:04, DRB1*04:05, DRB1*09:01, DRB1*11:01, DRB1*11:04, DRB1*13:01, DRB1*15:01, DRB1*15:02 | 15 |
| 714 | AIPFTYEQLDVLKHKLDE | DRB1*08:03 | DQA1*05:01/DQB1*02:01 (DQ2), DRB1*01:01, DRB1*03:01, DRB1*04:01, DRB1*04:04, DRB1*04:05, DRB1*07:01, DRB1*08:02, DRB1*08:03, DRB1*09:01, DRB1*11:01, DRB1*11:04, DRB1*13:02, DRB1*15:01, DRB1*15:02 | 15 |
| 715 | GLSTERVRELAVALAQKN | DQA1*05:01/DQB1*03:01 (DQ7) | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:02, DRB1*04:04, DRB1*04:05, DRB1*09:01, DRB1*11:01, DRB1*11:04, DRB1*13:01, DRB1*15:01, DRB1*15:02 | 15 |
| 717 | IPQGIVAAWRQRSSRDPS | DRB1*11:04 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*11:01, DRB1*11:04, DRB1*13:01, DRB1*15:01 | 13 |
| 720 | ALGGLACDLPGRFVAES | DQA1*05:01/DQB1*02:01 (DQ2) | DQA1*05:01/DQB1*02:01 (DQ2), DQA1*05:01/DQB1*03:01 (DQ7), DQB1*06:02, DRB1*01:01, DRB1*03:01, DRB1*04:05, DRB1*11:01, DRB1*11:04 | 8 |
| 721 | RELAVALAQKNVKLSTE | DQA1*05:01/DQB1*03:01 (DQ7) | DQA1*05:01/DQB1*03:01 (DQ7), DQB1*06:02, DRB1*01:01, DRB1*03:01, DRB1*04:01, DRB1*04:04, DRB1*04:05, DRB1*09:01, DRB1*11:04, DRB1*13:01, DRB1*15:01 | 11 |
| 722 | LKALLEVNKGHEMSPQ | DQA1*05:01/DQB1*02:01 (DQ2); DRB1*01:01; DRB1*04:05; DRB1*08:03; DRB1*11:04 | DQA1*05:01/DQB1*02:01 (DQ2), DQB1*06:02, DRB1*01:01, DRB1*03:01, DRB1*04:01, DRB1*04:02, DRB1*04:04, DRB1*04:05, DRB1*08:03, DRB1*11:01, DRB1*11:04, DRB1*13:01, DRB1*15:01 | 13 |
| 723 | TFMKLRTDAVLPLTVA | DRB1*01:01 | DQA1*05:01/DQB1*02:01 (DQ2), DRB1*01:01, DRB1*03:01, DRB1*04:01, DRB1*04:04, DRB1*04:05, DRB1*07:01, DRB1*08:02, DRB1*08:03, DRB1*09:01, DRB1*13:02, DRB1*15:01, DRB1*15:02 | 13 |
| 727 | TLGLGLQGGIPNGYLV | DQA1*05:01/DQB1*02:01 D(DQ2); RB1*01:01; | DQA1*05:01/DQB1*02:01 (DQ2), DRB1*01:01, DRB1*03:01, DRB1*04:01, | 9 |

TABLE 20-continued

Binding of the class II peptides to various HLA class II allotypes. Based on the prediction by the SYFPEITHI algorithm, the selected peptides are likely to bind to at least 4 of the HLA class II allotypes with known binding motif. Listed are all HLA class II alleles for which a SYFPEITHI prediction matrix is available.

| Seq ID No | Sequence | Best HLA class II binders | HLA Class II binders | No of HLA Class II binder |
|---|---|---|---|---|
| | | DRB1*15:01 | DRB1*04:02, DRB1*04:04, DRB1*07:01, DRB1*09:01, DRB1*15:01 | |
| 728 | DLPGRFVAESAEVLL | DQA1*05:01/DQB1*02:01 (DQ2) | DQA1*05:01/DQB1*02:01 (DQ2), DQA1*05:01/DQB1*03:01 (DQ7), DQB1*06:02, DRB1*01:01, DRB1*03:01, DRB1*04:01, DRB1*04:04, DRB1*04:05, DRB1*07:01, DRB1*09:01, DRB1*15:01, DRB1*15:02 | 12 |
| 732 | ERHRPVRDWILRQRQ | DRB1*15:01 | DQA1*05:01/DQB1*02:01 (DQ2), DRB1*04:01, DRB1*04:04, DRB1*15:01 | 4 |
| 733 | SPRQLLGFPCAEVSG | DRB1*01:01 | DQA1*05:01/DQB1*02:01 (DQ2), DQA1*05:01/DQB1*03:01 (DQ7), DQB1*06:02, DRB1*01:01, DRB1*04:01, DRB1*04:04, DRB1*15:01, DRB1*15:02 | 8 |
| 734 | SRTLAGETGQEAAPL | DRB1*01:01 | DQA1*05:01/DQB1*02:01 (DQ2), DRB1*01:01, DRB1*04:01, DRB1*04:04, DRB1*04:05, DRB1*15:01 | 6 |
| 735 | VTSLETLKALLEVNK | DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*08:03, DRB1*11:01, DRB1*11:04, DRB1*13:01, DRB1*15:01, DRB1*15:02 | 15 |
| 745 | WELSQLTNSVTELGPYTLDRD | DQA1*05:01/DQB1*02:01 (DQ2); DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:02, DRB1*04:04, DRB1*04:05, DRB1*07:01, DRB1*09:01, DRB1*13:01, DRB1*15:01, DRB1*15:02 | 13 |
| 746 | EITITTQTGYSLATSQVTLP | DRB1*01:01 | DQA1*05:01/DQB1*02:01 (DQ2), DQA1*05:01/DQB1*03:01 (DQ7), DRB1*01:01, DRB1*03:01, DRB1*04:01, DRB1*04:04, DRB1*04:05, DRB1*07:01, DRB1*09:01, DRB1*15:01 | 10 |
| 747 | ATTPSWVETHSIVIQGFPH | DRB1*07:01 | DQA1*05:01/DQB1*02:01 (DQ2), DQA1*05:01/DQB1*03:01 (DQ7), DRB1*01:01, DRB1*04:01, DRB1*04:04, DRB1*04:05, DRB1*07:01, DRB1*15:01, DRB1*15:02 | 9 |
| 748 | GIKELGPYTLDRNSLYVNG | DQA1*05:01/DQB1*02:01 (DQ2); DRB1*01:01 | DQA1*05:01/DQB1*02:01 (DQ2), DRB1*01:01, DRB1*03:01, DRB1*04:01, DRB1*04:02, DRB1*04:04, DRB1*04:05, DRB1*07:01, DRB1*08:02, DRB1*09:01, DRB1*13:02, DRB1*15:01, DRB1*15:02 | 13 |
| 755 | IELGPYLLDRGSLYVNG | DQA1*05:01/DQB1*02:01 (DQ2) | DQA1*05:01/DQB1*02:01 (DQ2), DRB1*01:01, DRB1*03:01, DRB1*04:01, DRB1*04:02, DRB1*04:04, DRB1*04:05, DRB1*07:01, DRB1*08:02, DRB1*09:01, DRB1*11:04, DRB1*13:02, DRB1*15:01, DRB1*15:02 | 14 |
| 759 | EELGPYTLDRNSLYVNG | DRB1*03:01 | DQA1*05:01/DQB1*02:01 (DQ2), DRB1*03:01, DRB1*04:01, DRB1*04:02, DRB1*04:04, DRB1*04:05, DRB1*07:01, DRB1*08:02, DRB1*09:01, DRB1*13:02, DRB1*15:01, DRB1*15:02 | 12 |
| 760 | LKPLFKSTSVGPLYSG | DRB1*11:04 | DQA1*05:01/DQB1*02:01 (DQ2), DRB1*01:01, DRB1*03:01, DRB1*04:01, DRB1*04:02, DRB1*04:04, DRB1*04:05, | 16 |

TABLE 20-continued

Binding of the class II peptides to various HLA class II allotypes. Based on the prediction by the SYFPEITHI algorithm, the selected peptides are likely to bind to at least 4 of the HLA class II allotypes with known binding motif. Listed are all HLA class II alleles for which a SYFPEITHI prediction matrix is available.

| Seq ID No | Sequence | Best HLA class II binders | HLA Class II binders | No of HLA Class II binder |
|---|---|---|---|---|
| | | | DRB1*07:01, DRB1*08:02, DRB1*08:03, DRB1*09:01, DRB1*11:01, DRB1*11:04, DRB1*13:01, DRB1*13:02, DRB1*15:01 | |
| 764 | FDKAFTAATTEVSRTE | DQA1*05:01/DQB1*03:01 (DQ7) | DQA1*05:01/DQB1*03:01 (DQ7), DRB1*01:01, DRB1*04:01, DRB1*04:04, DRB1*04:05, DRB1*07:01, DRB1*09:01, DRB1*11:01, DRB1*15:01 | 9 |
| 765 | ELGPYTLDRDSLYVN | DQA1*05:01/DQB1*02:01 (DQ2) | DQA1*05:01/DQB1*02:01 (DQ2), DRB1*03:01, DRB1*04:01, DRB1*04:02, DRB1*04:04, DRB1*04:05, DRB1*07:01, DRB1*08:02, DRB1*13:02, DRB1*15:01, DRB1*15:02 | 11 |
| 766 | GLLKPLFKSTSVGPL | DRB1*11:04 | DQA1*05:01/DQB1*02:01 (DQ2), DRB1*01:01, DRB1*03:01, DRB1*04:01, DRB1*04:02, DRB1*04:04, DRB1*04:05, DRB1*07:01, DRB1*08:02, DRB1*08:03, DRB1*09:01, DRB1*11:01, DRB1*11:04, DRB1*13:01, DRB1*13:02, DRB1*15:01 | 16 |
| 768 | SDPYKATSAVVITST | DQA1*05:01/DQB1*03:01 (DQ7) | DQA1*05:01/DQB1*02:01 (DQ2), DQA1*05:01/DQB1*03:01 (DQ7), DQB1*06:02, DRB1*01:01, DRB1*04:01, DRB1*04:04, DRB1*07:01, DRB1*09:01, DRB1*15:01, DRB1*15:02 | 10 |
| 770 | SRKFNTMESVLQGLL | DRB1*09:01 | DQA1*05:01/DQB1*03:01 (DQ7), DRB1*01:01, DRB1*03:01, DRB1*04:01, DRB1*04:04, DRB1*04:05, DRB1*07:01, DRB1*09:01, DRB1*13:02, DRB1*15:01 | 10 |

REFERENCE LIST

The Molecular Taxonomy of Primary Prostate Cancer. Cell 163 (2015): 1011-1025
Abba, M. C. et al., Mol. Cancer Res 5 (2007): 881-890
Abdelmalak, C. A. et al., Clin Lab 60 (2014): 55-61
Abe, A. et al., Genes Chromosomes. Cancer 55 (2016): 242-250
Aghajanova, L. et al., Hum. Reprod. 30 (2015): 232-238
Agherbi, H. et al., PLoS. One. 4 (2009): e5622
Aguilo, F. et al., Curr. Top. Microbiol. Immunol. 394 (2016): 29-39
Akagi, T. et al., J Biol Chem 290 (2015): 22460-22473
Al, Zeyadi M. et al., Biotechnol. Biotechnol. Equip. 29 (2015): 111-118
Albergaria, A. et al., Int. J Dev. Biol 55 (2011): 811-822
Alentorn, A. et al., Presse Med 42 (2013): 806-813
Alhosin, M. et al., J Exp. Clin Cancer Res 35 (2016): 174
Allison, J. P. et al., Science 270 (1995): 932-933
Alrawi, S. J. et al., Anticancer Res 26 (2006): 107-119
Alvarado-Ruiz, L. et al., Asian Pac. J Cancer Prev. 17 (2016): 1037-1047
Alzrigat, M. et al., Oncotarget. (2016)
Amsterdam, A. et al., Acta Histochem. 116 (2014): 781-787
Andersen, R. S. et al., Nat. Protoc. 7 (2012): 891-902
Andrade, V. C. et al., Cancer Immun. 8 (2008): 2
Andrade, V. C. et al., Exp. Hematol. 37 (2009): 446-449
Angelopoulou, K. et al., Mamm. Genome 21 (2010): 516-524
Angulo, J. C. et al., J Urol. 195 (2016): 619-626
Ansari, K. I. et al., J Mol. Endocrinol. 48 (2012): 61-75
Appay, V. et al., Eur. J Immunol. 36 (2006): 1805-1814
Aprelikova, O. et al., Cancer Res 69 (2009): 616-624
Arsenic, R. et al., BMC. Cancer 15 (2015): 784
Askew, E. B. et al., J Biol Chem 284 (2009): 34793-34808
Aung, P. P. et al., Oncogene 25 (2006): 2546-2557
Avasarala, S. et al., Biol Open. 2 (2013): 675-685
Avgustinova, A. et al., Nat Commun. 7 (2016): 10305
Aytes, A. et al., Proc. Natl. Acad. Sci. U.S.A 110 (2013): E3506-E3515
Bahnassy, A. A. et al., World J Gastroenterol. 20 (2014): 18240-18248
Bailey, V. J. et al., Methods 52 (2010): 237-241
Balaz, P. et al., Ann. Surg. 235 (2002): 519-527
Banchereau, J. et al., Cell 106 (2001): 271-274
Band, A. M. et al., J Mammary. Gland. Biol Neoplasia. 16 (2011): 109-115
Bao, L. et al., Cell Biol Toxicol. 32 (2016): 419-435
Baroy, T. et al., Mol. Cancer 13 (2014): 93
Bartolini, A. et al., Clin Cancer Res 22 (2016): 4923-4933
Baty, F. et al., J Biomed. Inform. 58 (2015): 175-185
Beard, R. E. et al., Clin Cancer Res 19 (2013): 4941-4950
Beatty, G. et al., J Immunol 166 (2001): 2276-2282
Beggs, J. D., Nature 275 (1978): 104-109
Beke, L. et al., Biosci. Rep. 35 (2015)
Bell, J. L. et al., J Clin Oncol 33 (2015): 1285-1293
Bell, J. L. et al., Cell Mol Life Sci. 70 (2013): 2657-2675
Benz, C. C. et al., Oncogene 15 (1997): 1513-1525
Bergamini, A. et al., Expert. Opin. Investig. Drugs 25 (2016): 1405-1412

Berger, C. et al., Curr. Mol. Med. 13 (2013): 1229-1240
Bernstein, M. B. et al., Cancer Biother. Radiopharm. 29 (2014): 153-161
Beyranvand, Nejad E. et al., Cancer Res 76 (2016): 6017-6029
Bhan, S. et al., Oncol Rep. 28 (2012): 1498-1502
Bierkens, M. et al., Genes Chromosomes. Cancer 52 (2013): 56-68
Bikkavilli, R. K. et al., Oncogene 34 (2015): 5317-5328
Bisig, B. et al., Best. Pract. Res Clin Haematol. 25 (2012): 13-28
Bode, P. K. et al., Mod. Pathol. 27 (2014): 899-905
Boeva, V. et al., PLoS. One. 8 (2013): e72182
Bogush, T. A. et al., Antibiot. Khimioter. 54 (2009): 41-49
Bonitsis, N. et al., Exp. Oncol 28 (2006): 187-193
Borgono, C. A. et al., Cancer Res 63 (2003): 9032-9041
Borgono, C. A. et al., Clin Cancer Res 12 (2006): 1487-1493
Borgono, C. A. et al., J Biol Chem 282 (2007): 2405-2422
Borowicz, S. et al., J Vis. Exp. (2014): e51998
Boulter, J. M. et al., Protein Eng 16 (2003): 707-711
Braumuller, H. et al., Nature (2013)
Brinkmann, U. et al., Proc. Natl. Acad. Sci. U.S.A 95 (1998): 10757-10762
Brossart, P. et al., Blood 90 (1997): 1594-1599
Bruckdorfer, T. et al., Curr. Pharm. Biotechnol. 5 (2004): 29-43
Bruey, J. M. et al., J Biol Chem 279 (2004): 51897-51907
Bryan, R. T., Philos. Trans. R Soc. Lond B Biol Sci. 370 (2015): 20140042
Bryan, R. T. et al., J Urol. 184 (2010): 423-431
Buchet-Poyau, K. et al., Nucleic Acids Res 35 (2007): 1289-1300
Bundela, S. et al., PLoS. One. 9 (2014): e102610
Burnett, R. M. et al., Oncotarget. 6 (2015): 12682-12696
Cano, A. et al., Future. Oncol 8 (2012): 1095-1108
Caputi, F. F. et al., J Mol. Neurosci. 51 (2013): 532-538
Card, K. F. et al., Cancer Immunol Immunother. 53 (2004): 345-357
Carrera, M. et al., Int. J Clin Exp. Pathol. 8 (2015): 3613-3623
Cerveira, N. et al., BMC. Cancer 10 (2010): 518
Chakrabarty, S. et al., J Cell Physiol 186 (2001): 47-52
Chan, M. H. et al., Pediatr. Blood Cancer 59 (2012): 1173-1179
Chandra, V. et al., Cell Death. Dis. 5 (2014): e1380
Chang, H. et al., Biochem. Biophys. Res Commun. 464 (2015a): 45-50
Chang, Q. et al., Oncotarget. 6 (2015b): 42838-42853
Chen, H. S. et al., Zhonghua Gan Zang. Bing. Za Zhi. 11 (2003): 145-148
Chen, S. T. et al., Cancer Sci. 102 (2011a): 2191-2198
Chen, Y. et al., Cancer Biol Ther. 11 (2011 b): 497-511
Chen, Y. et al., Onco. Targets. Ther. 7 (2014): 1465-1472
Chen, Y. C. et al., Taiwan. J Obstet. Gynecol. 54 (2015): 572-579
Chen, Y. L. et al., Int J Surg. 11 (2013): 85-91
Chen, Y. T. et al., Int. J Cancer 124 (2009): 2893-2898
Chen, Y. T. et al., Proc. Natl. Acad. Sci. U. S. A 102 (2005): 7940-7945
Cheng, Y. C. et al., J Neurochem. 110 (2009): 947-955
Cheung, A. et al., Oncotarget. 7 (2016): 52553-52574
Chevillard, G. et al., Blood 117 (2011): 2005-2008
Choi, M. R. et al., APMIS 123 (2015): 65-71
Choijamts, B. et al., Stem Cells 29 (2011): 1485-1495
Chung, H. et al., Biol Chem 393 (2012a): 413-420
Chung, S. et al., Oncotarget. 3 (2012b): 1629-1640
Ciruelos Gil, E. M., Cancer Treat. Rev 40 (2014): 862-871

Clancy, A. A. et al., Ann. Oncol 27 (2016): 1696-1705
Clermont, P. L. et al., Clin Epigenetics. 8 (2016): 16
Clermont, P. L. et al., Clin Epigenetics. 7 (2015): 40
Clermont, P. L. et al., Br. J Cancer 111 (2014): 1663-1672
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Colas, E. et al., Clin Transl. Oncol 14 (2012): 715-720
Coligan, J. E. et al., Current Protocols in Protein Science (1995)
Colombetti, S. et al., J Immunol. 176 (2006): 2730-2738
Colovai, A. I. et al., Cytometry B Clin Cytom. 72 (2007): 354-362
Cortesini, R., JOP. 8 (2007): 697-703
Coulie, P. G. et al., Immunol. Rev 188 (2002): 33-42
Coutte, L. et al., Gene 240 (1999): 201-207
Cui, X. P. et al., Dig. Dis. Sci. 59 (2014): 1442-1451
Curran, K. J. et al., Mol. Ther. 23 (2015): 769-778
Dai, W. et al., Am. J Cancer Res 5 (2015): 2697-2707
Dalerba, P. et al., Int. J Cancer 93 (2001): 85-90
Dannenmann, S. R. et al., Cancer Immunol. Res. 1 (2013): 288-295
Darda, L. et al., PLoS. One. 10 (2015): e0122285
Darling, M. R. et al., Head Neck Pathol. 2 (2008): 169-174
Dat, le T. et al., Int. J Oncol 40 (2012): 1455-1469
Davidson, B. et al., J Cell Mol. Med. 15 (2011): 535-544
Davis, M. P., Cleve. Clin J Med 79 Electronic Suppl 1 (2012): eS51-eS55
de Goeje, P. L. et al., Oncoimmunology 4 (2015): e1014242
de Matos, Simoes R. et al., BMC. Syst. Biol 9 (2015): 21
De, Meulenaere A. et al., Pathobiology 83 (2016): 327-333
De, Plaen E. et al., Immunogenetics 40 (1994): 360-369
Dengjel, J. et al., Clin Cancer Res 12 (2006): 4163-4170
Denkberg, G. et al., J Immunol 171 (2003): 2197-2207
Devetzi, M. et al., Thromb. Haemost. 109 (2013): 716-725
Dewar, R. et al., Arch. Pathol. Lab Med 135 (2011): 422-429
Dias, R. P. et al., Epigenomics. 5 (2013): 331-340
Dobrowolska, H. et al., Cytometry B Clin Cytom. 84 (2013): 21-29
Dong, Q. et al., Biomed. Res Int. 2015 (2015): 156432
Dorn, J. et al., Crit Rev Clin Lab Sci. 51 (2014): 63-84
Du, T. et al., Mol. Cancer 13 (2014): 100
Dua, P. et al., Cancer Res 73 (2013): 1934-1945
Duan, Z. et al., Clin Cancer Res 9 (2003): 2778-2785
Dufour, C. et al., Cancer 118 (2012): 3812-3821
Dyrskjot, L. et al., Br. J Cancer 107 (2012): 116-122
Ek, S. et al., Cancer Res 62 (2002): 4398-4405
Emmrich, S. et al., Genes Dev. 28 (2014): 858-874
Fabbri, C. et al., Dig. Endosc. (2017)
Falk, K. et al., Nature 351 (1991): 290-296
Fan, M. et al., Int. J Clin Exp. Pathol. 7 (2014): 6768-6775
Fang, F. et al., Clin Cancer Res 20 (2014a): 6504-6516
Fang, L. et al., Biochem. Biophys. Res Commun. 446 (2014b): 272-279
Faure, A. et al., Nat Rev Urol. 13 (2016): 141-150
Feng, X. et al., Mol. Biosyst. 11 (2015): 2946-2954
Ferre, H. et al., Protein Sci. 12 (2003): 551-559
Findeis-Hosey, J. J. et al., Biotech. Histochem. 87 (2012): 24-29
Fishman, W. H., Tumour. Biol 16 (1995): 394-402
Follenzi, A. et al., Nat Genet. 25 (2000): 217-222
Fong, L. et al., Proc. Natl. Acad. Sci. U. S. A 98 (2001): 8809-8814
Fontalba, A. et al., J Immunol. 179 (2007): 8519-8524
Forghanifard, M. M. et al., Cancer Biol Ther. 12 (2011): 191-197

Frasor, J. et al., Mol. Cell Endocrinol. 418 Pt 3 (2015): 235-239
Fritzsche, F. et al., Br. J Cancer 94 (2006): 540-547
Fry, E. A. et al., Int. J Cancer 140 (2017): 495-503
Fujiyama, T. et al., J Dermatol. Sci. 75 (2014): 43-48
Fukumoto, I. et al., J Hum. Genet. 61 (2016): 109-118
Fuqua, S. A. et al., Breast Cancer Res Treat. 144 (2014): 11-19
Gabrilovich, D. I. et al., Nat Med. 2 (1996): 1096-1103
Gan, X. et al., Dis. Markers 2016 (2016): 5259602
Ganguly, R. et al., Mol. Cancer Ther. 13 (2014): 1393-1398
Garg, M. et al., J Clin Endocrinol. Metab 99 (2014): E62-E72
Gattinoni, L. et al., Nat Rev. Immunol 6 (2006): 383-393
Ge, L. et al., J Biomed. Res 29 (2015a)
Ge, L. et al., Eur. Rev Med Pharmacol. Sci. 19 (2015b): 2703-2710
Geyer, C. R., Epigenetics. 5 (2010): 696-703
Ghodsi, M. et al., Int. J Surg. 13 (2015): 193-197
Gibbs, P. et al., Melanoma Res 10 (2000): 259-264
Gleize, V. et al., Ann. Neurol. 78 (2015): 355-374
Gnjatic, S. et al., Proc Natl. Acad. Sci. U. S. A 100 (2003): 8862-8867
Godkin, A. et al., Int. Immunol 9 (1997): 905-911
Gomez, A. et al., Mol. Pharmacol. 78 (2010): 1004-1011
Gong, Y. et al., Adv. Anat. Pathol. 21 (2014): 191-200
Gottlieb, H. B. et al., J Neuroendocrinol. 19 (2007): 531-542
Gragert, L. et al., Hum. Immunol. 74 (2013): 1313-1320
Grah, J. J. et al., Tumori 100 (2014): 60-68
Gratio, V. et al., Am. J Pathol. 179 (2011): 2625-2636
Green, M. R. et al., Molecular Cloning, A Laboratory Manual 4th (2012)
Greenfield, E. A., Antibodies: A Laboratory Manual 2nd (2014)
Gu, C. et al., Stem Cells 31 (2013): 870-881
Gu, Z. D. et al., Zhonghua Wei Chang Wai Ke. Za Zhi. 10 (2007): 365-367
Gualco, G. et al., Appl. Immunohistochem. Mol. Morphol. 18 (2010): 301-310
Guerrero, K. et al., Gynecol. Oncol 125 (2012): 720-726
Guo, J. T. et al., Zhonghua Zhong. Liu Za Zhi. 31 (2009): 528-531
Gupta, A. K. et al., Med J Armed. Forces. India 72 (2016): S37-S42
Gustafsson, C. et al., Trends Biotechnol. 22 (2004): 346-353
Haass, N. K. et al., Pigment Cell Res 18 (2005): 150-159
Haeberle, H. et al., Neoplasia. 14 (2012): 666-669
Hall, R. D. et al., Cancer Control 20 (2013): 22-31
Hamilton, K. E. et al., Mol. Cancer Res 13 (2015): 1478-1486
Han, J. et al., World J Surg. Oncol 10 (2012): 37
Han, Y. et al., Eur. J Cell Biol 94 (2015): 642-652
Han, Y. D. et al., Oncotarget. 8 (2017): 1871-1883
Hanafusa, H. et al., Seikagaku 83 (2011): 1127-1131
Harndahl, M. et al., Eur. J Immunol. 42 (2012): 1405-1416
Hase, H. et al., Mol. Cancer Res 12 (2014): 1807-1817
Hasegawa, H. et al., Arch. Pathol. Lab Med. 122 (1998): 551-554
Hashem, N. N. et al., Int. J Biol Markers 25 (2010): 32-37
Hashimoto, Y. et al., Oncotarget. (2017)
Hayashi, S. I. et al., Endocr. Relat Cancer 10 (2003): 193-202
Hayashida, T. et al., Proc. Natl. Acad. Sci. U. S. A 107 (2010): 1100-1105
Heeg, S. et al., Gastroenterology 151 (2016): 540-553
Heerma van Voss, M. R. et al., Histopathology 65 (2014): 814-827
Hemminger, J. A. et al., Mod. Pathol. 27 (2014): 1238-1245
Hennard, C. et al., J Pathol. 209 (2006): 430-435
Heubach, J. et al., Mol. Cancer 14 (2015): 108
Higgins, J. et al., Horm. Cancer 6 (2015): 67-86
Hildebrandt, M. O. et al., Bone Marrow Transplant. 22 (1998): 771-775
Hiramoto, T. et al., Oncogene 18 (1999): 3422-3426
Hirata, T. et al., Oncol Rep. 33 (2015): 2052-2060
Hiroumi, H. et al., Int. J Cancer 93 (2001): 786-791
Hoff, P. M. et al., Surg. Oncol Clin N. Am. 26 (2017): 57-71
Hoffmann, N. E. et al., Cancer 112 (2008): 1471-1479
Hofmann, M. C. et al., Eur. Urol. 23 (1993): 38-44
Holm, C. et al., Leuk. Res 30 (2006): 254-261
Honrado, E. et al., Crit Rev Oncol Hematol. 59 (2006): 27-39
Horiuchi, S. et al., J Pathol. 200 (2003): 568-576
Horvath, A. et al., World J Gastroenterol. 10 (2004): 152-154
Hoshino, Y. et al., Mol. Cancer 13 (2014): 102
Hou, Z. et al., Mol. Cancer Ther. (2017)
Hu, S. et al., J Cancer Res Clin Oncol 140 (2014): 883-893
Hu, X. T. et al., Cell Prolif. 47 (2014): 200-210
Huang, K. et al., Chin J Cancer Res 26 (2014): 72-80
Huang, X. et al., Cell Prolif. 48 (2015): 593-599
Hudolin, T. et al., J Transl. Med 11 (2013): 123
Hur, H. et al., J Cancer 7 (2016): 768-773
Hussein, Y. M. et al., Med. Oncol 29 (2012): 3055-3062
Hwang, M. L. et al., J Immunol. 179 (2007): 5829-5838
Iacobuzio-Donahue, C. A. et al., Cancer Res 63 (2003): 8614-8622
Idbaih, A., Rev Neurol. (Paris) 167 (2011): 691-698
Ingaramo, P. I. et al., Mol. Cell Endocrinol. 425 (2016): 37-47
Ioannidis, P. et al., Anticancer Res 23 (2003): 2179-2183
Ishida, S. et al., Biochem. Biophys. Res Commun. 339 (2006): 325-330
Ishikawa, K. et al., Mol. Biol Cell 23 (2012): 1294-1306
Ishikawa, S. et al., Cell Tissue Res 337 (2009): 381-391
Itesako, T. et al., PLoS. One. 9 (2014): e84311
Jacobs, J. et al., Pharmacol. Ther. 155 (2015a): 1-10
Jacobs, J. et al., Oncotarget. 6 (2015b): 13462-13475
James, S. R. et al., Epigenetics. 8 (2013): 849-863
Jang, B. G. et al., Virchows Arch. 467 (2015): 393-403
Jeng, Y. M. et al., Br. J Surg. 96 (2009): 66-73
Ji, P. et al., Oncogene 24 (2005): 2739-2744
Jiang, D. et al., PLoS. One. 9 (2014): e96822
Jiang, Y. et al., Mol. Oncol 10 (2016): 292-302
Jiang, Y. et al., Oncotarget. 6 (2015): 39865-39876
Jiao, T. T. et al., Int. J Clin Exp. Pathol. 6 (2013): 3036-3041
Jin, H. et al., Tumour. Biol 27 (2006): 274-282
Jnawali, H. N. et al., J Nat Prod. 77 (2014): 258-263
John, T. et al., Clin Cancer Res 14 (2008): 3291-3298
Jung, D. B. et al., Oncotarget. 6 (2015): 4992-5004
Jung, G. et al., Proc Natl Acad Sci USA 84 (1987): 4611-4615
Kalejs, M. et al., BMC. Cancer 6 (2006): 6
Kannan, K. et al., Proc. Natl. Acad. Sci. U. S. A 112 (2015): E1272-E1277
Karlgren, M. et al., Expert. Opin. Ther. Targets. 11 (2007): 61-67
Karpf, A. R. et al., Mol. Cancer Res 7 (2009): 523-535
Kasashima, H. et al., Cancer Lett. 354 (2014): 438-446
Kaufman, L. et al., J Am. Soc. Nephrol. 15 (2004): 1721-1730
Kazi, J. A. et al., Neuropeptides 41 (2007): 227-231
Kedage, V. et al., Cell Rep. 17 (2016): 1289-1301
Keld, R. et al., Br. J Cancer 105 (2011): 124-130
Keld, R. et al., Mol. Cancer 9 (2010): 313

Kelemen, L. E. et al., Nat Genet. 47 (2015): 888-897
Kelly, Z. et al., Int. J Cancer 139 (2016): 1608-1617
Kerns, S. L. et al., J Urol. 190 (2013): 102-108
Kevans, D. et al., Int J Surg. Pathol. 19 (2011): 751-760
Khan, F. S. et al., Hepatol. Int. 11 (2017): 45-53
Khan, M. F. et al., Transl. Oncol 5 (2012): 85-91
Kibbe, A. H., Handbook of Pharmaceutical Excipients rd (2000)
Kikkawa, Y. et al., Exp. Cell Res 328 (2014): 197-206
Kikkawa, Y. et al., J Biol Chem 288 (2013): 30990-31001
Kikkawa, Y. et al., Exp. Cell Res 314 (2008): 2579-2590
Kim, B. K. et al., J Dermatol. Sci. 79 (2015a): 137-147
Kim, B. R. et al., Cell Signal. 26 (2014): 1765-1773
Kim, T. D. et al., J Clin Invest 126 (2016): 706-720
Kim, T. H. et al., J Korean Med Sci. 30 (2015b): 155-161
Kim, Y. D. et al., Int. J Mol. Med. 29 (2012): 656-662
Kim, Y. H. et al., Ann. Surg. Oncol 18 (2011): 2338-2347
King, M. L. et al., Oncogene 34 (2015): 3452-3462
Kinoshita, T. et al., Int. Immunol. 18 (2006): 1701-1706
Kinoshita, T. et al., J Biol Chem 280 (2005): 21720-21725
Kirkova, M. et al., Pharmacol. Rep. 61 (2009): 1163-1172
Klatka, J. et al., Eur. Arch. Otorhinolaryngol. 270 (2013): 2683-2693
Klauke, K. et al., Nat Cell Biol 15 (2013): 353-362
Kleeff, J. et al., Nat Rev Dis. Primers. 2 (2016): 16022
Knudsen, K. A. et al., J Cell Biochem. 95 (2005): 488-496
Ko, A. et al., BMB. Rep. 49 (2016): 598-606
Kocak, H. et al., Cell Death. Dis. 4 (2013): e586
Kohrt, D. et al., Cell Cycle 13 (2014): 62-71
Kontos, C. K. et al., Clin Chem Lab Med 54 (2016): 315-324
Koonrungsesomboon, N. et al., Cancer Epidemiol. 39 (2015): 487-496
Korr, D. et al., Cell Signal. 18 (2006): 910-920
Kountourakis, P. et al., Thromb. Haemost. 101 (2009): 541-546
Krepischi, A. C. et al., Mol. Cytogenet. 9 (2016): 20
Krieg, A. M., Nat Rev. Drug Discov. 5 (2006): 471-484
Kruhlak, M. et al., Nature 447 (2007): 730-734
Kuball, J. et al., Blood 109 (2007): 2331-2338
Kuga, T. et al., J Cell Sci. 126 (2013): 4721-4731
Kuga, T. et al., Sci. Rep. 6 (2016): 26557
Kumar-Sinha, C. et al., Genome Med 7 (2015): 129
Kumari, A. et al., BMC. Res Notes 9 (2016): 92
Kuner, R. et al., J Mol. Med (Berl) 91 (2013): 237-248
Kuo, C. T. et al., Cancer Lett. 378 (2016): 104-110
Kuppers, R. et al., J Clin Invest 111 (2003): 529-537
Kuraishi, Y., Yakugaku Zasshi 134 (2014): 1125-1142
Kurscheid, S. et al., Genome Biol 16 (2015): 16
Kwon, O. S. et al., Oncotarget. 6 (2015): 41916-41928
La, Vecchia C., Eur. J Cancer Prev. 10 (2001): 125-129
Lally, K. M. et al., Int. J Cancer 93 (2001): 841-847
Lapin, V. et al., Oncogenesis. 3 (2014): e133
Latini, F. R. et al., Blood Cells Mol. Dis. 50 (2013): 161-165
Lawrenson, K. et al., Int. J Cancer 136 (2015a): 1390-1401
Lawrenson, K. et al., Nat Commun. 6 (2015b): 8234
Lazaro-Ibanez, E. et al., BMC. Cancer 17 (2017): 92
Lederer, M. et al., Semin. Cancer Biol 29 (2014): 3-12
Lee, E. et al., BMB. Rep. 46 (2013): 594-599
Lee, O. H. et al., Mol. Cell Proteomics. 10 (2011): M110
Leong, S. R. et al., Mol. Pharm. 12 (2015): 1717-1729
Leung, F. et al., Cancer Epidemiol. Biomarkers Prev. 25 (2016): 1333-1340
Li, B. et al., Cell Biochem. Biophys. 70 (2014a): 1363-1368
Li, B. et al., Oncotarget. (2016a)
Li, H. et al., Gynecol. Oncol 84 (2002): 216-221
Li, L. et al., Cytokine 89 (2017): 173-178
Li, L. et al., Zhongguo Shi Yan. Xue. Ye. Xue. Za Zhi. 24 (2016b): 326-331
Li, M. et al., Oncotarget. 7 (2016c): 51503-51514
Li, M. et al., Clin Cancer Res 11 (2005): 1809-1814
Li, Q. et al., J Gastroenterol. Hepatol. 29 (2014b): 835-842
Li, W. M. et al., J Surg. Oncol (2016d)
Li, Z. et al., Cancer Res 76 (2016e): 619-629
Liang, X. et al., Oncotarget. 7 (2016): 52207-52217
Liddy, N. et al., Nat Med. 18 (2012): 980-987
Lilja-Maula, L. et al., J Comp Pathol. 150 (2014): 399-407
Lim, J. Y. et al., World J Gastroenterol. 19 (2013): 7078-7088
Lin, J. et al., Clin Cancer Res 10 (2004): 5708-5716
Lin, L. et al., Oncol Lett. 6 (2013a): 740-744
Lin, Q. et al., J Cancer Res Clin Oncol 135 (2009): 1675-1684
Lin, Z. et al., Diagn. Pathol. 8 (2013b): 133
Linn, D. E. et al., PLoS. One. 10 (2015): e0120628
Linz, K. et al., J Pharmacol. Exp. Ther. 349 (2014): 535-548
Liu, D. B. et al., World J Gastroenterol. 11 (2005): 1562-1566
Liu, M. et al., Cell Mol. Neurobiol. 34 (2014a): 913-923
Liu, Q. et al., J Biol Chem 286 (2011): 29951-29963
Liu, R. et al., Cancer Biol Ther. 16 (2015a): 317-324
Liu, W. et al., Mol. Clin Oncol 2 (2014b): 219-225
Liu, X. et al., Biomed. Pharmacother. 88 (2017): 595-602
Liu, X. et al., Int. Immunopharmacol. 25 (2015b): 416-424
Liu, Y. et al., Int. J Gynecol. Cancer 23 (2013): 304-311
Ljunggren, H. G. et al., J Exp. Med. 162 (1985): 1745-1759
Llaurado, M. et al., Int. J Cancer 130 (2012a): 1532-1543
Llaurado, M. et al., Mol. Cancer Res 10 (2012b): 914-924
Longenecker, B. M. et al., Ann N.Y. Acad. Sci. 690 (1993): 276-291
Lopez, R. et al., Int. J Gynecol. Cancer 16 (2006): 1289-1296
Lopez-Romero, R. et al., Rev Med Inst. Mex. Seguro. Soc. 53 Suppl 2 (2015): S188-S193
Lorincz, A. T., Acta Cytol. 60 (2016): 501-512
Lose, F. et al., Biol Chem 393 (2012): 403-412
Low, G. M. et al., Oral Oncol 61 (2016): 27-30
Lukas, T. J. et al., Proc. Natl. Acad. Sci. U. S. A 78 (1981): 2791-2795
Lunardi, A. et al., Cancer Discov 5 (2015): 550-563
Lundblad, R. L., Chemical Reagents for Protein Modification 3rd (2004)
Luo, H. et al., Int. J Clin Exp. Med 7 (2014): 1244-1254
Luo, P. et al., Oncol Rep. (2017)
Luostari, K. et al., PLoS. One. 9 (2014): e102519
Lv, G. Q. et al., Biochem. Cell Biol 92 (2014): 379-389
Lv, L. et al., Cancer Lett. 357 (2015a): 105-113
Lv, X. et al., J Exp. Clin Cancer Res 34 (2015b): 133
Ma, K. et al., Clin Epigenetics. 8 (2016a): 43
Ma, Y. et al., Biosens. Bioelectron. 85 (2016b): 641-648
Ma, Z. et al., Int. J Clin Exp. Pathol. 8 (2015): 5071-5079
MacLean, J. A. et al., PLoS. One. 11 (2016): e0156109
Mahajan, A., Hum. Pathol. 51 (2016): 64-74
Maine, E. A. et al., Oncotarget. 7 (2016): 14708-14726
Maines-Bandiera, S. et al., Int. J Gynecol. Cancer 20 (2010): 16-22
Mamane, Y. et al., J Interferon Cytokine Res 22 (2002): 135-143
Mantia-Smaldone, G. M. et al., Hum. Vaccin. Immunother. 8 (2012): 1179-1191
Manzella, L. et al., Curr. Cancer Drug Targets. 16 (2016): 594-605
Mao, L. et al., Cancer Res 71 (2011): 4314-4324

Marcinkiewicz, K. M. et al., Exp. Cell Res 320 (2014a): 128-143
Marcinkiewicz, K. M. et al., J Cell Physiol 229 (2014b): 1405-1416
Marlow, L. A. et al., J Cell Sci. 125 (2012): 4253-4263
Maruta, S. et al., APMIS 117 (2009): 791-796
Marzese, D. M. et al., Hum. Mol. Genet. 23 (2014): 226-238
Masamoto, I. et al., Leuk. Lymphoma 57 (2016): 685-691
Mason, J. M. et al., Nucleic Acids Res. 43 (2015): 3180-3196
Mawrin, C. et al., J Neurooncol. 99 (2010): 379-391
McCormack, E. et al., Cancer Immunol. Immunother. 62 (2013): 773-785
Medina-Aguilar, R. et al., Data Brief. 11 (2017): 169-182
Mehta, A. et al., Breast 23 (2014): 2-9
Melin, B., Curr. Opin. Oncol 23 (2011): 643-647
Menezes, J. et al., Leukemia 28 (2014): 823-829
Mercer, K. E. et al., Adv. Exp. Med Biol 815 (2015): 185-195
Mercer, K. E. et al., Cancer Prev. Res (Phila) 7 (2014): 675-685
Mesquita, D. et al., Oncotarget. 6 (2015): 5217-5236
Meziere, C. et al., J Immunol 159 (1997): 3230-3237
Michaelidou, K. et al., Breast Cancer Res Treat. 152 (2015): 323-336
Millan, J. L. et al., Crit Rev Clin Lab Sci. 32 (1995): 1-39
Mitsuhashi, K. et al., Int. J Hematol. 100 (2014): 88-95
Miyazaki, M. et al., Immunity. 28 (2008): 231-245
Miyoshi, Y. et al., Med. Mol. Morphol. 43 (2010): 193-196
Mizuno, K. et al., Int. J Oncol 48 (2016): 450-460
Moon, H. J. et al., Bioorg. Chem 57 (2014): 231-241
Moore, K. N. et al., J Clin Oncol (2016): JCO2016699538
Morgan, R. A. et al., Science 314 (2006): 126-129
Moroy, T. et al., Semin. Immunol. 23 (2011): 379-387
Mortara, L. et al., Clin Cancer Res. 12 (2006): 3435-3443
Moskvina, L. V. et al., Arkh. Patol. 72 (2010): 58-61
Moussa, O. et al., J Cell Biochem. 108 (2009): 1389-1398
Mumberg, D. et al., Proc. Natl. Acad. Sci. U. S. A 96 (1999): 8633-8638
Nabeshima, K. et al., Diagn. Cytopathol. 44 (2016): 774-780
Nalla, A. K. et al., Mol. Carcinog 55 (2016): 1761-1771
Nawaz, I. et al., Oncotarget. 6 (2015): 31493-31507
Nishida, C. R. et al., Mol. Pharmacol. 78 (2010): 497-502
Niskakoski, A. et al., Epigenetics. 9 (2014): 1577-1587
Noah, T. K. et al., Gastroenterology 144 (2013): 1012-1023
Notaridou, M. et al., Int. J Cancer 128 (2011): 2063-2074
Notaro, S. et al., BMC. Cancer 16 (2016): 589
Noubissi, F. K. et al., J Invest Dermatol. 134 (2014): 1718-1724
Obiezu, C. V. et al., Cancer Lett. 224 (2005): 1-22
Oh, S. et al., Biochim. Biophys. Acta 1826 (2012): 1-12
Ohno, S. et al., Anticancer Res 28 (2008): 2493-2497
Okada, K. et al., Cancer Sci. 95 (2004): 949-954
Okamoto, O. K. et al., Biochim. Biophys. Acta 1769 (2007): 437-442
Oliveira-Costa, J. P. et al., Oncotarget. 6 (2015): 20902-20920
Orsini, G. et al., Pathol. Oncol Res 20 (2014): 267-276
Orwat, D. E. et al., Arch. Pathol. Lab Med 136 (2012): 333-338
Ostergaard, Pedersen L. et al., Eur. J Immunol. 31 (2001): 2986-2996
Ottaviani, S. et al., Cancer Immunol. Immunother. 55 (2006): 867-872
Otte, M. et al., Cancer Res 61 (2001): 6682-6687
Oue, N. et al., Cancer Sci. 106 (2015): 951-958
Pacholczyk, M. et al., Med Pr 67 (2016): 255-266
Pagnotta, S. M. et al., PLoS. One. 8 (2013): e72638
Pai, V. P. et al., Breast Cancer Res 11 (2009): R81
Pal, M. et al., J Biol Chem 288 (2013): 12222-12231
Palacios, J. et al., Pathobiology 75 (2008): 85-94
Paliouras, M. et al., Breast Cancer Res Treat. 102 (2007): 7-18
Paliouras, M. et al., Mol. Oncol 1 (2008a): 413-424
Paliouras, M. et al., Tumour. Biol 29 (2008b): 63-75
Palma, M. et al., BMC. Clin Pathol. 12 (2012): 2
Papachristopoulou, G. et al., Tumour. Biol 34 (2013): 369-378
Papadakis, A. I. et al., Cell Res 25 (2015): 445-458
Papadopoulou-Boutis, A. et al., Cancer Detect. Prev. 8 (1985): 141-150
Paredes, J. et al., Breast Cancer Res 9 (2007): 214
Paredes, J. et al., Biochim. Biophys. Acta 1826 (2012): 297-311
Parris, T. Z. et al., BMC. Cancer 14 (2014): 324
Parris, T. Z. et al., Clin Cancer Res 16 (2010): 3860-3874
Pathiraja, T. N. et al., Sci. Transl. Med 6 (2014): 229ra41
Patrick, A. N. et al., Nat Struct. Mol. Biol 20 (2013): 447-453
Pattani, K. M. et al., PLoS. One. 7 (2012): e45534
Peeters, M. C. et al., Cell Signal. 27 (2015): 2579-2588
Pelkonen, M. et al., BMC. Cancer 15 (2015): 431
Peng, H. X. et al., Biomed. Res Int. 2015 (2015): 326981
Pereira, B. et al., Nucleic Acids Res 41 (2013): 3986-3999
Perez, C. A. et al., Expert. Rev Anticancer Ther. 11 (2011): 1599-1605
Petersen, G. M., Semin. Oncol 43 (2016): 548-553
Petrau, C. et al., J Cancer 5 (2014): 761-764
Pich, C. et al., Br. J Cancer 114 (2016a): 63-70
Pich, C. et al., PLoS. One. 11 (2016b): e0148095
Pickard, M. R. et al., Breast Cancer Res 11 (2009): R60
Pineda, C. T. et al., Cell 160 (2015): 715-728
Piura, B. et al., Harefuah 144 (2005): 261-5, 303, 302
Planaguma, J. et al., Hum. Pathol. 42 (2011): 57-67
Planque, C. et al., Biol Chem 389 (2008a): 781-786
Planque, C. et al., Clin Chem 56 (2010): 987-997
Planque, C. et al., Clin Cancer Res 14 (2008b): 1355-1362
Plebanski, M. et al., Eur. J Immunol 25 (1995): 1783-1787
Pollack, S. M. et al., PLoS. One. 7 (2012): e32165
Pollard, C. et al., Expert. Rev Mol. Med 12 (2010): e10
Ponte, J. F. et al., Neoplasia. 18 (2016): 775-784
Ponzoni, M. et al., Ann. Oncol 25 (2014): 316-322
Popov, N. et al., Epigenetics. 5 (2010): 685-690
Porta, C. et al., Virology 202 (1994): 949-955
Power, P. F. et al., J Orthop. Res 31 (2013): 493-501
Prasad, M. L. et al., Head Neck 26 (2004): 1053-1057
Pu, X. et al., Clin Pharmacol. Ther. 96 (2014): 609-615
Pyle-Chenault, R. A. et al., Tumour. Biol 26 (2005): 245-257
Qin, Y. et al., Chin Med. J (Engl.) 127 (2014): 1666-1671
Rabien, A. et al., Tumour. Biol 29 (2008): 1-8
Raeisossadati, R. et al., Tumour. Biol 35 (2014): 5299-5305
Rahmatpanah, F. B. et al., Leukemia 20 (2006): 1855-1862
Rajapakse, S. et al., Zoolog. Sci. 24 (2007): 774-780
Rammensee, H. et al., Immunogenetics 50 (1999): 213-219
Ramos-Solano, M. et al., Exp. Cell Res 335 (2015): 39-50
Rapoport, A. P. et al., Nat Med 21 (2015): 914-921
Rasmussen, S. L. et al., Colorectal Dis. 18 (2016): 549-561
Rastelli, F. et al., Tumori 96 (2010): 875-888
Rauscher, G. H. et al., BMC. Cancer 15 (2015): 816
Ravenni, N. et al., MAbs. 6 (2014): 86-94
Reck, M., Ann. Oncol 23 Suppl 8 (2012): viii28-viii34
RefSeq, The NCBI handbook [Internet], Chapter 18, (2002),
Resende, C. et al., Helicobacter. 16 Suppl 1 (2011): 38-44

Reyes, C. et al., Appl. Immunohistochem. Mol. Morphol. 21 (2013): 283-286
Reyniers, L. et al., J Neurochem. 131 (2014): 239-250
Ribeiro, A. S. et al., Front Oncol 4 (2014): 371
Ricketts, C. J. et al., PLoS. One. 9 (2014): e85621
Riedel, S. S. et al., J Clin Invest 126 (2016): 1438-1450
Ries, J. et al., Int. J Oncol 26 (2005): 817-824
Rinaldi, A. et al., Pathobiology 77 (2010): 129-135
Rini, B. I. et al., Cancer 107 (2006): 67-74
Risch, H. A. et al., J Natl. Cancer Inst. 98 (2006): 1694-1706
Rock, K. L. et al., Science 249 (1990): 918-921
Rodenko, B. et al., Nat Protoc. 1 (2006): 1120-1132
Rodriguez-Rodero, S. et al., J Clin Endocrinol. Metab 98 (2013): 2811-2821
Roy, A. et al., J Cell Physiol 230 (2015): 504-509
Royce, L. S. et al., Invasion Metastasis 12 (1992): 149-155
Ruf, M. et al., Clin Cancer Res 21 (2015a): 889-898
Ruf, M. et al., Oncoimmunology 4 (2015b): e1049805
Rui, X. et al., Int. J Clin Exp. Pathol. 8 (2015): 5435-5442
S3-Leitlinie maligne Ovarialtumore, 032-0350L, (2013)
Sadik, H. et al., Cancer Res 76 (2016): 4443-4456
Saiki, R. K. et al., Science 239 (1988): 487-491
Salazar, M. D. et al., Breast Cancer Res 13 (2011): R18
Samaan, S. et al., Biol Chem 395 (2014): 991-1001
Sanchez, W. Y. et al., Endocrinology 153 (2012): 3179-3189
Savone, D. et al., Tumori 102 (2016): 450-458
Sawasaki, T. et al., Tumour. Biol 25 (2004): 141-148
Schaefer, J. S. et al., J Biol Chem 285 (2010): 11258-11269
Schmitt, T. M. et al., Hum. Gene Ther. 20 (2009): 1240-1248
Scholten, K. B. et al., Clin Immunol. 119 (2006): 135-145
Schulte, I. et al., BMC. Genomics 13 (2012): 719
Scrideli, C. A. et al., J Neurooncol. 88 (2008): 281-291
Sedgwick, A. E. et al., Cancers (Basel) 8 (2016)
Seeger, F. H. et al., Immunogenetics 49 (1999): 571-576
Seifi-Alan, M. et al., Asian Pac. J Cancer Prev. 14 (2014): 6625-6629
Seki, H. et al., Ann. Surg. Oncol 19 (2012): 1831-1840
Seliger, B., Methods Mol. Biol 1102 (2014): 367-380
Sha, L. et al., Clin Exp. Med 15 (2015): 55-64
Sha, S. et al., Dig. Liver Dis. 45 (2013): 422-429
Shabestarian, H. et al., Asian Pac. J Cancer Prev. 16 (2015): 8461-8465
Shaffer, A. L. et al., Clin Cancer Res 15 (2009): 2954-2961
Shang, B. et al., Cell Death. Dis. 5 (2014): e1285
Shantha Kumara, H. M. et al., Cancer Immun. 12 (2012): 16
Sharpe, D. J. et al., Oncotarget. 5 (2014): 8803-8815
Sher, Y. P. et al., Cancer Res 66 (2006): 11763-11770
Sherman, F. et al., Laboratory Course Manual for Methods in Yeast Genetics (1986)
Shi, H. et al., World J Surg. Oncol 12 (2014): 188
Shi, X. et al., Cancer Lett. 339 (2013): 159-166
Shima, H. et al., Int. J Hematol. 99 (2014): 21-31
Shrestha, B. et al., FEBS J 279 (2012): 3715-3726
Si, Y. Q. et al., Transplant. Proc. 44 (2012): 1407-1411
Simeone, A. et al., Mech. Dev. 33 (1991): 215-227
Simonova, O. A. et al., Mol. Biol (Mosk) 49 (2015): 667-677
Singh-Jasuja, H. et al., Cancer Immunol. Immunother. 53 (2004): 187-195
Skandalis, S. S. et al., Matrix Biol 35 (2014): 182-193
Skotheim, R. I. et al., Cancer Res 65 (2005): 5588-5598
Slim, R. et al., Mol. Hum. Reprod. 18 (2012): 52-56
Small, E. J. et al., J Clin Oncol. 24 (2006): 3089-3094
Smith, J. B. et al., Gynecol. Oncol 134 (2014): 181-189
Snijders, A. M. et al., Mol. Oncol 11 (2017): 167-179
Sohal, D. P. et al., Crit Rev Oncol Hematol. 107 (2016): 111-118
Song, D. G. et al., J Hematol. Oncol 9 (2016): 56
Sontakke, P. et al., PLoS. One. 11 (2016): e0153226
Spadaro, A. et al., World J Gastroenterol. 12 (2006): 4716-4720
Sriraksa, R. et al., Cancer Prev. Res (Phila) 6 (2013): 1348-1355
Stamer, U. M. et al., Br. J Anaesth. 106 (2011): 566-572
Steffan, J. J. et al., Cancer Lett. 310 (2011): 109-117
Stornaiuolo, A. et al., Cell Differ. Dev. 31 (1990): 119-127
Su, S. et al., J Biol Chem 287 (2012): 34809-34824
Suciu-Foca, N. et al., J Immunol. 178 (2007): 7432-7441
Sun, H. et al., J BUON. 20 (2015): 296-308
Sun, S. et al., Dig. Dis. Sci. 61 (2016): 2535-2544
Suzuki, N. et al., J Orthop. Res 32 (2014): 915-922
Sykes, D. B. et al., Cell 167 (2016): 171-186
Szajnik, M. et al., Gynecol. Obstet. (Sunnyvale.) Suppl 4 (2013): 3
Szalay, F. et al., World J Gastroenterol. 10 (2004): 42-45
Szarvas, T. et al., Int J Cancer 135 (2014): 1596-1604
Szczepanski, M. J. et al., Oral Oncol 49 (2013): 144-151
Szczepanski, M. J. et al., Biomark. Med. 7 (2013): 575-578
Ta, L. et al., Mol. Med Rep. 14 (2016): 1371-1378
Tabuse, M. et al., Mol. Cancer 10 (2011): 60
Talieri, M. et al., Br. J Cancer 100 (2009): 1659-1665
Tan, A. C. et al., Cancer Biol Ther. 7 (2008): 135-144
Tan, P. et al., Biochem. Biophys. Res Commun. 419 (2012): 801-808
Tanaka, F. et al., Int. J Oncol 10 (1997): 1113-1117
Tatarian, T. et al., Surg. Clin North Am. 96 (2016): 1207-1221
Tchabo, N. E. et al., Cancer Immun. 9 (2009): 6
Teufel, R. et al., Cell Mol Life Sci. 62 (2005): 1755-1762
Thomsen, H. et al., BMC. Cancer 16 (2016): 227
Thorne, A. et al., Cytotherapy. 17 (2015): 633-646
Tian, X. et al., J Transl. Med. 13 (2015): 337
Titz, B. et al., Oncogene 29 (2010): 5895-5910
Tjalma, W. A., Eur. J Obstet. Gynecol. Reprod. Biol 210 (2017): 275-280
Tomioka, N. et al., Cancer Genet. Cytogenet. 201 (2010): 6-14
Torres, S. et al., Clin Cancer Res 21 (2015): 4892-4902
Tran, E. et al., Science 344 (2014): 641-645
Trojandt, S. et al., Hum. Immunol. 77 (2016): 1223-1231
Tsukihara, H. et al., PLoS. One. 11 (2016): e0163961
Tung, P. Y. et al., Stem Cells 31 (2013): 2330-2342
Uehiro, N. et al., Breast Cancer Res 18 (2016): 129
Ulker, V. et al., Eur. J Obstet. Gynecol. Reprod. Biol 170 (2013): 188-192
Underwood, L. J. et al., Biochim. Biophys. Acta 1502 (2000): 337-350
Ushiku, T. et al., Histopathology 61 (2012): 1043-1056
van den Hurk, K. et al., Biochim. Biophys. Acta 1826 (2012): 89-102
van der Bruggen, P. et al., Immunol. Rev 188 (2002): 51-64
van, Duin M. et al., Haematologica 96 (2011): 1662-1669
Vanderstraeten, A. et al., Cancer Immunol. Immunother. 63 (2014): 545-557
Vardhini, N. V. et al., Tumour. Biol 35 (2014): 10855-10860
Vater, I. et al., Leukemia 29 (2015): 677-685
Vieira, A. F. et al., Mol. Cancer 14 (2015): 178
Vincent, A. et al., Oncotarget. 5 (2014): 2575-2587
Vlad, G. et al., Exp. Mol. Pathol. 93 (2012): 294-301
Vukovic, M. et al., J Exp. Med 212 (2015): 2223-2234
Walker, F. et al., Biol Chem 395 (2014): 1075-1086
Wallrapp, C. et al., Cancer Res 60 (2000): 2602-2606
Walter, S. et al., J Immunol 171 (2003): 4974-4978
Walter, S. et al., Nat Med. 18 (2012): 1254-1261
Wang, H. et al., Int. J Cancer 124 (2009): 1349-1357

Wang, J. et al., Cancer Epidemiol. Biomarkers Prev. 24 (2015a): 1332-1340
Wang, L. et al., Diagn. Pathol. 8 (2013): 190
Wang, Q. et al., Onco. Targets. Ther. 8 (2015b): 1971-1977
Wang, Q. J. et al., Clin Cancer Res (2016a)
Wang, X. et al., Med Oncol 28 (2011): 1225-1254
Wang, X. et al., Hum. Immunol. 75 (2014): 1203-1209
Wang, X. Z. et al., Oncogene 18 (1999): 5718-5721
Wang, Y. et al., BMC. Genomics 17 Suppl 7 (2016b): 515
Wang, Y. Y. et al., World J Surg. Oncol 13 (2015c): 259
Wanli, H. et al., Yi. Chuan 37 (2015): 1095-1104
Watabe, T., J Biochem. 152 (2012): 1-3
Wegiel, B. et al., J Natl. Cancer Inst. 100 (2008): 1022-1036
Wen, Y. et al., Zhongguo Fei. Ai. Za Zhi. 17 (2014): 30-33
Western, P. S. et al., PLoS. One. 6 (2011): e20736
Wielscher, M. et al., EBioMedicine 2 (2015): 929-936
Willcox, B. E. et al., Protein Sci. 8 (1999): 2418-2423
Wilson, E. M., Ther. Adv. Urol. 2 (2010): 105-117
Wilson, E. M., Methods Mol. Biol 776 (2011): 113-129
Wolff, L. et al., Blood Cells Mol. Dis. 50 (2013): 227-231
Wong, C. C. et al., Hepatology 60 (2014a): 1645-1658
Wong, N. A. et al., J Clin Pathol. 67 (2014b): 105-111
Woo, M. M. et al., Clin Cancer Res 10 (2004): 7958-7964
Wu, G. Q. et al., Plasmid 64 (2010): 41-50
Wu, L. et al., Int. J Mol. Med. 36 (2015): 1200-1204
Wu, P. et al., Nano. Lett. 13 (2013): 4632-4641
Wu, S. Y. et al., Nat Commun. 7 (2016): 11169
Wu, Z. Y. et al., Scand. J Immunol. 74 (2011): 561-567
Xiao, Z. D. et al., Int. J Clin Exp. Pathol. 7 (2014): 4039-4044
Xu, C. et al., Biomarkers 20 (2015a): 271-274
Xu, C. Q. et al., Alcohol Clin Exp. Res 39 (2015b): 969-979
Xu, D. et al., Mol. Biosyst. 12 (2016): 3067-3087
Xu, J. et al., Dig. Liver Dis. 46 (2014a): 750-757
Xu, L. et al., Zhongguo Fei. Ai. Za Zhi. 14 (2011): 727-732
Xu, Y. et al., Oncol Lett. 7 (2014b): 1474-1478
Xuan, F. et al., Neuro. Oncol 18 (2016): 819-829
Xylinas, E. et al., Biomolecules. 6 (2016)
Yakimchuk, K. et al., Mol. Cell Endocrinol. 375 (2013): 121-129
Yamada, R. et al., Tissue Antigens 81 (2013): 428-434
Yamagata, M. et al., J Neurosci. 32 (2012): 14402-14414
Yamamoto, H. et al., Carcinogenesis 25 (2004): 325-332
Yang, B. et al., Asian Pac. J Trop. Med 9 (2016a): 1105-1110
Yang, F. et al., Onco. Targets. Ther. 9 (2016b): 7039-7045
Yang, H. et al., Oncol Rep. 34 (2015a): 1681-1691
Yang, L. et al., Oncol Lett. 12 (2016c): 4068-4074
Yang, P. et al., Curr. Pharm. Des 21 (2015b): 1292-1300
Yang, W. et al., Cancer 91 (2001): 1277-1283
Yang, X. S. et al., Asian Pac. J Cancer Prev. 13 (2012): 1657-1662
Yao, J. et al., Cancer Immunol. Res. 2 (2014): 371-379
Yi, J. M. et al., Tumour. Biol 33 (2012): 363-372
Yi, Y. J. et al., Int. J Mol. Med 37 (2016): 1405-1411
Yilmaz-Ozcan, S. et al., PLoS. One. 9 (2014): e107905
Yin, B. et al., Int. J Clin Exp. Pathol. 7 (2014): 2934-2941
Yin, X. Y. et al., Oncogene 20 (2001): 2908-2917
Yin, X. Y. et al., Oncogene 18 (1999): 6621-6634
Yoon, H. et al., Tohoku J Exp. Med 224 (2011): 41-46
Yu, H. et al., Blood 124 (2014): 1737-1747
Yu, Y. et al., J Pharmacol. Sci. 112 (2010): 83-88
Yuan, R. et al., Cancer Res 74 (2014): 5287-5300
Yuan, R. H. et al., Ann Surg. Oncol 16 (2009): 1711-1719
Yue, W. et al., Sci. Rep. 5 (2015): 13390
Zamuner, F. T. et al., Mol. Cancer Ther. 14 (2015): 828-834
Zanaruddin, S. N. et al., Hum. Pathol. 44 (2013): 417-426
Zaremba, S. et al., Cancer Res. 57 (1997): 4570-4577
Zha, Y. et al., PLoS. One. 7 (2012): e40728
Zhai, Y. et al., Cancer Res 67 (2007): 10163-10172
Zhan, J. et al., Br. J Cancer 111 (2014): 883-893
Zhan, J. et al., Cancer Lett. 361 (2015): 75-85
Zhang, C. et al., J Surg. Res 197 (2015a): 301-306
Zhang, D. et al., Oncol Rep. 35 (2016a): 81-88
Zhang, G. et al., Int. J Biochem. Cell Biol 36 (2004): 1613-1623
Zhang, H. et al., J Exp. Clin Cancer Res 26 (2007): 361-366
Zhang, H. Y. et al., Oncol Rep. 34 (2015b): 1193-1202
Zhang, J. et al., Oncotarget. 6 (2015c): 42040-42052
Zhang, J. et al., Sci. Rep. 7 (2017): 42819
Zhang, K. et al., Tumour. Biol 35 (2014a): 7669-7673
Zhang, L. et al., Med Oncol 31 (2014b): 52
Zhang, L. et al., Cancer Res 65 (2005): 925-932
Zhang, M. et al., Onco. Targets. Ther. 9 (2016b): 2717-2723
Zhang, R. et al., Mol. Med Rep. 5 (2012a): 256-259
Zhang, W. et al., Epigenetics. 10 (2015d): 736-748
Zhang, W. et al., Acta Haematol. 130 (2013): 297-304
Zhang, X. et al., Int. J Oncol (2016c)
Zhang, X. et al., Med. Oncol 32 (2015e): 148
Zhang, Y. et al., Mol. Med. Rep. 5 (2012b): 910-916
Zhang, Z. et al., Tumour. Biol (2015f)
Zhao, H. et al., Zhonghua Gan Zang. Bing. Za Zhi. 10 (2002): 100-102
Zhao, L. et al., Oncogene (2017)
Zhao, R. et al., EBioMedicine 8 (2016): 30-39
Zheng, J. et al., J Surg. Oncol 107 (2013): 746-751
Zhou, B. et al., Biochim. Biophys. Acta 1784 (2008): 747-752
Zhou, Y. et al., Mol. Cell Endocrinol. 386 (2014): 16-33
Zhu, J. et al., Asian Pac. J Cancer Prev. 14 (2013): 3011-3015
Zhu, N. et al., J Clin Invest 126 (2016): 997-1011
Zhussupova, A. et al., PLoS. One. 9 (2014): e105285
Zou, C. et al., Cancer 118 (2012): 1845-1855
Zufferey, R. et al., J Virol. 73 (1999): 2886-2892
Neumann, F. et al., Cancer Immunol. Immunother. 53 (2004): 589-599
Rammensee, H. et al., Immunogenetics 50 (1999): 213-219
Sun, Y. et al., Int. J. Cancer 87 (2000): 399-404

The invention claimed is:

1. A method for killing target cells in a patient who has cancer, comprising administering to the patient an effective number of activated T cells that selectively recognize a cancer cell, which presents a peptide consisting of the amino acid sequence of MIPTFTALL (SEQ ID NO: 1), wherein the cancer is selected from the group consisting of ovarian cancer, colorectal cancer, gallbladder cancer, non-Hodgkin lymphoma, non-small cell lung cancer, and uterine and endometrial cancer.

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the population of activated T cells are administered in the form of a composition.

7. The method of claim 6, wherein the composition further comprises an adjuvant.

8. The method of claim 7, wherein the adjuvant is selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The method of claim 1, wherein the activated T cells are cytotoxic T cells produced by contacting T cells with an antigen presenting cell that presents the peptide in a complex with an MHC class I molecule on the surface of the antigen presenting cell, for a period of time sufficient to activate said T cell.

10. The method of claim 9, wherein the antigen presenting cell is infected with a recombinant virus expressing the peptide.

11. The method of claim 10, wherein the antigen presenting cell is a dendritic cell or a macrophage.

12. The method of claim 5, wherein the expansion is in the presence of an anti-CD28 antibody and IL-12.

13. The method of claim 1, wherein the population of activated T cells comprises CD8-positive cells.

14. The method of claim 9, wherein the contacting is in vitro.

15. The method of claim 1, wherein the cancer is ovarian cancer.

16. The method of claim 1, wherein the cancer is colorectal cancer.

17. The method of claim 1, wherein the cancer is gallbladder cancer.

18. The method of claim 1, wherein the cancer is non-Hodgkin lymphoma.

19. The method of claim 1, wherein the cancer is non-small cell lung cancer.

20. The method of claim 1, wherein the cancer is uterine and endometrial cancer.

* * * * *

SEQUENCE LISTING

<160> NUMBER OF SEQ ID NOS: 776

<210> SEQ ID NO 1
<211> LENGTH: 9
<212> TYPE: PRT
<213> ORGANISM: Homo sapiens

<400> SEQUENCE: 1

Met Ile Pro Thr Phe Thr Ala Leu Leu

```
1               5

<210> SEQ ID NO 2
<211> LENGTH: 9
<212> TYPE: PRT
<213> ORGANISM: Homo sapiens

<400> SEQUENCE: 2

Thr Leu Leu Lys Ala Leu Leu Glu Ile
1               5

<210> SEQ ID NO 3
<211> LENGTH: 9
<212> TYPE: PRT
<213> ORGANISM: Homo sapiens

<400> SEQUENCE: 3

Ala Leu Ile Tyr Asn Leu Val Gly Ile
1               5

<210> SEQ ID NO 4
<211> LENGTH: 8
<212> TYPE: PRT
<213> ORGANISM: Homo sapiens

<400> SEQUENCE: 4

Ala Leu Phe Lys Ala Trp Ala Leu
1               5

<210> SEQ ID NO 5
<211> LENGTH: 9
<212> TYPE: PRT
<213> ORGANISM: Homo sapiens

<400> SEQUENCE: 5

Arg Leu Leu Asp Phe Ile Asn Val Leu
1               5

<210> SEQ ID NO 6
<211> LENGTH: 9
<212> TYPE: PRT
<213> ORGANISM: Homo sapiens

<400> SEQUENCE: 6

Ser Leu Gly Lys His Thr Val Ala Leu
1               5

<210> SEQ ID NO 7
<211> LENGTH: 9
<212> TYPE: PRT
<213> ORGANISM: Homo sapiens

<400> SEQUENCE: 7

Ala Leu Gln Ala Phe Glu Phe Arg Val
1               5

<210> SEQ ID NO 8
<211> LENGTH: 9
<212> TYPE: PRT
<213> ORGANISM: Homo sapiens

<400> SEQUENCE: 8

Tyr Leu Val Thr Lys Val Val Ala Val
1               5
```

```
<210> SEQ ID NO 9
<211> LENGTH: 10
<212> TYPE: PRT
<213> ORGANISM: Homo sapiens

<400> SEQUENCE: 9

Val Leu Leu Ala Gly Phe Lys Pro Pro Leu
1               5                   10

<210> SEQ ID NO 10
<211> LENGTH: 11
<212> TYPE: PRT
<213> ORGANISM: Homo sapiens

<400> SEQUENCE: 10

Arg Tyr Ser Asp Ser Val Gly Arg Val Ser Phe
1               5                   10

<210> SEQ ID NO 11
<211> LENGTH: 9
<212> TYPE: PRT
<213> ORGANISM: Homo sapiens

<400> SEQUENCE: 11

Ser Tyr Ser Asp Leu His Tyr Gly Phe
1               5

<210> SEQ ID NO 12
<211> LENGTH: 9
<212> TYPE: PRT
<213> ORGANISM: Homo sapiens

<400> SEQUENCE: 12

Lys Tyr Glu Lys Ile Phe Glu Met Leu
1               5

<210> SEQ ID NO 13
<211> LENGTH: 9
<212> TYPE: PRT
<213> ORGANISM: Homo sapiens

<400> SEQUENCE: 13

Val Tyr Thr Phe Leu Ser Ser Thr Leu
1               5

<210> SEQ ID NO 14
<211> LENGTH: 9
<212> TYPE: PRT
<213> ORGANISM: Homo sapiens

<400> SEQUENCE: 14

Phe Tyr Phe Pro Thr Pro Thr Val Leu
1               5

<210> SEQ ID NO 15
<211> LENGTH: 10
<212> TYPE: PRT
<213> ORGANISM: Homo sapiens

<400> SEQUENCE: 15

Val Tyr His Asp Asp Lys Gln Pro Thr Phe
1               5                   10

<210> SEQ ID NO 16
```

```
<211> LENGTH: 9
<212> TYPE: PRT
<213> ORGANISM: Homo sapiens

<400> SEQUENCE: 16

Ile Tyr Ser Pro Gln Phe Ser Arg Leu
1               5

<210> SEQ ID NO 17
<211> LENGTH: 9
<212> TYPE: PRT
<213> ORGANISM: Homo sapiens

<400> SEQUENCE: 17

Arg Phe Thr Thr Met Leu Ser Thr Phe
1               5

<210> SEQ ID NO 18
<211> LENGTH: 9
<212> TYPE: PRT
<213> ORGANISM: Homo sapiens

<400> SEQUENCE: 18

Lys Tyr Pro Val His Ile Tyr Arg Leu
1               5

<210> SEQ ID NO 19
<211> LENGTH: 9
<212> TYPE: PRT
<213> ORGANISM: Homo sapiens

<400> SEQUENCE: 19

Lys Tyr Val Lys Val Phe His Gln Phe
1               5

<210> SEQ ID NO 20
<211> LENGTH: 9
<212> TYPE: PRT
<213> ORGANISM: Homo sapiens

<400> SEQUENCE: 20

Arg Met Ala Ser Pro Val Asn Val Lys
1               5

<210> SEQ ID NO 21
<211> LENGTH: 9
<212> TYPE: PRT
<213> ORGANISM: Homo sapiens

<400> SEQUENCE: 21

Ala Val Arg Lys Pro Ile Val Leu Lys
1               5

<210> SEQ ID NO 22
<211> LENGTH: 9
<212> TYPE: PRT
<213> ORGANISM: Homo sapiens

<400> SEQUENCE: 22

Ser Leu Lys Glu Arg Asn Pro Leu Lys
1               5

<210> SEQ ID NO 23
<211> LENGTH: 9
<212> TYPE: PRT
```

<213> ORGANISM: Homo sapiens

<400> SEQUENCE: 23

Gly Met Met Lys Gly Gly Ile Arg Lys
1               5

<210> SEQ ID NO 24
<211> LENGTH: 9
<212> TYPE: PRT
<213> ORGANISM: Homo sapiens

<400> SEQUENCE: 24

Ser Met Tyr Tyr Pro Leu Gln Leu Lys
1               5

<210> SEQ ID NO 25
<211> LENGTH: 9
<212> TYPE: PRT
<213> ORGANISM: Homo sapiens

<400> SEQUENCE: 25

Gly Thr Ser Pro Pro Ser Val Glu Lys
1               5

<210> SEQ ID NO 26
<211> LENGTH: 9
<212> TYPE: PRT
<213> ORGANISM: Homo sapiens

<400> SEQUENCE: 26

Arg Ile Ser Glu Tyr Leu Leu Glu Lys
1               5

<210> SEQ ID NO 27
<211> LENGTH: 10
<212> TYPE: PRT
<213> ORGANISM: Homo sapiens

<400> SEQUENCE: 27

Val Leu Tyr Gly Pro Ala Gly Leu Gly Lys
1               5                   10

<210> SEQ ID NO 28
<211> LENGTH: 11
<212> TYPE: PRT
<213> ORGANISM: Homo sapiens

<400> SEQUENCE: 28

Lys Thr Tyr Glu Thr Asn Leu Glu Ile Lys Lys
1               5                   10

<210> SEQ ID NO 29
<211> LENGTH: 9
<212> TYPE: PRT
<213> ORGANISM: Homo sapiens

<400> SEQUENCE: 29

Gln Gln Phe Leu Thr Ala Leu Phe Tyr
1               5

<210> SEQ ID NO 30
<211> LENGTH: 9
<212> TYPE: PRT
<213> ORGANISM: Homo sapiens

```
<400> SEQUENCE: 30

Ala Leu Glu Val Ala His Arg Leu Lys
1               5

<210> SEQ ID NO 31
<211> LENGTH: 10
<212> TYPE: PRT
<213> ORGANISM: Homo sapiens

<400> SEQUENCE: 31

Leu Leu Asp Glu Gly Ala Met Leu Leu Tyr
1               5                   10

<210> SEQ ID NO 32
<211> LENGTH: 9
<212> TYPE: PRT
<213> ORGANISM: Homo sapiens

<400> SEQUENCE: 32

Ser Pro Asn Lys Gly Thr Leu Ser Val
1               5

<210> SEQ ID NO 33
<211> LENGTH: 8
<212> TYPE: PRT
<213> ORGANISM: Homo sapiens

<400> SEQUENCE: 33

Ser Pro Thr Phe His Leu Thr Leu
1               5

<210> SEQ ID NO 34
<211> LENGTH: 10
<212> TYPE: PRT
<213> ORGANISM: Homo sapiens

<400> SEQUENCE: 34

Leu Pro Arg Gly Pro Leu Ala Ser Leu Leu
1               5                   10

<210> SEQ ID NO 35
<211> LENGTH: 9
<212> TYPE: PRT
<213> ORGANISM: Homo sapiens

<400> SEQUENCE: 35

Phe Pro Asp Asn Gln Arg Pro Ala Leu
1               5

<210> SEQ ID NO 36
<211> LENGTH: 9
<212> TYPE: PRT
<213> ORGANISM: Homo sapiens

<400> SEQUENCE: 36

Ala Pro Ala Ala Trp Leu Arg Ser Ala
1               5

<210> SEQ ID NO 37
<211> LENGTH: 9
<212> TYPE: PRT
<213> ORGANISM: Homo sapiens

<400> SEQUENCE: 37
```

Arg Pro Leu Phe Gln Lys Ser Ser Met
1               5

<210> SEQ ID NO 38
<211> LENGTH: 11
<212> TYPE: PRT
<213> ORGANISM: Homo sapiens

<400> SEQUENCE: 38

Ser Pro His Pro Val Thr Ala Leu Leu Thr Leu
1               5                   10

<210> SEQ ID NO 39
<211> LENGTH: 9
<212> TYPE: PRT
<213> ORGANISM: Homo sapiens

<400> SEQUENCE: 39

Arg Pro Ala Pro Phe Glu Val Val Phe
1               5

<210> SEQ ID NO 40
<211> LENGTH: 10
<212> TYPE: PRT
<213> ORGANISM: Homo sapiens

<400> SEQUENCE: 40

Lys Pro Gly Thr Ser Tyr Arg Val Thr Leu
1               5                   10

<210> SEQ ID NO 41
<211> LENGTH: 9
<212> TYPE: PRT
<213> ORGANISM: Homo sapiens

<400> SEQUENCE: 41

Arg Val Arg Ser Arg Ile Ser Asn Leu
1               5

<210> SEQ ID NO 42
<211> LENGTH: 8
<212> TYPE: PRT
<213> ORGANISM: Homo sapiens

<400> SEQUENCE: 42

Thr Leu Lys Val Thr Ser Ala Leu
1               5

<210> SEQ ID NO 43
<211> LENGTH: 9
<212> TYPE: PRT
<213> ORGANISM: Homo sapiens

<400> SEQUENCE: 43

Ala Leu Lys Ala Arg Thr Val Thr Phe
1               5

<210> SEQ ID NO 44
<211> LENGTH: 8
<212> TYPE: PRT
<213> ORGANISM: Homo sapiens

<400> SEQUENCE: 44

Leu Asn Lys Gln Lys Val Thr Phe
1               5

<210> SEQ ID NO 45
<211> LENGTH: 9
<212> TYPE: PRT
<213> ORGANISM: Homo sapiens

<400> SEQUENCE: 45

Val Gly Arg Glu Lys Lys Leu Ala Leu
1               5

<210> SEQ ID NO 46
<211> LENGTH: 9
<212> TYPE: PRT
<213> ORGANISM: Homo sapiens

<400> SEQUENCE: 46

Asp Met Lys Lys Ala Lys Glu Gln Leu
1               5

<210> SEQ ID NO 47
<211> LENGTH: 9
<212> TYPE: PRT
<213> ORGANISM: Homo sapiens

<400> SEQUENCE: 47

Met Pro Asn Leu Arg Ser Val Asp Leu
1               5

<210> SEQ ID NO 48
<211> LENGTH: 9
<212> TYPE: PRT
<213> ORGANISM: Homo sapiens

<400> SEQUENCE: 48

Asp Val Lys Lys Lys Ile Lys Glu Val
1               5

<210> SEQ ID NO 49
<211> LENGTH: 9
<212> TYPE: PRT
<213> ORGANISM: Homo sapiens

<400> SEQUENCE: 49

Leu Pro Arg Leu Lys Ala Phe Met Ile
1               5

<210> SEQ ID NO 50
<211> LENGTH: 8
<212> TYPE: PRT
<213> ORGANISM: Homo sapiens

<400> SEQUENCE: 50

Asp Met Lys Tyr Lys Asn Arg Val
1               5

<210> SEQ ID NO 51
<211> LENGTH: 9
<212> TYPE: PRT
<213> ORGANISM: Homo sapiens

<400> SEQUENCE: 51

Ser Leu Arg Leu Lys Asn Val Gln Leu
1               5

```
<210> SEQ ID NO 52
<211> LENGTH: 9
<212> TYPE: PRT
<213> ORGANISM: Homo sapiens

<400> SEQUENCE: 52

Ala Glu Phe Leu Leu Arg Ile Phe Leu
1               5

<210> SEQ ID NO 53
<211> LENGTH: 9
<212> TYPE: PRT
<213> ORGANISM: Homo sapiens

<400> SEQUENCE: 53

Met Glu His Pro Gly Lys Leu Leu Phe
1               5

<210> SEQ ID NO 54
<211> LENGTH: 11
<212> TYPE: PRT
<213> ORGANISM: Homo sapiens

<400> SEQUENCE: 54

Ala Glu Ile Thr Ile Thr Thr Gln Thr Gly Tyr
1               5                   10

<210> SEQ ID NO 55
<211> LENGTH: 9
<212> TYPE: PRT
<213> ORGANISM: Homo sapiens

<400> SEQUENCE: 55

His Glu Thr Glu Thr Arg Thr Thr Trp
1               5

<210> SEQ ID NO 56
<211> LENGTH: 9
<212> TYPE: PRT
<213> ORGANISM: Homo sapiens

<400> SEQUENCE: 56

Ser Glu Pro Asp Thr Thr Ala Ser Trp
1               5

<210> SEQ ID NO 57
<211> LENGTH: 9
<212> TYPE: PRT
<213> ORGANISM: Homo sapiens

<400> SEQUENCE: 57

Gln Glu Ser Asp Leu Arg Leu Phe Leu
1               5

<210> SEQ ID NO 58
<211> LENGTH: 8
<212> TYPE: PRT
<213> ORGANISM: Homo sapiens

<400> SEQUENCE: 58

Gly Glu Met Glu Gln Lys Gln Leu
1               5

<210> SEQ ID NO 59
<211> LENGTH: 9
```

```
<212> TYPE: PRT
<213> ORGANISM: Homo sapiens

<400> SEQUENCE: 59

Ser Glu Asn Val Thr Met Lys Val Val
1               5

<210> SEQ ID NO 60
<211> LENGTH: 11
<212> TYPE: PRT
<213> ORGANISM: Homo sapiens

<400> SEQUENCE: 60

Gly Leu Leu Ser Leu Thr Ser Thr Leu Tyr Leu
1               5                   10

<210> SEQ ID NO 61
<211> LENGTH: 9
<212> TYPE: PRT
<213> ORGANISM: Homo sapiens

<400> SEQUENCE: 61

Tyr Met Val His Ile Gln Val Thr Leu
1               5

<210> SEQ ID NO 62
<211> LENGTH: 9
<212> TYPE: PRT
<213> ORGANISM: Homo sapiens

<400> SEQUENCE: 62

Lys Val Leu Gly Val Asn Val Met Leu
1               5

<210> SEQ ID NO 63
<211> LENGTH: 9
<212> TYPE: PRT
<213> ORGANISM: Homo sapiens

<400> SEQUENCE: 63

Met Met Glu Glu Met Ile Phe Asn Leu
1               5

<210> SEQ ID NO 64
<211> LENGTH: 9
<212> TYPE: PRT
<213> ORGANISM: Homo sapiens

<400> SEQUENCE: 64

Phe Leu Asp Pro Asp Arg His Phe Leu
1               5

<210> SEQ ID NO 65
<211> LENGTH: 9
<212> TYPE: PRT
<213> ORGANISM: Homo sapiens

<400> SEQUENCE: 65

Thr Met Phe Leu Arg Glu Thr Ser Leu
1               5

<210> SEQ ID NO 66
<211> LENGTH: 9
<212> TYPE: PRT
<213> ORGANISM: Homo sapiens
```

<400> SEQUENCE: 66

Gly Leu Leu Gln Glu Leu Ser Ser Ile
1               5

<210> SEQ ID NO 67
<211> LENGTH: 9
<212> TYPE: PRT
<213> ORGANISM: Homo sapiens

<400> SEQUENCE: 67

Ser Leu Leu Leu Pro Ser Ile Phe Leu
1               5

<210> SEQ ID NO 68
<211> LENGTH: 9
<212> TYPE: PRT
<213> ORGANISM: Homo sapiens

<400> SEQUENCE: 68

Lys Leu Phe Asp Thr Gln Gln Phe Leu
1               5

<210> SEQ ID NO 69
<211> LENGTH: 9
<212> TYPE: PRT
<213> ORGANISM: Homo sapiens

<400> SEQUENCE: 69

Thr Thr Tyr Glu Gly Ser Ile Thr Val
1               5

<210> SEQ ID NO 70
<211> LENGTH: 9
<212> TYPE: PRT
<213> ORGANISM: Homo sapiens

<400> SEQUENCE: 70

Val Leu Gln Gly Leu Leu Arg Ser Leu
1               5

<210> SEQ ID NO 71
<211> LENGTH: 9
<212> TYPE: PRT
<213> ORGANISM: Homo sapiens

<400> SEQUENCE: 71

Tyr Leu Glu Asp Thr Asp Arg Asn Leu
1               5

<210> SEQ ID NO 72
<211> LENGTH: 9
<212> TYPE: PRT
<213> ORGANISM: Homo sapiens

<400> SEQUENCE: 72

Tyr Leu Thr Asp Leu Gln Val Ser Leu
1               5

<210> SEQ ID NO 73
<211> LENGTH: 9
<212> TYPE: PRT
<213> ORGANISM: Homo sapiens

<400> SEQUENCE: 73

Phe Leu Ile Glu Glu Leu Leu Phe Ala
1               5

<210> SEQ ID NO 74
<211> LENGTH: 9
<212> TYPE: PRT
<213> ORGANISM: Homo sapiens

<400> SEQUENCE: 74

Ser Gln Ser Pro Ser Val Ser Gln Leu
1               5

<210> SEQ ID NO 75
<211> LENGTH: 9
<212> TYPE: PRT
<213> ORGANISM: Homo sapiens

<400> SEQUENCE: 75

Lys Val Val Ser Val Leu Tyr Asn Val
1               5

<210> SEQ ID NO 76
<211> LENGTH: 9
<212> TYPE: PRT
<213> ORGANISM: Homo sapiens

<400> SEQUENCE: 76

Lys Tyr Val Ala Glu Leu Ser Leu Leu
1               5

<210> SEQ ID NO 77
<211> LENGTH: 8
<212> TYPE: PRT
<213> ORGANISM: Homo sapiens

<400> SEQUENCE: 77

Arg Tyr Gly Pro Val Phe Thr Val
1               5

<210> SEQ ID NO 78
<211> LENGTH: 9
<212> TYPE: PRT
<213> ORGANISM: Homo sapiens

<400> SEQUENCE: 78

Ser Phe Ala Pro Arg Ser Ala Val Phe
1               5

<210> SEQ ID NO 79
<211> LENGTH: 9
<212> TYPE: PRT
<213> ORGANISM: Homo sapiens

<400> SEQUENCE: 79

Ser Tyr Asn Glu His Trp Asn Tyr Leu
1               5

<210> SEQ ID NO 80
<211> LENGTH: 10
<212> TYPE: PRT
<213> ORGANISM: Homo sapiens

<400> SEQUENCE: 80

Thr Ala Tyr Met Val Ser Val Ala Ala Phe

```
1               5              10
```

<210> SEQ ID NO 81
<211> LENGTH: 9
<212> TYPE: PRT
<213> ORGANISM: Homo sapiens

<400> SEQUENCE: 81

```
Val Tyr Asn His Thr Thr Arg Pro Leu
1               5
```

<210> SEQ ID NO 82
<211> LENGTH: 9
<212> TYPE: PRT
<213> ORGANISM: Homo sapiens

<400> SEQUENCE: 82

```
Ser Tyr Phe Arg Gly Phe Thr Leu Ile
1               5
```

<210> SEQ ID NO 83
<211> LENGTH: 9
<212> TYPE: PRT
<213> ORGANISM: Homo sapiens

<400> SEQUENCE: 83

```
Gly Thr Tyr Ala His Thr Val Asn Arg
1               5
```

<210> SEQ ID NO 84
<211> LENGTH: 10
<212> TYPE: PRT
<213> ORGANISM: Homo sapiens

<400> SEQUENCE: 84

```
Lys Leu Gln Pro Ala Gln Thr Ala Ala Lys
1               5              10
```

<210> SEQ ID NO 85
<211> LENGTH: 10
<212> TYPE: PRT
<213> ORGANISM: Homo sapiens

<400> SEQUENCE: 85

```
Val Leu Leu Gly Ser Leu Phe Ser Arg Lys
1               5              10
```

<210> SEQ ID NO 86
<211> LENGTH: 11
<212> TYPE: PRT
<213> ORGANISM: Homo sapiens

<400> SEQUENCE: 86

```
Val Val Leu Leu Gly Ser Leu Phe Ser Arg Lys
1               5              10
```

<210> SEQ ID NO 87
<211> LENGTH: 10
<212> TYPE: PRT
<213> ORGANISM: Homo sapiens

<400> SEQUENCE: 87

```
Ala Val Ala Pro Pro Thr Pro Ala Ser Lys
1               5              10
```

```
<210> SEQ ID NO 88
<211> LENGTH: 9
<212> TYPE: PRT
<213> ORGANISM: Homo sapiens

<400> SEQUENCE: 88

Val Val His Ala Val Phe Ala Leu Lys
1               5

<210> SEQ ID NO 89
<211> LENGTH: 9
<212> TYPE: PRT
<213> ORGANISM: Homo sapiens

<400> SEQUENCE: 89

Arg Val Ala Glu Leu Leu Leu Leu His
1               5

<210> SEQ ID NO 90
<211> LENGTH: 10
<212> TYPE: PRT
<213> ORGANISM: Homo sapiens

<400> SEQUENCE: 90

Lys Val Ala Gly Glu Arg Tyr Val Tyr Lys
1               5                   10

<210> SEQ ID NO 91
<211> LENGTH: 9
<212> TYPE: PRT
<213> ORGANISM: Homo sapiens

<400> SEQUENCE: 91

Arg Ser Leu Arg Tyr Tyr Tyr Glu Lys
1               5

<210> SEQ ID NO 92
<211> LENGTH: 9
<212> TYPE: PRT
<213> ORGANISM: Homo sapiens

<400> SEQUENCE: 92

Ser Val Phe Pro Ile Glu Asn Ile Tyr
1               5

<210> SEQ ID NO 93
<211> LENGTH: 9
<212> TYPE: PRT
<213> ORGANISM: Homo sapiens

<400> SEQUENCE: 93

Lys Ile Leu Glu Glu His Thr Asn Lys
1               5

<210> SEQ ID NO 94
<211> LENGTH: 9
<212> TYPE: PRT
<213> ORGANISM: Homo sapiens

<400> SEQUENCE: 94

Ala Thr Phe Glu Arg Val Leu Leu Arg
1               5

<210> SEQ ID NO 95
```

```
<211> LENGTH: 10
<212> TYPE: PRT
<213> ORGANISM: Homo sapiens

<400> SEQUENCE: 95

Gln Ser Met Tyr Tyr Pro Leu Gln Leu Lys
1               5                   10

<210> SEQ ID NO 96
<211> LENGTH: 9
<212> TYPE: PRT
<213> ORGANISM: Homo sapiens

<400> SEQUENCE: 96

Thr Ala Phe Gly Gly Phe Leu Lys Tyr
1               5

<210> SEQ ID NO 97
<211> LENGTH: 10
<212> TYPE: PRT
<213> ORGANISM: Homo sapiens

<400> SEQUENCE: 97

Thr Met Leu Asp Val Glu Gly Leu Phe Tyr
1               5                   10

<210> SEQ ID NO 98
<211> LENGTH: 10
<212> TYPE: PRT
<213> ORGANISM: Homo sapiens

<400> SEQUENCE: 98

Leu Leu Gln Pro Pro Pro Leu Leu Ala Arg
1               5                   10

<210> SEQ ID NO 99
<211> LENGTH: 9
<212> TYPE: PRT
<213> ORGANISM: Homo sapiens

<400> SEQUENCE: 99

Lys Val Val Asp Arg Trp Asn Glu Lys
1               5

<210> SEQ ID NO 100
<211> LENGTH: 10
<212> TYPE: PRT
<213> ORGANISM: Homo sapiens

<400> SEQUENCE: 100

Arg Leu Phe Thr Ser Pro Ile Met Thr Lys
1               5                   10

<210> SEQ ID NO 101
<211> LENGTH: 10
<212> TYPE: PRT
<213> ORGANISM: Homo sapiens

<400> SEQUENCE: 101

Arg Val Phe Thr Ser Ser Ile Lys Thr Lys
1               5                   10

<210> SEQ ID NO 102
<211> LENGTH: 9
<212> TYPE: PRT
```

<213> ORGANISM: Homo sapiens

<400> SEQUENCE: 102

Ser Val Leu Thr Ser Ser Leu Val Lys
1               5

<210> SEQ ID NO 103
<211> LENGTH: 9
<212> TYPE: PRT
<213> ORGANISM: Homo sapiens

<400> SEQUENCE: 103

Thr Ser Arg Ser Val Asp Glu Ala Tyr
1               5

<210> SEQ ID NO 104
<211> LENGTH: 9
<212> TYPE: PRT
<213> ORGANISM: Homo sapiens

<400> SEQUENCE: 104

Val Leu Ala Asp Ser Val Thr Thr Lys
1               5

<210> SEQ ID NO 105
<211> LENGTH: 9
<212> TYPE: PRT
<213> ORGANISM: Homo sapiens

<400> SEQUENCE: 105

Arg Leu Phe Ser Trp Leu Val Asn Arg
1               5

<210> SEQ ID NO 106
<211> LENGTH: 9
<212> TYPE: PRT
<213> ORGANISM: Homo sapiens

<400> SEQUENCE: 106

Ala Ala Phe Val Pro Leu Leu Leu Lys
1               5

<210> SEQ ID NO 107
<211> LENGTH: 9
<212> TYPE: PRT
<213> ORGANISM: Homo sapiens

<400> SEQUENCE: 107

Arg Leu Gln Glu Trp Lys Ala Leu Lys
1               5

<210> SEQ ID NO 108
<211> LENGTH: 10
<212> TYPE: PRT
<213> ORGANISM: Homo sapiens

<400> SEQUENCE: 108

Val Leu Tyr Pro Val Pro Leu Glu Ser Tyr
1               5                   10

<210> SEQ ID NO 109
<211> LENGTH: 11
<212> TYPE: PRT
<213> ORGANISM: Homo sapiens

```
<400> SEQUENCE: 109

Lys Thr Phe Thr Ile Lys Arg Phe Leu Ala Lys
1               5                   10

<210> SEQ ID NO 110
<211> LENGTH: 9
<212> TYPE: PRT
<213> ORGANISM: Homo sapiens

<400> SEQUENCE: 110

Ser Ala Ala Pro Pro Ser Tyr Phe Arg
1               5

<210> SEQ ID NO 111
<211> LENGTH: 10
<212> TYPE: PRT
<213> ORGANISM: Homo sapiens

<400> SEQUENCE: 111

Thr Leu Pro Gln Phe Arg Glu Leu Gly Tyr
1               5                   10

<210> SEQ ID NO 112
<211> LENGTH: 10
<212> TYPE: PRT
<213> ORGANISM: Homo sapiens

<400> SEQUENCE: 112

Thr Val Thr Gly Ala Glu Gln Ile Gln Tyr
1               5                   10

<210> SEQ ID NO 113
<211> LENGTH: 9
<212> TYPE: PRT
<213> ORGANISM: Homo sapiens

<400> SEQUENCE: 113

Gln Leu Asp Ser Asn Arg Leu Thr Tyr
1               5

<210> SEQ ID NO 114
<211> LENGTH: 10
<212> TYPE: PRT
<213> ORGANISM: Homo sapiens

<400> SEQUENCE: 114

Val Met Glu Gln Ser Ala Gly Ile Met Tyr
1               5                   10

<210> SEQ ID NO 115
<211> LENGTH: 9
<212> TYPE: PRT
<213> ORGANISM: Homo sapiens

<400> SEQUENCE: 115

Phe Val Asp Asn Gln Tyr Trp Arg Tyr
1               5

<210> SEQ ID NO 116
<211> LENGTH: 11
<212> TYPE: PRT
<213> ORGANISM: Homo sapiens

<400> SEQUENCE: 116
```

```
Val Leu Leu Asp Glu Gly Ala Met Leu Tyr
1               5                   10

<210> SEQ ID NO 117
<211> LENGTH: 10
<212> TYPE: PRT
<213> ORGANISM: Homo sapiens

<400> SEQUENCE: 117

Ala Pro Arg Leu Leu Leu Ala Val Leu
1               5                   10

<210> SEQ ID NO 118
<211> LENGTH: 9
<212> TYPE: PRT
<213> ORGANISM: Homo sapiens

<400> SEQUENCE: 118

Ser Pro Ala Ser Arg Ser Ile Ser Leu
1               5

<210> SEQ ID NO 119
<211> LENGTH: 10
<212> TYPE: PRT
<213> ORGANISM: Homo sapiens

<400> SEQUENCE: 119

Ala Pro Leu Pro Arg Pro Gly Ala Val Leu
1               5                   10

<210> SEQ ID NO 120
<211> LENGTH: 9
<212> TYPE: PRT
<213> ORGANISM: Homo sapiens

<400> SEQUENCE: 120

Arg Pro Ala Met Asn Tyr Asp Lys Leu
1               5

<210> SEQ ID NO 121
<211> LENGTH: 9
<212> TYPE: PRT
<213> ORGANISM: Homo sapiens

<400> SEQUENCE: 121

Val Pro Asn Gln Ser Ser Glu Ser Leu
1               5

<210> SEQ ID NO 122
<211> LENGTH: 9
<212> TYPE: PRT
<213> ORGANISM: Homo sapiens

<400> SEQUENCE: 122

Tyr Pro Gly Phe Pro Gln Ser Gln Tyr
1               5

<210> SEQ ID NO 123
<211> LENGTH: 10
<212> TYPE: PRT
<213> ORGANISM: Homo sapiens

<400> SEQUENCE: 123

Lys Pro Ser Glu Ser Ile Tyr Ser Ala Leu
1               5                   10
```

<210> SEQ ID NO 124
<211> LENGTH: 11
<212> TYPE: PRT
<213> ORGANISM: Homo sapiens

<400> SEQUENCE: 124

Leu Pro Ser Asp Ser His Phe Lys Ile Thr Phe
1               5                   10

<210> SEQ ID NO 125
<211> LENGTH: 10
<212> TYPE: PRT
<213> ORGANISM: Homo sapiens

<400> SEQUENCE: 125

Val Pro Val Tyr Ile Leu Leu Asp Glu Met
1               5                   10

<210> SEQ ID NO 126
<211> LENGTH: 8
<212> TYPE: PRT
<213> ORGANISM: Homo sapiens

<400> SEQUENCE: 126

Lys Pro Gly Pro Glu Asp Lys Leu
1               5

<210> SEQ ID NO 127
<211> LENGTH: 9
<212> TYPE: PRT
<213> ORGANISM: Homo sapiens

<400> SEQUENCE: 127

Ala Pro Arg Ala Gly Ser Gln Val Val
1               5

<210> SEQ ID NO 128
<211> LENGTH: 9
<212> TYPE: PRT
<213> ORGANISM: Homo sapiens

<400> SEQUENCE: 128

Tyr Pro Arg Thr Ile Thr Pro Gly Met
1               5

<210> SEQ ID NO 129
<211> LENGTH: 8
<212> TYPE: PRT
<213> ORGANISM: Homo sapiens

<400> SEQUENCE: 129

Ala Pro Arg Pro Ala Ser Ser Leu
1               5

<210> SEQ ID NO 130
<211> LENGTH: 9
<212> TYPE: PRT
<213> ORGANISM: Homo sapiens

<400> SEQUENCE: 130

Phe Pro Arg Leu Val Gly Pro Asp Phe
1               5

<210> SEQ ID NO 131
<211> LENGTH: 9
<212> TYPE: PRT
<213> ORGANISM: Homo sapiens

<400> SEQUENCE: 131

Ala Pro Thr Glu Asp Leu Lys Ala Leu
1               5

<210> SEQ ID NO 132
<211> LENGTH: 9
<212> TYPE: PRT
<213> ORGANISM: Homo sapiens

<400> SEQUENCE: 132

Ile Pro Gly Pro Ala Gln Ser Thr Ile
1               5

<210> SEQ ID NO 133
<211> LENGTH: 10
<212> TYPE: PRT
<213> ORGANISM: Homo sapiens

<400> SEQUENCE: 133

Met Pro Asn Leu Pro Ser Thr Thr Ser Leu
1               5                   10

<210> SEQ ID NO 134
<211> LENGTH: 9
<212> TYPE: PRT
<213> ORGANISM: Homo sapiens

<400> SEQUENCE: 134

Arg Pro Ile Val Pro Gly Pro Leu Leu
1               5

<210> SEQ ID NO 135
<211> LENGTH: 9
<212> TYPE: PRT
<213> ORGANISM: Homo sapiens

<400> SEQUENCE: 135

Arg Val Arg Ser Thr Ile Ser Ser Leu
1               5

<210> SEQ ID NO 136
<211> LENGTH: 11
<212> TYPE: PRT
<213> ORGANISM: Homo sapiens

<400> SEQUENCE: 136

Ser Pro Phe Ser Ala Glu Glu Ala Asn Ser Leu
1               5                   10

<210> SEQ ID NO 137
<211> LENGTH: 10
<212> TYPE: PRT
<213> ORGANISM: Homo sapiens

<400> SEQUENCE: 137

Ser Pro Gly Ala Thr Ser Arg Gly Thr Leu
1               5                   10

<210> SEQ ID NO 138
<211> LENGTH: 9

```
<212> TYPE: PRT
<213> ORGANISM: Homo sapiens

<400> SEQUENCE: 138

Ser Pro Met Ala Thr Thr Ser Thr Leu
1               5

<210> SEQ ID NO 139
<211> LENGTH: 9
<212> TYPE: PRT
<213> ORGANISM: Homo sapiens

<400> SEQUENCE: 139

Ser Pro Gln Ser Met Ser Asn Thr Leu
1               5

<210> SEQ ID NO 140
<211> LENGTH: 11
<212> TYPE: PRT
<213> ORGANISM: Homo sapiens

<400> SEQUENCE: 140

Ser Pro Arg Thr Glu Ala Ser Ser Ala Val Leu
1               5                   10

<210> SEQ ID NO 141
<211> LENGTH: 11
<212> TYPE: PRT
<213> ORGANISM: Homo sapiens

<400> SEQUENCE: 141

Ser Pro Met Thr Ser Leu Leu Thr Ser Gly Leu
1               5                   10

<210> SEQ ID NO 142
<211> LENGTH: 9
<212> TYPE: PRT
<213> ORGANISM: Homo sapiens

<400> SEQUENCE: 142

Thr Pro Gly Leu Arg Glu Thr Ser Ile
1               5

<210> SEQ ID NO 143
<211> LENGTH: 9
<212> TYPE: PRT
<213> ORGANISM: Homo sapiens

<400> SEQUENCE: 143

Ser Pro Ala Met Thr Ser Thr Ser Phe
1               5

<210> SEQ ID NO 144
<211> LENGTH: 9
<212> TYPE: PRT
<213> ORGANISM: Homo sapiens

<400> SEQUENCE: 144

Ser Pro Ser Pro Val Ser Ser Thr Leu
1               5

<210> SEQ ID NO 145
<211> LENGTH: 9
<212> TYPE: PRT
<213> ORGANISM: Homo sapiens
```

```
<400> SEQUENCE: 145

Ser Pro Ser Ser Pro Met Ser Thr Phe
1               5

<210> SEQ ID NO 146
<211> LENGTH: 9
<212> TYPE: PRT
<213> ORGANISM: Homo sapiens

<400> SEQUENCE: 146

Ile Pro Arg Pro Glu Val Gln Ala Leu
1               5

<210> SEQ ID NO 147
<211> LENGTH: 11
<212> TYPE: PRT
<213> ORGANISM: Homo sapiens

<400> SEQUENCE: 147

Ala Pro Arg Trp Phe Pro Gln Pro Thr Val Val
1               5                   10

<210> SEQ ID NO 148
<211> LENGTH: 9
<212> TYPE: PRT
<213> ORGANISM: Homo sapiens

<400> SEQUENCE: 148

Lys Pro Tyr Gly Gly Ser Gly Pro Leu
1               5

<210> SEQ ID NO 149
<211> LENGTH: 9
<212> TYPE: PRT
<213> ORGANISM: Homo sapiens

<400> SEQUENCE: 149

Gly Pro Arg Glu Ala Leu Ser Arg Leu
1               5

<210> SEQ ID NO 150
<211> LENGTH: 8
<212> TYPE: PRT
<213> ORGANISM: Homo sapiens

<400> SEQUENCE: 150

Met Ala Ala Val Lys Gln Ala Leu
1               5

<210> SEQ ID NO 151
<211> LENGTH: 9
<212> TYPE: PRT
<213> ORGANISM: Homo sapiens

<400> SEQUENCE: 151

His Leu Leu Leu Lys Val Leu Ala Phe
1               5

<210> SEQ ID NO 152
<211> LENGTH: 9
<212> TYPE: PRT
<213> ORGANISM: Homo sapiens

<400> SEQUENCE: 152
```

Met Gly Ser Ala Arg Val Ala Glu Leu
1               5

<210> SEQ ID NO 153
<211> LENGTH: 9
<212> TYPE: PRT
<213> ORGANISM: Homo sapiens

<400> SEQUENCE: 153

Asn Ala Met Leu Arg Lys Val Ala Val
1               5

<210> SEQ ID NO 154
<211> LENGTH: 9
<212> TYPE: PRT
<213> ORGANISM: Homo sapiens

<400> SEQUENCE: 154

Met Leu Arg Lys Ile Ala Val Ala Ala
1               5

<210> SEQ ID NO 155
<211> LENGTH: 9
<212> TYPE: PRT
<213> ORGANISM: Homo sapiens

<400> SEQUENCE: 155

Asn Lys Lys Met Met Lys Arg Leu Met
1               5

<210> SEQ ID NO 156
<211> LENGTH: 8
<212> TYPE: PRT
<213> ORGANISM: Homo sapiens

<400> SEQUENCE: 156

His Val Lys Glu Lys Phe Leu Leu
1               5

<210> SEQ ID NO 157
<211> LENGTH: 9
<212> TYPE: PRT
<213> ORGANISM: Homo sapiens

<400> SEQUENCE: 157

Glu Ala Met Lys Arg Leu Ser Tyr Ile
1               5

<210> SEQ ID NO 158
<211> LENGTH: 8
<212> TYPE: PRT
<213> ORGANISM: Homo sapiens

<400> SEQUENCE: 158

Leu Pro Lys Leu Ala Gly Leu Leu
1               5

<210> SEQ ID NO 159
<211> LENGTH: 9
<212> TYPE: PRT
<213> ORGANISM: Homo sapiens

<400> SEQUENCE: 159

Val Leu Lys His Lys Leu Asp Glu Leu

```
1               5

<210> SEQ ID NO 160
<211> LENGTH: 8
<212> TYPE: PRT
<213> ORGANISM: Homo sapiens

<400> SEQUENCE: 160

Tyr Pro Lys Ala Arg Leu Ala Phe
1               5

<210> SEQ ID NO 161
<211> LENGTH: 9
<212> TYPE: PRT
<213> ORGANISM: Homo sapiens

<400> SEQUENCE: 161

Ala Leu Lys Thr Thr Thr Thr Ala Leu
1               5

<210> SEQ ID NO 162
<211> LENGTH: 8
<212> TYPE: PRT
<213> ORGANISM: Homo sapiens

<400> SEQUENCE: 162

Gln Ala Lys Thr His Ser Thr Leu
1               5

<210> SEQ ID NO 163
<211> LENGTH: 8
<212> TYPE: PRT
<213> ORGANISM: Homo sapiens

<400> SEQUENCE: 163

Gln Gly Leu Leu Arg Pro Val Phe
1               5

<210> SEQ ID NO 164
<211> LENGTH: 9
<212> TYPE: PRT
<213> ORGANISM: Homo sapiens

<400> SEQUENCE: 164

Ser Ile Lys Thr Lys Ser Ala Glu Met
1               5

<210> SEQ ID NO 165
<211> LENGTH: 8
<212> TYPE: PRT
<213> ORGANISM: Homo sapiens

<400> SEQUENCE: 165

Ser Pro Arg Phe Lys Thr Gly Leu
1               5

<210> SEQ ID NO 166
<211> LENGTH: 9
<212> TYPE: PRT
<213> ORGANISM: Homo sapiens

<400> SEQUENCE: 166

Thr Pro Lys Leu Arg Glu Thr Ser Ile
1               5
```

<210> SEQ ID NO 167
<211> LENGTH: 9
<212> TYPE: PRT
<213> ORGANISM: Homo sapiens

<400> SEQUENCE: 167

Thr Ser His Glu Arg Leu Thr Thr Leu
1               5

<210> SEQ ID NO 168
<211> LENGTH: 9
<212> TYPE: PRT
<213> ORGANISM: Homo sapiens

<400> SEQUENCE: 168

Thr Ser His Glu Arg Leu Thr Thr Tyr
1               5

<210> SEQ ID NO 169
<211> LENGTH: 9
<212> TYPE: PRT
<213> ORGANISM: Homo sapiens

<400> SEQUENCE: 169

Thr Ser Met Pro Arg Ser Ser Ala Met
1               5

<210> SEQ ID NO 170
<211> LENGTH: 9
<212> TYPE: PRT
<213> ORGANISM: Homo sapiens

<400> SEQUENCE: 170

Tyr Leu Leu Glu Lys Ser Arg Val Ile
1               5

<210> SEQ ID NO 171
<211> LENGTH: 8
<212> TYPE: PRT
<213> ORGANISM: Homo sapiens

<400> SEQUENCE: 171

Phe Ala Phe Arg Lys Glu Ala Leu
1               5

<210> SEQ ID NO 172
<211> LENGTH: 9
<212> TYPE: PRT
<213> ORGANISM: Homo sapiens

<400> SEQUENCE: 172

Lys Leu Lys Glu Arg Asn Arg Glu Leu
1               5

<210> SEQ ID NO 173
<211> LENGTH: 11
<212> TYPE: PRT
<213> ORGANISM: Homo sapiens

<400> SEQUENCE: 173

Ala Glu Ala Gln Val Gly Asp Glu Arg Asp Tyr
1               5                   10

<210> SEQ ID NO 174

-continued

```
<211> LENGTH: 10
<212> TYPE: PRT
<213> ORGANISM: Homo sapiens

<400> SEQUENCE: 174

Ala Glu Ala Thr Ala Arg Leu Asn Val Phe
1               5                   10

<210> SEQ ID NO 175
<211> LENGTH: 9
<212> TYPE: PRT
<213> ORGANISM: Homo sapiens

<400> SEQUENCE: 175

Ala Glu Ile Glu Pro Lys Ala Asp Gly
1               5

<210> SEQ ID NO 176
<211> LENGTH: 11
<212> TYPE: PRT
<213> ORGANISM: Homo sapiens

<400> SEQUENCE: 176

Ala Glu Ile Glu Pro Lys Ala Asp Gly Ser Trp
1               5                   10

<210> SEQ ID NO 177
<211> LENGTH: 9
<212> TYPE: PRT
<213> ORGANISM: Homo sapiens

<400> SEQUENCE: 177

Thr Glu Val Gly Thr Met Asn Leu Phe
1               5

<210> SEQ ID NO 178
<211> LENGTH: 10
<212> TYPE: PRT
<213> ORGANISM: Homo sapiens

<400> SEQUENCE: 178

Asn Glu Leu Phe Arg Asp Gly Val Asn Trp
1               5                   10

<210> SEQ ID NO 179
<211> LENGTH: 9
<212> TYPE: PRT
<213> ORGANISM: Homo sapiens

<400> SEQUENCE: 179

Arg Glu Ala Gly Asp Glu Phe Glu Leu
1               5

<210> SEQ ID NO 180
<211> LENGTH: 11
<212> TYPE: PRT
<213> ORGANISM: Homo sapiens

<400> SEQUENCE: 180

Arg Glu Ala Gly Asp Glu Phe Glu Leu Arg Tyr
1               5                   10

<210> SEQ ID NO 181
<211> LENGTH: 8
<212> TYPE: PRT
```

```
<213> ORGANISM: Homo sapiens

<400> SEQUENCE: 181

Gly Glu Gly Pro Lys Thr Ser Trp
1               5

<210> SEQ ID NO 182
<211> LENGTH: 9
<212> TYPE: PRT
<213> ORGANISM: Homo sapiens

<400> SEQUENCE: 182

Lys Glu Ala Thr Glu Ala Gln Ser Leu
1               5

<210> SEQ ID NO 183
<211> LENGTH: 9
<212> TYPE: PRT
<213> ORGANISM: Homo sapiens

<400> SEQUENCE: 183

Tyr Glu Lys Gly Ile Met Gln Lys Val
1               5

<210> SEQ ID NO 184
<211> LENGTH: 10
<212> TYPE: PRT
<213> ORGANISM: Homo sapiens

<400> SEQUENCE: 184

Ala Glu Leu Glu Ala Leu Thr Asp Leu Trp
1               5                   10

<210> SEQ ID NO 185
<211> LENGTH: 10
<212> TYPE: PRT
<213> ORGANISM: Homo sapiens

<400> SEQUENCE: 185

Ala Glu Arg Gln Pro Gly Ala Ala Ser Leu
1               5                   10

<210> SEQ ID NO 186
<211> LENGTH: 9
<212> TYPE: PRT
<213> ORGANISM: Homo sapiens

<400> SEQUENCE: 186

Arg Glu Gly Pro Glu Glu Pro Gly Leu
1               5

<210> SEQ ID NO 187
<211> LENGTH: 9
<212> TYPE: PRT
<213> ORGANISM: Homo sapiens

<400> SEQUENCE: 187

Gly Glu Ala Gln Thr Arg Ile Ala Trp
1               5

<210> SEQ ID NO 188
<211> LENGTH: 10
<212> TYPE: PRT
<213> ORGANISM: Homo sapiens
```

```
<400> SEQUENCE: 188

Ala Glu Phe Ala Lys Lys Gln Pro Trp Trp
1               5                   10

<210> SEQ ID NO 189
<211> LENGTH: 8
<212> TYPE: PRT
<213> ORGANISM: Homo sapiens

<400> SEQUENCE: 189

Lys Glu Phe Leu Phe Asn Met Tyr
1               5

<210> SEQ ID NO 190
<211> LENGTH: 9
<212> TYPE: PRT
<213> ORGANISM: Homo sapiens

<400> SEQUENCE: 190

Tyr Glu Val Ala Arg Ile Leu Asn Leu
1               5

<210> SEQ ID NO 191
<211> LENGTH: 10
<212> TYPE: PRT
<213> ORGANISM: Homo sapiens

<400> SEQUENCE: 191

Glu Glu Asp Ala Ala Leu Phe Lys Ala Trp
1               5                   10

<210> SEQ ID NO 192
<211> LENGTH: 9
<212> TYPE: PRT
<213> ORGANISM: Homo sapiens

<400> SEQUENCE: 192

Tyr Glu Phe Lys Phe Pro Asn Arg Leu
1               5

<210> SEQ ID NO 193
<211> LENGTH: 8
<212> TYPE: PRT
<213> ORGANISM: Homo sapiens

<400> SEQUENCE: 193

Leu Glu Ala Gln Gln Glu Ala Leu
1               5

<210> SEQ ID NO 194
<211> LENGTH: 10
<212> TYPE: PRT
<213> ORGANISM: Homo sapiens

<400> SEQUENCE: 194

Lys Glu Val Asp Pro Thr Ser His Ser Tyr
1               5                   10

<210> SEQ ID NO 195
<211> LENGTH: 9
<212> TYPE: PRT
<213> ORGANISM: Homo sapiens

<400> SEQUENCE: 195
```

```
Ala Glu Asp Lys Arg His Tyr Ser Val
1               5
```

<210> SEQ ID NO 196
<211> LENGTH: 9
<212> TYPE: PRT
<213> ORGANISM: Homo sapiens

<400> SEQUENCE: 196

```
Arg Glu Met Pro Gly Gly Pro Val Trp
1               5
```

<210> SEQ ID NO 197
<211> LENGTH: 9
<212> TYPE: PRT
<213> ORGANISM: Homo sapiens

<400> SEQUENCE: 197

```
Ala Glu Val Leu Leu Pro Arg Leu Val
1               5
```

<210> SEQ ID NO 198
<211> LENGTH: 8
<212> TYPE: PRT
<213> ORGANISM: Homo sapiens

<400> SEQUENCE: 198

```
Gln Glu Ala Ala Arg Ala Ala Leu
1               5
```

<210> SEQ ID NO 199
<211> LENGTH: 10
<212> TYPE: PRT
<213> ORGANISM: Homo sapiens

<400> SEQUENCE: 199

```
Arg Glu Ile Asp Glu Ser Leu Ile Phe Tyr
1               5                   10
```

<210> SEQ ID NO 200
<211> LENGTH: 9
<212> TYPE: PRT
<213> ORGANISM: Homo sapiens

<400> SEQUENCE: 200

```
Ala Glu Ser Ile Pro Thr Val Ser Phe
1               5
```

<210> SEQ ID NO 201
<211> LENGTH: 10
<212> TYPE: PRT
<213> ORGANISM: Homo sapiens

<400> SEQUENCE: 201

```
Ala Glu Thr Ile Leu Thr Phe His Ala Phe
1               5                   10
```

<210> SEQ ID NO 202
<211> LENGTH: 9
<212> TYPE: PRT
<213> ORGANISM: Homo sapiens

<400> SEQUENCE: 202

```
His Glu Ser Glu Ala Thr Ala Ser Trp
1               5
```

<210> SEQ ID NO 203
<211> LENGTH: 11
<212> TYPE: PRT
<213> ORGANISM: Homo sapiens

<400> SEQUENCE: 203

Ile Glu His Ser Thr Gln Ala Gln Asp Thr Leu
1               5                   10

<210> SEQ ID NO 204
<211> LENGTH: 11
<212> TYPE: PRT
<213> ORGANISM: Homo sapiens

<400> SEQUENCE: 204

Arg Glu Thr Ser Thr Ser Glu Glu Thr Ser Leu
1               5                   10

<210> SEQ ID NO 205
<211> LENGTH: 8
<212> TYPE: PRT
<213> ORGANISM: Homo sapiens

<400> SEQUENCE: 205

Ser Glu Ile Thr Arg Ile Glu Met
1               5

<210> SEQ ID NO 206
<211> LENGTH: 10
<212> TYPE: PRT
<213> ORGANISM: Homo sapiens

<400> SEQUENCE: 206

Ser Glu Ser Val Thr Ser Arg Thr Ser Tyr
1               5                   10

<210> SEQ ID NO 207
<211> LENGTH: 10
<212> TYPE: PRT
<213> ORGANISM: Homo sapiens

<400> SEQUENCE: 207

Thr Glu Ala Arg Ala Thr Ser Asp Ser Trp
1               5                   10

<210> SEQ ID NO 208
<211> LENGTH: 9
<212> TYPE: PRT
<213> ORGANISM: Homo sapiens

<400> SEQUENCE: 208

Thr Glu Val Ser Arg Thr Glu Ala Ile
1               5

<210> SEQ ID NO 209
<211> LENGTH: 8
<212> TYPE: PRT
<213> ORGANISM: Homo sapiens

<400> SEQUENCE: 209

Thr Glu Val Ser Arg Thr Glu Leu
1               5

<210> SEQ ID NO 210
<211> LENGTH: 10
<212> TYPE: PRT
<213> ORGANISM: Homo sapiens

<400> SEQUENCE: 210

Val Glu Ala Ala Asp Ile Phe Gln Asn Phe
1               5                   10

<210> SEQ ID NO 211
<211> LENGTH: 10
<212> TYPE: PRT
<213> ORGANISM: Homo sapiens

<400> SEQUENCE: 211

Glu Glu Lys Val Phe Pro Ser Pro Leu Trp
1               5                   10

<210> SEQ ID NO 212
<211> LENGTH: 10
<212> TYPE: PRT
<213> ORGANISM: Homo sapiens

<400> SEQUENCE: 212

Met Glu Gln Lys Gln Leu Gln Lys Arg Phe
1               5                   10

<210> SEQ ID NO 213
<211> LENGTH: 9
<212> TYPE: PRT
<213> ORGANISM: Homo sapiens

<400> SEQUENCE: 213

Lys Glu Ser Ile Pro Arg Trp Tyr Tyr
1               5

<210> SEQ ID NO 214
<211> LENGTH: 10
<212> TYPE: PRT
<213> ORGANISM: Homo sapiens

<400> SEQUENCE: 214

Val Glu Gln Thr Arg Ala Gly Ser Leu Leu
1               5                   10

<210> SEQ ID NO 215
<211> LENGTH: 11
<212> TYPE: PRT
<213> ORGANISM: Homo sapiens

<400> SEQUENCE: 215

Ser Glu Asp Gly Leu Pro Glu Gly Ile His Leu
1               5                   10

<210> SEQ ID NO 216
<211> LENGTH: 10
<212> TYPE: PRT
<213> ORGANISM: Homo sapiens

<400> SEQUENCE: 216

Ile Met Phe Asp Asp Ala Ile Glu Arg Ala
1               5                   10

<210> SEQ ID NO 217
<211> LENGTH: 9

```
<212> TYPE: PRT
<213> ORGANISM: Homo sapiens

<400> SEQUENCE: 217

Val Ser Ser Leu Thr Leu Lys Val
1               5

<210> SEQ ID NO 218
<211> LENGTH: 10
<212> TYPE: PRT
<213> ORGANISM: Homo sapiens

<400> SEQUENCE: 218

Thr Ile Ala Ser Gln Arg Leu Thr Pro Leu
1               5                   10

<210> SEQ ID NO 219
<211> LENGTH: 9
<212> TYPE: PRT
<213> ORGANISM: Homo sapiens

<400> SEQUENCE: 219

Pro Leu Pro Arg Pro Gly Ala Val Leu
1               5

<210> SEQ ID NO 220
<211> LENGTH: 9
<212> TYPE: PRT
<213> ORGANISM: Homo sapiens

<400> SEQUENCE: 220

Arg Met Thr Thr Gln Leu Leu Leu Leu
1               5

<210> SEQ ID NO 221
<211> LENGTH: 8
<212> TYPE: PRT
<213> ORGANISM: Homo sapiens

<400> SEQUENCE: 221

Ser Leu Leu Asp Leu Tyr Gln Leu
1               5

<210> SEQ ID NO 222
<211> LENGTH: 10
<212> TYPE: PRT
<213> ORGANISM: Homo sapiens

<400> SEQUENCE: 222

Ala Leu Met Arg Leu Ile Gly Cys Pro Leu
1               5                   10

<210> SEQ ID NO 223
<211> LENGTH: 8
<212> TYPE: PRT
<213> ORGANISM: Homo sapiens

<400> SEQUENCE: 223

Phe Ala His His Gly Arg Ser Leu
1               5

<210> SEQ ID NO 224
<211> LENGTH: 9
<212> TYPE: PRT
<213> ORGANISM: Homo sapiens
```

-continued

<400> SEQUENCE: 224

Ser Leu Pro Arg Phe Gln Val Thr Leu
1               5

<210> SEQ ID NO 225
<211> LENGTH: 9
<212> TYPE: PRT
<213> ORGANISM: Homo sapiens

<400> SEQUENCE: 225

Ser Val Phe Ala His Pro Arg Lys Leu
1               5

<210> SEQ ID NO 226
<211> LENGTH: 10
<212> TYPE: PRT
<213> ORGANISM: Homo sapiens

<400> SEQUENCE: 226

Gln Val Asp Pro Lys Lys Arg Ile Ser Met
1               5                   10

<210> SEQ ID NO 227
<211> LENGTH: 9
<212> TYPE: PRT
<213> ORGANISM: Homo sapiens

<400> SEQUENCE: 227

Tyr Thr Phe Arg Tyr Pro Leu Ser Leu
1               5

<210> SEQ ID NO 228
<211> LENGTH: 9
<212> TYPE: PRT
<213> ORGANISM: Homo sapiens

<400> SEQUENCE: 228

Arg Leu Trp Asp Trp Val Pro Leu Ala
1               5

<210> SEQ ID NO 229
<211> LENGTH: 9
<212> TYPE: PRT
<213> ORGANISM: Homo sapiens

<400> SEQUENCE: 229

Ile Ser Val Pro Ala Lys Thr Ser Leu
1               5

<210> SEQ ID NO 230
<211> LENGTH: 9
<212> TYPE: PRT
<213> ORGANISM: Homo sapiens

<400> SEQUENCE: 230

Ser Ala Phe Arg Glu Gly Thr Ser Leu
1               5

<210> SEQ ID NO 231
<211> LENGTH: 9
<212> TYPE: PRT
<213> ORGANISM: Homo sapiens

<400> SEQUENCE: 231

Ser Val Thr Glu Ser Thr His His Leu
1               5

<210> SEQ ID NO 232
<211> LENGTH: 9
<212> TYPE: PRT
<213> ORGANISM: Homo sapiens

<400> SEQUENCE: 232

Thr Ile Ser Ser Leu Thr His Glu Leu
1               5

<210> SEQ ID NO 233
<211> LENGTH: 9
<212> TYPE: PRT
<213> ORGANISM: Homo sapiens

<400> SEQUENCE: 233

Gly Ser Asp Thr Ser Ser Lys Ser Leu
1               5

<210> SEQ ID NO 234
<211> LENGTH: 9
<212> TYPE: PRT
<213> ORGANISM: Homo sapiens

<400> SEQUENCE: 234

Gly Val Ala Thr Arg Val Asp Ala Ile
1               5

<210> SEQ ID NO 235
<211> LENGTH: 9
<212> TYPE: PRT
<213> ORGANISM: Homo sapiens

<400> SEQUENCE: 235

Ser Ala Ile Glu Thr Ser Ala Val Leu
1               5

<210> SEQ ID NO 236
<211> LENGTH: 9
<212> TYPE: PRT
<213> ORGANISM: Homo sapiens

<400> SEQUENCE: 236

Ser Ala Ile Pro Phe Ser Met Thr Leu
1               5

<210> SEQ ID NO 237
<211> LENGTH: 9
<212> TYPE: PRT
<213> ORGANISM: Homo sapiens

<400> SEQUENCE: 237

Ser Ala Met Gly Thr Ile Ser Ile Met
1               5

<210> SEQ ID NO 238
<211> LENGTH: 8
<212> TYPE: PRT
<213> ORGANISM: Homo sapiens

<400> SEQUENCE: 238

Pro Leu Leu Val Leu Phe Thr Ile

```
1               5

<210> SEQ ID NO 239
<211> LENGTH: 9
<212> TYPE: PRT
<213> ORGANISM: Homo sapiens

<400> SEQUENCE: 239

Phe Ala Val Pro Thr Gly Ile Ser Met
1               5

<210> SEQ ID NO 240
<211> LENGTH: 9
<212> TYPE: PRT
<213> ORGANISM: Homo sapiens

<400> SEQUENCE: 240

Phe Ser Thr Asp Thr Ser Ile Val Leu
1               5

<210> SEQ ID NO 241
<211> LENGTH: 9
<212> TYPE: PRT
<213> ORGANISM: Homo sapiens

<400> SEQUENCE: 241

Arg Gln Pro Asn Ile Leu Val His Leu
1               5

<210> SEQ ID NO 242
<211> LENGTH: 9
<212> TYPE: PRT
<213> ORGANISM: Homo sapiens

<400> SEQUENCE: 242

Ser Thr Ile Pro Ala Leu His Glu Ile
1               5

<210> SEQ ID NO 243
<211> LENGTH: 9
<212> TYPE: PRT
<213> ORGANISM: Homo sapiens

<400> SEQUENCE: 243

Tyr Ala Ser Glu Gly Val Lys Gln Val
1               5

<210> SEQ ID NO 244
<211> LENGTH: 10
<212> TYPE: PRT
<213> ORGANISM: Homo sapiens

<400> SEQUENCE: 244

Asp Thr Asp Ser Ser Val His Val Gln Val
1               5                   10

<210> SEQ ID NO 245
<211> LENGTH: 9
<212> TYPE: PRT
<213> ORGANISM: Homo sapiens

<400> SEQUENCE: 245

Leu Ala Val Glu Gly Gly Gln Ser Leu
1               5
```

<210> SEQ ID NO 246
<211> LENGTH: 10
<212> TYPE: PRT
<213> ORGANISM: Homo sapiens

<400> SEQUENCE: 246

Arg Tyr Leu Ala Val Val His Ala Val Phe
1               5                   10

<210> SEQ ID NO 247
<211> LENGTH: 9
<212> TYPE: PRT
<213> ORGANISM: Homo sapiens

<400> SEQUENCE: 247

Ala Arg Pro Pro Trp Met Trp Val Leu
1               5

<210> SEQ ID NO 248
<211> LENGTH: 8
<212> TYPE: PRT
<213> ORGANISM: Homo sapiens

<400> SEQUENCE: 248

Ser Val Ile Gln His Leu Gly Tyr
1               5

<210> SEQ ID NO 249
<211> LENGTH: 9
<212> TYPE: PRT
<213> ORGANISM: Homo sapiens

<400> SEQUENCE: 249

Val Tyr Thr Pro Thr Leu Gly Thr Leu
1               5

<210> SEQ ID NO 250
<211> LENGTH: 10
<212> TYPE: PRT
<213> ORGANISM: Homo sapiens

<400> SEQUENCE: 250

His Phe Pro Glu Lys Thr Thr His Ser Phe
1               5                   10

<210> SEQ ID NO 251
<211> LENGTH: 9
<212> TYPE: PRT
<213> ORGANISM: Homo sapiens

<400> SEQUENCE: 251

Lys Gln Arg Gln Val Leu Ile Phe Phe
1               5

<210> SEQ ID NO 252
<211> LENGTH: 9
<212> TYPE: PRT
<213> ORGANISM: Homo sapiens

<400> SEQUENCE: 252

Leu Tyr Gln Pro Arg Ala Ser Glu Met
1               5

<210> SEQ ID NO 253

```
<211> LENGTH: 8
<212> TYPE: PRT
<213> ORGANISM: Homo sapiens

<400> SEQUENCE: 253

Ala Tyr Pro Glu Ile Glu Lys Phe
1               5

<210> SEQ ID NO 254
<211> LENGTH: 9
<212> TYPE: PRT
<213> ORGANISM: Homo sapiens

<400> SEQUENCE: 254

Ile Ile Gln His Leu Thr Glu Gln Phe
1               5

<210> SEQ ID NO 255
<211> LENGTH: 9
<212> TYPE: PRT
<213> ORGANISM: Homo sapiens

<400> SEQUENCE: 255

Val Phe Val Ser Phe Ser Ser Leu Phe
1               5

<210> SEQ ID NO 256
<211> LENGTH: 10
<212> TYPE: PRT
<213> ORGANISM: Homo sapiens

<400> SEQUENCE: 256

Arg Thr Glu Glu Val Leu Leu Thr Phe Lys
1               5                   10

<210> SEQ ID NO 257
<211> LENGTH: 9
<212> TYPE: PRT
<213> ORGANISM: Homo sapiens

<400> SEQUENCE: 257

Val Thr Ala Asp His Ser His Val Phe
1               5

<210> SEQ ID NO 258
<211> LENGTH: 9
<212> TYPE: PRT
<213> ORGANISM: Homo sapiens

<400> SEQUENCE: 258

Gly Ala Tyr Ala His Thr Val Asn Arg
1               5

<210> SEQ ID NO 259
<211> LENGTH: 9
<212> TYPE: PRT
<213> ORGANISM: Homo sapiens

<400> SEQUENCE: 259

Lys Thr Leu Glu Leu Arg Val Ala Tyr
1               5

<210> SEQ ID NO 260
<211> LENGTH: 9
<212> TYPE: PRT
```

```
<213> ORGANISM: Homo sapiens

<400> SEQUENCE: 260

Gly Thr Asn Thr Val Ile Leu Glu Tyr
1               5

<210> SEQ ID NO 261
<211> LENGTH: 9
<212> TYPE: PRT
<213> ORGANISM: Homo sapiens

<400> SEQUENCE: 261

His Thr Phe Gly Leu Phe Tyr Gln Arg
1               5

<210> SEQ ID NO 262
<211> LENGTH: 10
<212> TYPE: PRT
<213> ORGANISM: Homo sapiens

<400> SEQUENCE: 262

Arg Ser Arg Leu Asn Pro Leu Val Gln Arg
1               5                   10

<210> SEQ ID NO 263
<211> LENGTH: 9
<212> TYPE: PRT
<213> ORGANISM: Homo sapiens

<400> SEQUENCE: 263

Ser Ser Ser Ser Ala Thr Ile Ser Lys
1               5

<210> SEQ ID NO 264
<211> LENGTH: 10
<212> TYPE: PRT
<213> ORGANISM: Homo sapiens

<400> SEQUENCE: 264

Ala Ile Lys Val Ile Pro Thr Val Phe Lys
1               5                   10

<210> SEQ ID NO 265
<211> LENGTH: 9
<212> TYPE: PRT
<213> ORGANISM: Homo sapiens

<400> SEQUENCE: 265

Gln Ile His Asp His Val Asn Pro Lys
1               5

<210> SEQ ID NO 266
<211> LENGTH: 10
<212> TYPE: PRT
<213> ORGANISM: Homo sapiens

<400> SEQUENCE: 266

Ile Ser Tyr Ser Gly Gln Phe Leu Val Lys
1               5                   10

<210> SEQ ID NO 267
<211> LENGTH: 9
<212> TYPE: PRT
<213> ORGANISM: Homo sapiens
```

```
<400> SEQUENCE: 267

Val Thr Asp Leu Ile Ser Pro Arg Lys
1               5

<210> SEQ ID NO 268
<211> LENGTH: 9
<212> TYPE: PRT
<213> ORGANISM: Homo sapiens

<400> SEQUENCE: 268

Gly Leu Leu Gly Leu Ser Leu Arg Tyr
1               5

<210> SEQ ID NO 269
<211> LENGTH: 10
<212> TYPE: PRT
<213> ORGANISM: Homo sapiens

<400> SEQUENCE: 269

Arg Leu Lys Gly Asp Ala Trp Val Tyr Lys
1               5                   10

<210> SEQ ID NO 270
<211> LENGTH: 11
<212> TYPE: PRT
<213> ORGANISM: Homo sapiens

<400> SEQUENCE: 270

Ala Val Phe Asn Pro Arg Phe Tyr Arg Thr Tyr
1               5                   10

<210> SEQ ID NO 271
<211> LENGTH: 12
<212> TYPE: PRT
<213> ORGANISM: Homo sapiens

<400> SEQUENCE: 271

Arg Met Phe Ala Asp Asp Leu His Asn Leu Asn Lys
1               5                   10

<210> SEQ ID NO 272
<211> LENGTH: 11
<212> TYPE: PRT
<213> ORGANISM: Homo sapiens

<400> SEQUENCE: 272

Arg Gln Pro Glu Arg Thr Ile Leu Arg Pro Arg
1               5                   10

<210> SEQ ID NO 273
<211> LENGTH: 9
<212> TYPE: PRT
<213> ORGANISM: Homo sapiens

<400> SEQUENCE: 273

Arg Val Asn Ala Ile Pro Phe Thr Tyr
1               5

<210> SEQ ID NO 274
<211> LENGTH: 9
<212> TYPE: PRT
<213> ORGANISM: Homo sapiens

<400> SEQUENCE: 274
```

Lys Thr Phe Pro Ala Ser Thr Val Phe
1               5

<210> SEQ ID NO 275
<211> LENGTH: 9
<212> TYPE: PRT
<213> ORGANISM: Homo sapiens

<400> SEQUENCE: 275

Ser Thr Thr Phe Pro Thr Leu Thr Lys
1               5

<210> SEQ ID NO 276
<211> LENGTH: 9
<212> TYPE: PRT
<213> ORGANISM: Homo sapiens

<400> SEQUENCE: 276

Val Ser Lys Thr Thr Gly Met Glu Phe
1               5

<210> SEQ ID NO 277
<211> LENGTH: 9
<212> TYPE: PRT
<213> ORGANISM: Homo sapiens

<400> SEQUENCE: 277

Thr Thr Ala Leu Lys Thr Thr Ser Arg
1               5

<210> SEQ ID NO 278
<211> LENGTH: 9
<212> TYPE: PRT
<213> ORGANISM: Homo sapiens

<400> SEQUENCE: 278

Asn Leu Ser Ser Ile Thr His Glu Arg
1               5

<210> SEQ ID NO 279
<211> LENGTH: 11
<212> TYPE: PRT
<213> ORGANISM: Homo sapiens

<400> SEQUENCE: 279

Ser Val Ser Ser Glu Thr Thr Lys Ile Lys Arg
1               5                   10

<210> SEQ ID NO 280
<211> LENGTH: 9
<212> TYPE: PRT
<213> ORGANISM: Homo sapiens

<400> SEQUENCE: 280

Ser Val Ser Gly Val Lys Thr Thr Phe
1               5

<210> SEQ ID NO 281
<211> LENGTH: 9
<212> TYPE: PRT
<213> ORGANISM: Homo sapiens

<400> SEQUENCE: 281

Arg Ala Lys Glu Leu Glu Ala Thr Phe
1               5

<210> SEQ ID NO 282
<211> LENGTH: 11
<212> TYPE: PRT
<213> ORGANISM: Homo sapiens

<400> SEQUENCE: 282

Cys Leu Thr Arg Thr Gly Leu Phe Leu Arg Phe
1               5                   10

<210> SEQ ID NO 283
<211> LENGTH: 9
<212> TYPE: PRT
<213> ORGANISM: Homo sapiens

<400> SEQUENCE: 283

Ile Val Gln Glu Pro Thr Glu Glu Lys
1               5

<210> SEQ ID NO 284
<211> LENGTH: 9
<212> TYPE: PRT
<213> ORGANISM: Homo sapiens

<400> SEQUENCE: 284

Lys Ser Leu Ile Lys Ser Trp Lys Lys
1               5

<210> SEQ ID NO 285
<211> LENGTH: 9
<212> TYPE: PRT
<213> ORGANISM: Homo sapiens

<400> SEQUENCE: 285

Gly Thr Val Asn Pro Thr Val Gly Lys
1               5

<210> SEQ ID NO 286
<211> LENGTH: 10
<212> TYPE: PRT
<213> ORGANISM: Homo sapiens

<400> SEQUENCE: 286

Thr Val Ala Pro Pro Gln Gly Val Val Lys
1               5                   10

<210> SEQ ID NO 287
<211> LENGTH: 11
<212> TYPE: PRT
<213> ORGANISM: Homo sapiens

<400> SEQUENCE: 287

Arg Arg Ile His Thr Gly Glu Lys Pro Tyr Lys
1               5                   10

<210> SEQ ID NO 288
<211> LENGTH: 11
<212> TYPE: PRT
<213> ORGANISM: Homo sapiens

<400> SEQUENCE: 288

Ser Pro Val Thr Ser Val His Gly Gly Thr Tyr
1               5                   10

<210> SEQ ID NO 289
<211> LENGTH: 9
<212> TYPE: PRT
<213> ORGANISM: Homo sapiens

<400> SEQUENCE: 289

Arg Trp Glu Lys Thr Asp Leu Thr Tyr
1               5

<210> SEQ ID NO 290
<211> LENGTH: 10
<212> TYPE: PRT
<213> ORGANISM: Homo sapiens

<400> SEQUENCE: 290

Asp Met Asp Glu Glu Ile Glu Ala Glu Tyr
1               5                   10

<210> SEQ ID NO 291
<211> LENGTH: 9
<212> TYPE: PRT
<213> ORGANISM: Homo sapiens

<400> SEQUENCE: 291

Glu Thr Ile Arg Ser Val Gly Tyr Tyr
1               5

<210> SEQ ID NO 292
<211> LENGTH: 11
<212> TYPE: PRT
<213> ORGANISM: Homo sapiens

<400> SEQUENCE: 292

Asn Val Thr Met Lys Val Val Ser Val Leu Tyr
1               5                   10

<210> SEQ ID NO 293
<211> LENGTH: 11
<212> TYPE: PRT
<213> ORGANISM: Homo sapiens

<400> SEQUENCE: 293

Val Pro Asp Ser Gly Ala Thr Ala Thr Ala Tyr
1               5                   10

<210> SEQ ID NO 294
<211> LENGTH: 9
<212> TYPE: PRT
<213> ORGANISM: Homo sapiens

<400> SEQUENCE: 294

Tyr Pro Leu Arg Gly Ser Ser Ile Phe
1               5

<210> SEQ ID NO 295
<211> LENGTH: 11
<212> TYPE: PRT
<213> ORGANISM: Homo sapiens

<400> SEQUENCE: 295

Tyr Pro Leu Arg Gly Ser Ser Ile Phe Gly Leu
1               5                   10

<210> SEQ ID NO 296
<211> LENGTH: 8

```
<212> TYPE: PRT
<213> ORGANISM: Homo sapiens

<400> SEQUENCE: 296

Tyr Pro Leu Arg Gly Ser Ser Ile
1               5

<210> SEQ ID NO 297
<211> LENGTH: 9
<212> TYPE: PRT
<213> ORGANISM: Homo sapiens

<400> SEQUENCE: 297

Thr Val Arg Glu Ala Ser Gly Leu Leu
1               5

<210> SEQ ID NO 298
<211> LENGTH: 8
<212> TYPE: PRT
<213> ORGANISM: Homo sapiens

<400> SEQUENCE: 298

Tyr Pro Thr Glu His Val Gln Phe
1               5

<210> SEQ ID NO 299
<211> LENGTH: 9
<212> TYPE: PRT
<213> ORGANISM: Homo sapiens

<400> SEQUENCE: 299

His Pro Gly Ser Ser Ala Leu His Tyr
1               5

<210> SEQ ID NO 300
<211> LENGTH: 10
<212> TYPE: PRT
<213> ORGANISM: Homo sapiens

<400> SEQUENCE: 300

Ile Pro Met Ala Ala Val Lys Gln Ala Leu
1               5                   10

<210> SEQ ID NO 301
<211> LENGTH: 10
<212> TYPE: PRT
<213> ORGANISM: Homo sapiens

<400> SEQUENCE: 301

Ser Pro Arg Arg Ser Pro Arg Ile Ser Phe
1               5                   10

<210> SEQ ID NO 302
<211> LENGTH: 9
<212> TYPE: PRT
<213> ORGANISM: Homo sapiens

<400> SEQUENCE: 302

Arg Val Glu Glu Val Arg Ala Leu Leu
1               5

<210> SEQ ID NO 303
<211> LENGTH: 9
<212> TYPE: PRT
<213> ORGANISM: Homo sapiens
```

<400> SEQUENCE: 303

Leu Pro Met Trp Lys Val Thr Ala Phe
1               5

<210> SEQ ID NO 304
<211> LENGTH: 8
<212> TYPE: PRT
<213> ORGANISM: Homo sapiens

<400> SEQUENCE: 304

Leu Pro Arg Pro Gly Ala Val Leu
1               5

<210> SEQ ID NO 305
<211> LENGTH: 10
<212> TYPE: PRT
<213> ORGANISM: Homo sapiens

<400> SEQUENCE: 305

Thr Pro Trp Ala Glu Ser Ser Thr Lys Phe
1               5                   10

<210> SEQ ID NO 306
<211> LENGTH: 9
<212> TYPE: PRT
<213> ORGANISM: Homo sapiens

<400> SEQUENCE: 306

Ala Pro Val Ile Phe Ser His Ser Ala
1               5

<210> SEQ ID NO 307
<211> LENGTH: 12
<212> TYPE: PRT
<213> ORGANISM: Homo sapiens

<400> SEQUENCE: 307

Leu Pro Tyr Gly Pro Gly Ser Glu Ala Ala Ala Phe
1               5                   10

<210> SEQ ID NO 308
<211> LENGTH: 9
<212> TYPE: PRT
<213> ORGANISM: Homo sapiens

<400> SEQUENCE: 308

Tyr Pro Glu Gly Ala Ala Tyr Glu Phe
1               5

<210> SEQ ID NO 309
<211> LENGTH: 9
<212> TYPE: PRT
<213> ORGANISM: Homo sapiens

<400> SEQUENCE: 309

Phe Pro Gln Ser Gln Tyr Pro Gln Tyr
1               5

<210> SEQ ID NO 310
<211> LENGTH: 9
<212> TYPE: PRT
<213> ORGANISM: Homo sapiens

<400> SEQUENCE: 310

```
Arg Pro Asn Pro Ile Thr Ile Ile Leu
1               5

<210> SEQ ID NO 311
<211> LENGTH: 9
<212> TYPE: PRT
<213> ORGANISM: Homo sapiens

<400> SEQUENCE: 311

Arg Pro Leu Phe Tyr Val Val Ser Leu
1               5

<210> SEQ ID NO 312
<211> LENGTH: 9
<212> TYPE: PRT
<213> ORGANISM: Homo sapiens

<400> SEQUENCE: 312

Leu Pro Tyr Phe Arg Glu Phe Ser Met
1               5

<210> SEQ ID NO 313
<211> LENGTH: 9
<212> TYPE: PRT
<213> ORGANISM: Homo sapiens

<400> SEQUENCE: 313

Lys Val Lys Ser Asp Arg Ser Val Phe
1               5

<210> SEQ ID NO 314
<211> LENGTH: 9
<212> TYPE: PRT
<213> ORGANISM: Homo sapiens

<400> SEQUENCE: 314

Val Pro Asp Gln Pro His Pro Glu Ile
1               5

<210> SEQ ID NO 315
<211> LENGTH: 10
<212> TYPE: PRT
<213> ORGANISM: Homo sapiens

<400> SEQUENCE: 315

Ser Pro Arg Glu Asn Phe Pro Asp Thr Leu
1               5                   10

<210> SEQ ID NO 316
<211> LENGTH: 8
<212> TYPE: PRT
<213> ORGANISM: Homo sapiens

<400> SEQUENCE: 316

Glu Pro Lys Thr Ala Thr Val Leu
1               5

<210> SEQ ID NO 317
<211> LENGTH: 8
<212> TYPE: PRT
<213> ORGANISM: Homo sapiens

<400> SEQUENCE: 317

Phe Pro Phe Gln Pro Gly Ser Val
```

<210> SEQ ID NO 318
<211> LENGTH: 9
<212> TYPE: PRT
<213> ORGANISM: Homo sapiens

<400> SEQUENCE: 318

Phe Pro Asn Arg Leu Asn Leu Glu Ala
1               5

<210> SEQ ID NO 319
<211> LENGTH: 11
<212> TYPE: PRT
<213> ORGANISM: Homo sapiens

<400> SEQUENCE: 319

Ser Pro Ala Glu Pro Ser Val Tyr Ala Thr Leu
1               5                   10

<210> SEQ ID NO 320
<211> LENGTH: 9
<212> TYPE: PRT
<213> ORGANISM: Homo sapiens

<400> SEQUENCE: 320

Phe Pro Met Ser Pro Val Thr Ser Val
1               5

<210> SEQ ID NO 321
<211> LENGTH: 9
<212> TYPE: PRT
<213> ORGANISM: Homo sapiens

<400> SEQUENCE: 321

Ser Pro Met Asp Thr Phe Leu Leu Ile
1               5

<210> SEQ ID NO 322
<211> LENGTH: 9
<212> TYPE: PRT
<213> ORGANISM: Homo sapiens

<400> SEQUENCE: 322

Ser Pro Asp Pro Ser Lys His Leu Leu
1               5

<210> SEQ ID NO 323
<211> LENGTH: 9
<212> TYPE: PRT
<213> ORGANISM: Homo sapiens

<400> SEQUENCE: 323

Arg Pro Met Pro Asn Leu Arg Ser Val
1               5

<210> SEQ ID NO 324
<211> LENGTH: 8
<212> TYPE: PRT
<213> ORGANISM: Homo sapiens

<400> SEQUENCE: 324

Val Pro Tyr Arg Val Val Gly Leu
1               5

<210> SEQ ID NO 325
<211> LENGTH: 9
<212> TYPE: PRT
<213> ORGANISM: Homo sapiens

<400> SEQUENCE: 325

Gly Pro Arg Asn Ala Gln Arg Val Leu
1               5

<210> SEQ ID NO 326
<211> LENGTH: 9
<212> TYPE: PRT
<213> ORGANISM: Homo sapiens

<400> SEQUENCE: 326

Val Pro Ser Glu Ile Asp Ala Ala Phe
1               5

<210> SEQ ID NO 327
<211> LENGTH: 9
<212> TYPE: PRT
<213> ORGANISM: Homo sapiens

<400> SEQUENCE: 327

Ser Pro Leu Pro Val Thr Ser Leu Ile
1               5

<210> SEQ ID NO 328
<211> LENGTH: 10
<212> TYPE: PRT
<213> ORGANISM: Homo sapiens

<400> SEQUENCE: 328

Glu Pro Val Thr Ser Ser Leu Pro Asn Phe
1               5                   10

<210> SEQ ID NO 329
<211> LENGTH: 12
<212> TYPE: PRT
<213> ORGANISM: Homo sapiens

<400> SEQUENCE: 329

Phe Pro Ala Met Thr Glu Ser Gly Gly Met Ile Leu
1               5                   10

<210> SEQ ID NO 330
<211> LENGTH: 10
<212> TYPE: PRT
<213> ORGANISM: Homo sapiens

<400> SEQUENCE: 330

Phe Pro Phe Val Thr Gly Ser Thr Glu Met
1               5                   10

<210> SEQ ID NO 331
<211> LENGTH: 10
<212> TYPE: PRT
<213> ORGANISM: Homo sapiens

<400> SEQUENCE: 331

Phe Pro His Pro Glu Met Thr Thr Ser Met
1               5                   10

<210> SEQ ID NO 332

```
<211> LENGTH: 9
<212> TYPE: PRT
<213> ORGANISM: Homo sapiens

<400> SEQUENCE: 332

Phe Pro His Ser Glu Met Thr Thr Leu
1               5

<210> SEQ ID NO 333
<211> LENGTH: 10
<212> TYPE: PRT
<213> ORGANISM: Homo sapiens

<400> SEQUENCE: 333

Phe Pro His Ser Glu Met Thr Thr Val Met
1               5                   10

<210> SEQ ID NO 334
<211> LENGTH: 9
<212> TYPE: PRT
<213> ORGANISM: Homo sapiens

<400> SEQUENCE: 334

Phe Pro Tyr Ser Glu Val Thr Thr Leu
1               5

<210> SEQ ID NO 335
<211> LENGTH: 9
<212> TYPE: PRT
<213> ORGANISM: Homo sapiens

<400> SEQUENCE: 335

His Pro Asp Pro Val Gly Pro Gly Leu
1               5

<210> SEQ ID NO 336
<211> LENGTH: 12
<212> TYPE: PRT
<213> ORGANISM: Homo sapiens

<400> SEQUENCE: 336

His Pro Lys Thr Glu Ser Ala Thr Pro Ala Ala Tyr
1               5                   10

<210> SEQ ID NO 337
<211> LENGTH: 9
<212> TYPE: PRT
<213> ORGANISM: Homo sapiens

<400> SEQUENCE: 337

His Pro Val Glu Thr Ser Ser Ala Leu
1               5

<210> SEQ ID NO 338
<211> LENGTH: 9
<212> TYPE: PRT
<213> ORGANISM: Homo sapiens

<400> SEQUENCE: 338

His Val Thr Lys Thr Gln Ala Thr Phe
1               5

<210> SEQ ID NO 339
<211> LENGTH: 11
<212> TYPE: PRT
```

<213> ORGANISM: Homo sapiens

<400> SEQUENCE: 339

Leu Pro Ala Gly Thr Thr Gly Ser Leu Val Phe
1               5                   10

<210> SEQ ID NO 340
<211> LENGTH: 9
<212> TYPE: PRT
<213> ORGANISM: Homo sapiens

<400> SEQUENCE: 340

Leu Pro Glu Ile Ser Thr Arg Thr Met
1               5

<210> SEQ ID NO 341
<211> LENGTH: 9
<212> TYPE: PRT
<213> ORGANISM: Homo sapiens

<400> SEQUENCE: 341

Leu Pro Leu Asp Thr Ser Thr Thr Leu
1               5

<210> SEQ ID NO 342
<211> LENGTH: 9
<212> TYPE: PRT
<213> ORGANISM: Homo sapiens

<400> SEQUENCE: 342

Leu Pro Leu Gly Thr Ser Met Thr Phe
1               5

<210> SEQ ID NO 343
<211> LENGTH: 11
<212> TYPE: PRT
<213> ORGANISM: Homo sapiens

<400> SEQUENCE: 343

Leu Pro Ser Val Ser Gly Val Lys Thr Thr Phe
1               5                   10

<210> SEQ ID NO 344
<211> LENGTH: 9
<212> TYPE: PRT
<213> ORGANISM: Homo sapiens

<400> SEQUENCE: 344

Leu Pro Thr Gln Thr Thr Ser Ser Leu
1               5

<210> SEQ ID NO 345
<211> LENGTH: 10
<212> TYPE: PRT
<213> ORGANISM: Homo sapiens

<400> SEQUENCE: 345

Leu Pro Thr Ser Glu Ser Leu Val Ser Phe
1               5                   10

<210> SEQ ID NO 346
<211> LENGTH: 10
<212> TYPE: PRT
<213> ORGANISM: Homo sapiens

```
<400> SEQUENCE: 346

Leu Pro Trp Asp Thr Ser Thr Thr Leu Phe
1               5                   10

<210> SEQ ID NO 347
<211> LENGTH: 10
<212> TYPE: PRT
<213> ORGANISM: Homo sapiens

<400> SEQUENCE: 347

Met Pro Leu Thr Thr Gly Ser Gln Gly Met
1               5                   10

<210> SEQ ID NO 348
<211> LENGTH: 10
<212> TYPE: PRT
<213> ORGANISM: Homo sapiens

<400> SEQUENCE: 348

Met Pro Asn Ser Ala Ile Pro Phe Ser Met
1               5                   10

<210> SEQ ID NO 349
<211> LENGTH: 11
<212> TYPE: PRT
<213> ORGANISM: Homo sapiens

<400> SEQUENCE: 349

Met Pro Ser Leu Ser Glu Ala Met Thr Ser Phe
1               5                   10

<210> SEQ ID NO 350
<211> LENGTH: 9
<212> TYPE: PRT
<213> ORGANISM: Homo sapiens

<400> SEQUENCE: 350

Asn Pro Ser Ser Thr Thr Thr Glu Phe
1               5

<210> SEQ ID NO 351
<211> LENGTH: 9
<212> TYPE: PRT
<213> ORGANISM: Homo sapiens

<400> SEQUENCE: 351

Asn Val Leu Thr Ser Thr Pro Ala Phe
1               5

<210> SEQ ID NO 352
<211> LENGTH: 9
<212> TYPE: PRT
<213> ORGANISM: Homo sapiens

<400> SEQUENCE: 352

Ser Pro Ala Glu Thr Ser Thr Asn Met
1               5

<210> SEQ ID NO 353
<211> LENGTH: 9
<212> TYPE: PRT
<213> ORGANISM: Homo sapiens

<400> SEQUENCE: 353
```

```
Ser Pro Ala Met Thr Thr Pro Ser Leu
1               5

<210> SEQ ID NO 354
<211> LENGTH: 9
<212> TYPE: PRT
<213> ORGANISM: Homo sapiens

<400> SEQUENCE: 354

Ser Pro Leu Pro Val Thr Ser Leu Leu
1               5

<210> SEQ ID NO 355
<211> LENGTH: 9
<212> TYPE: PRT
<213> ORGANISM: Homo sapiens

<400> SEQUENCE: 355

Ser Pro Leu Val Thr Ser His Ile Met
1               5

<210> SEQ ID NO 356
<211> LENGTH: 9
<212> TYPE: PRT
<213> ORGANISM: Homo sapiens

<400> SEQUENCE: 356

Ser Pro Asn Glu Phe Tyr Phe Thr Val
1               5

<210> SEQ ID NO 357
<211> LENGTH: 9
<212> TYPE: PRT
<213> ORGANISM: Homo sapiens

<400> SEQUENCE: 357

Ser Pro Ser Pro Val Pro Thr Thr Leu
1               5

<210> SEQ ID NO 358
<211> LENGTH: 9
<212> TYPE: PRT
<213> ORGANISM: Homo sapiens

<400> SEQUENCE: 358

Ser Pro Ser Pro Val Thr Ser Thr Leu
1               5

<210> SEQ ID NO 359
<211> LENGTH: 9
<212> TYPE: PRT
<213> ORGANISM: Homo sapiens

<400> SEQUENCE: 359

Ser Pro Ser Thr Ile Lys Leu Thr Met
1               5

<210> SEQ ID NO 360
<211> LENGTH: 9
<212> TYPE: PRT
<213> ORGANISM: Homo sapiens

<400> SEQUENCE: 360

Ser Pro Ser Val Ser Ser Asn Thr Tyr
1               5
```

<210> SEQ ID NO 361
<211> LENGTH: 9
<212> TYPE: PRT
<213> ORGANISM: Homo sapiens

<400> SEQUENCE: 361

Ser Pro Thr His Val Thr Gln Ser Leu
1               5

<210> SEQ ID NO 362
<211> LENGTH: 9
<212> TYPE: PRT
<213> ORGANISM: Homo sapiens

<400> SEQUENCE: 362

Ser Pro Val Pro Val Thr Ser Leu Phe
1               5

<210> SEQ ID NO 363
<211> LENGTH: 9
<212> TYPE: PRT
<213> ORGANISM: Homo sapiens

<400> SEQUENCE: 363

Thr Ala Lys Thr Pro Asp Ala Thr Phe
1               5

<210> SEQ ID NO 364
<211> LENGTH: 9
<212> TYPE: PRT
<213> ORGANISM: Homo sapiens

<400> SEQUENCE: 364

Thr Pro Leu Ala Thr Thr Gln Arg Phe
1               5

<210> SEQ ID NO 365
<211> LENGTH: 11
<212> TYPE: PRT
<213> ORGANISM: Homo sapiens

<400> SEQUENCE: 365

Thr Pro Leu Ala Thr Thr Gln Arg Phe Thr Tyr
1               5                   10

<210> SEQ ID NO 366
<211> LENGTH: 11
<212> TYPE: PRT
<213> ORGANISM: Homo sapiens

<400> SEQUENCE: 366

Thr Pro Leu Thr Thr Thr Gly Ser Ala Glu Met
1               5                   10

<210> SEQ ID NO 367
<211> LENGTH: 9
<212> TYPE: PRT
<213> ORGANISM: Homo sapiens

<400> SEQUENCE: 367

Thr Pro Ser Val Val Thr Glu Gly Phe
1               5

```
<210> SEQ ID NO 368
<211> LENGTH: 9
<212> TYPE: PRT
<213> ORGANISM: Homo sapiens

<400> SEQUENCE: 368

Val Pro Thr Pro Val Phe Pro Thr Met
1               5

<210> SEQ ID NO 369
<211> LENGTH: 9
<212> TYPE: PRT
<213> ORGANISM: Homo sapiens

<400> SEQUENCE: 369

Phe Pro His Ser Glu Met Thr Thr Val
1               5

<210> SEQ ID NO 370
<211> LENGTH: 8
<212> TYPE: PRT
<213> ORGANISM: Homo sapiens

<400> SEQUENCE: 370

Pro Gly Gly Thr Arg Gln Ser Leu
1               5

<210> SEQ ID NO 371
<211> LENGTH: 9
<212> TYPE: PRT
<213> ORGANISM: Homo sapiens

<400> SEQUENCE: 371

Leu Tyr Val Asp Gly Phe Thr His Trp
1               5

<210> SEQ ID NO 372
<211> LENGTH: 10
<212> TYPE: PRT
<213> ORGANISM: Homo sapiens

<400> SEQUENCE: 372

Ile Pro Arg Asn Pro Pro Pro Thr Leu Leu
1               5                   10

<210> SEQ ID NO 373
<211> LENGTH: 11
<212> TYPE: PRT
<213> ORGANISM: Homo sapiens

<400> SEQUENCE: 373

Arg Pro Arg Ala Leu Arg Asp Leu Arg Ile Leu
1               5                   10

<210> SEQ ID NO 374
<211> LENGTH: 10
<212> TYPE: PRT
<213> ORGANISM: Homo sapiens

<400> SEQUENCE: 374

Asn Pro Ile Gly Asp Thr Gly Val Lys Phe
1               5                   10

<210> SEQ ID NO 375
<211> LENGTH: 9
```

```
<212> TYPE: PRT
<213> ORGANISM: Homo sapiens

<400> SEQUENCE: 375

Ala Ala Ala Ser Pro Leu Leu Leu Leu
1               5

<210> SEQ ID NO 376
<211> LENGTH: 10
<212> TYPE: PRT
<213> ORGANISM: Homo sapiens

<400> SEQUENCE: 376

Arg Pro Arg Ser Pro Ala Gly Gln Val Ala
1               5                   10

<210> SEQ ID NO 377
<211> LENGTH: 12
<212> TYPE: PRT
<213> ORGANISM: Homo sapiens

<400> SEQUENCE: 377

Arg Pro Arg Ser Pro Ala Gly Gln Val Ala Ala Ala
1               5                   10

<210> SEQ ID NO 378
<211> LENGTH: 11
<212> TYPE: PRT
<213> ORGANISM: Homo sapiens

<400> SEQUENCE: 378

Arg Pro Arg Ser Pro Ala Gly Gln Val Ala Ala
1               5                   10

<210> SEQ ID NO 379
<211> LENGTH: 9
<212> TYPE: PRT
<213> ORGANISM: Homo sapiens

<400> SEQUENCE: 379

Gly Pro Phe Pro Leu Val Tyr Val Leu
1               5

<210> SEQ ID NO 380
<211> LENGTH: 8
<212> TYPE: PRT
<213> ORGANISM: Homo sapiens

<400> SEQUENCE: 380

Ile Pro Thr Tyr Gly Arg Thr Phe
1               5

<210> SEQ ID NO 381
<211> LENGTH: 9
<212> TYPE: PRT
<213> ORGANISM: Homo sapiens

<400> SEQUENCE: 381

Leu Pro Glu Gln Thr Pro Leu Ala Phe
1               5

<210> SEQ ID NO 382
<211> LENGTH: 9
<212> TYPE: PRT
<213> ORGANISM: Homo sapiens
```

```
<400> SEQUENCE: 382

Ser Pro Met His Asp Arg Trp Thr Phe
1               5

<210> SEQ ID NO 383
<211> LENGTH: 9
<212> TYPE: PRT
<213> ORGANISM: Homo sapiens

<400> SEQUENCE: 383

Thr Pro Thr Lys Glu Thr Val Ser Leu
1               5

<210> SEQ ID NO 384
<211> LENGTH: 9
<212> TYPE: PRT
<213> ORGANISM: Homo sapiens

<400> SEQUENCE: 384

Tyr Pro Gly Leu Arg Gly Ser Pro Met
1               5

<210> SEQ ID NO 385
<211> LENGTH: 9
<212> TYPE: PRT
<213> ORGANISM: Homo sapiens

<400> SEQUENCE: 385

Ser Pro Ala Leu His Ile Gly Ser Val
1               5

<210> SEQ ID NO 386
<211> LENGTH: 8
<212> TYPE: PRT
<213> ORGANISM: Homo sapiens

<400> SEQUENCE: 386

Phe Pro Phe Asn Pro Leu Asp Phe
1               5

<210> SEQ ID NO 387
<211> LENGTH: 10
<212> TYPE: PRT
<213> ORGANISM: Homo sapiens

<400> SEQUENCE: 387

Ala Pro Leu Lys Leu Ser Arg Thr Pro Ala
1               5                   10

<210> SEQ ID NO 388
<211> LENGTH: 12
<212> TYPE: PRT
<213> ORGANISM: Homo sapiens

<400> SEQUENCE: 388

Ser Pro Ala Pro Leu Lys Leu Ser Arg Thr Pro Ala
1               5                   10

<210> SEQ ID NO 389
<211> LENGTH: 11
<212> TYPE: PRT
<213> ORGANISM: Homo sapiens

<400> SEQUENCE: 389
```

Ser Pro Gly Ala Gln Arg Thr Phe Phe Gln Leu
1               5                   10

<210> SEQ ID NO 390
<211> LENGTH: 9
<212> TYPE: PRT
<213> ORGANISM: Homo sapiens

<400> SEQUENCE: 390

Asn Pro Asp Leu Arg Arg Asn Val Leu
1               5

<210> SEQ ID NO 391
<211> LENGTH: 10
<212> TYPE: PRT
<213> ORGANISM: Homo sapiens

<400> SEQUENCE: 391

Ala Pro Ser Thr Pro Arg Ile Thr Thr Phe
1               5                   10

<210> SEQ ID NO 392
<211> LENGTH: 9
<212> TYPE: PRT
<213> ORGANISM: Homo sapiens

<400> SEQUENCE: 392

Lys Pro Ile Glu Ser Thr Leu Val Ala
1               5

<210> SEQ ID NO 393
<211> LENGTH: 8
<212> TYPE: PRT
<213> ORGANISM: Homo sapiens

<400> SEQUENCE: 393

Ala Ser Lys Pro His Val Glu Ile
1               5

<210> SEQ ID NO 394
<211> LENGTH: 8
<212> TYPE: PRT
<213> ORGANISM: Homo sapiens

<400> SEQUENCE: 394

Met Tyr Lys Met Lys Lys Pro Ile
1               5

<210> SEQ ID NO 395
<211> LENGTH: 9
<212> TYPE: PRT
<213> ORGANISM: Homo sapiens

<400> SEQUENCE: 395

Val Leu Leu Pro Arg Leu Val Ser Cys
1               5

<210> SEQ ID NO 396
<211> LENGTH: 9
<212> TYPE: PRT
<213> ORGANISM: Homo sapiens

<400> SEQUENCE: 396

Arg Glu Ala Ser Gly Leu Leu Ser Leu

<210> SEQ ID NO 397
<211> LENGTH: 9
<212> TYPE: PRT
<213> ORGANISM: Homo sapiens

<400> SEQUENCE: 397

Arg Glu Gly Asp Thr Val Gln Leu Leu
1               5

<210> SEQ ID NO 398
<211> LENGTH: 10
<212> TYPE: PRT
<213> ORGANISM: Homo sapiens

<400> SEQUENCE: 398

Ser Phe Glu Gln Val Val Asn Glu Leu Phe
1               5                   10

<210> SEQ ID NO 399
<211> LENGTH: 9
<212> TYPE: PRT
<213> ORGANISM: Homo sapiens

<400> SEQUENCE: 399

Arg Glu Leu Leu His Leu Val Thr Leu
1               5

<210> SEQ ID NO 400
<211> LENGTH: 8
<212> TYPE: PRT
<213> ORGANISM: Homo sapiens

<400> SEQUENCE: 400

Gly Glu Ile Glu Ile His Leu Leu
1               5

<210> SEQ ID NO 401
<211> LENGTH: 9
<212> TYPE: PRT
<213> ORGANISM: Homo sapiens

<400> SEQUENCE: 401

Glu Asp Leu Lys Glu Glu Leu Leu Leu
1               5

<210> SEQ ID NO 402
<211> LENGTH: 10
<212> TYPE: PRT
<213> ORGANISM: Homo sapiens

<400> SEQUENCE: 402

Arg Glu Leu Ala Asn Asp Glu Leu Ile Leu
1               5                   10

<210> SEQ ID NO 403
<211> LENGTH: 9
<212> TYPE: PRT
<213> ORGANISM: Homo sapiens

<400> SEQUENCE: 403

Glu Glu Ala Gln Trp Val Arg Lys Tyr
1               5

```
<210> SEQ ID NO 404
<211> LENGTH: 8
<212> TYPE: PRT
<213> ORGANISM: Homo sapiens

<400> SEQUENCE: 404

Asn Glu Ala Ile Met His Gln Tyr
1               5

<210> SEQ ID NO 405
<211> LENGTH: 8
<212> TYPE: PRT
<213> ORGANISM: Homo sapiens

<400> SEQUENCE: 405

Asn Glu Ile Trp Thr His Ser Tyr
1               5

<210> SEQ ID NO 406
<211> LENGTH: 9
<212> TYPE: PRT
<213> ORGANISM: Homo sapiens

<400> SEQUENCE: 406

Glu Asp Gly Arg Leu Val Ile Glu Phe
1               5

<210> SEQ ID NO 407
<211> LENGTH: 9
<212> TYPE: PRT
<213> ORGANISM: Homo sapiens

<400> SEQUENCE: 407

Ala Glu His Glu Gly Val Ser Val Leu
1               5

<210> SEQ ID NO 408
<211> LENGTH: 8
<212> TYPE: PRT
<213> ORGANISM: Homo sapiens

<400> SEQUENCE: 408

Leu Glu Lys Ala Leu Gln Val Phe
1               5

<210> SEQ ID NO 409
<211> LENGTH: 12
<212> TYPE: PRT
<213> ORGANISM: Homo sapiens

<400> SEQUENCE: 409

Arg Glu Phe Val Leu Ser Lys Gly Asp Ala Gly Leu
1               5                   10

<210> SEQ ID NO 410
<211> LENGTH: 9
<212> TYPE: PRT
<213> ORGANISM: Homo sapiens

<400> SEQUENCE: 410

Ser Glu Asp Pro Ser Lys Leu Glu Ala
1               5

<210> SEQ ID NO 411
```

```
<211> LENGTH: 9
<212> TYPE: PRT
<213> ORGANISM: Homo sapiens

<400> SEQUENCE: 411

Leu Glu Leu Pro Pro Ile Leu Val Tyr
1               5

<210> SEQ ID NO 412
<211> LENGTH: 9
<212> TYPE: PRT
<213> ORGANISM: Homo sapiens

<400> SEQUENCE: 412

Gln Glu Ile Leu Thr Gln Val Lys Gln
1               5

<210> SEQ ID NO 413
<211> LENGTH: 10
<212> TYPE: PRT
<213> ORGANISM: Homo sapiens

<400> SEQUENCE: 413

Ile Glu Ala Leu Ser Gly Lys Ile Glu Leu
1               5                   10

<210> SEQ ID NO 414
<211> LENGTH: 9
<212> TYPE: PRT
<213> ORGANISM: Homo sapiens

<400> SEQUENCE: 414

Glu Asp Ala Ala Leu Phe Lys Ala Trp
1               5

<210> SEQ ID NO 415
<211> LENGTH: 11
<212> TYPE: PRT
<213> ORGANISM: Homo sapiens

<400> SEQUENCE: 415

Arg Glu Glu Asp Ala Ala Leu Phe Lys Ala Trp
1               5                   10

<210> SEQ ID NO 416
<211> LENGTH: 9
<212> TYPE: PRT
<213> ORGANISM: Homo sapiens

<400> SEQUENCE: 416

Ser Glu Glu Glu Thr Arg Val Val Phe
1               5

<210> SEQ ID NO 417
<211> LENGTH: 9
<212> TYPE: PRT
<213> ORGANISM: Homo sapiens

<400> SEQUENCE: 417

Ala Glu His Phe Ser Met Ile Arg Ala
1               5

<210> SEQ ID NO 418
<211> LENGTH: 9
<212> TYPE: PRT
```

```
<213> ORGANISM: Homo sapiens

<400> SEQUENCE: 418

Phe Glu Asp Ala Gln Gly His Ile Trp
1               5

<210> SEQ ID NO 419
<211> LENGTH: 9
<212> TYPE: PRT
<213> ORGANISM: Homo sapiens

<400> SEQUENCE: 419

His Glu Phe Gly His Val Leu Gly Leu
1               5

<210> SEQ ID NO 420
<211> LENGTH: 9
<212> TYPE: PRT
<213> ORGANISM: Homo sapiens

<400> SEQUENCE: 420

Phe Glu Ser His Ser Thr Val Ser Ala
1               5

<210> SEQ ID NO 421
<211> LENGTH: 9
<212> TYPE: PRT
<213> ORGANISM: Homo sapiens

<400> SEQUENCE: 421

Gly Glu Pro Ala Thr Thr Val Ser Leu
1               5

<210> SEQ ID NO 422
<211> LENGTH: 9
<212> TYPE: PRT
<213> ORGANISM: Homo sapiens

<400> SEQUENCE: 422

Ser Glu Thr Thr Phe Ser Leu Ile Phe
1               5

<210> SEQ ID NO 423
<211> LENGTH: 9
<212> TYPE: PRT
<213> ORGANISM: Homo sapiens

<400> SEQUENCE: 423

Ser Glu Val Pro Thr Gly Thr Thr Ala
1               5

<210> SEQ ID NO 424
<211> LENGTH: 9
<212> TYPE: PRT
<213> ORGANISM: Homo sapiens

<400> SEQUENCE: 424

Thr Glu Phe Pro Leu Phe Ser Ala Ala
1               5

<210> SEQ ID NO 425
<211> LENGTH: 9
<212> TYPE: PRT
<213> ORGANISM: Homo sapiens
```

```
<400> SEQUENCE: 425

Ser Glu Val Pro Leu Pro Met Ala Ile
1               5

<210> SEQ ID NO 426
<211> LENGTH: 8
<212> TYPE: PRT
<213> ORGANISM: Homo sapiens

<400> SEQUENCE: 426

Pro Glu Lys Thr Thr His Ser Phe
1               5

<210> SEQ ID NO 427
<211> LENGTH: 9
<212> TYPE: PRT
<213> ORGANISM: Homo sapiens

<400> SEQUENCE: 427

His Glu Ser Ser Ser His His Asp Leu
1               5

<210> SEQ ID NO 428
<211> LENGTH: 8
<212> TYPE: PRT
<213> ORGANISM: Homo sapiens

<400> SEQUENCE: 428

Leu Asp Leu Gly Leu Asn His Ile
1               5

<210> SEQ ID NO 429
<211> LENGTH: 9
<212> TYPE: PRT
<213> ORGANISM: Homo sapiens

<400> SEQUENCE: 429

Arg Glu Lys Phe Ile Ala Ser Val Ile
1               5

<210> SEQ ID NO 430
<211> LENGTH: 9
<212> TYPE: PRT
<213> ORGANISM: Homo sapiens

<400> SEQUENCE: 430

Asp Glu Lys Ile Leu Tyr Pro Glu Phe
1               5

<210> SEQ ID NO 431
<211> LENGTH: 11
<212> TYPE: PRT
<213> ORGANISM: Homo sapiens

<400> SEQUENCE: 431

Ala Glu Gln Asp Pro Asp Glu Leu Asn Lys Ala
1               5                   10

<210> SEQ ID NO 432
<211> LENGTH: 8
<212> TYPE: PRT
<213> ORGANISM: Homo sapiens

<400> SEQUENCE: 432
```

Glu Glu Gln Tyr Ile Ala Gln Phe
1               5

<210> SEQ ID NO 433
<211> LENGTH: 8
<212> TYPE: PRT
<213> ORGANISM: Homo sapiens

<400> SEQUENCE: 433

Ser Asp Ser Gln Val Arg Ala Phe
1               5

<210> SEQ ID NO 434
<211> LENGTH: 9
<212> TYPE: PRT
<213> ORGANISM: Homo sapiens

<400> SEQUENCE: 434

Lys Glu Ala Ile Arg Glu His Gln Met
1               5

<210> SEQ ID NO 435
<211> LENGTH: 10
<212> TYPE: PRT
<213> ORGANISM: Homo sapiens

<400> SEQUENCE: 435

Arg Glu Glu Phe Val Ser Ile Asp His Leu
1               5                   10

<210> SEQ ID NO 436
<211> LENGTH: 10
<212> TYPE: PRT
<213> ORGANISM: Homo sapiens

<400> SEQUENCE: 436

Arg Glu Pro Gly Asp Ile Phe Ser Glu Leu
1               5                   10

<210> SEQ ID NO 437
<211> LENGTH: 9
<212> TYPE: PRT
<213> ORGANISM: Homo sapiens

<400> SEQUENCE: 437

Thr Glu Ala Val Val Thr Asn Glu Leu
1               5

<210> SEQ ID NO 438
<211> LENGTH: 9
<212> TYPE: PRT
<213> ORGANISM: Homo sapiens

<400> SEQUENCE: 438

Ser Glu Val Asp Ser Pro Asn Val Leu
1               5

<210> SEQ ID NO 439
<211> LENGTH: 9
<212> TYPE: PRT
<213> ORGANISM: Homo sapiens

<400> SEQUENCE: 439

Glu Ala Leu Ala Lys Leu Met Ser Leu
1               5

<210> SEQ ID NO 440
<211> LENGTH: 9
<212> TYPE: PRT
<213> ORGANISM: Homo sapiens

<400> SEQUENCE: 440

Glu Leu Phe Glu Gly Leu Lys Ala Phe
1               5

<210> SEQ ID NO 441
<211> LENGTH: 9
<212> TYPE: PRT
<213> ORGANISM: Homo sapiens

<400> SEQUENCE: 441

His Gln Ile Thr Glu Val Gly Thr Met
1               5

<210> SEQ ID NO 442
<211> LENGTH: 10
<212> TYPE: PRT
<213> ORGANISM: Homo sapiens

<400> SEQUENCE: 442

Ile Leu Ser Lys Leu Thr Asp Ile Gln Tyr
1               5                   10

<210> SEQ ID NO 443
<211> LENGTH: 9
<212> TYPE: PRT
<213> ORGANISM: Homo sapiens

<400> SEQUENCE: 443

Gly Thr Phe Asn Pro Val Ser Leu Trp
1               5

<210> SEQ ID NO 444
<211> LENGTH: 9
<212> TYPE: PRT
<213> ORGANISM: Homo sapiens

<400> SEQUENCE: 444

Lys Leu Ser Gln Lys Gly Tyr Ser Trp
1               5

<210> SEQ ID NO 445
<211> LENGTH: 9
<212> TYPE: PRT
<213> ORGANISM: Homo sapiens

<400> SEQUENCE: 445

Leu His Ile Thr Pro Gly Thr Ala Tyr
1               5

<210> SEQ ID NO 446
<211> LENGTH: 9
<212> TYPE: PRT
<213> ORGANISM: Homo sapiens

<400> SEQUENCE: 446

Gly Arg Ile Val Ala Phe Phe Ser Phe
1               5

```
<210> SEQ ID NO 447
<211> LENGTH: 8
<212> TYPE: PRT
<213> ORGANISM: Homo sapiens

<400> SEQUENCE: 447

Met Gln Val Leu Val Ser Arg Ile
1               5

<210> SEQ ID NO 448
<211> LENGTH: 8
<212> TYPE: PRT
<213> ORGANISM: Homo sapiens

<400> SEQUENCE: 448

Leu Ser Gln Lys Gly Tyr Ser Trp
1               5

<210> SEQ ID NO 449
<211> LENGTH: 10
<212> TYPE: PRT
<213> ORGANISM: Homo sapiens

<400> SEQUENCE: 449

Arg Ala Phe Ser Asp Leu Thr Ser Gln Leu
1               5                   10

<210> SEQ ID NO 450
<211> LENGTH: 9
<212> TYPE: PRT
<213> ORGANISM: Homo sapiens

<400> SEQUENCE: 450

Lys Gln Thr Phe Pro Phe Pro Thr Ile
1               5

<210> SEQ ID NO 451
<211> LENGTH: 10
<212> TYPE: PRT
<213> ORGANISM: Homo sapiens

<400> SEQUENCE: 451

Asp Tyr Leu Asn Glu Trp Gly Ser Arg Phe
1               5                   10

<210> SEQ ID NO 452
<211> LENGTH: 9
<212> TYPE: PRT
<213> ORGANISM: Homo sapiens

<400> SEQUENCE: 452

Leu Lys Val Leu Gly Val Asn Val Met
1               5

<210> SEQ ID NO 453
<211> LENGTH: 8
<212> TYPE: PRT
<213> ORGANISM: Homo sapiens

<400> SEQUENCE: 453

Asp Val Lys Leu Glu Lys Pro Lys
1               5

<210> SEQ ID NO 454
<211> LENGTH: 9
```

```
<212> TYPE: PRT
<213> ORGANISM: Homo sapiens

<400> SEQUENCE: 454

Ala Gln Thr Asp Pro Thr Thr Gly Tyr
1               5

<210> SEQ ID NO 455
<211> LENGTH: 9
<212> TYPE: PRT
<213> ORGANISM: Homo sapiens

<400> SEQUENCE: 455

Ala Ala Ala Ala Asn Ala Gln Val Tyr
1               5

<210> SEQ ID NO 456
<211> LENGTH: 11
<212> TYPE: PRT
<213> ORGANISM: Homo sapiens

<400> SEQUENCE: 456

Ile Pro Leu Glu Arg Pro Leu Gly Glu Val Tyr
1               5                   10

<210> SEQ ID NO 457
<211> LENGTH: 11
<212> TYPE: PRT
<213> ORGANISM: Homo sapiens

<400> SEQUENCE: 457

Asn Ala Ala Ala Ala Ala Asn Ala Gln Val Tyr
1               5                   10

<210> SEQ ID NO 458
<211> LENGTH: 8
<212> TYPE: PRT
<213> ORGANISM: Homo sapiens

<400> SEQUENCE: 458

Thr Asp Thr Leu Ile His Leu Met
1               5

<210> SEQ ID NO 459
<211> LENGTH: 9
<212> TYPE: PRT
<213> ORGANISM: Homo sapiens

<400> SEQUENCE: 459

Lys Val Ala Gly Glu Arg Tyr Val Tyr
1               5

<210> SEQ ID NO 460
<211> LENGTH: 11
<212> TYPE: PRT
<213> ORGANISM: Homo sapiens

<400> SEQUENCE: 460

Arg Leu Ser Ser Ala Thr Ala Asn Ala Leu Tyr
1               5                   10

<210> SEQ ID NO 461
<211> LENGTH: 9
<212> TYPE: PRT
<213> ORGANISM: Homo sapiens
```

<400> SEQUENCE: 461

Ala Gln Arg Met Thr Thr Gln Leu Leu
1               5

<210> SEQ ID NO 462
<211> LENGTH: 9
<212> TYPE: PRT
<213> ORGANISM: Homo sapiens

<400> SEQUENCE: 462

Gln Arg Met Thr Thr Gln Leu Leu Leu
1               5

<210> SEQ ID NO 463
<211> LENGTH: 9
<212> TYPE: PRT
<213> ORGANISM: Homo sapiens

<400> SEQUENCE: 463

Val Asn Gln Ser Leu Leu Asp Leu Tyr
1               5

<210> SEQ ID NO 464
<211> LENGTH: 8
<212> TYPE: PRT
<213> ORGANISM: Homo sapiens

<400> SEQUENCE: 464

Met Ser Ala Leu Arg Pro Leu Leu
1               5

<210> SEQ ID NO 465
<211> LENGTH: 9
<212> TYPE: PRT
<213> ORGANISM: Homo sapiens

<400> SEQUENCE: 465

Asp Leu Ile Glu Ser Gly Gln Leu Arg
1               5

<210> SEQ ID NO 466
<211> LENGTH: 11
<212> TYPE: PRT
<213> ORGANISM: Homo sapiens

<400> SEQUENCE: 466

Asp Leu Ile Glu Ser Gly Gln Leu Arg Glu Arg
1               5                   10

<210> SEQ ID NO 467
<211> LENGTH: 9
<212> TYPE: PRT
<213> ORGANISM: Homo sapiens

<400> SEQUENCE: 467

Met Gln Met Gln Glu Arg Asp Thr Leu
1               5

<210> SEQ ID NO 468
<211> LENGTH: 8
<212> TYPE: PRT
<213> ORGANISM: Homo sapiens

<400> SEQUENCE: 468

Ala Leu Ala Lys Leu Leu Pro Leu
1               5

<210> SEQ ID NO 469
<211> LENGTH: 9
<212> TYPE: PRT
<213> ORGANISM: Homo sapiens

<400> SEQUENCE: 469

Gln Glu Gln Ser Ser Val Val Arg Ala
1               5

<210> SEQ ID NO 470
<211> LENGTH: 10
<212> TYPE: PRT
<213> ORGANISM: Homo sapiens

<400> SEQUENCE: 470

Gln Gly Glu Arg Leu Leu Gly Ala Ala Val
1               5                   10

<210> SEQ ID NO 471
<211> LENGTH: 9
<212> TYPE: PRT
<213> ORGANISM: Homo sapiens

<400> SEQUENCE: 471

Ala Gln Arg Leu Asp Pro Val Tyr Phe
1               5

<210> SEQ ID NO 472
<211> LENGTH: 8
<212> TYPE: PRT
<213> ORGANISM: Homo sapiens

<400> SEQUENCE: 472

Met Arg Leu Leu Val Ala Pro Leu
1               5

<210> SEQ ID NO 473
<211> LENGTH: 10
<212> TYPE: PRT
<213> ORGANISM: Homo sapiens

<400> SEQUENCE: 473

Met Leu Asn Asn Asn Ala Leu Ser Ala Leu
1               5                   10

<210> SEQ ID NO 474
<211> LENGTH: 12
<212> TYPE: PRT
<213> ORGANISM: Homo sapiens

<400> SEQUENCE: 474

Ala Ala Asp Gly Gly Leu Arg Ala Ser Val Thr Leu
1               5                   10

<210> SEQ ID NO 475
<211> LENGTH: 10
<212> TYPE: PRT
<213> ORGANISM: Homo sapiens

<400> SEQUENCE: 475

Gly Arg Asp Pro Thr Ser Tyr Pro Ser Leu

<210> SEQ ID NO 476
<211> LENGTH: 9
<212> TYPE: PRT
<213> ORGANISM: Homo sapiens

<400> SEQUENCE: 476

Ile Ser Tyr Pro Pro Leu His Glu Trp
1               5

<210> SEQ ID NO 477
<211> LENGTH: 9
<212> TYPE: PRT
<213> ORGANISM: Homo sapiens

<400> SEQUENCE: 477

Arg Ile Gln Gln Gln Thr Asn Thr Tyr
1               5

<210> SEQ ID NO 478
<211> LENGTH: 9
<212> TYPE: PRT
<213> ORGANISM: Homo sapiens

<400> SEQUENCE: 478

Val Val Gly Pro Lys Gly Ala Thr Ile
1               5

<210> SEQ ID NO 479
<211> LENGTH: 9
<212> TYPE: PRT
<213> ORGANISM: Homo sapiens

<400> SEQUENCE: 479

Thr Glu Gly Ser His Phe Val Glu Ala
1               5

<210> SEQ ID NO 480
<211> LENGTH: 9
<212> TYPE: PRT
<213> ORGANISM: Homo sapiens

<400> SEQUENCE: 480

Gly Arg Ala Asp Ile Met Ile Asp Phe
1               5

<210> SEQ ID NO 481
<211> LENGTH: 10
<212> TYPE: PRT
<213> ORGANISM: Homo sapiens

<400> SEQUENCE: 481

Gly Arg Trp Glu Lys Thr Asp Leu Thr Tyr
1               5                   10

<210> SEQ ID NO 482
<211> LENGTH: 11
<212> TYPE: PRT
<213> ORGANISM: Homo sapiens

<400> SEQUENCE: 482

Gly Arg Trp Glu Lys Thr Asp Leu Thr Tyr Arg
1               5                   10

<210> SEQ ID NO 483
<211> LENGTH: 11
<212> TYPE: PRT
<213> ORGANISM: Homo sapiens

<400> SEQUENCE: 483

Val Arg Phe Pro Val His Ala Ala Leu Val Trp
1               5                   10

<210> SEQ ID NO 484
<211> LENGTH: 8
<212> TYPE: PRT
<213> ORGANISM: Homo sapiens

<400> SEQUENCE: 484

Ala Trp Leu Arg Ser Ala Ala Ala
1               5

<210> SEQ ID NO 485
<211> LENGTH: 9
<212> TYPE: PRT
<213> ORGANISM: Homo sapiens

<400> SEQUENCE: 485

Val Arg Phe Pro Val His Ala Ala Leu
1               5

<210> SEQ ID NO 486
<211> LENGTH: 8
<212> TYPE: PRT
<213> ORGANISM: Homo sapiens

<400> SEQUENCE: 486

Asp Arg Phe Phe Trp Leu Lys Val
1               5

<210> SEQ ID NO 487
<211> LENGTH: 9
<212> TYPE: PRT
<213> ORGANISM: Homo sapiens

<400> SEQUENCE: 487

Gly Met Ala Asp Ile Leu Val Val Phe
1               5

<210> SEQ ID NO 488
<211> LENGTH: 9
<212> TYPE: PRT
<213> ORGANISM: Homo sapiens

<400> SEQUENCE: 488

Arg Ser Phe Ser Leu Gly Val Pro Arg
1               5

<210> SEQ ID NO 489
<211> LENGTH: 9
<212> TYPE: PRT
<213> ORGANISM: Homo sapiens

<400> SEQUENCE: 489

Glu Val Ser Gly Leu Ser Thr Glu Arg
1               5

<210> SEQ ID NO 490

```
<211> LENGTH: 9
<212> TYPE: PRT
<213> ORGANISM: Homo sapiens

<400> SEQUENCE: 490

Ala Glu Val Gln Lys Leu Leu Gly Pro
1               5

<210> SEQ ID NO 491
<211> LENGTH: 9
<212> TYPE: PRT
<213> ORGANISM: Homo sapiens

<400> SEQUENCE: 491

Glu Ala Tyr Ser Ser Thr Ser Ser Trp
1               5

<210> SEQ ID NO 492
<211> LENGTH: 10
<212> TYPE: PRT
<213> ORGANISM: Homo sapiens

<400> SEQUENCE: 492

Glu Val Thr Pro Trp Ile Ser Leu Thr Leu
1               5                   10

<210> SEQ ID NO 493
<211> LENGTH: 9
<212> TYPE: PRT
<213> ORGANISM: Homo sapiens

<400> SEQUENCE: 493

Asp Thr Asn Leu Glu Pro Val Thr Arg
1               5

<210> SEQ ID NO 494
<211> LENGTH: 9
<212> TYPE: PRT
<213> ORGANISM: Homo sapiens

<400> SEQUENCE: 494

Glu Thr Thr Ala Ser Leu Val Ser Arg
1               5

<210> SEQ ID NO 495
<211> LENGTH: 12
<212> TYPE: PRT
<213> ORGANISM: Homo sapiens

<400> SEQUENCE: 495

Glu Val Pro Ser Gly Ala Thr Thr Glu Val Ser Arg
1               5                   10

<210> SEQ ID NO 496
<211> LENGTH: 12
<212> TYPE: PRT
<213> ORGANISM: Homo sapiens

<400> SEQUENCE: 496

Glu Val Pro Thr Gly Thr Thr Ala Glu Val Ser Arg
1               5                   10

<210> SEQ ID NO 497
<211> LENGTH: 11
<212> TYPE: PRT
```

<213> ORGANISM: Homo sapiens

<400> SEQUENCE: 497

Glu Val Ser Arg Thr Glu Val Ile Ser Ser Arg
1               5                   10

<210> SEQ ID NO 498
<211> LENGTH: 11
<212> TYPE: PRT
<213> ORGANISM: Homo sapiens

<400> SEQUENCE: 498

Glu Val Tyr Pro Glu Leu Gly Thr Gln Gly Arg
1               5                   10

<210> SEQ ID NO 499
<211> LENGTH: 9
<212> TYPE: PRT
<213> ORGANISM: Homo sapiens

<400> SEQUENCE: 499

Ser Ser Glu Thr Thr Lys Ile Lys Arg
1               5

<210> SEQ ID NO 500
<211> LENGTH: 8
<212> TYPE: PRT
<213> ORGANISM: Homo sapiens

<400> SEQUENCE: 500

Ala His Val Leu His Ser Thr Leu
1               5

<210> SEQ ID NO 501
<211> LENGTH: 9
<212> TYPE: PRT
<213> ORGANISM: Homo sapiens

<400> SEQUENCE: 501

Ile Gln Ile Glu Pro Thr Ser Ser Leu
1               5

<210> SEQ ID NO 502
<211> LENGTH: 9
<212> TYPE: PRT
<213> ORGANISM: Homo sapiens

<400> SEQUENCE: 502

Ser Gly Asp Gln Gly Ile Thr Ser Leu
1               5

<210> SEQ ID NO 503
<211> LENGTH: 10
<212> TYPE: PRT
<213> ORGANISM: Homo sapiens

<400> SEQUENCE: 503

Thr Val Phe Asp Lys Ala Phe Thr Ala Ala
1               5                   10

<210> SEQ ID NO 504
<211> LENGTH: 9
<212> TYPE: PRT
<213> ORGANISM: Homo sapiens

```
<400> SEQUENCE: 504

Thr Val Ser Ser Val Asn Gln Gly Leu
1               5

<210> SEQ ID NO 505
<211> LENGTH: 10
<212> TYPE: PRT
<213> ORGANISM: Homo sapiens

<400> SEQUENCE: 505

Tyr Val Pro Thr Gly Ala Ile Thr Gln Ala
1               5                   10

<210> SEQ ID NO 506
<211> LENGTH: 10
<212> TYPE: PRT
<213> ORGANISM: Homo sapiens

<400> SEQUENCE: 506

His Gln Phe Ile Thr Ser Thr Asn Thr Phe
1               5                   10

<210> SEQ ID NO 507
<211> LENGTH: 9
<212> TYPE: PRT
<213> ORGANISM: Homo sapiens

<400> SEQUENCE: 507

Thr Ser Ile Phe Ser Gly Gln Ser Leu
1               5

<210> SEQ ID NO 508
<211> LENGTH: 9
<212> TYPE: PRT
<213> ORGANISM: Homo sapiens

<400> SEQUENCE: 508

Thr Val Ala Lys Thr Thr Thr Thr Phe
1               5

<210> SEQ ID NO 509
<211> LENGTH: 9
<212> TYPE: PRT
<213> ORGANISM: Homo sapiens

<400> SEQUENCE: 509

Gly Arg Gly Pro Gly Gly Val Ser Trp
1               5

<210> SEQ ID NO 510
<211> LENGTH: 9
<212> TYPE: PRT
<213> ORGANISM: Homo sapiens

<400> SEQUENCE: 510

Arg Arg Ile Pro Thr Glu Pro Thr Phe
1               5

<210> SEQ ID NO 511
<211> LENGTH: 9
<212> TYPE: PRT
<213> ORGANISM: Homo sapiens

<400> SEQUENCE: 511
```

```
Ser Arg Ile Pro Gln Asp Val Ser Trp
1               5
```

<210> SEQ ID NO 512
<211> LENGTH: 9
<212> TYPE: PRT
<213> ORGANISM: Homo sapiens

<400> SEQUENCE: 512

```
Ser Arg Ser Pro Glu Asn Pro Ser Trp
1               5
```

<210> SEQ ID NO 513
<211> LENGTH: 9
<212> TYPE: PRT
<213> ORGANISM: Homo sapiens

<400> SEQUENCE: 513

```
Ser Arg Thr Glu Ile Ser Ser Ser Arg
1               5
```

<210> SEQ ID NO 514
<211> LENGTH: 9
<212> TYPE: PRT
<213> ORGANISM: Homo sapiens

<400> SEQUENCE: 514

```
Ser Arg Thr Glu Val Ala Ser Ser Arg
1               5
```

<210> SEQ ID NO 515
<211> LENGTH: 9
<212> TYPE: PRT
<213> ORGANISM: Homo sapiens

<400> SEQUENCE: 515

```
Thr Arg Ile Glu Met Glu Ser Thr Phe
1               5
```

<210> SEQ ID NO 516
<211> LENGTH: 9
<212> TYPE: PRT
<213> ORGANISM: Homo sapiens

<400> SEQUENCE: 516

```
Thr Ala Ser Thr Pro Ile Ser Thr Phe
1               5
```

<210> SEQ ID NO 517
<211> LENGTH: 11
<212> TYPE: PRT
<213> ORGANISM: Homo sapiens

<400> SEQUENCE: 517

```
Thr Ala Glu Thr Ile Leu Thr Phe His Ala Phe
1               5                   10
```

<210> SEQ ID NO 518
<211> LENGTH: 9
<212> TYPE: PRT
<213> ORGANISM: Homo sapiens

<400> SEQUENCE: 518

```
Thr Ser Asp Phe Pro Thr Ile Thr Val
1               5
```

<210> SEQ ID NO 519
<211> LENGTH: 10
<212> TYPE: PRT
<213> ORGANISM: Homo sapiens

<400> SEQUENCE: 519

Val Thr Ser Leu Leu Thr Pro Gly Met Val
1               5                   10

<210> SEQ ID NO 520
<211> LENGTH: 9
<212> TYPE: PRT
<213> ORGANISM: Homo sapiens

<400> SEQUENCE: 520

Thr His Ser Ala Met Thr His Gly Phe
1               5

<210> SEQ ID NO 521
<211> LENGTH: 9
<212> TYPE: PRT
<213> ORGANISM: Homo sapiens

<400> SEQUENCE: 521

Thr His Ser Thr Ala Ser Gln Gly Phe
1               5

<210> SEQ ID NO 522
<211> LENGTH: 9
<212> TYPE: PRT
<213> ORGANISM: Homo sapiens

<400> SEQUENCE: 522

Thr His Ser Thr Ile Ser Gln Gly Phe
1               5

<210> SEQ ID NO 523
<211> LENGTH: 12
<212> TYPE: PRT
<213> ORGANISM: Homo sapiens

<400> SEQUENCE: 523

Ala Pro Lys Gly Ile Pro Val Lys Pro Thr Ser Ala
1               5                   10

<210> SEQ ID NO 524
<211> LENGTH: 9
<212> TYPE: PRT
<213> ORGANISM: Homo sapiens

<400> SEQUENCE: 524

Ala Val Ser Pro Thr Val Gln Gly Leu
1               5

<210> SEQ ID NO 525
<211> LENGTH: 8
<212> TYPE: PRT
<213> ORGANISM: Homo sapiens

<400> SEQUENCE: 525

Gln Arg Phe Pro His Ser Glu Met
1               5

```
<210> SEQ ID NO 526
<211> LENGTH: 8
<212> TYPE: PRT
<213> ORGANISM: Homo sapiens

<400> SEQUENCE: 526

Ser Val Pro Asp Ile Leu Ser Thr
1               5

<210> SEQ ID NO 527
<211> LENGTH: 9
<212> TYPE: PRT
<213> ORGANISM: Homo sapiens

<400> SEQUENCE: 527

Gln Ser Thr Pro Tyr Val Asn Ser Val
1               5

<210> SEQ ID NO 528
<211> LENGTH: 9
<212> TYPE: PRT
<213> ORGANISM: Homo sapiens

<400> SEQUENCE: 528

Thr Arg Thr Gly Leu Phe Leu Arg Phe
1               5

<210> SEQ ID NO 529
<211> LENGTH: 8
<212> TYPE: PRT
<213> ORGANISM: Homo sapiens

<400> SEQUENCE: 529

Pro Phe Ser Asn Pro Arg Val Leu
1               5

<210> SEQ ID NO 530
<211> LENGTH: 8
<212> TYPE: PRT
<213> ORGANISM: Homo sapiens

<400> SEQUENCE: 530

Met Leu Pro Arg Ala Ala Leu Leu
1               5

<210> SEQ ID NO 531
<211> LENGTH: 9
<212> TYPE: PRT
<213> ORGANISM: Homo sapiens

<400> SEQUENCE: 531

Gln Gly Ala Gln Leu Arg Gly Ala Leu
1               5

<210> SEQ ID NO 532
<211> LENGTH: 9
<212> TYPE: PRT
<213> ORGANISM: Homo sapiens

<400> SEQUENCE: 532

Ala Ile Ser Phe Ser Tyr Lys Ala Trp
1               5

<210> SEQ ID NO 533
<211> LENGTH: 9
```

<212> TYPE: PRT
<213> ORGANISM: Homo sapiens

<400> SEQUENCE: 533

Gly Gln His Leu His Leu Glu Thr Phe
1               5

<210> SEQ ID NO 534
<211> LENGTH: 10
<212> TYPE: PRT
<213> ORGANISM: Homo sapiens

<400> SEQUENCE: 534

Cys Arg Pro Gly Ala Leu Gln Ile Glu Leu
1               5                   10

<210> SEQ ID NO 535
<211> LENGTH: 8
<212> TYPE: PRT
<213> ORGANISM: Homo sapiens

<400> SEQUENCE: 535

Ile Lys Asp Val Arg Lys Ile Lys
1               5

<210> SEQ ID NO 536
<211> LENGTH: 10
<212> TYPE: PRT
<213> ORGANISM: Homo sapiens

<400> SEQUENCE: 536

Val Gln Asp Gln Ala Cys Val Ala Lys Phe
1               5                   10

<210> SEQ ID NO 537
<211> LENGTH: 10
<212> TYPE: PRT
<213> ORGANISM: Homo sapiens

<400> SEQUENCE: 537

Ile Arg Arg Leu Lys Glu Leu Lys Asp Gln
1               5                   10

<210> SEQ ID NO 538
<211> LENGTH: 9
<212> TYPE: PRT
<213> ORGANISM: Homo sapiens

<400> SEQUENCE: 538

Gln Leu Glu Lys Ala Leu Lys Glu Ile
1               5

<210> SEQ ID NO 539
<211> LENGTH: 11
<212> TYPE: PRT
<213> ORGANISM: Homo sapiens

<400> SEQUENCE: 539

Ile Pro Ile Pro Ser Thr Gly Ser Val Glu Met
1               5                   10

<210> SEQ ID NO 540
<211> LENGTH: 9
<212> TYPE: PRT
<213> ORGANISM: Homo sapiens

<400> SEQUENCE: 540

Ala Gly Ile Pro Ala Val Ala Leu Trp
1               5

<210> SEQ ID NO 541
<211> LENGTH: 9
<212> TYPE: PRT
<213> ORGANISM: Homo sapiens

<400> SEQUENCE: 541

Arg Leu Ser Pro Ala Pro Leu Lys Leu
1               5

<210> SEQ ID NO 542
<211> LENGTH: 10
<212> TYPE: PRT
<213> ORGANISM: Homo sapiens

<400> SEQUENCE: 542

Gln Ile Ile Asp Glu Glu Glu Thr Gln Phe
1               5                   10

<210> SEQ ID NO 543
<211> LENGTH: 9
<212> TYPE: PRT
<213> ORGANISM: Homo sapiens

<400> SEQUENCE: 543

Met Arg Leu Ser Pro Ala Pro Leu Lys
1               5

<210> SEQ ID NO 544
<211> LENGTH: 9
<212> TYPE: PRT
<213> ORGANISM: Homo sapiens

<400> SEQUENCE: 544

Leu Arg Asn Pro Ser Ile Gln Lys Leu
1               5

<210> SEQ ID NO 545
<211> LENGTH: 8
<212> TYPE: PRT
<213> ORGANISM: Homo sapiens

<400> SEQUENCE: 545

Arg Val Gly Pro Pro Leu Leu Ile
1               5

<210> SEQ ID NO 546
<211> LENGTH: 9
<212> TYPE: PRT
<213> ORGANISM: Homo sapiens

<400> SEQUENCE: 546

Gly Arg Ala Phe Phe Ala Ala Ala Phe
1               5

<210> SEQ ID NO 547
<211> LENGTH: 10
<212> TYPE: PRT
<213> ORGANISM: Homo sapiens

<400> SEQUENCE: 547

```
Glu Val Asn Lys Pro Gly Val Tyr Thr Arg
1               5                   10

<210> SEQ ID NO 548
<211> LENGTH: 10
<212> TYPE: PRT
<213> ORGANISM: Homo sapiens

<400> SEQUENCE: 548

Val Ser Glu Ala Ser Leu Val Ser Ser Ile
1               5                   10

<210> SEQ ID NO 549
<211> LENGTH: 9
<212> TYPE: PRT
<213> ORGANISM: Homo sapiens

<400> SEQUENCE: 549

Ala Arg Ser Lys Leu Gln Gln Gly Leu
1               5

<210> SEQ ID NO 550
<211> LENGTH: 9
<212> TYPE: PRT
<213> ORGANISM: Homo sapiens

<400> SEQUENCE: 550

Arg Arg Phe Lys Glu Pro Trp Phe Leu
1               5

<210> SEQ ID NO 551
<211> LENGTH: 10
<212> TYPE: PRT
<213> ORGANISM: Homo sapiens

<400> SEQUENCE: 551

Arg Leu His Thr Gly Glu Lys Pro Tyr Lys
1               5                   10

<210> SEQ ID NO 552
<211> LENGTH: 20
<212> TYPE: PRT
<213> ORGANISM: Homo sapiens

<400> SEQUENCE: 552

Gly Val Asn Ala Met Leu Arg Lys Val Ala Val Ala Ala Ala Ser Lys
1               5                   10                  15

Pro His Val Glu
            20

<210> SEQ ID NO 553
<211> LENGTH: 19
<212> TYPE: PRT
<213> ORGANISM: Homo sapiens

<400> SEQUENCE: 553

Val Asn Ala Met Leu Arg Lys Val Ala Val Ala Ala Ala Ser Lys Pro
1               5                   10                  15

His Val Glu

<210> SEQ ID NO 554
<211> LENGTH: 18
<212> TYPE: PRT
```

<210> SEQ ID NO 554
<211> LENGTH: 18 (not visible, inferring from context — omit)
<213> ORGANISM: Homo sapiens

<400> SEQUENCE: 554

Gly Val Asn Ala Met Leu Arg Lys Val Ala Val Ala Ala Ala Ser Lys
1               5                   10                  15
Pro His

<210> SEQ ID NO 555
<211> LENGTH: 17
<212> TYPE: PRT
<213> ORGANISM: Homo sapiens

<400> SEQUENCE: 555

Val Asn Ala Met Leu Arg Lys Val Ala Val Ala Ala Ala Ser Lys Pro
1               5                   10                  15
His

<210> SEQ ID NO 556
<211> LENGTH: 16
<212> TYPE: PRT
<213> ORGANISM: Homo sapiens

<400> SEQUENCE: 556

Asn Ala Met Leu Arg Lys Val Ala Val Ala Ala Ala Ser Lys Pro His
1               5                   10                  15

<210> SEQ ID NO 557
<211> LENGTH: 15
<212> TYPE: PRT
<213> ORGANISM: Homo sapiens

<400> SEQUENCE: 557

Ala Met Leu Arg Lys Val Ala Val Ala Ala Ala Ser Lys Pro His
1               5                   10                  15

<210> SEQ ID NO 558
<211> LENGTH: 13
<212> TYPE: PRT
<213> ORGANISM: Homo sapiens

<400> SEQUENCE: 558

Leu Arg Lys Val Ala Val Ala Ala Ala Ser Lys Pro His
1               5                   10

<210> SEQ ID NO 559
<211> LENGTH: 12
<212> TYPE: PRT
<213> ORGANISM: Homo sapiens

<400> SEQUENCE: 559

Arg Lys Val Ala Val Ala Ala Ala Ser Lys Pro His
1               5                   10

<210> SEQ ID NO 560
<211> LENGTH: 20
<212> TYPE: PRT
<213> ORGANISM: Homo sapiens

<400> SEQUENCE: 560

Pro Asn Phe Ser Gly Asn Trp Lys Ile Ile Arg Ser Glu Asn Phe Glu
1               5                   10                  15
Glu Leu Leu Lys
            20

<210> SEQ ID NO 561
<211> LENGTH: 19
<212> TYPE: PRT
<213> ORGANISM: Homo sapiens

<400> SEQUENCE: 561

Pro Asn Phe Ser Gly Asn Trp Lys Ile Ile Arg Ser Glu Asn Phe Glu
1               5                   10                  15

Glu Leu Leu

<210> SEQ ID NO 562
<211> LENGTH: 18
<212> TYPE: PRT
<213> ORGANISM: Homo sapiens

<400> SEQUENCE: 562

Gly Asn Trp Lys Ile Ile Arg Ser Glu Asn Phe Glu Glu Leu Leu Lys
1               5                   10                  15

Val Leu

<210> SEQ ID NO 563
<211> LENGTH: 18
<212> TYPE: PRT
<213> ORGANISM: Homo sapiens

<400> SEQUENCE: 563

Pro Asn Phe Ser Gly Asn Trp Lys Ile Ile Arg Ser Glu Asn Phe Glu
1               5                   10                  15

Glu Leu

<210> SEQ ID NO 564
<211> LENGTH: 17
<212> TYPE: PRT
<213> ORGANISM: Homo sapiens

<400> SEQUENCE: 564

Gly Asn Trp Lys Ile Ile Arg Ser Glu Asn Phe Glu Glu Leu Leu Lys
1               5                   10                  15

Val

<210> SEQ ID NO 565
<211> LENGTH: 16
<212> TYPE: PRT
<213> ORGANISM: Homo sapiens

<400> SEQUENCE: 565

Asn Trp Lys Ile Ile Arg Ser Glu Asn Phe Glu Glu Leu Leu Lys Val
1               5                   10                  15

<210> SEQ ID NO 566
<211> LENGTH: 15
<212> TYPE: PRT
<213> ORGANISM: Homo sapiens

<400> SEQUENCE: 566

Asn Trp Lys Ile Ile Arg Ser Glu Asn Phe Glu Glu Leu Leu Lys
1               5                   10                  15

<210> SEQ ID NO 567
<211> LENGTH: 14
<212> TYPE: PRT

-continued

<213> ORGANISM: Homo sapiens

<400> SEQUENCE: 567

Asn Trp Lys Ile Ile Arg Ser Glu Asn Phe Glu Glu Leu Leu
1               5                   10

<210> SEQ ID NO 568
<211> LENGTH: 14
<212> TYPE: PRT
<213> ORGANISM: Homo sapiens

<400> SEQUENCE: 568

Trp Lys Ile Ile Arg Ser Glu Asn Phe Glu Glu Leu Leu Lys
1               5                   10

<210> SEQ ID NO 569
<211> LENGTH: 13
<212> TYPE: PRT
<213> ORGANISM: Homo sapiens

<400> SEQUENCE: 569

Trp Lys Ile Ile Arg Ser Glu Asn Phe Glu Glu Leu Leu
1               5                   10

<210> SEQ ID NO 570
<211> LENGTH: 11
<212> TYPE: PRT
<213> ORGANISM: Homo sapiens

<400> SEQUENCE: 570

Gly Asn Trp Lys Ile Ile Arg Ser Glu Asn Phe
1               5                   10

<210> SEQ ID NO 571
<211> LENGTH: 11
<212> TYPE: PRT
<213> ORGANISM: Homo sapiens

<400> SEQUENCE: 571

Pro Asn Phe Ser Gly Asn Trp Lys Ile Ile Arg
1               5                   10

<210> SEQ ID NO 572
<211> LENGTH: 14
<212> TYPE: PRT
<213> ORGANISM: Homo sapiens

<400> SEQUENCE: 572

Ile Asn Phe Lys Val Gly Glu Glu Phe Glu Glu Gln Thr Val
1               5                   10

<210> SEQ ID NO 573
<211> LENGTH: 14
<212> TYPE: PRT
<213> ORGANISM: Homo sapiens

<400> SEQUENCE: 573

Arg Leu Leu Ser Ala Asp Thr Lys Gly Trp Val Arg Leu Gln
1               5                   10

<210> SEQ ID NO 574
<211> LENGTH: 18
<212> TYPE: PRT
<213> ORGANISM: Homo sapiens

```
<400> SEQUENCE: 574

Leu Pro Asp Phe Tyr Asn Asp Trp Met Phe Ile Ala Lys His Leu Pro
1               5                   10                  15

Asp Leu

<210> SEQ ID NO 575
<211> LENGTH: 17
<212> TYPE: PRT
<213> ORGANISM: Homo sapiens

<400> SEQUENCE: 575

Val Gly Asp Asp His Leu Leu Leu Gln Gly Glu Gln Leu Arg Arg
1               5                   10                  15

Thr

<210> SEQ ID NO 576
<211> LENGTH: 16
<212> TYPE: PRT
<213> ORGANISM: Homo sapiens

<400> SEQUENCE: 576

Val Gly Asp Asp His Leu Leu Leu Gln Gly Glu Gln Leu Arg Arg
1               5                   10                  15

<210> SEQ ID NO 577
<211> LENGTH: 15
<212> TYPE: PRT
<213> ORGANISM: Homo sapiens

<400> SEQUENCE: 577

Gly Asp Asp His Leu Leu Leu Gln Gly Glu Gln Leu Arg Arg
1               5                   10                  15

<210> SEQ ID NO 578
<211> LENGTH: 14
<212> TYPE: PRT
<213> ORGANISM: Homo sapiens

<400> SEQUENCE: 578

Asp Asp His Leu Leu Leu Gln Gly Glu Gln Leu Arg Arg
1               5                   10

<210> SEQ ID NO 579
<211> LENGTH: 16
<212> TYPE: PRT
<213> ORGANISM: Homo sapiens

<400> SEQUENCE: 579

Ser Gly Gly Pro Leu Val Cys Asp Glu Thr Leu Gln Gly Ile Leu Ser
1               5                   10                  15

<210> SEQ ID NO 580
<211> LENGTH: 15
<212> TYPE: PRT
<213> ORGANISM: Homo sapiens

<400> SEQUENCE: 580

Gly Gly Pro Leu Val Cys Asp Glu Thr Leu Gln Gly Ile Leu Ser
1               5                   10                  15

<210> SEQ ID NO 581
<211> LENGTH: 14
<212> TYPE: PRT
```

<213> ORGANISM: Homo sapiens

<400> SEQUENCE: 581

Gly Gly Pro Leu Val Cys Asp Glu Thr Leu Gln Gly Ile Leu
1               5                   10

<210> SEQ ID NO 582
<211> LENGTH: 16
<212> TYPE: PRT
<213> ORGANISM: Homo sapiens

<400> SEQUENCE: 582

Gly Ser Gln Pro Trp Gln Val Ser Leu Phe Asn Gly Leu Ser Phe His
1               5                   10                  15

<210> SEQ ID NO 583
<211> LENGTH: 24
<212> TYPE: PRT
<213> ORGANISM: Homo sapiens

<400> SEQUENCE: 583

Leu Thr Val Lys Leu Pro Asp Gly Tyr Glu Phe Lys Phe Pro Asn Arg
1               5                   10                  15

Leu Asn Leu Glu Ala Ile Asn Tyr
            20

<210> SEQ ID NO 584
<211> LENGTH: 23
<212> TYPE: PRT
<213> ORGANISM: Homo sapiens

<400> SEQUENCE: 584

Thr Val Lys Leu Pro Asp Gly Tyr Glu Phe Lys Phe Pro Asn Arg Leu
1               5                   10                  15

Asn Leu Glu Ala Ile Asn Tyr
            20

<210> SEQ ID NO 585
<211> LENGTH: 19
<212> TYPE: PRT
<213> ORGANISM: Homo sapiens

<400> SEQUENCE: 585

Leu Thr Val Lys Leu Pro Asp Gly Tyr Glu Phe Lys Phe Pro Asn Arg
1               5                   10                  15

Leu Asn Leu

<210> SEQ ID NO 586
<211> LENGTH: 18
<212> TYPE: PRT
<213> ORGANISM: Homo sapiens

<400> SEQUENCE: 586

Thr Val Lys Leu Pro Asp Gly Tyr Glu Phe Lys Phe Pro Asn Arg Leu
1               5                   10                  15

Asn Leu

<210> SEQ ID NO 587
<211> LENGTH: 23
<212> TYPE: PRT
<213> ORGANISM: Homo sapiens

<400> SEQUENCE: 587

Asp Gln Ala Asn Leu Thr Val Lys Leu Pro Asp Gly Tyr Glu Phe Lys
1               5                   10                  15

Phe Pro Asn Arg Leu Asn Leu
            20

<210> SEQ ID NO 588
<211> LENGTH: 19
<212> TYPE: PRT
<213> ORGANISM: Homo sapiens

<400> SEQUENCE: 588

Val Ala Pro Asp Ala Lys Ser Phe Val Leu Asn Leu Gly Lys Asp Ser
1               5                   10                  15

Asn Asn Leu

<210> SEQ ID NO 589
<211> LENGTH: 18
<212> TYPE: PRT
<213> ORGANISM: Homo sapiens

<400> SEQUENCE: 589

Ala Pro Asp Ala Lys Ser Phe Val Leu Asn Leu Gly Lys Asp Ser Asn
1               5                   10                  15

Asn Leu

<210> SEQ ID NO 590
<211> LENGTH: 18
<212> TYPE: PRT
<213> ORGANISM: Homo sapiens

<400> SEQUENCE: 590

Arg Val Arg Gly Glu Val Ala Pro Asp Ala Lys Ser Phe Val Leu Asn
1               5                   10                  15

Leu Gly

<210> SEQ ID NO 591
<211> LENGTH: 16
<212> TYPE: PRT
<213> ORGANISM: Homo sapiens

<400> SEQUENCE: 591

Val Arg Gly Glu Val Ala Pro Asp Ala Lys Ser Phe Val Leu Asn Leu
1               5                   10                  15

<210> SEQ ID NO 592
<211> LENGTH: 17
<212> TYPE: PRT
<213> ORGANISM: Homo sapiens

<400> SEQUENCE: 592

Val Arg Gly Glu Val Ala Pro Asp Ala Lys Ser Phe Val Leu Asn Leu
1               5                   10                  15

Gly

<210> SEQ ID NO 593
<211> LENGTH: 15
<212> TYPE: PRT
<213> ORGANISM: Homo sapiens

<400> SEQUENCE: 593

Gly Glu Val Ala Pro Asp Ala Lys Ser Phe Val Leu Asn Leu Gly

```
<210> SEQ ID NO 594
<211> LENGTH: 15
<212> TYPE: PRT
<213> ORGANISM: Homo sapiens

<400> SEQUENCE: 594

Val Arg Gly Glu Val Ala Pro Asp Ala Lys Ser Phe Val Leu Asn
1               5                   10                  15

<210> SEQ ID NO 595
<211> LENGTH: 14
<212> TYPE: PRT
<213> ORGANISM: Homo sapiens

<400> SEQUENCE: 595

Val Arg Gly Glu Val Ala Pro Asp Ala Lys Ser Phe Val Leu
1               5                   10

<210> SEQ ID NO 596
<211> LENGTH: 15
<212> TYPE: PRT
<213> ORGANISM: Homo sapiens

<400> SEQUENCE: 596

Met Ala Ala Asp Gly Asp Phe Lys Ile Lys Cys Val Ala Phe Asp
1               5                   10                  15

<210> SEQ ID NO 597
<211> LENGTH: 19
<212> TYPE: PRT
<213> ORGANISM: Homo sapiens

<400> SEQUENCE: 597

Ser Pro Asp Ala Glu Ser Leu Phe Arg Glu Ala Leu Ser Asn Lys Val
1               5                   10                  15

Asp Glu Leu

<210> SEQ ID NO 598
<211> LENGTH: 16
<212> TYPE: PRT
<213> ORGANISM: Homo sapiens

<400> SEQUENCE: 598

Ala Glu Ser Leu Phe Arg Glu Ala Leu Ser Asn Lys Val Asp Glu Leu
1               5                   10                  15

<210> SEQ ID NO 599
<211> LENGTH: 15
<212> TYPE: PRT
<213> ORGANISM: Homo sapiens

<400> SEQUENCE: 599

Ala Glu Ser Leu Phe Arg Glu Ala Leu Ser Asn Lys Val Asp Glu
1               5                   10                  15

<210> SEQ ID NO 600
<211> LENGTH: 11
<212> TYPE: PRT
<213> ORGANISM: Homo sapiens

<400> SEQUENCE: 600

Phe Arg Glu Ala Leu Ser Asn Lys Val Asp Glu
```

```
1               5                   10
```

<210> SEQ ID NO 601
<211> LENGTH: 15
<212> TYPE: PRT
<213> ORGANISM: Homo sapiens

<400> SEQUENCE: 601

```
Leu Ser Asn Lys Val Asp Glu Leu Ala His Phe Leu Leu Arg Lys
1               5                   10                  15
```

<210> SEQ ID NO 602
<211> LENGTH: 13
<212> TYPE: PRT
<213> ORGANISM: Homo sapiens

<400> SEQUENCE: 602

```
Lys Asp Pro Val Ala Trp Glu Ala Gly Met Leu Met His
1               5                   10
```

<210> SEQ ID NO 603
<211> LENGTH: 13
<212> TYPE: PRT
<213> ORGANISM: Homo sapiens

<400> SEQUENCE: 603

```
Lys Ala Arg Asp Glu Thr Arg Gly Leu Asn Val Pro Gln
1               5                   10
```

<210> SEQ ID NO 604
<211> LENGTH: 17
<212> TYPE: PRT
<213> ORGANISM: Homo sapiens

<400> SEQUENCE: 604

```
Lys Leu Ile Thr Gln Asp Leu Val Lys Leu Lys Tyr Leu Glu Tyr Arg
1               5                   10                  15

Gln
```

<210> SEQ ID NO 605
<211> LENGTH: 25
<212> TYPE: PRT
<213> ORGANISM: Homo sapiens

<400> SEQUENCE: 605

```
Leu Thr Val Ala Glu Val Gln Lys Leu Leu Gly Pro His Val Glu Gly
1               5                   10                  15

Leu Lys Ala Glu Glu Arg His Arg Pro
                20                  25
```

<210> SEQ ID NO 606
<211> LENGTH: 22
<212> TYPE: PRT
<213> ORGANISM: Homo sapiens

<400> SEQUENCE: 606

```
Leu Thr Val Ala Glu Val Gln Lys Leu Leu Gly Pro His Val Glu Gly
1               5                   10                  15

Leu Lys Ala Glu Glu Arg
                20
```

<210> SEQ ID NO 607
<211> LENGTH: 21

<210> SEQ ID NO 607
<211> LENGTH: 20 [not shown, inferred]
<212> TYPE: PRT
<213> ORGANISM: Homo sapiens

<400> SEQUENCE: 607

Leu Thr Val Ala Glu Val Gln Lys Leu Leu Gly Pro His Val Glu Gly
1               5                   10                  15

Leu Lys Ala Glu Glu
            20

<210> SEQ ID NO 608
<211> LENGTH: 20
<212> TYPE: PRT
<213> ORGANISM: Homo sapiens

<400> SEQUENCE: 608

Leu Thr Val Ala Glu Val Gln Lys Leu Leu Gly Pro His Val Glu Gly
1               5                   10                  15

Leu Lys Ala Glu
            20

<210> SEQ ID NO 609
<211> LENGTH: 19
<212> TYPE: PRT
<213> ORGANISM: Homo sapiens

<400> SEQUENCE: 609

Leu Thr Val Ala Glu Val Gln Lys Leu Leu Gly Pro His Val Glu Gly
1               5                   10                  15

Leu Lys Ala

<210> SEQ ID NO 610
<211> LENGTH: 18
<212> TYPE: PRT
<213> ORGANISM: Homo sapiens

<400> SEQUENCE: 610

Leu Thr Val Ala Glu Val Gln Lys Leu Leu Gly Pro His Val Glu Gly
1               5                   10                  15

Leu Lys

<210> SEQ ID NO 611
<211> LENGTH: 17
<212> TYPE: PRT
<213> ORGANISM: Homo sapiens

<400> SEQUENCE: 611

Leu Thr Val Ala Glu Val Gln Lys Leu Leu Gly Pro His Val Glu Gly
1               5                   10                  15

Leu

<210> SEQ ID NO 612
<211> LENGTH: 17
<212> TYPE: PRT
<213> ORGANISM: Homo sapiens

<400> SEQUENCE: 612

Thr Val Ala Glu Val Gln Lys Leu Leu Gly Pro His Val Glu Gly Leu
1               5                   10                  15

Lys

<210> SEQ ID NO 613

-continued

```
<211> LENGTH: 16
<212> TYPE: PRT
<213> ORGANISM: Homo sapiens

<400> SEQUENCE: 613

Leu Thr Val Ala Glu Val Gln Lys Leu Leu Gly Pro His Val Glu Gly
1               5                   10                  15

<210> SEQ ID NO 614
<211> LENGTH: 16
<212> TYPE: PRT
<213> ORGANISM: Homo sapiens

<400> SEQUENCE: 614

Thr Val Ala Glu Val Gln Lys Leu Leu Gly Pro His Val Glu Gly Leu
1               5                   10                  15

<210> SEQ ID NO 615
<211> LENGTH: 16
<212> TYPE: PRT
<213> ORGANISM: Homo sapiens

<400> SEQUENCE: 615

Val Ala Glu Val Gln Lys Leu Leu Gly Pro His Val Glu Gly Leu Lys
1               5                   10                  15

<210> SEQ ID NO 616
<211> LENGTH: 15
<212> TYPE: PRT
<213> ORGANISM: Homo sapiens

<400> SEQUENCE: 616

Thr Val Ala Glu Val Gln Lys Leu Leu Gly Pro His Val Glu Gly
1               5                   10                  15

<210> SEQ ID NO 617
<211> LENGTH: 15
<212> TYPE: PRT
<213> ORGANISM: Homo sapiens

<400> SEQUENCE: 617

Val Ala Glu Val Gln Lys Leu Leu Gly Pro His Val Glu Gly Leu
1               5                   10                  15

<210> SEQ ID NO 618
<211> LENGTH: 14
<212> TYPE: PRT
<213> ORGANISM: Homo sapiens

<400> SEQUENCE: 618

Val Ala Glu Val Gln Lys Leu Leu Gly Pro His Val Glu Gly
1               5                   10

<210> SEQ ID NO 619
<211> LENGTH: 13
<212> TYPE: PRT
<213> ORGANISM: Homo sapiens

<400> SEQUENCE: 619

Val Ala Glu Val Gln Lys Leu Leu Gly Pro His Val Glu
1               5                   10

<210> SEQ ID NO 620
<211> LENGTH: 12
<212> TYPE: PRT
```

```
<213> ORGANISM: Homo sapiens

<400> SEQUENCE: 620

Glu Val Gln Lys Leu Leu Gly Pro His Val Glu Gly
1               5                   10

<210> SEQ ID NO 621
<211> LENGTH: 11
<212> TYPE: PRT
<213> ORGANISM: Homo sapiens

<400> SEQUENCE: 621

Leu Thr Val Ala Glu Val Gln Lys Leu Leu Gly
1               5                   10

<210> SEQ ID NO 622
<211> LENGTH: 25
<212> TYPE: PRT
<213> ORGANISM: Homo sapiens

<400> SEQUENCE: 622

Met Asp Ala Leu Arg Gly Leu Leu Pro Val Leu Gly Gln Pro Ile Ile
1               5                   10                  15

Arg Ser Ile Pro Gln Gly Ile Val Ala
            20                  25

<210> SEQ ID NO 623
<211> LENGTH: 23
<212> TYPE: PRT
<213> ORGANISM: Homo sapiens

<400> SEQUENCE: 623

Ala Leu Arg Gly Leu Leu Pro Val Leu Gly Gln Pro Ile Ile Arg Ser
1               5                   10                  15

Ile Pro Gln Gly Ile Val Ala
            20

<210> SEQ ID NO 624
<211> LENGTH: 22
<212> TYPE: PRT
<213> ORGANISM: Homo sapiens

<400> SEQUENCE: 624

Leu Arg Gly Leu Leu Pro Val Leu Gly Gln Pro Ile Ile Arg Ser Ile
1               5                   10                  15

Pro Gln Gly Ile Val Ala
            20

<210> SEQ ID NO 625
<211> LENGTH: 21
<212> TYPE: PRT
<213> ORGANISM: Homo sapiens

<400> SEQUENCE: 625

Asp Ala Leu Arg Gly Leu Leu Pro Val Leu Gly Gln Pro Ile Ile Arg
1               5                   10                  15

Ser Ile Pro Gln Gly
            20

<210> SEQ ID NO 626
<211> LENGTH: 21
<212> TYPE: PRT
<213> ORGANISM: Homo sapiens
```

-continued

<400> SEQUENCE: 626

Arg Gly Leu Leu Pro Val Leu Gly Gln Pro Ile Ile Arg Ser Ile Pro
1               5                   10                  15

Gln Gly Ile Val Ala
            20

<210> SEQ ID NO 627
<211> LENGTH: 20
<212> TYPE: PRT
<213> ORGANISM: Homo sapiens

<400> SEQUENCE: 627

Ala Leu Arg Gly Leu Leu Pro Val Leu Gly Gln Pro Ile Ile Arg Ser
1               5                   10                  15

Ile Pro Gln Gly
            20

<210> SEQ ID NO 628
<211> LENGTH: 20
<212> TYPE: PRT
<213> ORGANISM: Homo sapiens

<400> SEQUENCE: 628

Asp Ala Leu Arg Gly Leu Leu Pro Val Leu Gly Gln Pro Ile Ile Arg
1               5                   10                  15

Ser Ile Pro Gln
            20

<210> SEQ ID NO 629
<211> LENGTH: 20
<212> TYPE: PRT
<213> ORGANISM: Homo sapiens

<400> SEQUENCE: 629

Gly Leu Leu Pro Val Leu Gly Gln Pro Ile Ile Arg Ser Ile Pro Gln
1               5                   10                  15

Gly Ile Val Ala
            20

<210> SEQ ID NO 630
<211> LENGTH: 19
<212> TYPE: PRT
<213> ORGANISM: Homo sapiens

<400> SEQUENCE: 630

Ala Leu Arg Gly Leu Leu Pro Val Leu Gly Gln Pro Ile Ile Arg Ser
1               5                   10                  15

Ile Pro Gln

<210> SEQ ID NO 631
<211> LENGTH: 19
<212> TYPE: PRT
<213> ORGANISM: Homo sapiens

<400> SEQUENCE: 631

Asp Ala Leu Arg Gly Leu Leu Pro Val Leu Gly Gln Pro Ile Ile Arg
1               5                   10                  15

Ser Ile Pro

<210> SEQ ID NO 632

<211> LENGTH: 19
<212> TYPE: PRT
<213> ORGANISM: Homo sapiens

<400> SEQUENCE: 632

Leu Leu Pro Val Leu Gly Gln Pro Ile Ile Arg Ser Ile Pro Gln Gly
1               5                   10                  15

Ile Val Ala

<210> SEQ ID NO 633
<211> LENGTH: 18
<212> TYPE: PRT
<213> ORGANISM: Homo sapiens

<400> SEQUENCE: 633

Leu Arg Gly Leu Leu Pro Val Leu Gly Gln Pro Ile Ile Arg Ser Ile
1               5                   10                  15

Pro Gln

<210> SEQ ID NO 634
<211> LENGTH: 17
<212> TYPE: PRT
<213> ORGANISM: Homo sapiens

<400> SEQUENCE: 634

Asp Ala Leu Arg Gly Leu Leu Pro Val Leu Gly Gln Pro Ile Ile Arg
1               5                   10                  15

Ser

<210> SEQ ID NO 635
<211> LENGTH: 16
<212> TYPE: PRT
<213> ORGANISM: Homo sapiens

<400> SEQUENCE: 635

Ala Leu Arg Gly Leu Leu Pro Val Leu Gly Gln Pro Ile Ile Arg Ser
1               5                   10                  15

<210> SEQ ID NO 636
<211> LENGTH: 16
<212> TYPE: PRT
<213> ORGANISM: Homo sapiens

<400> SEQUENCE: 636

Asp Ala Leu Arg Gly Leu Leu Pro Val Leu Gly Gln Pro Ile Ile Arg
1               5                   10                  15

<210> SEQ ID NO 637
<211> LENGTH: 15
<212> TYPE: PRT
<213> ORGANISM: Homo sapiens

<400> SEQUENCE: 637

Ala Leu Arg Gly Leu Leu Pro Val Leu Gly Gln Pro Ile Ile Arg
1               5                   10                  15

<210> SEQ ID NO 638
<211> LENGTH: 15
<212> TYPE: PRT
<213> ORGANISM: Homo sapiens

<400> SEQUENCE: 638

Leu Arg Gly Leu Leu Pro Val Leu Gly Gln Pro Ile Ile Arg Ser

-continued

```
1               5                   10                  15
```

<210> SEQ ID NO 639
<211> LENGTH: 14
<212> TYPE: PRT
<213> ORGANISM: Homo sapiens

<400> SEQUENCE: 639

```
Ala Leu Arg Gly Leu Leu Pro Val Leu Gly Gln Pro Ile Ile
1               5                   10
```

<210> SEQ ID NO 640
<211> LENGTH: 13
<212> TYPE: PRT
<213> ORGANISM: Homo sapiens

<400> SEQUENCE: 640

```
Ala Leu Arg Gly Leu Leu Pro Val Leu Gly Gln Pro Ile
1               5                   10
```

<210> SEQ ID NO 641
<211> LENGTH: 13
<212> TYPE: PRT
<213> ORGANISM: Homo sapiens

<400> SEQUENCE: 641

```
Arg Gly Leu Leu Pro Val Leu Gly Gln Pro Ile Ile Arg
1               5                   10
```

<210> SEQ ID NO 642
<211> LENGTH: 12
<212> TYPE: PRT
<213> ORGANISM: Homo sapiens

<400> SEQUENCE: 642

```
Gly Leu Leu Pro Val Leu Gly Gln Pro Ile Ile Arg
1               5                   10
```

<210> SEQ ID NO 643
<211> LENGTH: 12
<212> TYPE: PRT
<213> ORGANISM: Homo sapiens

<400> SEQUENCE: 643

```
Leu Arg Gly Leu Leu Pro Val Leu Gly Gln Pro Ile
1               5                   10
```

<210> SEQ ID NO 644
<211> LENGTH: 11
<212> TYPE: PRT
<213> ORGANISM: Homo sapiens

<400> SEQUENCE: 644

```
Arg Gly Leu Leu Pro Val Leu Gly Gln Pro Ile
1               5                   10
```

<210> SEQ ID NO 645
<211> LENGTH: 25
<212> TYPE: PRT
<213> ORGANISM: Homo sapiens

<400> SEQUENCE: 645

```
Arg Gly Leu Leu Pro Val Leu Gly Gln Pro Ile Ile Arg Ser Ile Pro
1               5                   10                  15
```

Gln Gly Ile Val Ala Ala Trp Arg Gln
            20                  25

<210> SEQ ID NO 646
<211> LENGTH: 24
<212> TYPE: PRT
<213> ORGANISM: Homo sapiens

<400> SEQUENCE: 646

Gly Leu Leu Pro Val Leu Gly Gln Pro Ile Ile Arg Ser Ile Pro Gln
1               5                   10                  15

Gly Ile Val Ala Ala Trp Arg Gln
            20

<210> SEQ ID NO 647
<211> LENGTH: 22
<212> TYPE: PRT
<213> ORGANISM: Homo sapiens

<400> SEQUENCE: 647

Leu Pro Val Leu Gly Gln Pro Ile Ile Arg Ser Ile Pro Gln Gly Ile
1               5                   10                  15

Val Ala Ala Trp Arg Gln
            20

<210> SEQ ID NO 648
<211> LENGTH: 21
<212> TYPE: PRT
<213> ORGANISM: Homo sapiens

<400> SEQUENCE: 648

Gly Leu Leu Pro Val Leu Gly Gln Pro Ile Ile Arg Ser Ile Pro Gln
1               5                   10                  15

Gly Ile Val Ala Ala
            20

<210> SEQ ID NO 649
<211> LENGTH: 20
<212> TYPE: PRT
<213> ORGANISM: Homo sapiens

<400> SEQUENCE: 649

Leu Leu Pro Val Leu Gly Gln Pro Ile Ile Arg Ser Ile Pro Gln Gly
1               5                   10                  15

Ile Val Ala Ala
            20

<210> SEQ ID NO 650
<211> LENGTH: 20
<212> TYPE: PRT
<213> ORGANISM: Homo sapiens

<400> SEQUENCE: 650

Leu Pro Val Leu Gly Gln Pro Ile Ile Arg Ser Ile Pro Gln Gly Ile
1               5                   10                  15

Val Ala Ala Trp
            20

<210> SEQ ID NO 651
<211> LENGTH: 19
<212> TYPE: PRT
<213> ORGANISM: Homo sapiens

```
<400> SEQUENCE: 651

Leu Pro Val Leu Gly Gln Pro Ile Ile Arg Ser Ile Pro Gln Gly Ile
1               5                   10                  15

Val Ala Ala

<210> SEQ ID NO 652
<211> LENGTH: 19
<212> TYPE: PRT
<213> ORGANISM: Homo sapiens

<400> SEQUENCE: 652

Pro Val Leu Gly Gln Pro Ile Ile Arg Ser Ile Pro Gln Gly Ile Val
1               5                   10                  15

Ala Ala Trp

<210> SEQ ID NO 653
<211> LENGTH: 18
<212> TYPE: PRT
<213> ORGANISM: Homo sapiens

<400> SEQUENCE: 653

Leu Pro Val Leu Gly Gln Pro Ile Ile Arg Ser Ile Pro Gln Gly Ile
1               5                   10                  15

Val Ala

<210> SEQ ID NO 654
<211> LENGTH: 17
<212> TYPE: PRT
<213> ORGANISM: Homo sapiens

<400> SEQUENCE: 654

Pro Val Leu Gly Gln Pro Ile Ile Arg Ser Ile Pro Gln Gly Ile Val
1               5                   10                  15

Ala

<210> SEQ ID NO 655
<211> LENGTH: 16
<212> TYPE: PRT
<213> ORGANISM: Homo sapiens

<400> SEQUENCE: 655

Leu Gly Gln Pro Ile Ile Arg Ser Ile Pro Gln Gly Ile Val Ala Ala
1               5                   10                  15

<210> SEQ ID NO 656
<211> LENGTH: 16
<212> TYPE: PRT
<213> ORGANISM: Homo sapiens

<400> SEQUENCE: 656

Val Leu Gly Gln Pro Ile Ile Arg Ser Ile Pro Gln Gly Ile Val Ala
1               5                   10                  15

<210> SEQ ID NO 657
<211> LENGTH: 13
<212> TYPE: PRT
<213> ORGANISM: Homo sapiens

<400> SEQUENCE: 657

Gln Pro Ile Ile Arg Ser Ile Pro Gln Gly Ile Val Ala
1               5                   10
```

<210> SEQ ID NO 658
<211> LENGTH: 25
<212> TYPE: PRT
<213> ORGANISM: Homo sapiens

<400> SEQUENCE: 658

Val Ser Thr Met Asp Ala Leu Arg Gly Leu Leu Pro Val Leu Gly Gln
1               5                   10                  15

Pro Ile Ile Arg Ser Ile Pro Gln Gly
            20                  25

<210> SEQ ID NO 659
<211> LENGTH: 24
<212> TYPE: PRT
<213> ORGANISM: Homo sapiens

<400> SEQUENCE: 659

Val Ser Thr Met Asp Ala Leu Arg Gly Leu Leu Pro Val Leu Gly Gln
1               5                   10                  15

Pro Ile Ile Arg Ser Ile Pro Gln
            20

<210> SEQ ID NO 660
<211> LENGTH: 20
<212> TYPE: PRT
<213> ORGANISM: Homo sapiens

<400> SEQUENCE: 660

Val Ser Thr Met Asp Ala Leu Arg Gly Leu Leu Pro Val Leu Gly Gln
1               5                   10                  15

Pro Ile Ile Arg
            20

<210> SEQ ID NO 661
<211> LENGTH: 19
<212> TYPE: PRT
<213> ORGANISM: Homo sapiens

<400> SEQUENCE: 661

Leu Arg Gly Leu Leu Pro Val Leu Gly Gln Pro Ile Ile Arg Ser Ile
1               5                   10                  15

Pro Gln Gly

<210> SEQ ID NO 662
<211> LENGTH: 24
<212> TYPE: PRT
<213> ORGANISM: Homo sapiens

<400> SEQUENCE: 662

Leu Arg Thr Asp Ala Val Leu Pro Leu Thr Val Ala Glu Val Gln Lys
1               5                   10                  15

Leu Leu Gly Pro His Val Glu Gly
            20

<210> SEQ ID NO 663
<211> LENGTH: 23
<212> TYPE: PRT
<213> ORGANISM: Homo sapiens

<400> SEQUENCE: 663

Arg Thr Asp Ala Val Leu Pro Leu Thr Val Ala Glu Val Gln Lys Leu
1               5                   10                  15

```
Leu Gly Pro His Val Glu Gly
            20

<210> SEQ ID NO 664
<211> LENGTH: 20
<212> TYPE: PRT
<213> ORGANISM: Homo sapiens

<400> SEQUENCE: 664

Ala Val Leu Pro Leu Thr Val Ala Glu Val Gln Lys Leu Leu Gly Pro
1               5                   10                  15

His Val Glu Gly
            20

<210> SEQ ID NO 665
<211> LENGTH: 19
<212> TYPE: PRT
<213> ORGANISM: Homo sapiens

<400> SEQUENCE: 665

Val Leu Pro Leu Thr Val Ala Glu Val Gln Lys Leu Leu Gly Pro His
1               5                   10                  15

Val Glu Gly

<210> SEQ ID NO 666
<211> LENGTH: 18
<212> TYPE: PRT
<213> ORGANISM: Homo sapiens

<400> SEQUENCE: 666

Leu Pro Leu Thr Val Ala Glu Val Gln Lys Leu Leu Gly Pro His Val
1               5                   10                  15

Glu Gly

<210> SEQ ID NO 667
<211> LENGTH: 13
<212> TYPE: PRT
<213> ORGANISM: Homo sapiens

<400> SEQUENCE: 667

Thr Asp Ala Val Leu Pro Leu Thr Val Ala Glu Val Gln
1               5                   10

<210> SEQ ID NO 668
<211> LENGTH: 12
<212> TYPE: PRT
<213> ORGANISM: Homo sapiens

<400> SEQUENCE: 668

Ala Val Leu Pro Leu Thr Val Ala Glu Val Gln Lys
1               5                   10

<210> SEQ ID NO 669
<211> LENGTH: 24
<212> TYPE: PRT
<213> ORGANISM: Homo sapiens

<400> SEQUENCE: 669

Val Leu Pro Leu Thr Val Ala Glu Val Gln Lys Leu Leu Gly Pro His
1               5                   10                  15

Val Glu Gly Leu Lys Ala Glu Glu
            20
```

```
<210> SEQ ID NO 670
<211> LENGTH: 21
<212> TYPE: PRT
<213> ORGANISM: Homo sapiens

<400> SEQUENCE: 670

Val Leu Pro Leu Thr Val Ala Glu Val Gln Lys Leu Leu Gly Pro His
1               5                   10                  15

Val Glu Gly Leu Lys
            20

<210> SEQ ID NO 671
<211> LENGTH: 20
<212> TYPE: PRT
<213> ORGANISM: Homo sapiens

<400> SEQUENCE: 671

Leu Pro Leu Thr Val Ala Glu Val Gln Lys Leu Leu Gly Pro His Val
1               5                   10                  15

Glu Gly Leu Lys
            20

<210> SEQ ID NO 672
<211> LENGTH: 23
<212> TYPE: PRT
<213> ORGANISM: Homo sapiens

<400> SEQUENCE: 672

Leu Arg Gly Leu Leu Pro Val Leu Gly Gln Pro Ile Ile Arg Ser Ile
1               5                   10                  15

Pro Gln Gly Ile Val Ala Ala
            20

<210> SEQ ID NO 673
<211> LENGTH: 21
<212> TYPE: PRT
<213> ORGANISM: Homo sapiens

<400> SEQUENCE: 673

Ile Pro Phe Thr Tyr Glu Gln Leu Asp Val Leu Lys His Lys Leu Asp
1               5                   10                  15

Glu Leu Tyr Pro Gln
            20

<210> SEQ ID NO 674
<211> LENGTH: 17
<212> TYPE: PRT
<213> ORGANISM: Homo sapiens

<400> SEQUENCE: 674

Ile Pro Phe Thr Tyr Glu Gln Leu Asp Val Leu Lys His Lys Leu Asp
1               5                   10                  15

Glu

<210> SEQ ID NO 675
<211> LENGTH: 16
<212> TYPE: PRT
<213> ORGANISM: Homo sapiens

<400> SEQUENCE: 675

Ile Pro Phe Thr Tyr Glu Gln Leu Asp Val Leu Lys His Lys Leu Asp
```

-continued

```
1               5                   10                  15
```

<210> SEQ ID NO 676
<211> LENGTH: 20
<212> TYPE: PRT
<213> ORGANISM: Homo sapiens

<400> SEQUENCE: 676

Val Pro Pro Ser Ser Ile Trp Ala Val Arg Pro Gln Asp Leu Asp Thr
1               5                   10                  15

Cys Asp Pro Arg
            20

<210> SEQ ID NO 677
<211> LENGTH: 15
<212> TYPE: PRT
<213> ORGANISM: Homo sapiens

<400> SEQUENCE: 677

Ile Trp Ala Val Arg Pro Gln Asp Leu Asp Thr Cys Asp Pro Arg
1               5                   10                  15

<210> SEQ ID NO 678
<211> LENGTH: 13
<212> TYPE: PRT
<213> ORGANISM: Homo sapiens

<400> SEQUENCE: 678

Ala Val Arg Pro Gln Asp Leu Asp Thr Cys Asp Pro Arg
1               5                   10

<210> SEQ ID NO 679
<211> LENGTH: 20
<212> TYPE: PRT
<213> ORGANISM: Homo sapiens

<400> SEQUENCE: 679

Trp Gly Val Arg Gly Ser Leu Leu Ser Glu Ala Asp Val Arg Ala Leu
1               5                   10                  15

Gly Gly Leu Ala
            20

<210> SEQ ID NO 680
<211> LENGTH: 19
<212> TYPE: PRT
<213> ORGANISM: Homo sapiens

<400> SEQUENCE: 680

Gly Val Arg Gly Ser Leu Leu Ser Glu Ala Asp Val Arg Ala Leu Gly
1               5                   10                  15

Gly Leu Ala

<210> SEQ ID NO 681
<211> LENGTH: 19
<212> TYPE: PRT
<213> ORGANISM: Homo sapiens

<400> SEQUENCE: 681

Trp Gly Val Arg Gly Ser Leu Leu Ser Glu Ala Asp Val Arg Ala Leu
1               5                   10                  15

Gly Gly Leu

```
<210> SEQ ID NO 682
<211> LENGTH: 18
<212> TYPE: PRT
<213> ORGANISM: Homo sapiens

<400> SEQUENCE: 682

Gly Val Arg Gly Ser Leu Leu Ser Glu Ala Asp Val Arg Ala Leu Gly
1               5                   10                  15

Gly Leu

<210> SEQ ID NO 683
<211> LENGTH: 18
<212> TYPE: PRT
<213> ORGANISM: Homo sapiens

<400> SEQUENCE: 683

Val Arg Gly Ser Leu Leu Ser Glu Ala Asp Val Arg Ala Leu Gly Gly
1               5                   10                  15

Leu Ala

<210> SEQ ID NO 684
<211> LENGTH: 18
<212> TYPE: PRT
<213> ORGANISM: Homo sapiens

<400> SEQUENCE: 684

Trp Gly Val Arg Gly Ser Leu Leu Ser Glu Ala Asp Val Arg Ala Leu
1               5                   10                  15

Gly Gly

<210> SEQ ID NO 685
<211> LENGTH: 17
<212> TYPE: PRT
<213> ORGANISM: Homo sapiens

<400> SEQUENCE: 685

Gly Val Arg Gly Ser Leu Leu Ser Glu Ala Asp Val Arg Ala Leu Gly
1               5                   10                  15

Gly

<210> SEQ ID NO 686
<211> LENGTH: 17
<212> TYPE: PRT
<213> ORGANISM: Homo sapiens

<400> SEQUENCE: 686

Val Arg Gly Ser Leu Leu Ser Glu Ala Asp Val Arg Ala Leu Gly Gly
1               5                   10                  15

Leu

<210> SEQ ID NO 687
<211> LENGTH: 17
<212> TYPE: PRT
<213> ORGANISM: Homo sapiens

<400> SEQUENCE: 687

Trp Gly Val Arg Gly Ser Leu Leu Ser Glu Ala Asp Val Arg Ala Leu
1               5                   10                  15

Gly

<210> SEQ ID NO 688
```

```
<211> LENGTH: 16
<212> TYPE: PRT
<213> ORGANISM: Homo sapiens

<400> SEQUENCE: 688

Gly Val Arg Gly Ser Leu Leu Ser Glu Ala Asp Val Arg Ala Leu Gly
1               5                   10                  15

<210> SEQ ID NO 689
<211> LENGTH: 16
<212> TYPE: PRT
<213> ORGANISM: Homo sapiens

<400> SEQUENCE: 689

Trp Gly Val Arg Gly Ser Leu Leu Ser Glu Ala Asp Val Arg Ala Leu
1               5                   10                  15

<210> SEQ ID NO 690
<211> LENGTH: 15
<212> TYPE: PRT
<213> ORGANISM: Homo sapiens

<400> SEQUENCE: 690

Gly Ser Leu Leu Ser Glu Ala Asp Val Arg Ala Leu Gly Gly Leu
1               5                   10                  15

<210> SEQ ID NO 691
<211> LENGTH: 15
<212> TYPE: PRT
<213> ORGANISM: Homo sapiens

<400> SEQUENCE: 691

Gly Val Arg Gly Ser Leu Leu Ser Glu Ala Asp Val Arg Ala Leu
1               5                   10                  15

<210> SEQ ID NO 692
<211> LENGTH: 15
<212> TYPE: PRT
<213> ORGANISM: Homo sapiens

<400> SEQUENCE: 692

Arg Gly Ser Leu Leu Ser Glu Ala Asp Val Arg Ala Leu Gly Gly
1               5                   10                  15

<210> SEQ ID NO 693
<211> LENGTH: 15
<212> TYPE: PRT
<213> ORGANISM: Homo sapiens

<400> SEQUENCE: 693

Trp Gly Val Arg Gly Ser Leu Leu Ser Glu Ala Asp Val Arg Ala
1               5                   10                  15

<210> SEQ ID NO 694
<211> LENGTH: 14
<212> TYPE: PRT
<213> ORGANISM: Homo sapiens

<400> SEQUENCE: 694

Gly Ser Leu Leu Ser Glu Ala Asp Val Arg Ala Leu Gly Gly
1               5                   10

<210> SEQ ID NO 695
<211> LENGTH: 14
<212> TYPE: PRT
```

<213> ORGANISM: Homo sapiens

<400> SEQUENCE: 695

Arg Gly Ser Leu Leu Ser Glu Ala Asp Val Arg Ala Leu Gly
1               5                   10

<210> SEQ ID NO 696
<211> LENGTH: 14
<212> TYPE: PRT
<213> ORGANISM: Homo sapiens

<400> SEQUENCE: 696

Trp Gly Val Arg Gly Ser Leu Leu Ser Glu Ala Asp Val Arg
1               5                   10

<210> SEQ ID NO 697
<211> LENGTH: 13
<212> TYPE: PRT
<213> ORGANISM: Homo sapiens

<400> SEQUENCE: 697

Gly Ser Leu Leu Ser Glu Ala Asp Val Arg Ala Leu Gly
1               5                   10

<210> SEQ ID NO 698
<211> LENGTH: 13
<212> TYPE: PRT
<213> ORGANISM: Homo sapiens

<400> SEQUENCE: 698

Val Arg Gly Ser Leu Leu Ser Glu Ala Asp Val Arg Ala
1               5                   10

<210> SEQ ID NO 699
<211> LENGTH: 12
<212> TYPE: PRT
<213> ORGANISM: Homo sapiens

<400> SEQUENCE: 699

Leu Leu Ser Glu Ala Asp Val Arg Ala Leu Gly Gly
1               5                   10

<210> SEQ ID NO 700
<211> LENGTH: 12
<212> TYPE: PRT
<213> ORGANISM: Homo sapiens

<400> SEQUENCE: 700

Ser Leu Leu Ser Glu Ala Asp Val Arg Ala Leu Gly
1               5                   10

<210> SEQ ID NO 701
<211> LENGTH: 11
<212> TYPE: PRT
<213> ORGANISM: Homo sapiens

<400> SEQUENCE: 701

Gly Ser Leu Leu Ser Glu Ala Asp Val Arg Ala
1               5                   10

<210> SEQ ID NO 702
<211> LENGTH: 11
<212> TYPE: PRT
<213> ORGANISM: Homo sapiens

```
<400> SEQUENCE: 702

Leu Leu Ser Glu Ala Asp Val Arg Ala Leu Gly
1               5                   10

<210> SEQ ID NO 703
<211> LENGTH: 11
<212> TYPE: PRT
<213> ORGANISM: Homo sapiens

<400> SEQUENCE: 703

Leu Ser Glu Ala Asp Val Arg Ala Leu Gly Gly
1               5                   10

<210> SEQ ID NO 704
<211> LENGTH: 10
<212> TYPE: PRT
<213> ORGANISM: Homo sapiens

<400> SEQUENCE: 704

Ser Glu Ala Asp Val Arg Ala Leu Gly Gly
1               5                   10

<210> SEQ ID NO 705
<211> LENGTH: 9
<212> TYPE: PRT
<213> ORGANISM: Homo sapiens

<400> SEQUENCE: 705

Glu Ala Asp Val Arg Ala Leu Gly Gly
1               5

<210> SEQ ID NO 706
<211> LENGTH: 19
<212> TYPE: PRT
<213> ORGANISM: Homo sapiens

<400> SEQUENCE: 706

Leu Ser Thr Glu Arg Val Arg Glu Leu Ala Val Ala Leu Ala Gln Lys
1               5                   10                  15

Asn Val Lys

<210> SEQ ID NO 707
<211> LENGTH: 17
<212> TYPE: PRT
<213> ORGANISM: Homo sapiens

<400> SEQUENCE: 707

Leu Ser Thr Glu Arg Val Arg Glu Leu Ala Val Ala Leu Ala Gln Lys
1               5                   10                  15

Asn

<210> SEQ ID NO 708
<211> LENGTH: 16
<212> TYPE: PRT
<213> ORGANISM: Homo sapiens

<400> SEQUENCE: 708

Glu Arg Val Arg Glu Leu Ala Val Ala Leu Ala Gln Lys Asn Val Lys
1               5                   10                  15

<210> SEQ ID NO 709
<211> LENGTH: 16
<212> TYPE: PRT
```

```
<213> ORGANISM: Homo sapiens

<400> SEQUENCE: 709

Leu Ser Thr Glu Arg Val Arg Glu Leu Ala Val Ala Leu Ala Gln Lys
1               5                   10                  15

<210> SEQ ID NO 710
<211> LENGTH: 15
<212> TYPE: PRT
<213> ORGANISM: Homo sapiens

<400> SEQUENCE: 710

Leu Ser Thr Glu Arg Val Arg Glu Leu Ala Val Ala Leu Ala Gln
1               5                   10                  15

<210> SEQ ID NO 711
<211> LENGTH: 15
<212> TYPE: PRT
<213> ORGANISM: Homo sapiens

<400> SEQUENCE: 711

Ser Thr Glu Arg Val Arg Glu Leu Ala Val Ala Leu Ala Gln Lys
1               5                   10                  15

<210> SEQ ID NO 712
<211> LENGTH: 15
<212> TYPE: PRT
<213> ORGANISM: Homo sapiens

<400> SEQUENCE: 712

Thr Glu Arg Val Arg Glu Leu Ala Val Ala Leu Ala Gln Lys Asn
1               5                   10                  15

<210> SEQ ID NO 713
<211> LENGTH: 14
<212> TYPE: PRT
<213> ORGANISM: Homo sapiens

<400> SEQUENCE: 713

Val Arg Glu Leu Ala Val Ala Leu Ala Gln Lys Asn Val Lys
1               5                   10

<210> SEQ ID NO 714
<211> LENGTH: 18
<212> TYPE: PRT
<213> ORGANISM: Homo sapiens

<400> SEQUENCE: 714

Ala Ile Pro Phe Thr Tyr Glu Gln Leu Asp Val Leu Lys His Lys Leu
1               5                   10                  15

Asp Glu

<210> SEQ ID NO 715
<211> LENGTH: 18
<212> TYPE: PRT
<213> ORGANISM: Homo sapiens

<400> SEQUENCE: 715

Gly Leu Ser Thr Glu Arg Val Arg Glu Leu Ala Val Ala Leu Ala Gln
1               5                   10                  15

Lys Asn

<210> SEQ ID NO 716
```

```
<211> LENGTH: 16
<212> TYPE: PRT
<213> ORGANISM: Homo sapiens

<400> SEQUENCE: 716

Gly Leu Ser Thr Glu Arg Val Arg Glu Leu Ala Val Ala Leu Ala Gln
1               5                   10                  15

<210> SEQ ID NO 717
<211> LENGTH: 18
<212> TYPE: PRT
<213> ORGANISM: Homo sapiens

<400> SEQUENCE: 717

Ile Pro Gln Gly Ile Val Ala Ala Trp Arg Gln Arg Ser Ser Arg Asp
1               5                   10                  15

Pro Ser

<210> SEQ ID NO 718
<211> LENGTH: 15
<212> TYPE: PRT
<213> ORGANISM: Homo sapiens

<400> SEQUENCE: 718

Gly Ile Val Ala Ala Trp Arg Gln Arg Ser Ser Arg Asp Pro Ser
1               5                   10                  15

<210> SEQ ID NO 719
<211> LENGTH: 15
<212> TYPE: PRT
<213> ORGANISM: Homo sapiens

<400> SEQUENCE: 719

Ile Pro Gln Gly Ile Val Ala Ala Trp Arg Gln Arg Ser Ser Arg
1               5                   10                  15

<210> SEQ ID NO 720
<211> LENGTH: 17
<212> TYPE: PRT
<213> ORGANISM: Homo sapiens

<400> SEQUENCE: 720

Ala Leu Gly Gly Leu Ala Cys Asp Leu Pro Gly Arg Phe Val Ala Glu
1               5                   10                  15

Ser

<210> SEQ ID NO 721
<211> LENGTH: 17
<212> TYPE: PRT
<213> ORGANISM: Homo sapiens

<400> SEQUENCE: 721

Arg Glu Leu Ala Val Ala Leu Ala Gln Lys Asn Val Lys Leu Ser Thr
1               5                   10                  15

Glu

<210> SEQ ID NO 722
<211> LENGTH: 16
<212> TYPE: PRT
<213> ORGANISM: Homo sapiens

<400> SEQUENCE: 722

Leu Lys Ala Leu Leu Glu Val Asn Lys Gly His Glu Met Ser Pro Gln
```

<210> SEQ ID NO 723
<211> LENGTH: 16
<212> TYPE: PRT
<213> ORGANISM: Homo sapiens

<400> SEQUENCE: 723

Thr Phe Met Lys Leu Arg Thr Asp Ala Val Leu Pro Leu Thr Val Ala
1               5                   10                  15

<210> SEQ ID NO 724
<211> LENGTH: 15
<212> TYPE: PRT
<213> ORGANISM: Homo sapiens

<400> SEQUENCE: 724

Phe Met Lys Leu Arg Thr Asp Ala Val Leu Pro Leu Thr Val Ala
1               5                   10                  15

<210> SEQ ID NO 725
<211> LENGTH: 13
<212> TYPE: PRT
<213> ORGANISM: Homo sapiens

<400> SEQUENCE: 725

Phe Met Lys Leu Arg Thr Asp Ala Val Leu Pro Leu Thr
1               5                   10

<210> SEQ ID NO 726
<211> LENGTH: 12
<212> TYPE: PRT
<213> ORGANISM: Homo sapiens

<400> SEQUENCE: 726

Phe Met Lys Leu Arg Thr Asp Ala Val Leu Pro Leu
1               5                   10

<210> SEQ ID NO 727
<211> LENGTH: 16
<212> TYPE: PRT
<213> ORGANISM: Homo sapiens

<400> SEQUENCE: 727

Thr Leu Gly Leu Gly Leu Gln Gly Gly Ile Pro Asn Gly Tyr Leu Val
1               5                   10                  15

<210> SEQ ID NO 728
<211> LENGTH: 15
<212> TYPE: PRT
<213> ORGANISM: Homo sapiens

<400> SEQUENCE: 728

Asp Leu Pro Gly Arg Phe Val Ala Glu Ser Ala Glu Val Leu Leu
1               5                   10                  15

<210> SEQ ID NO 729
<211> LENGTH: 14
<212> TYPE: PRT
<213> ORGANISM: Homo sapiens

<400> SEQUENCE: 729

Asp Leu Pro Gly Arg Phe Val Ala Glu Ser Ala Glu Val Leu
1               5                   10

<210> SEQ ID NO 730
<211> LENGTH: 13
<212> TYPE: PRT
<213> ORGANISM: Homo sapiens

<400> SEQUENCE: 730

Leu Pro Gly Arg Phe Val Ala Glu Ser Ala Glu Val Leu
1               5                   10

<210> SEQ ID NO 731
<211> LENGTH: 11
<212> TYPE: PRT
<213> ORGANISM: Homo sapiens

<400> SEQUENCE: 731

Asp Leu Pro Gly Arg Phe Val Ala Glu Ser Ala
1               5                   10

<210> SEQ ID NO 732
<211> LENGTH: 15
<212> TYPE: PRT
<213> ORGANISM: Homo sapiens

<400> SEQUENCE: 732

Glu Arg His Arg Pro Val Arg Asp Trp Ile Leu Arg Gln Arg Gln
1               5                   10                  15

<210> SEQ ID NO 733
<211> LENGTH: 15
<212> TYPE: PRT
<213> ORGANISM: Homo sapiens

<400> SEQUENCE: 733

Ser Pro Arg Gln Leu Leu Gly Phe Pro Cys Ala Glu Val Ser Gly
1               5                   10                  15

<210> SEQ ID NO 734
<211> LENGTH: 15
<212> TYPE: PRT
<213> ORGANISM: Homo sapiens

<400> SEQUENCE: 734

Ser Arg Thr Leu Ala Gly Glu Thr Gly Gln Glu Ala Ala Pro Leu
1               5                   10                  15

<210> SEQ ID NO 735
<211> LENGTH: 15
<212> TYPE: PRT
<213> ORGANISM: Homo sapiens

<400> SEQUENCE: 735

Val Thr Ser Leu Glu Thr Leu Lys Ala Leu Leu Glu Val Asn Lys
1               5                   10                  15

<210> SEQ ID NO 736
<211> LENGTH: 14
<212> TYPE: PRT
<213> ORGANISM: Homo sapiens

<400> SEQUENCE: 736

Leu Gly Leu Gln Gly Gly Ile Pro Asn Gly Tyr Leu Val Leu
1               5                   10

<210> SEQ ID NO 737

-continued

```
<211> LENGTH: 12
<212> TYPE: PRT
<213> ORGANISM: Homo sapiens

<400> SEQUENCE: 737

Leu Gln Gly Gly Ile Pro Asn Gly Tyr Leu Val Leu
1               5                   10

<210> SEQ ID NO 738
<211> LENGTH: 10
<212> TYPE: PRT
<213> ORGANISM: Homo sapiens

<400> SEQUENCE: 738

Gly Gly Ile Pro Asn Gly Tyr Leu Val Leu
1               5                   10

<210> SEQ ID NO 739
<211> LENGTH: 14
<212> TYPE: PRT
<213> ORGANISM: Homo sapiens

<400> SEQUENCE: 739

Leu Gln Gly Gly Ile Pro Asn Gly Tyr Leu Val Leu Asp Leu
1               5                   10

<210> SEQ ID NO 740
<211> LENGTH: 13
<212> TYPE: PRT
<213> ORGANISM: Homo sapiens

<400> SEQUENCE: 740

Ala Pro Glu Arg Gln Arg Leu Leu Pro Ala Ala Leu Ala
1               5                   10

<210> SEQ ID NO 741
<211> LENGTH: 13
<212> TYPE: PRT
<213> ORGANISM: Homo sapiens

<400> SEQUENCE: 741

Phe Val Lys Ile Gln Ser Phe Leu Gly Gly Ala Pro Thr
1               5                   10

<210> SEQ ID NO 742
<211> LENGTH: 10
<212> TYPE: PRT
<213> ORGANISM: Homo sapiens

<400> SEQUENCE: 742

Phe Val Lys Ile Gln Ser Phe Leu Gly Gly
1               5                   10

<210> SEQ ID NO 743
<211> LENGTH: 9
<212> TYPE: PRT
<213> ORGANISM: Homo sapiens

<400> SEQUENCE: 743

Phe Val Lys Ile Gln Ser Phe Leu Gly
1               5

<210> SEQ ID NO 744
<211> LENGTH: 11
<212> TYPE: PRT
```

<213> ORGANISM: Homo sapiens

<400> SEQUENCE: 744

Phe Leu Lys Met Ser Pro Glu Asp Ile Arg Lys
1               5                   10

<210> SEQ ID NO 745
<211> LENGTH: 21
<212> TYPE: PRT
<213> ORGANISM: Homo sapiens

<400> SEQUENCE: 745

Trp Glu Leu Ser Gln Leu Thr Asn Ser Val Thr Glu Leu Gly Pro Tyr
1               5                   10                  15

Thr Leu Asp Arg Asp
            20

<210> SEQ ID NO 746
<211> LENGTH: 20
<212> TYPE: PRT
<213> ORGANISM: Homo sapiens

<400> SEQUENCE: 746

Glu Ile Thr Ile Thr Thr Gln Thr Gly Tyr Ser Leu Ala Thr Ser Gln
1               5                   10                  15

Val Thr Leu Pro
            20

<210> SEQ ID NO 747
<211> LENGTH: 19
<212> TYPE: PRT
<213> ORGANISM: Homo sapiens

<400> SEQUENCE: 747

Ala Thr Thr Pro Ser Trp Val Glu Thr His Ser Ile Val Ile Gln Gly
1               5                   10                  15

Phe Pro His

<210> SEQ ID NO 748
<211> LENGTH: 19
<212> TYPE: PRT
<213> ORGANISM: Homo sapiens

<400> SEQUENCE: 748

Gly Ile Lys Glu Leu Gly Pro Tyr Thr Leu Asp Arg Asn Ser Leu Tyr
1               5                   10                  15

Val Asn Gly

<210> SEQ ID NO 749
<211> LENGTH: 15
<212> TYPE: PRT
<213> ORGANISM: Homo sapiens

<400> SEQUENCE: 749

Gly Ile Lys Glu Leu Gly Pro Tyr Thr Leu Asp Arg Asn Ser Leu
1               5                   10                  15

<210> SEQ ID NO 750
<211> LENGTH: 14
<212> TYPE: PRT
<213> ORGANISM: Homo sapiens

<400> SEQUENCE: 750

Gly Pro Tyr Thr Leu Asp Arg Asn Ser Leu Tyr Val Asn Gly
1               5                   10

<210> SEQ ID NO 751
<211> LENGTH: 13
<212> TYPE: PRT
<213> ORGANISM: Homo sapiens

<400> SEQUENCE: 751

Gly Ile Lys Glu Leu Gly Pro Tyr Thr Leu Asp Arg Asn
1               5                   10

<210> SEQ ID NO 752
<211> LENGTH: 13
<212> TYPE: PRT
<213> ORGANISM: Homo sapiens

<400> SEQUENCE: 752

Leu Gly Pro Tyr Thr Leu Asp Arg Asn Ser Leu Tyr Val
1               5                   10

<210> SEQ ID NO 753
<211> LENGTH: 12
<212> TYPE: PRT
<213> ORGANISM: Homo sapiens

<400> SEQUENCE: 753

Leu Gly Pro Tyr Thr Leu Asp Arg Asn Ser Leu Tyr
1               5                   10

<210> SEQ ID NO 754
<211> LENGTH: 11
<212> TYPE: PRT
<213> ORGANISM: Homo sapiens

<400> SEQUENCE: 754

Leu Gly Pro Tyr Thr Leu Asp Arg Asn Ser Leu
1               5                   10

<210> SEQ ID NO 755
<211> LENGTH: 17
<212> TYPE: PRT
<213> ORGANISM: Homo sapiens

<400> SEQUENCE: 755

Ile Glu Leu Gly Pro Tyr Leu Leu Asp Arg Gly Ser Leu Tyr Val Asn
1               5                   10                  15

Gly

<210> SEQ ID NO 756
<211> LENGTH: 15
<212> TYPE: PRT
<213> ORGANISM: Homo sapiens

<400> SEQUENCE: 756

Leu Gly Pro Tyr Leu Leu Asp Arg Gly Ser Leu Tyr Val Asn Gly
1               5                   10                  15

<210> SEQ ID NO 757
<211> LENGTH: 14
<212> TYPE: PRT
<213> ORGANISM: Homo sapiens

<400> SEQUENCE: 757

```
Leu Gly Pro Tyr Leu Leu Asp Arg Gly Ser Leu Tyr Val Asn
1               5                   10

<210> SEQ ID NO 758
<211> LENGTH: 13
<212> TYPE: PRT
<213> ORGANISM: Homo sapiens

<400> SEQUENCE: 758

Leu Gly Pro Tyr Leu Leu Asp Arg Gly Ser Leu Tyr Val
1               5                   10

<210> SEQ ID NO 759
<211> LENGTH: 17
<212> TYPE: PRT
<213> ORGANISM: Homo sapiens

<400> SEQUENCE: 759

Glu Glu Leu Gly Pro Tyr Thr Leu Asp Arg Asn Ser Leu Tyr Val Asn
1               5                   10                  15

Gly

<210> SEQ ID NO 760
<211> LENGTH: 16
<212> TYPE: PRT
<213> ORGANISM: Homo sapiens

<400> SEQUENCE: 760

Leu Lys Pro Leu Phe Lys Ser Thr Ser Val Gly Pro Leu Tyr Ser Gly
1               5                   10                  15

<210> SEQ ID NO 761
<211> LENGTH: 15
<212> TYPE: PRT
<213> ORGANISM: Homo sapiens

<400> SEQUENCE: 761

Leu Lys Pro Leu Phe Lys Ser Thr Ser Val Gly Pro Leu Tyr Ser
1               5                   10                  15

<210> SEQ ID NO 762
<211> LENGTH: 14
<212> TYPE: PRT
<213> ORGANISM: Homo sapiens

<400> SEQUENCE: 762

Leu Lys Pro Leu Phe Lys Ser Thr Ser Val Gly Pro Leu Tyr
1               5                   10

<210> SEQ ID NO 763
<211> LENGTH: 13
<212> TYPE: PRT
<213> ORGANISM: Homo sapiens

<400> SEQUENCE: 763

Leu Lys Pro Leu Phe Lys Ser Thr Ser Val Gly Pro Leu
1               5                   10

<210> SEQ ID NO 764
<211> LENGTH: 16
<212> TYPE: PRT
<213> ORGANISM: Homo sapiens

<400> SEQUENCE: 764
```

Phe Asp Lys Ala Phe Thr Ala Ala Thr Thr Glu Val Ser Arg Thr Glu
1               5                   10                  15

<210> SEQ ID NO 765
<211> LENGTH: 15
<212> TYPE: PRT
<213> ORGANISM: Homo sapiens

<400> SEQUENCE: 765

Glu Leu Gly Pro Tyr Thr Leu Asp Arg Asp Ser Leu Tyr Val Asn
1               5                   10                  15

<210> SEQ ID NO 766
<211> LENGTH: 15
<212> TYPE: PRT
<213> ORGANISM: Homo sapiens

<400> SEQUENCE: 766

Gly Leu Leu Lys Pro Leu Phe Lys Ser Thr Ser Val Gly Pro Leu
1               5                   10                  15

<210> SEQ ID NO 767
<211> LENGTH: 14
<212> TYPE: PRT
<213> ORGANISM: Homo sapiens

<400> SEQUENCE: 767

Leu Leu Lys Pro Leu Phe Lys Ser Thr Ser Val Gly Pro Leu
1               5                   10

<210> SEQ ID NO 768
<211> LENGTH: 15
<212> TYPE: PRT
<213> ORGANISM: Homo sapiens

<400> SEQUENCE: 768

Ser Asp Pro Tyr Lys Ala Thr Ser Ala Val Val Ile Thr Ser Thr
1               5                   10                  15

<210> SEQ ID NO 769
<211> LENGTH: 14
<212> TYPE: PRT
<213> ORGANISM: Homo sapiens

<400> SEQUENCE: 769

Ser Asp Pro Tyr Lys Ala Thr Ser Ala Val Val Ile Thr Ser
1               5                   10

<210> SEQ ID NO 770
<211> LENGTH: 15
<212> TYPE: PRT
<213> ORGANISM: Homo sapiens

<400> SEQUENCE: 770

Ser Arg Lys Phe Asn Thr Met Glu Ser Val Leu Gln Gly Leu Leu
1               5                   10                  15

<210> SEQ ID NO 771
<211> LENGTH: 13
<212> TYPE: PRT
<213> ORGANISM: Homo sapiens

<400> SEQUENCE: 771

Ser Arg Lys Phe Asn Thr Met Glu Ser Val Leu Gln Gly

```
<210> SEQ ID NO 772
<211> LENGTH: 14
<212> TYPE: PRT
<213> ORGANISM: Homo sapiens

<400> SEQUENCE: 772

Leu Gly Phe Tyr Val Leu Asp Arg Asp Ser Leu Phe Ile Asn
1               5                   10

<210> SEQ ID NO 773
<211> LENGTH: 9
<212> TYPE: PRT
<213> ORGANISM: Homo sapiens

<400> SEQUENCE: 773

Ala Leu Tyr Gly Lys Leu Leu Lys Leu
1               5

<210> SEQ ID NO 774
<211> LENGTH: 9
<212> TYPE: PRT
<213> ORGANISM: Homo sapiens

<400> SEQUENCE: 774

Val Tyr Val Asp Asp Ile Tyr Val Ile
1               5

<210> SEQ ID NO 775
<211> LENGTH: 10
<212> TYPE: PRT
<213> ORGANISM: Homo sapiens

<400> SEQUENCE: 775

Glu Leu Ala Gly Ile Gly Ile Leu Thr Val
1               5                   10

<210> SEQ ID NO 776
<211> LENGTH: 9
<212> TYPE: PRT
<213> ORGANISM: Homo sapiens

<400> SEQUENCE: 776

Tyr Leu Leu Pro Ala Ile Val His Ile
1               5
```